(12) United States Patent
Bartlett et al.

(10) Patent No.: US 11,040,033 B2
(45) Date of Patent: *Jun. 22, 2021

(54) THERAPEUTIC HETEROCYCLIC COMPOUNDS

(71) Applicant: Gilead Sciences, Inc., Foster City, CA (US)

(72) Inventors: Mark J. Bartlett, Castro Valley, CA (US); Britton Kenneth Corkey, Redwood City, CA (US); Jennifer Leigh Cosman, Foster City, CA (US); Kristyna M. Elbel, South San Francisco, CA (US); Elfatih Elzein, Mountain House, CA (US); Rao V. Kalla, Cupertino, CA (US); Dmitry Koltun, Foster City, CA (US); Xiaofen Li, Mountain View, CA (US); Eric Q. Parkhill, Union City, CA (US); Thao Perry, San Jose, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/999,548

(22) Filed: Aug. 20, 2018

(65) Prior Publication Data

US 2019/0192504 A1 Jun. 27, 2019

Related U.S. Application Data

(60) Provisional application No. 62/649,052, filed on Mar. 28, 2018, provisional application No. 62/556,748, filed on Sep. 11, 2017, provisional application No. 62/548,616, filed on Aug. 22, 2017.

(51) Int. Cl.

| | |
|---|---|
| *A61K 31/4745* | (2006.01) |
| *A61P 35/00* | (2006.01) |
| *A61K 31/497* | (2006.01) |
| *A61K 31/4985* | (2006.01) |
| *A61K 31/5025* | (2006.01) |
| *A61K 31/506* | (2006.01) |
| *A61K 31/519* | (2006.01) |
| *A61K 35/17* | (2015.01) |
| *A61K 35/26* | (2015.01) |
| *A61K 45/06* | (2006.01) |
| *C07D 471/04* | (2006.01) |
| *C07D 487/04* | (2006.01) |
| *A61K 31/437* | (2006.01) |

(Continued)

(52) U.S. Cl.
CPC ........ *A61K 31/4745* (2013.01); *A61K 31/437* (2013.01); *A61K 31/497* (2013.01); *A61K 31/4985* (2013.01); *A61K 31/506* (2013.01); *A61K 31/5025* (2013.01); *A61K 31/519* (2013.01); *A61K 35/17* (2013.01); *A61K 35/26* (2013.01); *A61K 39/3955* (2013.01); *A61K 45/06* (2013.01); *A61P 35/00* (2018.01); *C07D 471/04* (2013.01); *C07D 487/04* (2013.01); *C07K 16/2827* (2013.01); *C07K 2317/24* (2013.01)

(58) Field of Classification Search
USPC ........................................................ 514/223
See application file for complete search history.

(56) References Cited

FOREIGN PATENT DOCUMENTS

| WO | WO-03044021 A2 | 5/2003 |
|---|---|---|
| WO | WO-2008/107125 A1 | 9/2008 |

(Continued)

OTHER PUBLICATIONS

Intl. Search Report—Written Opinion dated Nov. 22, 2018 for PCT/US2018/000349.

(Continued)

*Primary Examiner* — Jared Barsky
(74) *Attorney, Agent, or Firm* — Sheppard Mullin Richter & Hampton LLP.

(57) ABSTRACT

Compounds having the following Formula I and/or Formula II and methods of their use and preparation are disclosed:

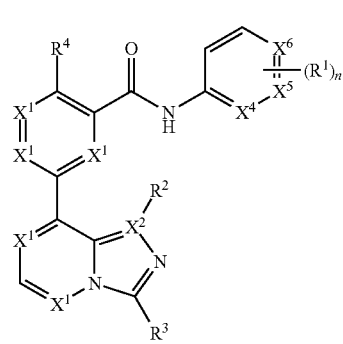

I

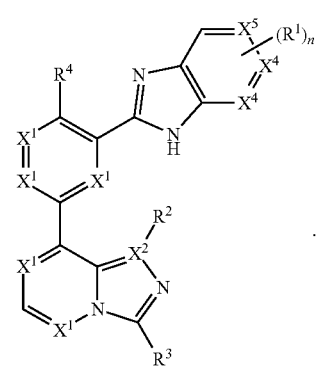

II

22 Claims, No Drawings

(51) Int. Cl.
*A61K 39/395* (2006.01)
*C07K 16/28* (2006.01)

(56) References Cited

FOREIGN PATENT DOCUMENTS

WO  WO-2016/106623 A1  7/2016
WO  WO-2016/161960 A1  10/2016

OTHER PUBLICATIONS

Examination Report dated May 4, 2020 for Australian Appl. No. 2018319538.
Examination Report dated Oct. 6, 2020 for Indian Appl. No. 202017010015.

THERAPEUTIC HETEROCYCLIC COMPOUNDS

This Application is a Continuation of Application 62/649,052 filed on Mar. 28, 2018. This Application claims the benefit of U.S. Provisional Application 62/556,748 filed on Sep. 11, 2017. This Application claims the benefit of U.S. Provisional Application 62/548,616 filed on Aug. 22, 2017. The entire contents of these applications are incorporated herein by reference in their entirety.

FIELD

The present disclosure relates generally to inhibitors of indoleamine 2,3-dioxygenase 1 (IDO1) activity and methods of use and manufacture thereof.

BACKGROUND

Catabolism of the essential amino acid tryptophan by the inducible heme-containing enzyme indoleamine 2,3-dioxygenase 1 (IDO1) is a central pathway maintaining the immunosuppressive microenvironment in many cancers. IDO1 catalyzes the degradation of tryptophan to kynurenine, and its effects on immune suppression are due to decreased tryptophan availability and the generation of tryptophan metabolites resulting in multipronged negative effects on cytotoxic T lymphocytes, as well as expansion of immunosuppressive regulatory T cells. IDO1 is elevated in multiple cancers, and is induced by chemotherapy, targeted therapy, or immunotherapy. IDO1 expression in the tumor microenvironment is correlated with poor prognosis in a variety of cancers. IDO1 inhibitors are positioned to potentiate the efficacy of multiple oncology therapeutics including immunotherapies, targeted agents, and chemotherapies. Indeed, epacadostat (INCB24360), a potent and selective IDO1 inhibitor, entered clinical trials and is demonstrating activity in combination with ipilimumab (anti-CTLA4) in melanoma.

In addition to the above, IDO1 has been shown to play a role in chronic infections, HIV and AIDS, autoimmune diseases or disorders (e.g., rheumatoid arthritis), and immunologic tolerance, such as prevention of fetal rejection in utero. Inhibition of IDO1 may also be an important treatment strategy for patients with neurological or neuropsychiatric diseases or disorders, such as depression.

A need remains for additional therapeutic agents useful to treat proliferative disorders or diseases that are mediated by IDO1.

SUMMARY

The present disclosure provides compounds that function as inhibitors of IDO1. The disclosure also provides compositions, including pharmaceutical compositions, kits that include the compounds, and methods of using and making the compounds. The compounds provided herein are useful in treating diseases, disorders, or conditions that are mediated by IDO1. The disclosure also provides compounds for use in therapy. The disclosure further provides compounds for use in a method of treating a disease, disorder, or condition that is mediated by IDO1. Moreover, the disclosure provides uses of the compounds in the manufacture of a medicament for the treatment of a disease, disorder or condition that is mediated by IDO1.

In some embodiments, provided is a compound having the structure of Formula I:

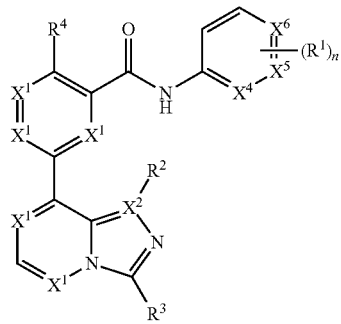

Formula I wherein
- $X^1$ at each location in Formula I is independently N, CH, or $CX^R$;
- $X^2$ is N or C, wherein $R^2$ is absent when $X^2$ is N;
- $X^4$ at each location in Formula I is independently N, CH, or $CR^1$;
- $X^5$ is CH, $CX^R$, or $CR^1$;
- $X^R$ is hydrogen, halogen, $C_{1-3}$ haloalkyl, or $C_{1-6}$ alkyl;
- $R^1$ is hydrogen, deuterium, halogen, —CN, —OCF$_3$, —OCHF$_2$, or —CF$_3$, wherein n is 0-5 and where if n is >1, $R^1$ can be independently the same or different from each other;
- $R^2$ is hydrogen, halogen, $C_{1-6}$ alkyl, or an unsubstituted or substituted aryl with one, two, or three substituents independently selected from halogen, —CN, $C_{1-6}$ haloalkyl, and $C_{1-6}$ alkyl;
- $R^3$ is $C_{3-6}$ cycloalkyl, $C_{3-6}$ heterocycle, mono or bicyclic aryl or heteroaryl, wherein each mono or bicyclic aryl or heteroaryl is unsubstituted or substituted with one, two, or three substituents independently selected from halogen, —CN, $C_{1-6}$ haloalkyl, and $C_{1-6}$ alkyl; and
- $R^4$ is halogen, $C_{1-6}$ alkyl, $C_{1-6}$ haloalkyl, —OCF$_3$, $C_{3-6}$ cycloalkyl, or a 4-12 membered heterocycle, or a pharmaceutically acceptable salt thereof.

Another embodiment provides a compound having the following Formula $I_a$:

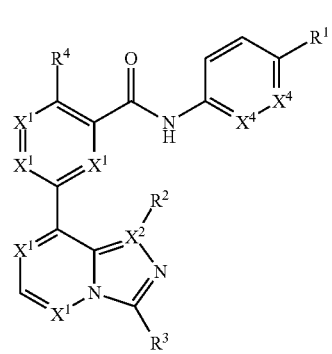

Formula $I_a$ wherein
- $X^1$ at each location of Formula Ia is independently N, CH, or $CX^R$;
- $X^2$ is N or C, wherein $R^2$ is absent when $X^2$ is N;
- $X^4$ at each location of Formula Ia is independently N, CH, or $CR^1$;
- $X^R$ is hydrogen, halogen, $C_{1-3}$ haloalkyl, or $C_{1-6}$ alkyl;
- $R^1$ is hydrogen, deuterium, halogen, —CN, —OCF$_3$, —OCHF$_2$, or —CF$_3$;

R² is absent when X² is N; or R² is hydrogen, halogen, C$_{1-6}$ alkyl, or an unsubstituted or substituted aryl with one, two, or three substituents independently selected from halogen, —CN, C$_{1-6}$ haloalkyl, and C$_{1-6}$ alkyl;

R³ is C$_{3-6}$ cycloalkyl, C$_{3-6}$ heterocycle, mono or bicyclic aryl or heteroaryl, wherein each mono or bicyclic aryl or heteroaryl is unsubstituted or substituted with one, two, or three substituents independently selected from halogen, —CN, C$_{1-6}$ haloalkyl, and C$_{1-6}$ alkyl; and R⁴ is halogen, C$_{1-6}$ alkyl, C$_{1-6}$ haloalkyl, —OCF$_3$, C$_{3-6}$ cycloalkyl, or a 4-12 membered heterocycle, or a pharmaceutically acceptable salt thereof.

Another embodiment provides a compound having the following Formula I$_b$:

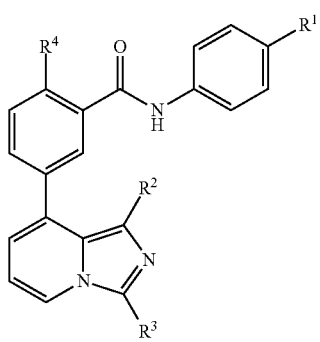

Formula I$_b$ wherein
R¹ is halogen;
R² is hydrogen, C$_{1-3}$ alkyl, or an unsubstituted or substituted aryl with one, two, or three substituents independently selected from halogen, —CN, C$_{1-3}$ haloalkyl, and C$_{1-3}$ alkyl;
R³ is a C$_{3-6}$ cycloalkyl, C$_{3-6}$ heterocycle, mono or bicyclic aryl or heteroaryl, wherein each mono or bicyclic aryl or heteroaryl is unsubstituted or substituted with one, two, or three substituents independently selected from halogen, —CN, C$_{1-3}$ haloalkyl, and C$_{1-3}$ alkyl; and
R⁴ is halogen, C$_{1-3}$ alkyl, C$_{1-3}$ haloalkyl, —OCF$_3$, C$_{3-6}$cycloalkyl, or 4-12 membered heterocycle,
or a pharmaceutically acceptable salt thereof.

Another embodiment provides a compound having the following Formula I$_c$:

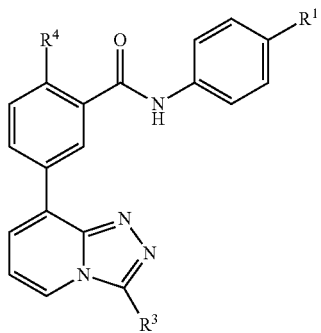

Formula I$_c$

R¹ is halogen;
R³ is a C$_{3-6}$ cycloalkyl, C$_{3-6}$ heterocycle, mono or bicyclic aryl or heteroaryl, wherein each mono or bicyclic aryl or heteroaryl is unsubstituted or substituted with one, two, or three substituents independently selected from halogen, —CN, C$_{1-3}$ haloalkyl, and C$_{1-3}$ alkyl; and R⁴ is halogen, C$_{1-3}$ alkyl, C$_{1-3}$ haloalkyl, —OCF$_3$, C$_{3-6}$ cycloalkyl, or 4-12 membered heterocycle, or a pharmaceutically acceptable salt thereof.

Another embodiment provides a compound having the following Formula I$_d$:

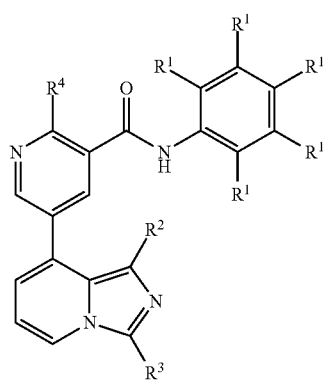

Formula I$_d$ wherein
R¹ is hydrogen, deuterium, halogen, —CN, —OCF$_3$, —OCHF$_2$, or —CF$_3$, wherein R¹ can be independently the same or different from each other;
R² is halogen, C$_{1-3}$ alkyl, C$_{1-3}$ haloalkyl, C$_{3-6}$ cycloalkyl, or 4-12 membered heterocycle;
R³ is a C$_{3-6}$ cycloalkyl, C$_{3-6}$ heterocycle, mono or bicyclic aryl or heteroaryl, wherein each mono or bicyclic aryl or heteroaryl is unsubstituted or substituted with one, two, or three substituents independently selected from halogen, —CN, C$_{1-3}$ haloalkyl, and C$_{1-3}$ alkyl; and
R⁴ is halogen, C$_{1-6}$ alkyl, C$_{1-6}$ haloalkyl, —OCF$_3$, C$_{3-6}$ cycloalkyl, or a 4-12 membered heterocycle,
or a pharmaceutically acceptable salt thereof.

Another embodiment provides a compound having the following Formula I$_e$:

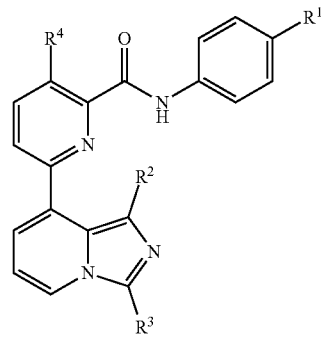

Formula I$_e$ wherein
R¹ is halogen;
R² is hydrogen, halogen, C$_{1-3}$ alkyl, C$_{1-3}$ haloalkyl, —OCF$_3$, C$_{3-6}$ cycloalkyl, or 4-12 membered heterocycle;
R³ is a C$_{3-6}$ cycloalkyl, C$_{3-6}$ heterocycle, mono or bicyclic aryl or heteroaryl, wherein each mono or bicyclic aryl or heteroaryl is unsubstituted or substituted with one, two, or three substituents independently selected from halogen, —CN, haloalkyl, and $C_{1-3}$ alkyl; and $R^4$ is halogen, $C_{1-6}$ alkyl, $C_{1-6}$ haloalkyl, —OCF$_3$, $C_{3-6}$ cycloalkyl, or a 4-12 membered heterocycle, or a pharmaceutically acceptable salt thereof.

Another embodiment provides a compound having the following Formula $I_f$:

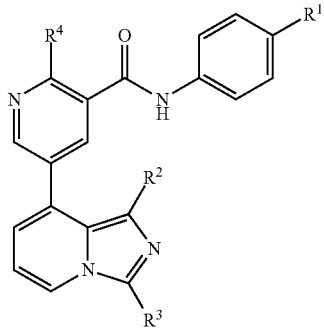

Formula $I_f$ wherein
$R^1$ is halogen;
$R^2$ is absent, hydrogen, $C_{1-3}$ alkyl, or an unsubstituted or substituted aryl with one, two, or three substituents independently selected from halogen, —CN, $C_{1-3}$ haloalkyl, and $C_{1-3}$ alkyl;
$R^3$ is a $C_{3-6}$ cycloalkyl, $C_{3-6}$ heterocycle, mono or bicyclic aryl or heteroaryl, wherein each mono or bicyclic aryl or heteroaryl is unsubstituted or substituted with one, two, or three substituents independently selected from halogen, —CN, $C_{1-3}$ haloalkyl, and $C_{1-3}$ alkyl; and
$R^4$ is halogen, $C_{1-3}$ alkyl, $C_{1-3}$ haloalkyl, $C_{3-6}$ cycloalkyl, or 4-12 membered heterocycle, wherein each $R^7$ can be the same or different from each other, or a pharmaceutically acceptable salt thereof.

Another embodiment provides a compound having the following Formula $I_g$:

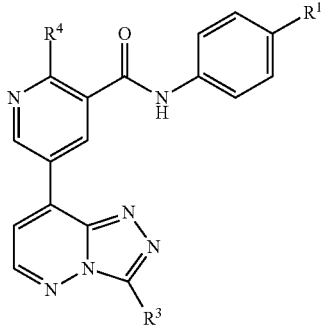

Formula $I_g$ wherein
$R^1$ is halogen;
$R^2$ is $C_{1-3}$ alkyl or $C_{1-3}$ haloalkyl; and
$R^3$ is a 5-10 membered mono or bicyclic aryl or heteroaryl, wherein each mono or bicyclic aryl or heteroaryl is unsubstituted or substituted with one, two, or three substituents independently selected from halogen, —CN, $C_{1-3}$ haloalkyl, and $C_{1-3}$ alkyl, or a pharmaceutically acceptable salt thereof.

Another embodiment provides a compound having the following Formula $I_h$:

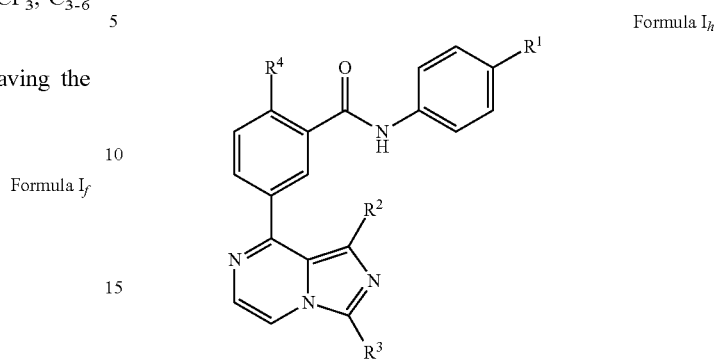

Formula $I_h$ wherein
$R^1$ is halogen;
$R^2$ is hydrogen, $C_{1-3}$ alkyl, or an unsubstituted or substituted aryl with one, two, or three substituents independently selected from halogen, —CN, $C_{1-3}$ haloalkyl, and $C_{1-3}$ alkyl;
$R^3$ is a 5-10 membered mono or bicyclic aryl or heteroaryl, wherein each mono or bicyclic aryl or heteroaryl is unsubstituted or substituted with one, two, or three substituents independently selected from halogen, —CN, $C_{1-3}$ haloalkyl, and $C_{1-3}$ alkyl; and
$R^4$ is $C_{1-3}$ alkyl or $C_{1-3}$ haloalkyl, or a pharmaceutically acceptable salt thereof.

In some embodiments, provided is a compound having the structure of Formula Ii:

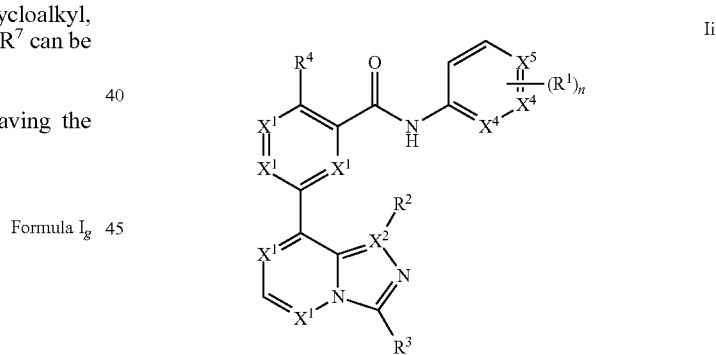

Ii wherein
$X^1$ at each location in Formula Ii is independently N, CH, or $CX^R$;
$X^2$ is N or C, wherein $R^2$ is absent when $X^2$ is N;
$X^4$ at each location in Formula Ii is independently N, CH, or $CR^1$;
$X^5$ is N, CH, or $CR^1$;
$X^R$ is hydrogen, halogen, $C_{1-3}$ haloalkyl, or $C_{1-6}$ alkyl;
$R^1$ is hydrogen, deuterium, halogen, —CN, —OCF$_3$, —OCHF$_2$, $C_{1-3}$ haloalkyl, or $C_{1-6}$ alkyl, wherein n is 0-5 and $R^1$ can be independently the same or different from each other;
$R^2$ is hydrogen, halogen, $C_{1-6}$ alkyl, or an unsubstituted or substituted aryl with one, two, or three substituents independently selected from halogen, —CN, $C_{1-6}$ haloalkyl, and $C_{1-6}$ alkyl;

R³ is C₃₋₆ cycloalkyl, C₃₋₆ heterocycle, or mono or bicyclic aryl or heteroaryl, wherein each mono or bicyclic aryl or heteroaryl is unsubstituted or substituted with one, two, or three substituents independently selected from halogen, —CN, $C_{1-6}$ haloalkyl, $C_{1-6}$ alkyl, and —C(O)N(R⁵)(R⁶);

R⁴ is halogen, $C_{1-6}$ alkyl, $C_{1-6}$ haloalkyl, —OCF₃, $C_{3-6}$ cycloalkyl, or a 4-12 membered heterocycle;

R⁵ is hydrogen or $C_{1-6}$ alkyl; and

R⁶ is hydrogen or $C_{1-6}$ alkyl, or a pharmaceutically acceptable salt thereof.

In some embodiments, provided is a compound having the structure of Formula II:

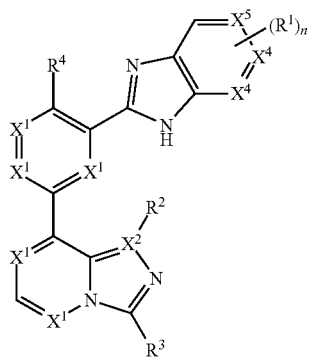

Formula II wherein

X¹ at each location in Formula II is independently N, CH, or CX^R;

X² is N or C, wherein R² is absent when X² is N;

X⁴ at each location in Formula II is independently N, CH, or CR¹;

X⁵ is CH, CX^R, or CR¹;

X^R is hydrogen, halogen, $C_{1-3}$ haloalkyl, or $C_{1-6}$ alkyl;

R¹ is hydrogen, deuterium, halogen, —CN, —OCF₃, —OCHF₂, or —CF₃, wherein n is 0-4 and where if n is >1, R¹ can be independently the same or different from each other;

R² is hydrogen, halogen, $C_{1-6}$ alkyl, or an unsubstituted or substituted aryl with one, two, or three substituents independently selected from halogen, —CN, $C_{1-6}$ haloalkyl, and $C_{1-6}$ alkyl;

R³ is C₃₋₆ cycloalkyl, C₃₋₆ heterocycle, mono or bicyclic aryl or heteroaryl, wherein each mono or bicyclic aryl or heteroaryl is unsubstituted or substituted with one, two, or three substituents independently selected from halogen, —CN, $C_{1-6}$ haloalkyl, and $C_{1-6}$ alkyl; and R⁴ is halogen, $C_{1-6}$ alkyl, $C_{1-6}$ haloalkyl, —OCF₃, $C_{3-6}$ cycloalkyl, or a 4-12 membered heterocycle, or a pharmaceutically acceptable salt thereof.

In some embodiments, provided is a compound having the structure of Formula IIa:

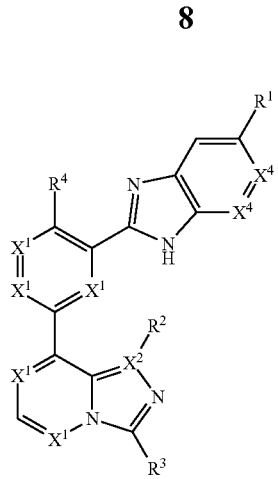

Formula IIa wherein

X¹ at each location of Formula IIa is independently N, CH, or CX^R;

X² is N or C, wherein R² is absent when X² is N;

X⁴ at each location of Formula IIa is independently N, CH, or CR¹;

X^R is hydrogen, halogen, $C_{1-3}$ haloalkyl, or $C_{1-6}$ alkyl;

R¹ is hydrogen, deuterium, halogen, —CN, —OCHF₂, or —CF₃, wherein R¹ can be independently the same or different from each other;

R² is absent when X² is N; or R² is hydrogen, halogen, $C_{1-6}$ alkyl, or an unsubstituted or substituted aryl with one, two, or three substituents independently selected from halogen, —CN, $C_{1-6}$ haloalkyl, and $C_{1-6}$ alkyl;

R³ is C₃₋₆ cycloalkyl, C₃₋₆ heterocycle, mono or bicyclic aryl or heteroaryl, wherein each mono or bicyclic aryl or heteroaryl is unsubstituted or substituted with one, two, or three substituents independently selected from halogen, —CN, $C_{1-6}$ haloalkyl, and $C_{1-6}$ alkyl; and R⁴ is halogen, $C_{1-6}$ alkyl, $C_{1-6}$ haloalkyl, —OCF₃, $C_{3-6}$ cycloalkyl, or a 4-12 membered heterocycle, or a pharmaceutically acceptable salt thereof.

In some embodiments, provided herein is a compound having the structure of formula IIb:

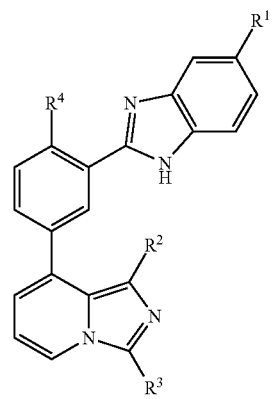

Formula IIb wherein

R¹ is halogen or hydrogen;

R² is hydrogen, $C_{1-3}$ alkyl, or an unsubstituted or substituted aryl with one, two, or three substituents independently selected from halogen, —CN, $C_{1-3}$ haloalkyl, and $C_{1-3}$ alkyl;

$R^3$ is a $C_{3-6}$ cycloalkyl, $C_{3-6}$ heterocycle, mono or bicyclic aryl or heteroaryl, wherein each mono or bicyclic aryl or heteroaryl is unsubstituted or substituted with one, two, or three substituents independently selected from halogen, —CN, $C_{1-3}$ haloalkyl, and $C_{1-3}$ alkyl; and $R^4$ is halogen, $C_{1-3}$ alkyl, $C_{1-3}$ haloalkyl, —OCF$_3$, $C_{3-6}$ cycloalkyl, or 4-12 membered heterocycle, or a pharmaceutically acceptable salt thereof.

In some embodiments, provided herein is a compound having the structure of formula IIc:

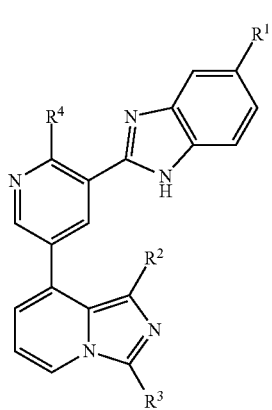

Formula IIc $R^1$ is halogen or hydrogen;

$R^2$ is hydrogen, $C_{1-3}$ alkyl, or an unsubstituted or substituted aryl with one, two, or three substituents independently selected from halogen, —CN, $C_{1-3}$ haloalkyl, and $C_{1-3}$ alkyl;

$R^3$ is a $C_{3-6}$ cycloalkyl, $C_{3-6}$ heterocycle, mono or bicyclic aryl or heteroaryl, wherein each mono or bicyclic aryl or heteroaryl is unsubstituted or substituted with one, two, or three substituents independently selected from halogen, —CN, $C_{1-3}$ haloalkyl, and $C_{1-3}$ alkyl; and $R^4$ is halogen, $C_{1-3}$ alkyl, $C_{1-3}$ haloalkyl, —OCF$_3$, $C_{3-6}$ cycloalkyl, or 4-12 membered heterocycle, or a pharmaceutically acceptable salt thereof.

In some embodiments, a method of treating a subject having a disease or condition responsive to the inhibition of IDO1 activity with a pharmaceutical composition having a compound of Formula I, Ia, Ib, Ic, Id, Ie, If, Ig, or Ih, or a pharmaceutically acceptable salt thereof is provided.

In some embodiments, a method of treating a subject having a disease or condition responsive to the inhibition of IDO1 activity with a pharmaceutical composition having a compound of Formula I, Ia, Ib, Ic, Id, Ie, If, Ig, Ih, Ii, II, IIa, IIb, or IIc, or a pharmaceutically acceptable salt thereof, is provided.

In some embodiments, a method of inhibiting the activity of an IDO1 protein by contacting the protein with the a compound of Formula I, Ia, Ib, Ic, Id, Ie, If, Ig, or Ih, or a pharmaceutically acceptable salt thereof is provided.

In some embodiments, a method of inhibiting the activity of an IDO1 protein by contacting the protein with a compound of Formula I, Ia, Ib, Ic, Id, Ie, If, Ig, Ih, Ii, II, IIa, IIb, or IIc, or a pharmaceutically acceptable salt thereof, is provided.

In some embodiments, a method of inhibiting growth or a proliferation of cancer cells, by administering a therapeutically effective amount of a compound of any of Formula I, Ia, Ib, Ic, Id, Ie, If, Ig, or Ih, or a pharmaceutically acceptable salt thereof is provided.

In some embodiments, a method of inhibiting growth or a proliferation of cancer cells, by administering a therapeutically effective amount of a compound of any of Formula I, Ia, Ib, Ic, Id, Ie, If, Ig, Ih, Ii, II, IIa, IIb, or IIc, or a pharmaceutically acceptable salt thereof, is provided.

In some embodiments, a method of inhibiting immunosuppression in a subject by administering a therapeutically effective amount of a compound of any of Formula I, Ia, Ib, Ic, Id, Ie, If, Ig, or Ih, or a pharmaceutically acceptable salt thereof is provided.

In some embodiments, a method of inhibiting immunosuppression in a subject by administering a therapeutically effective amount of a compound of any of Formula I, Ia, Ib, Ic, Id, Ie, If, Ig, Ih, Ii, II, IIa, IIb, or IIc, or a pharmaceutically acceptable salt thereof is provided.

In some embodiments, a method of treating cancer or viral infection in a subject by administering a therapeutically effective amount of a compound of any of Formula I, Ia, Ib, Ic, Id, Ie, If, Ig, or Ih, or a pharmaceutically acceptable salt thereof is provided. In some embodiments, the viral infection is hepatitis B virus (HBV) or human immunodeficiency virus (HIV). In some embodiments, the cancer is selected from the group consisting of melanoma, non-small cell lung cancer, colorectal cancer, pancreatic cancer, and bladder cancer.

In some embodiments, a method of treating cancer or viral infection in a subject by administering a therapeutically effective amount of a compound of any of Formula I, Ia, Ib, Ic, Id, Ie, If, Ig, Ih, Ii, II, IIa, IIb, or IIc, or a pharmaceutically acceptable salt thereof is provided. In some embodiments, the viral infection is hepatitis B virus (HBV) or human immunodeficiency virus (HIV). In some embodiments, the cancer is selected from the group consisting of melanoma, non-small cell lung cancer, colorectal cancer, pancreatic cancer, and bladder cancer.

In some embodiments, the method of inhibiting IDO1 protein activity, the method of inhibiting growth or proliferation of cancer cells, the method of inhibiting immunosuppression, the method of treating cancer, or the method of treating a viral infection further includes administering to the subject a therapeutically effective amount of an anti-viral agent, a chemotherapeutic, an immunosuppressant, radiation, an anti-tumor vaccine, an antiviral vaccine, cytokine therapy, a checkpoint inhibitor, or a tyrosine kinase inhibitor.

In some embodiments, the method of inhibiting IDO1 protein activity, the method of inhibiting growth or proliferation of cancer cells, the method of inhibiting immunosuppression, the method of treating cancer, or the method of treating a viral infection further includes administering to the subject a therapeutically effective amount of an HBV inhibitor or an HIV inhibitor.

In some embodiments, the method of inhibiting IDO1 protein activity, the method of inhibiting growth or proliferation of cancer cells, the method of inhibiting immunosuppression, the method of treating cancer, or the method of treating a viral infection further includes administering to the subject a therapeutically effective amount of a checkpoint inhibitor, where the checkpoint inhibitor is a PD1 inhibitor, a PD-L1 inhibitor, a PD1 and a PD-L1 inhibitor, a TIM-3 inhibitor, a TIM-3 and PD1 inhibitor, a LAG-3 inhibitor, or a LAG-3 and PD-1 inhibitor, In some embodiments, the checkpoint inhibitor is a monoclonal antibody. In some embodiments, the checkpoint inhibitor is a small molecule. In some embodiments, the checkpoint inhibitor is nivolumab, pembrolizumab, lambrolizumab, pidilizumab, durvalumab, avelumab, atezolizumab, PDR001, TSR-042, or BMS-986016, or a pharmaceutically acceptable salt or solvate of any of the forgoing.

In some embodiments, the method of inhibiting IDO1 protein activity, the method of inhibiting growth or proliferation of cancer cells, the method of inhibiting immunosuppression, the method of treating cancer, or the method of treating a viral infection further includes administering to the subject a therapeutically effective amount of at least one additional therapeutic agent selected from the following group: Inducible T-cell costimulator (ICOS) agonists, cytotoxic T-lymphocyte antigen 4 (CTLA-4)-blocking antibodies, PD1 and/or PD-L1 inhibitors, Cluster of Differentiation 47 (CD47) inhibitors, Hematopoietic Progenitor Kinase (HPK1) inhibitors, Toll-like receptor 7 (TLR7) agonists, OX40 agonists, GITR agonists, CD40 agonists, CD137 agonists, Indoleamine-pyrrole-2,3-dioxygenase (IDO1) inhibitors, Toll-like receptor 8 (TLR8) agonists, T cell immunoglobulin and mucin domain-3 (TIM-3) inhibitors, lymphocyte activation gene 3 (LAG-3) inhibitors, CEACAM1 inhibitors, T cell immunoreceptor with Ig and ITIM domains (TIGIT) inhibitors, V-domain immunoglobulin (Ig)-containing suppressor of T-cell activation (VISTA) inhibitors, anti-Killer IgG-like receptors (KIR) inhibitors, STING agonists, C-X-C chemokine receptor type 4 (CXCR-4) inhibitors, B7-H3 inhibitors, and CD73 inhibitors.

In some embodiments, the method of inhibiting IDO1 protein activity, the method of inhibiting growth or proliferation of cancer cells, the method of inhibiting immunosuppression, the method of treating cancer, or the method of treating a viral infection further includes administering to the subject a therapeutically effective amount of at least one additional therapeutic agent selected from the following group of PD1 inhibitors: nivolumab, lambrolizumab, pembrolizumab, pidilizumab, PDR001, or TSR-001, or a pharmaceutically acceptable salt or solvate of any of the forgoing.

In some embodiments, the method of inhibiting IDO1 protein activity, the method of inhibiting growth or proliferation of cancer cells, the method of inhibiting immunosuppression, the method of treating cancer, or the method of treating a viral infection further includes administering to the subject a therapeutically effective amount of at least one additional therapeutic agent selected from the following group of PD-L1 inhibitors: atezolizumab, durvalumab, or avelumab, or a pharmaceutically acceptable salt or solvate of any of the forgoing.

In some embodiments, the method of inhibiting IDO1 protein activity, the method of inhibiting growth or proliferation of cancer cells, the method of inhibiting immunosuppression, the method of treating cancer, or the method of treating a viral infection further includes administering to the subject a therapeutically effective amount of Toll-like receptor 7 (TLR7) agonist. In some embodiments, the Toll-like receptor 7 (TLR7) agonist is vesatolimod.

In some embodiments, the method of inhibiting IDO1 protein activity, the method of inhibiting growth or proliferation of cancer cells, the method of inhibiting immunosuppression, the method of treating cancer, or the method of treating a viral infection further includes administering to the subject a therapeutically effective amount of a Toll-like receptor 8 (TLR8) agonist. In some embodiments, the method of inhibiting IDO1 protein activity, the method of inhibiting growth or proliferation of cancer cells, the method of inhibiting immunosuppression, the method of treating cancer, or the method of treating a viral infection further includes administering to the subject a therapeutically effective amount of a Toll-like receptor 8 (TLR8) agonist and a therapeutically effective amount of a Programmed Death 1 (PD-1) inhibitor and/or a Programmed Death Ligand 1 (PD-L1) inhibitor.

In some embodiments, the method of inhibiting IDO1 protein activity, the method of inhibiting growth or proliferation of cancer cells, the method of inhibiting immunosuppression, the method of treating cancer, or the method of treating a viral infection further includes administering to the subject a therapeutically effective amount of an additional therapeutic agent selected from T cell immunomodulators along with the compounds of Formula I, Ia, Ib, Ic, Id, Ie, If, Ig, or Ih, or a pharmaceutically acceptable salt thereof. In some embodiments, the T cell immunomodulator is selected from the group consisting of inhibitory RNA, HPK1 inhibitors, IL2/15/17 fusion proteins, OX40 agonists, CD27 agonists, MKNK1/2 inhibitors, CD40 agonists, CD137 agonists, CD28 agonists, and GITR agonists.

In some embodiments, the method of inhibiting IDO1 protein activity, the method of inhibiting growth or proliferation of cancer cells, the method of inhibiting immunosuppression, the method of treating cancer, or the method of treating a viral infection further includes administering to the subject a therapeutically effective amount of an additional therapeutic agent selected from T cell immunomodulators along with the compounds of Formula I, Ia, Ib, Ic, Id, Ie, If, Ig, Ih, Ii, II, IIa, IIb, or IIc, or a pharmaceutically acceptable salt thereof. In some embodiments, the T cell immunomodulator is selected from the group consisting of inhibitory RNA, HPK1 inhibitors, IL2/15/17 fusion proteins, OX40 agonists, CD27 agonists, MKNK1/2 inhibitors, CD40 agonists, CD137 agonists, CD28 agonists, and GITR agonists.

Some embodiments provide a method of using a compound of Formula I, Ia, Ib, Ic, Id, Ie, If, Ig, Ih, or additional Formulas described throughout, in the treatment of a disease or condition in a mammal, particularly a human, that is amenable to treatment by an IDO1 inhibitor (e.g., cancer, HBV, etc.).

Some embodiments provide a method of using a compound of Formula I, Ia, Ib, Ic, Id, Ie, If, Ig, Ih, Ii, II, IIa, IIb, or IIc, or additional Formulas described throughout, or a pharmaceutically acceptable salt thereof, in the treatment of a disease or condition in a mammal, particularly a human, that is amenable to treatment by an IDO1 inhibitor (e.g., cancer, HBV, etc.).

In some embodiments, the disclosure herein provides pharmaceutical compositions comprising a therapeutically effective amount of a compound of the disclosure (e.g., a compound of Formula I, Ia, Ib, Ic, Id, Ie, If, Ig, Ih, or additional Formulas described throughout), and at least one pharmaceutically acceptable excipient.

In some embodiments, the disclosure herein provides pharmaceutical compositions comprising a therapeutically effective amount of a compound of the disclosure (e.g., a compound of Formula I, Ia, Ib, Ic, Id, Ie, If, Ig, Ih, Ii, II, IIa, IIb, or IIc, or additional Formulas described throughout), or a pharmaceutically acceptable salt thereof, and at least one pharmaceutically acceptable excipient.

In some embodiments, the disclosure herein provides an article of manufacture comprising a unit dosage of a compound of the disclosure (e.g., a compound of Formula I, Ia, Ib, Ic, Id, Ie, If, Ig, Ih, or additional Formulas described throughout).

In some embodiments, the disclosure herein provides an article of manufacture comprising a unit dosage of a compound of the disclosure (e.g., a compound of Formula I, Ia, Ib, Ic, Id, Ie, If, Ig, Ih, Ii, II, IIa, IIb, or IIc, or additional Formulas described throughout, or a pharmaceutically acceptable salt thereof).

In some embodiments, the disclosure herein provides a compound of the disclosure (e.g., a compound of Formula I, $I_a$, $I_b$, $I_c$, $I_d$, $I_e$, $I_f$, $I_g$, $I_h$, or additional Formulas described throughout) for use in medical therapy.

In some embodiments, the disclosure herein provides a compound of the disclosure (e.g., a compound of Formula I, Ia, Ib, Ic, Id, Ie, If, Ig, Ih, Ii, II, IIa, IIb, or IIc, or additional Formulas described throughout) for use in medical therapy.

In some embodiments, the disclosure herein provides a compound of the disclosure (e.g., a compound of Formula I, Ia, Ib, Ic, Id, Ie, If, Ig, Ih, or additional Formulas described throughout) for the manufacture of a medicament for the treatment of a disease or condition in a mammal, particularly a human, that is amenable to treatment by an IDO1 inhibitor (e.g., cancer, HBV, etc.).

In some embodiments, the disclosure herein provides a compound of the disclosure (e.g., a compound of Formula I, Ia, Ib, Ic, Id, Ie, If, Ig, Ih, Ii, II, IIa, IIb, or IIc, or additional Formulas described throughout, or a pharmaceutically acceptable salt thereof) for the manufacture of a medicament for the treatment of a disease or condition in a mammal, particularly a human, that is amenable to treatment by an IDO1 inhibitor (e.g., cancer, HBV, etc.).

The inventions of this disclosure are described throughout. In addition, specific embodiments of the invention are as disclosed herein.

DETAILED DESCRIPTION

Definitions and General Parameters

The following description sets forth exemplary methods, parameters and the like. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

A dash ("—") that is not between two letters or symbols is used to indicate a point of attachment for a substituent. For example, —CONH$_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named.

The prefix "$C_{u-v}$" indicates that the following group has from u to v carbon atoms. For example, "$C_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_{1-20}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e. —(CH$_2$)$_3$CH$_3$), sec-butyl (i.e. —CH(CH$_3$)CH$_2$CH$_3$), isobutyl (i.e. —CH$_2$CH(CH$_3$)$_2$) and tert-butyl (i.e. —C(CH$_3$)$_3$); and "propyl" includes n-propyl (i.e. —(CH$_2$)$_2$CH$_3$) and isopropyl (i.e. —CH(CH$_3$)$_2$).

"Alkenyl" refers to an aliphatic group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$ alkenyl). Examples of alkenyl groups include ethenyl, propenyl, butadienyl (including 1,2-butadienyl and 1,1-butadienyl)

"Alkynyl" refers to an aliphatic group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term "alkynyl" also includes those groups having one triple bond and one double bond.

"Alkoxy" refers to the group "alkyl-O—". Examples of alkoxy groups include methoxy, ethoxy, n-propoxy, iso-propoxy, n-butoxy, tert-butoxy, sec-butoxy, n-pentoxy, n-hexoxy, and 1,2-dimethylbutoxy. "Haloalkoxy" refers to an alkoxy group as defined above, wherein one or more hydrogen atoms are replaced by a halogen.

"Acyl" refers to a group —C(=O)R, wherein R is hydrogen, alkyl, cycloalkyl, heterocyclyl, aryl, heteroalkyl, or heteroaryl; each of which may be optionally substituted, as defined herein. Examples of acyl include formyl, acetyl, cyclohexylcarbonyl, cyclohexylmethyl-carbonyl, and benzoyl.

"Amido" refers to both a "C-amido" group which refers to the group —C(=O)NR$^y$R$^z$ and an "N-amido" group which refers to the group —NR$^y$C(=O)R$^z$, wherein R$^y$ and R$^z$ are independently selected from the group consisting of hydrogen, alkyl, aryl, haloalkyl, or heteroaryl; each of which may be optionally substituted.

"Amino" refers to the group —NR$^y$R$^z$ wherein R$^y$ and R$^z$ are independently selected from the group consisting of hydrogen, alkyl, haloalkyl, aryl, or heteroaryl; each of which may be optionally substituted.

"Aryl" refers to an aromatic carbocyclic group having a single ring (e.g. monocyclic) or multiple rings (e.g. bicyclic or tricyclic) including fused systems. As used herein, aryl has 6 to 20 ring carbon atoms (i.e., $C_{6-20}$ aryl), 6 to 12 carbon ring atoms (i.e., $C_{6-12}$ aryl), or 6 to 10 carbon ring atoms (i.e., $C_{6-10}$ aryl). Examples of aryl groups include phenyl, naphthyl, fluorenyl, and anthryl. Aryl, however, does not encompass or overlap in any way with heteroaryl defined below. If one or more aryl groups are fused with a heteroaryl ring, the resulting ring system is heteroaryl.

"Cyano" or "carbonitrile" refers to the group —CN.

"Cycloalkyl" refers to a saturated or partially saturated cyclic alkyl group having a single ring or multiple rings including fused, bridged, and Spiro ring systems. The term "cycloalkyl" includes cycloalkenyl groups (i.e. the cyclic group having at least one double bond). As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Examples of cycloalkyl groups include cyclopropyl, cyclobutyl, cyclopentyl, and cyclohexyl.

"Bridged" refers to a ring fusion wherein non-adjacent atoms on a ring are joined by a divalent substituent, such as an alkylenyl or heteroalkenyl group or a single heteroatom. Quinuclidinyl and adamantanyl are examples of bridged ring systems.

The term "fused" refers to a ring which is bound to an adjacent ring.

"Spiro" refers to a ring substituent which is joined by two bonds at the same carbon atom. Examples of spiro groups include 1,1-diethylcyclopentane, dimethyl-dioxolane, and 4-benzyl-4-methylpiperidine, wherein the cyclopentane and piperidine, respectively, are the spiro substituents.

"Halogen" or "halo" includes fluoro, chloro, bromo, and iodo. "Haloalkyl" refers to an unbranched or branched alkyl group as defined above, wherein one or more hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include difluoromethyl (—$CHF_2$) and trifluoromethyl (—$CF_3$).

"Heteroalkyl" refers to an alkyl group in which one or more of the carbon atoms (and any associated hydrogen atoms) are each independently replaced with the same or different heteroatomic group. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —NR—, —O—, —S—, —S(O)—, —$S(O)_2$—, and the like, where R is H, alkyl, aryl, cycloalkyl, heteroalkyl, heteroaryl or heterocyclyl, each of which may be optionally substituted. Examples of heteroalkyl groups include —$OCH_3$, —$CH_2OCH_3$, —$SCH_3$, —$CH_2SCH_3$, $NRCH_3$, and —$CH_2NRCH_3$, where R is hydrogen, alkyl, aryl, arylalkyl, heteroalkyl, or heteroaryl, each of which may be optionally substituted. As used herein, heteroalkyl include 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to an aromatic group having a single ring, multiple rings, or multiple fused rings, with one or more ring heteroatoms independently selected from nitrogen, oxygen, and sulfur. As used herein, heteroaryl include 1 to 20 ring carbon atoms (i.e., $C_{1-20}$ heteroaryl), 3 to 12 ring carbon atoms (i.e., $C_{3-12}$ heteroaryl), or 3 to 8 carbon ring atoms (i.e., $C_{3-8}$ heteroaryl); and 1 to 5 heteroatoms, 1 to 4 heteroatoms, 1 to 3 ring heteroatoms, 1 to 2 ring heteroatoms, or 1 ring heteroatom independently selected from nitrogen, oxygen, and sulfur. Examples of heteroaryl groups include pyrimidinyl, purinyl, pyridyl, pyridazinyl, benzothiazolyl, and pyrazolyl. Heteroaryl does not encompass or overlap with aryl as defined above.

"Heterocyclyl" or "heterocyclic ring" refers to an unsaturated non-aromatic cyclic alkyl group, with one or more ring heteroatoms independently selected from nitrogen, oxygen and sulfur. As used herein, "heterocyclyl" or "heterocyclic ring" refers to rings that are saturated or partially saturated unless otherwise indicated, e.g., in some embodiments "heterocyclyl" or "heterocyclic ring" refers to rings that are partially saturated where specified. The term "heterocyclyl" or "heterocyclic ring" includes heterocycloalkenyl groups (i.e., the heterocyclyl group having at least one double bond). A heterocyclyl may be a single ring or multiple rings wherein the multiple rings may be fused, bridged, or Spiro. As used herein, heterocyclyl has 2 to 20 ring carbon atoms (i.e., $C_{2-20}$ heterocyclyl), 2 to 12 ring carbon atoms (i.e., $C_{2-12}$ heterocyclyl), 2 to 10 ring carbon atoms (i.e., $C_{2-10}$ heterocyclyl), 2 to 8 ring carbon atoms (i.e., $C_{2-8}$ heterocyclyl), 3 to 12 ring carbon atoms (i.e., $C_{3-12}$ heterocyclyl), 3 to 8 ring carbon atoms (i.e., $C_{3-8}$ heterocyclyl), or 3 to 6 ring carbon atoms (i.e., $C_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. Examples of heterocyclyl groups include pyrrolidinyl, piperidinyl, piperazinyl, oxetanyl, dioxolanyl, azetidinyl, and morpholinyl. As used herein, the term "bridged-heterocyclyl" refers to a four- to ten-membered cyclic moiety connected at two non-adjacent atoms of the heterocyclyl with one or more (e.g., 1 or 2) four- to ten-membered cyclic moiety having at least one heteroatom where each heteroatom is independently selected from nitrogen, oxygen, and sulfur. As used herein, "bridged-heterocyclyl" includes bicyclic and tricyclic ring systems. Also as used herein, the term "spiro-heterocyclyl" refers to a ring system in which a three- to ten-membered heterocyclyl has one or more additional ring, wherein the one or more additional ring is three- to ten-membered cycloalkyl or three- to ten-membered heterocyclyl, where a single atom of the one or more additional ring is also an atom of the three- to ten-membered heterocyclyl. Examples of the spiro-heterocyclyl include bicyclic and tricyclic ring systems, such as 2-oxa-7-azaspiro[3.5]nonanyl, 2-oxa-6-azaspiro[3.4]octanyl, and 6-oxa-1-azaspiro[3.3]heptanyl. As used herein, the terms "heterocycle", "heterocyclyl", and "heterocyclic ring" are used interchangeably.

"Hydroxy" or "hydroxyl" refers to the group —OH.

"Oxo" refers to the group (=O) or (O).

"Sulfonyl" refers to the group —$S(O)_2R$, where R is alkyl, haloalkyl, heterocyclyl, cycloalkyl, heteroaryl, or aryl. Examples of sulfonyl are methylsulfonyl, ethylsulfonyl, phenylsulfonyl, and toluenesulfonyl.

Whenever the graphical representation of a group terminates in a singly bonded nitrogen atom, that group represents an —NH group unless otherwise indicated. Similarly, unless otherwise expressed, hydrogen atom(s) are implied and deemed present where necessary in view of the knowledge of one of skill in the art to complete valency or provide stability.

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g.

arylalkyl, the last mentioned group contains the atom by which the moiety is attached to the rest of the molecule.

The terms "optional" or "optionally" means that the subsequently described event or circumstance may or may not occur, and that the description includes instances where said event or circumstance occurs and instances in which it does not. Also, the term "optionally substituted" refers to any one or more hydrogen atoms on the designated atom or group may or may not be replaced by a moiety other than hydrogen.

The term "substituted" means that any one or more hydrogen atoms on the designated atom or group is replaced with One or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl)substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. For example, the term "substituted aryl" includes, but is not limited to, "alkylaryl." Unless specified otherwise, where a group is described as optionally substituted, any substituents of the group are themselves unsubstituted.

In some embodiments, the term "substituted alkyl" refers to an alkyl group having one or more substituents including hydroxyl, halo, alkoxy, cycloalkyl, heterocyclyl, aryl, and heteroaryl. In additional embodiments, "substituted cycloalkyl" refers to a cycloalkyl group having one or more substituents including alkyl, haloalkyl, cycloalkyl, heterocyclyl, aryl, heteroaryl, alkoxy, halo, oxo, and hydroxyl; "substituted heterocyclyl" refers to a heterocyclyl group having one or more substituents including alkyl, haloalkyl, heterocyclyl, cycloalkyl, aryl, heteroaryl, alkoxy, halo, oxo, and hydroxyl; "substituted aryl" refers to an aryl group having one or more substituents including halo, alkyl, haloalkyl, cycloalkyl, heterocyclyl, heteroaryl, alkoxy, and cyano; "substituted heteroaryl" refers to an heteroaryl group having one or more substituents including halo, alkyl, haloalkyl, heterocyclyl, heteroaryl, alkoxy, and cyano and "substituted sulfonyl" refers to a group —S(O)$_2$R, in which R is substituted with one or more substituents including alkyl, cycloalkyl, heterocyclyl, aryl, and heteroaryl. In other embodiments, the one or more substituents may be further substituted with halo, alkyl, haloalkyl, hydroxyl, alkoxy, cycloalkyl, heterocyclyl, aryl, or heteroaryl, each of which is substituted. In other embodiments, the substituents may be further substituted with halo, alkyl, haloalkyl, alkoxy, hydroxyl, cycloalkyl, heterocyclyl, aryl, or heteroaryl, each of which is unsubstituted.

Some of the compounds exist as tautomeric isomers. Tautomeric isomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

Any formula or structure given herein, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure, for example those into which radioactive isotopes such as $^3$H, $^{13}$C and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also included compounds of Formula I in which from 1 to n hydrogens attached to a carbon atom is/are replaced by deuterium, in which n is the number of hydrogens in the molecule. Such compounds exhibit increased resistance to metabolism and are thus useful for increasing the half-life of any compound of Formula I when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

The disclosure also included compounds of Formula I, Ia, Ib, Ic, Id, Ie, If, Ig, Ih, Ii, II, IIa, IIb, or IIc in which from 1 to n hydrogens attached to a carbon atom is/are replaced by deuterium, in which n is the number of hydrogens in the molecule. Such compounds exhibit increased resistance to metabolism and are thus useful for increasing the half-life of any compound of Formula I, Ia, Ib, Ic, Id, Ie, If, Ig, Ih, Ii, II, IIa, IIb, or IIc when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I, la, Ib, Ic, Id, Ie, If, Ig, Ih, Ii, II, IIa, IIb, or IIc.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino and/or carboxyl groups or groups similar thereto.

The term "pharmaceutically acceptable salt" of a given compound refers to salts that retain the biological effectiveness and properties of the given compound, and which are not biologically or otherwise undesirable. Pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, mono, di or tri cycloalkyl amines, mono, di or tri arylamines or mixed amines, etc. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human.

The term "therapeutically effective amount" or "effective amount" of a compound described herein or pharmaceutically acceptable salts, isomer, or a mixture thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition responsive to inhibition of IDO1 activity. The therapeutically effective amount may vary depending on the subject, and disease or condition being treated, the weight and age of the subject, the severity of the disease or condition, and the manner of administering, which can readily be determined by one or ordinary skill in the art.

The term "inhibition" indicates a decrease in the baseline activity of a biological activity or process. "Inhibition of activity of IDO1" or variants thereof refers to a decrease in activity in IDO1 as a direct or indirect response to the presence of a compound of the present application relative to the activity IDO1 in the absence of the compound of the present application. "Inhibition of IDO1" refers to a decrease in IDO1 activity as a direct or indirect response to the presence of a compound described herein relative to the activity of IDO1 in the absence of the compound described herein. In some embodiments, the inhibition of IDO1 activity may be compared in the same subject prior to treatment, or other subjects not receiving the treatment.

Compounds

Provided herein are compounds that function as inhibitors of IDO1. In one aspect, provided is a compound having structure of Formula I:

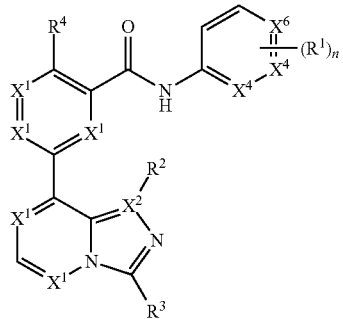

I or a pharmaceutically acceptable salt thereof.

In some embodiments, compounds of formula I are compounds of formula Ia:

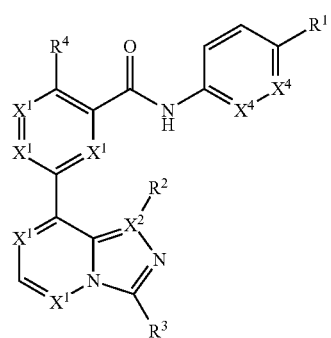

Ia or a pharmaceutically acceptable salt thereof.

In some embodiments, compounds of formula I are compounds of formula Ib:

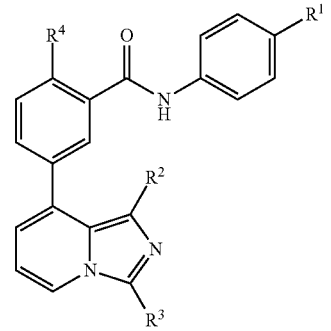

Ib or a pharmaceutically acceptable salt thereof.

In some embodiments, compounds of formula I are compounds of formula Ic:

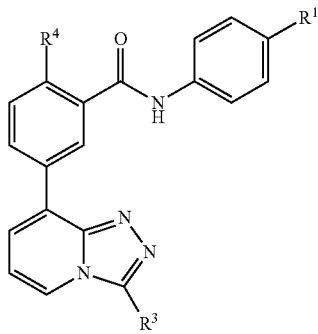

Ic or a pharmaceutically acceptable salt thereof.

In some embodiments, compounds of formula I are compounds of formula Id:

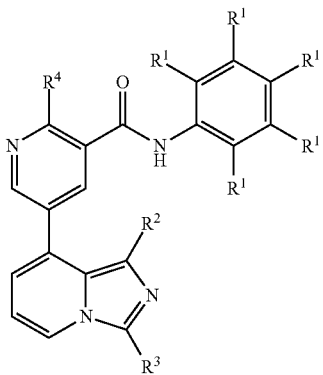

Id or a pharmaceutically acceptable salt thereof.

In some embodiments, compounds of formula I are compounds of formula Ie:

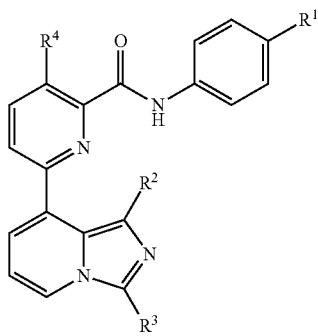

Ie or a pharmaceutically acceptable salt thereof.

In some embodiments, compounds of formula I are compounds of formula If

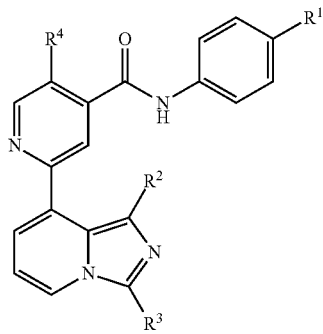

If or a pharmaceutically acceptable salt thereof.

In some embodiments, compounds of formula I are compounds of formula Ig:


Ig or a pharmaceutically acceptable salt thereof.

In some embodiments, compounds of formula I are compounds of formula Ih:

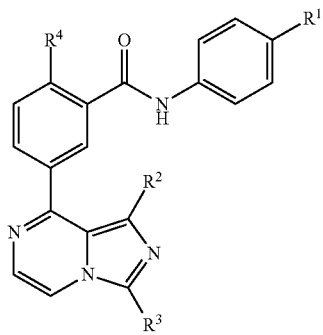

Ih or a pharmaceutically acceptable salt thereof.

In some embodiments, provided is a compound having the structure of Formula Ii:

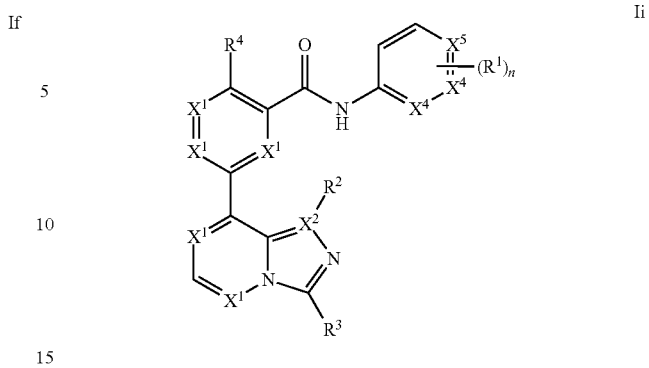

Ii wherein
$X^1$ at each location in Formula Ii is independently N, CH, or $CX^R$;
$X^2$ is N or C, wherein $R^2$ is absent when $X^2$ is N;
$X^4$ at each location in Formula Ii is independently N, CH, or $CR^1$;
$X^5$ is N, CH, or $CR^1$;
$X^R$ is hydrogen, halogen, $C_{1-3}$ haloalkyl, or $C_{1-6}$ alkyl;
$R^1$ is hydrogen, deuterium, halogen, —CN, —OCF$_3$, —OCHF$_2$, $C_{1-3}$ haloalkyl, or $C_{1-6}$ alkyl, wherein n is 0-5 and $R^1$ can be independently the same or different from each other;
$R^2$ is hydrogen, halogen, $C_{1-6}$ alkyl, or an unsubstituted or substituted aryl with one, two, or three substituents independently selected from halogen, —CN, $C_{1-6}$ haloalkyl, and $C_{1-6}$ alkyl;
$R^3$ is $C_{3-6}$ cycloalkyl, $C_{3-6}$ heterocycle, or mono or bicyclic aryl or heteroaryl, wherein each mono or bicyclic aryl or heteroaryl is unsubstituted or substituted with one, two, or three substituents independently selected from halogen, —CN, $C_{1-6}$ haloalkyl, $C_{1-6}$ alkyl, and —C(O)N($R^5$)($R^6$);
$R^4$ is halogen, $C_{1-6}$ alkyl, $C_{1-6}$ haloalkyl, —OCF$_3$, $C_{3-6}$ cycloalkyl, or a 4-12 membered heterocycle;
$R^5$ is hydrogen or $C_{1-6}$ alkyl; and
$R^6$ is hydrogen or $C_{1-6}$ alkyl,
or a pharmaceutically acceptable salt thereof.

Specific values listed below are values for compounds of formula I as well as all related formulas (e.g., Ia, Ib, Ic, Id, Ie, If, Ig, and Ih). Specific values listed below are values for compounds of formula I as well as all related formulas (e.g., Ia, Ib, Ic, Id, Ie, If, Ig, Ih, and Ii), or pharmaceutically acceptable salts thereof. It is to be understood that two or more values may combined. Thus, it is to be understood that any variable for compounds of formula I may be combined with any other variable for compounds of formula I the same as if each and every combination of variables were specifically and individually listed. For example, it is understood that any specific value of $R^1$ detailed herein for compounds of Formula I may be combined with any other specific value for one or more of the variables $X^1$, $X^2$, $X^4$, $X^5$, $X^6$, $X^R$, $R^2$, $R^3$, or $R^4$ the same as if each and every combination were specifically and individually listed.

In some embodiments, a group of compounds of formula I are compounds where $X^1$ is selected from nitrogen, methine (—CH), or a carbon further attached to a group denoted as $X^R$. The specific group of compounds of formula I are compounds where $X^R$ is selected from hydrogen, halogen, $C_{1-3}$ haloalkyl, or $C_{1-6}$ alkyl.

In some embodiments, a group of compounds of formula I are compounds where $X^1$ is either nitrogen or —CH group.

In some embodiments, a group of compound of formula I are compounds where $X^1$ is a carbon having a hydrogen, halogen, $C_{1-3}$ haloalkyl, or $C_{1-6}$ alkyl as a substituent.

In some embodiments, a group of compounds of formula I are compounds where $X^2$ is selected from nitrogen, —CH group, or a carbon further substituted with substituents denoted by $R^2$.

In some embodiments, a group of compounds of formula I are compounds where $X^2$ is nitrogen.

In some embodiments, a group of compounds of formula I are compounds where $X^2$ is carbon attached to $R^2$ where $R^2$ is hydrogen, halogen, $C_{1-6}$ alkyl, or an unsubstituted or substituted aryl with one, two, or three substituents independently selected from halogen, —CN, $C_{1-6}$ haloalkyl, and $C_{1-6}$ alkyl.

In some embodiments, a group of compounds of formula I are compounds where $R^2$ is bromo, chloro, or fluoro.

In some embodiments, a group of compounds of formula I are compounds where $R^2$ is methyl, ethyl, propyl, isopropyl, butyl, n-butyl, sec-butyl, isobutyl, t-butyl, pentyl, or hexyl.

In some embodiment, compounds of formula I are compounds where $R^2$ is absent.

In some embodiments, a group of compounds of formula I are compounds where $X^4$ is selected from nitrogen, a —CH group, or a carbon substituted with $X^1$.

In some embodiments, a group of compounds of formula I are compounds where $X^4$ is selected from a carbon substituted with a hydrogen or a carbon substituted with $X^R$, where $X^R$ is either hydrogen, halogen, $C_{1-3}$ haloalkyl, or $C_{1-6}$ alkyl.

In some embodiments, a group of compounds of formula I are compounds where $X^5$ is selected from nitrogen, —CH group, or carbon substituted with $R^1$.

In some embodiments, a group of compounds of formula I are compounds substituted with one $R^1$ group.

In some embodiments, a group of compounds of formula I are compounds that are substituted with more than one $R^1$ group, where the $R^1$ groups may be either the same or different from one another.

In some embodiments, $R^1$ is hydrogen, deuterium, halogen, cyano (—CN), —OC($R^7$)$_3$, —OCH($R^7$)$_2$, or —C($R^7$)$_3$, where $R^7$ is halogen and where when there is more than one $R^7$ group attached, $R^7$ may be the same or different from each other.

In some embodiments, $R^1$ is fluoro, bromo, or chloro.

In some embodiments, $R^1$ is a halo methoxy.

In some embodiments, $R^1$ is a fluoro methoxy, difluoro methoxy, or trifluoro methoxy.

In some embodiments, $R^1$ is a fluoro methyl, difluoro methyl, or trifluoro methyl.

In some embodiments, $R^1$ is —OCF$_3$.

In some embodiments, $R^1$ is —OCHF$_2$.

In some embodiments, $R^1$ is —CF$_3$.

In some embodiments, $R^1$ is —CN.

In some embodiments, a group of compounds of formula I are compounds where $R^3$ is $C_{3-6}$ cycloalkyl, $C_{3-6}$ heterocycle, mono or bicyclic aryl or heteroaryl, wherein each mono or bicyclic aryl or heteroaryl is unsubstituted or substituted with one, two, or three substituents independently selected from halogen, —CN, $C_{1-6}$ haloalkyl, $C_{1-6}$ alkyl, and —C(O)N($R^5$)($R^6$).

In some embodiments, a group of compounds of formula I are compounds where within $R^3$, $R^5$ and $R^6$, together with the atoms they are bound to, join to form a $C_{3-6}$ cycloalkyl, where the $C_{3-6}$ cycloalkyl can be further substituted with $X^R$.

In some embodiments, a group of compounds of formula I are compounds where within $R^3$, $R^5$ and $R^6$, together with the atoms they are bound to, join to form a $C_{3-6}$ heterocycle, where the $C_{3-6}$ heterocycle can be further substituted with $X^R$.

In some embodiments, a group of compounds of formula I are compounds where $R^3$ is cyclopropyl, cyclobutyl, cyclopentyl, or cyclohexyl.

In some embodiments, a group of compounds of formula I are compounds where $R^3$ is tetrahydrofuranyl or tetrahydro-2H-pyranyl.

In some embodiments, a group of compounds of formula I are compounds where $R^3$ is oxazole.

In some embodiments, a group of compounds of formula I are compounds where $R^3$ is oxadiazole.

In some embodiments, a group of compounds of formula I are compounds where $R^3$ is 1,3,4-oxadiazole.

In some embodiments, a group of compounds of formula I are compounds where $R^3$ is $C_{1-3}$ alkyl-substituted oxadiazole.

In some embodiments, a group of compounds of formula I are compounds where $R^3$ is methyl substituted 1,3,4-oxadiazole.

In some embodiments, a group of compounds of formula I are compounds where $R^3$ is imidazole, pyrazole, triazole, or tetrazole.

In some embodiments, a group of compounds of formula I are compounds where $R^3$ is $C_{1-3}$ alkyl substituted imidazole, pyrazole, triazole, or tetrazole.

In some embodiments, a group of compounds of formula I are compounds where $R^3$ is methyl substituted pyrazole, imidazole, triazole, or tetrazole.

In some embodiments, a group of compounds of formula I are compounds where $R^3$ is phenyl, 1-3 halo substituted phenyl, $C_{1-3}$ alkyl substituted phenyl, or $C_{1-3}$ haloalkyl substituted phenyl.

In some embodiments, a group of compounds of formula I are compounds where $R^3$ is a dihalo substituted phenyl, where the halo atoms can be either the same or different.

In some embodiments, a group of compounds of formula I are compounds where $R^3$ is singly halo substituted $C_{1-3}$ haloalkyl phenyl.

In some embodiments, a group of compounds of formula I are compounds where $R^3$ is doubly halo substituted $C_{1-3}$ haloalkyl phenyl where the halo atoms may be the same or different.

In some embodiments, a group of compounds of formula I are compounds where $R^3$ is triply halo substituted $C_{1-3}$ haloalkyl phenyl where the halo atoms may be the same or different.

In some embodiments, a group of compounds of formula I are compounds where $R^3$ is phenyl substituted with halo and $C_{1-3}$ alkyl In some embodiments, a group of compounds of formula I are compounds where $R^3$ is phenyl substituted with a halo and a $C_{1-3}$ haloalkyl group.

In some embodiments, a group of compounds of formula I are compounds where $R^3$ is pyridine, pyridazine, pyrimidine, or pyrazine.

In some embodiments, a group of compounds of formula I are compounds where $R^3$ is halo substituted pyridine, pyridazine, pyrimidine, or pyrazine.

In some embodiments, a group of compounds of formula I are compounds where $R^3$ is $C_{1-3}$ alkyl substituted pyridine, pyridazine, pyrimidine, or pyrazine.

In some embodiments, a group of compounds of formula I are compounds where R³ is cyano substituted pyridine, pyridazine, pyrimidine, or pyrazine.

In some embodiments, a group of compounds of formula I are compounds where R³ is naphthyl or hetero-naphthyl.

In some embodiments, a group of compounds of formula I are compounds where R³ is nitrogen substituted napthyl.

In some embodiments, a group of compounds of formula I are compounds where R³ is quinolone or isoquinolone.

In some embodiments, R³ is selected from the following:

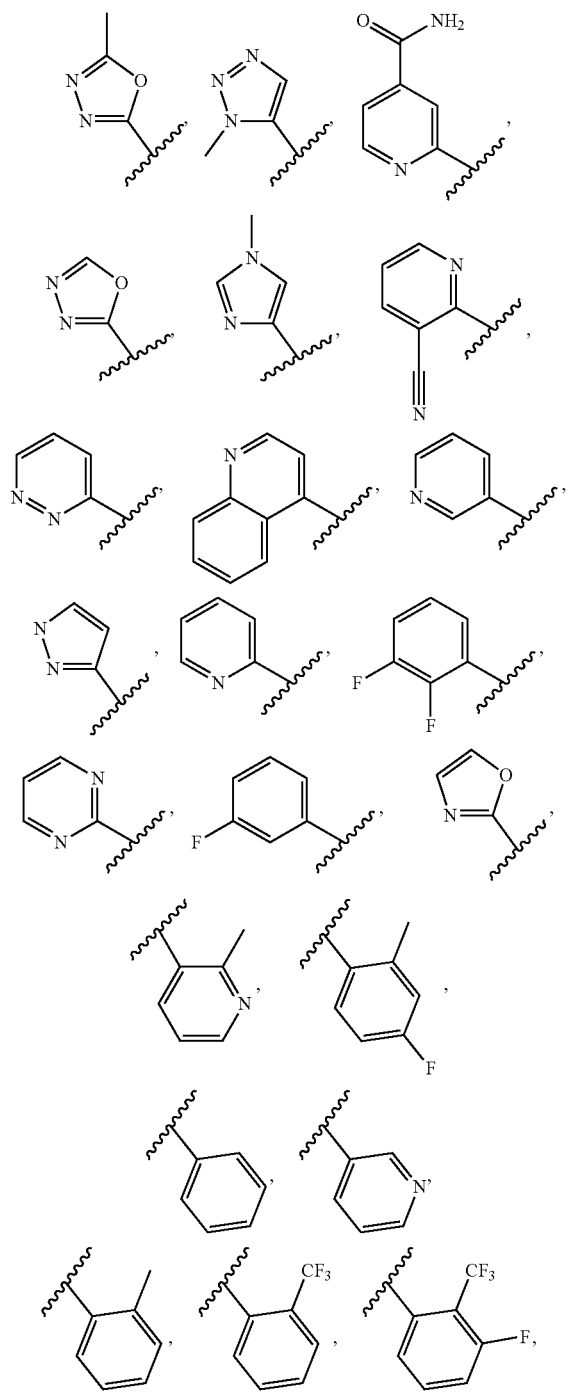

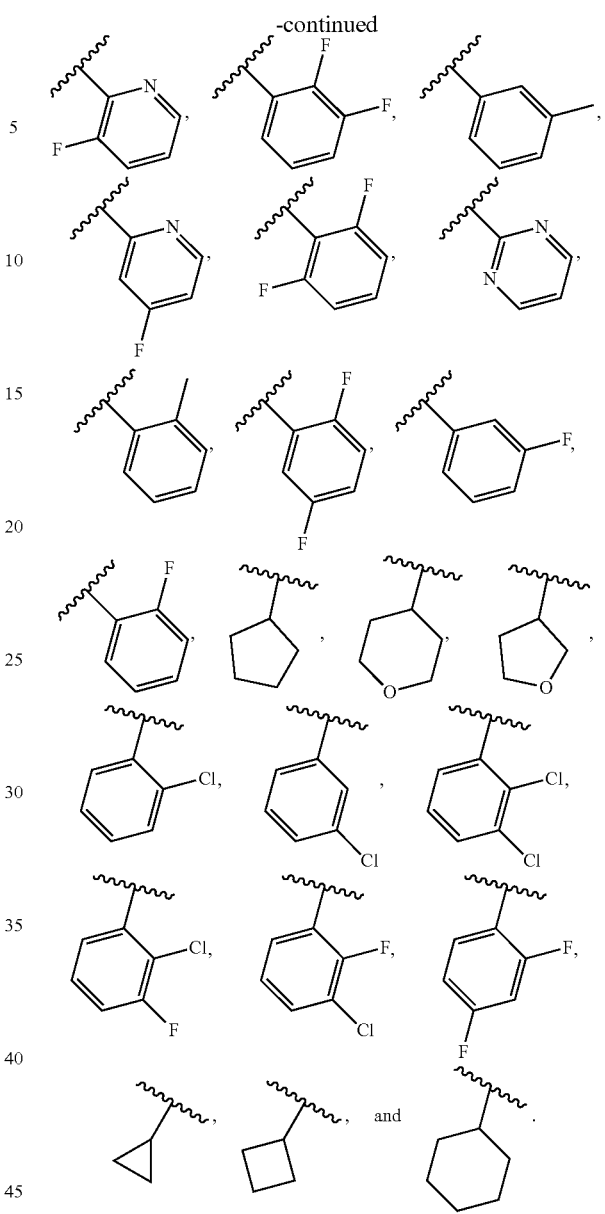

In some embodiments, a group of compounds of formula I are compounds where R⁴ is halogen, $C_{1-6}$ alkyl, $C_{1-6}$ haloalkyl, $C_{1-3}$ haloalkoxy, $C_{3-6}$ cycloalkyl, or a 4-12 membered heterocycle.

In some embodiments, a group of compounds of formula I are compounds where R⁴ is chloro, fluoro, or bromo.

In some embodiments, a group of compounds of formula I are compounds where R⁴ is trifluoro methyl, tribromo methyl, or trichloro methyl.

In some embodiments, a group of compounds of formula I are compounds where R⁴ is difluoro methyl, dichloro methyl, or dibromo methyl.

In some embodiments, a group of compounds of formula I are compounds where R⁴ is fluoro methyl, chloro methyl, or bromo methyl.

In some embodiments, a group of compounds of formula I are compounds where R⁴ is halo methoxy.

In some embodiments, a group of compounds of formula I are compounds where R⁴ is fluoro methoxy, difluoro methoxy, or trifluoro methoxy.

In some embodiments, a group of compounds of formula I are compounds where $R^4$ is cyclopropyl, cyclobutyl, cyclopentyl, or cyclohexyl.

In some embodiments, a group of compounds of formula I are compounds where $R^4$ is azetidine.

In some embodiments, a group of compounds of formula I are compounds where $R^4$ is pyrrolidine.

In some embodiments, a group of compounds of formula I are compounds where $R^4$ is piperidine.

In any of the embodiments above, a group of compounds of formula I are compounds where $X^R$ is fluoro, bromo, or chloro.

In any of the embodiments above, a group of compounds of formula I are compounds where $X^R$ is methyl, ethyl, propyl, isopropyl, butyl, n-butyl, sec-butyl, isobutyl, t-butyl, pentyl, or hexyl.

In any of the embodiments above, a group of compounds of formula I are compounds where $X^R$ is a fluoromethyl, a bromomethyl, or a chloromethyl.

In any of the embodiments above, a group of compounds of formula I are compounds where $X^R$ is a difluoromethyl, a dibromo methyl, or dichloro methyl.

In any of the embodiments above, a group of compounds of formula I are compounds where $X^R$ is a trifluoromethyl, a tribromo methyl, or a trichloro methyl.

In some embodiments, compounds of formula I are compounds where $R^4$ is either hydrogen, halogen, $C_{1-6}$ alkyl, or an unsubstituted or substituted aryl with one, two, or three substituents independently selected from halogen, —CN, $C_{1-6}$ haloalkyl, and $C_{1-6}$ alkyl.

In some embodiments, compounds of formula I are compounds where $R^4$ is methyl or ethyl.

In some embodiments, compounds of formula I are compounds where $R^4$ is fluoro, chloro, or bromo.

In some embodiments, compounds of formula I are compounds where $R^4$ is absent.

In some embodiments, $R^5$ is selected from hydrogen, or $C_{1-6}$ alkyl.

In some embodiments, $R^5$ is methyl.

In some embodiments, $R^6$ is selected from hydrogen, or $C_{1-6}$ alkyl.

In some embodiments, $R^7$ is halogen.

In some embodiments, $R^7$ is fluoro.

In one embodiment, the compound of the present disclosure is selected from the group consisting of:

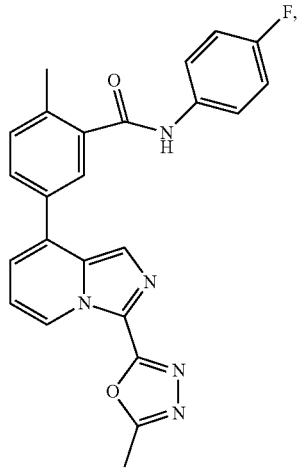

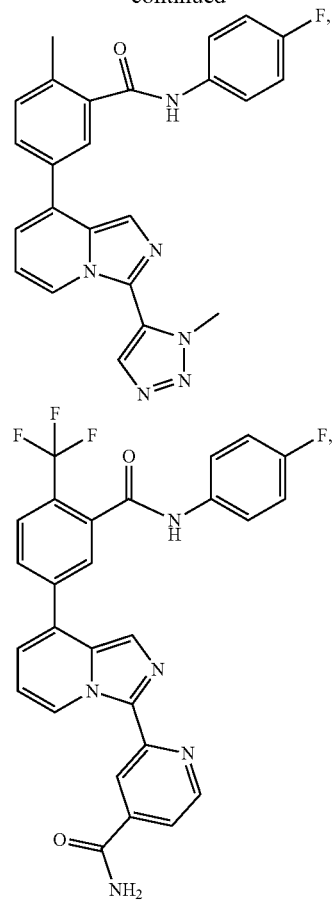

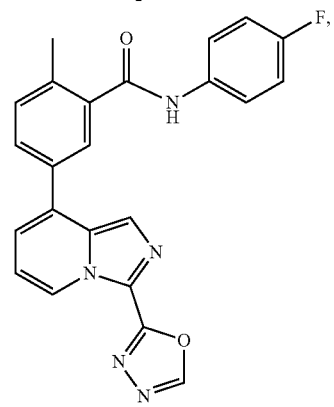

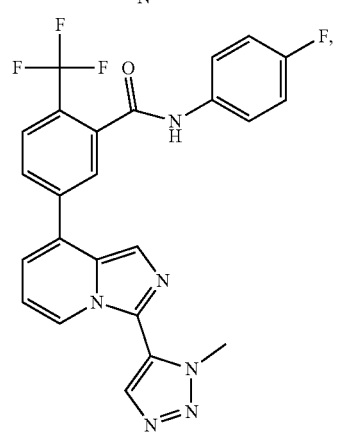

-continued
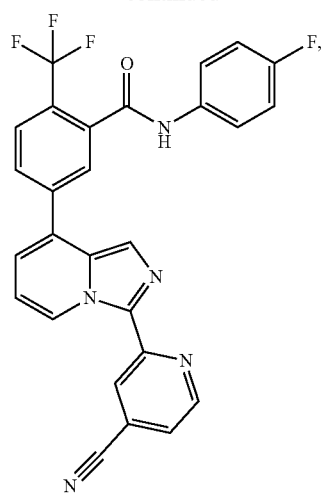
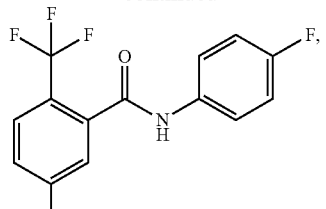
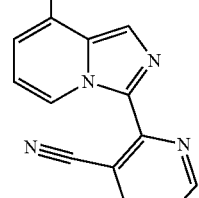
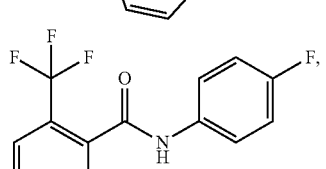
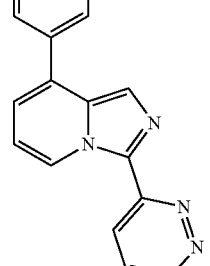
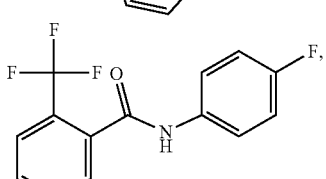
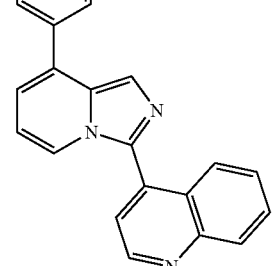
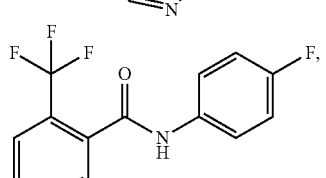
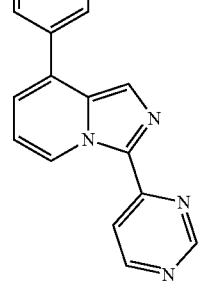

33
-continued
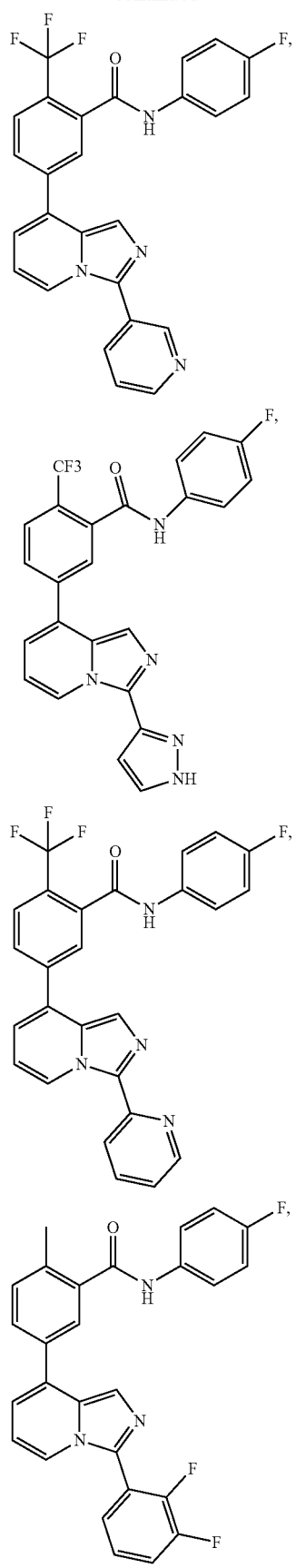
34
-continued
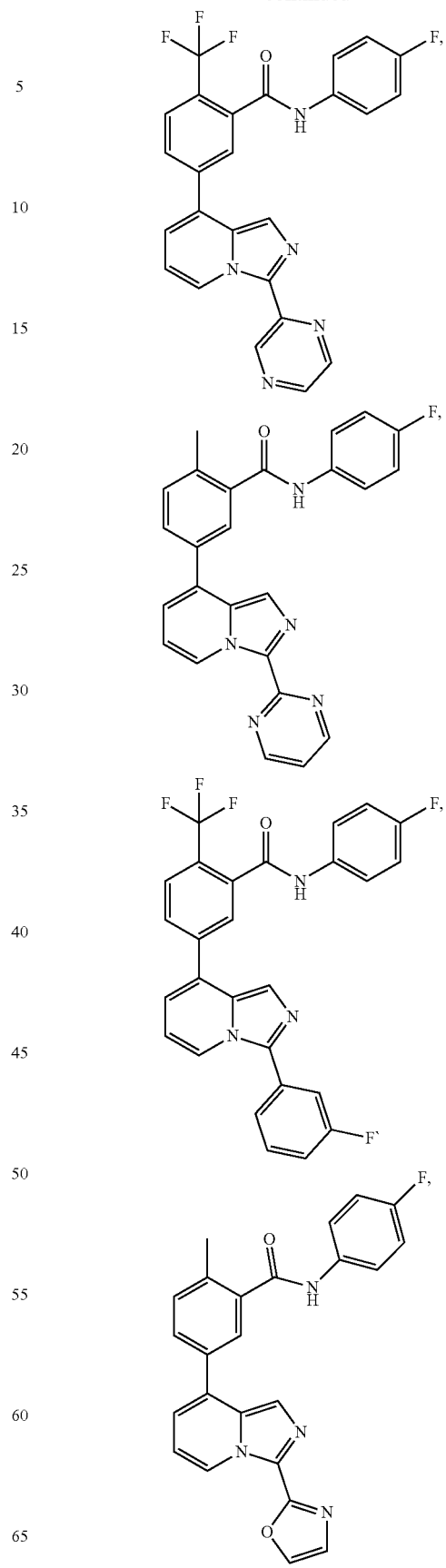

-continued
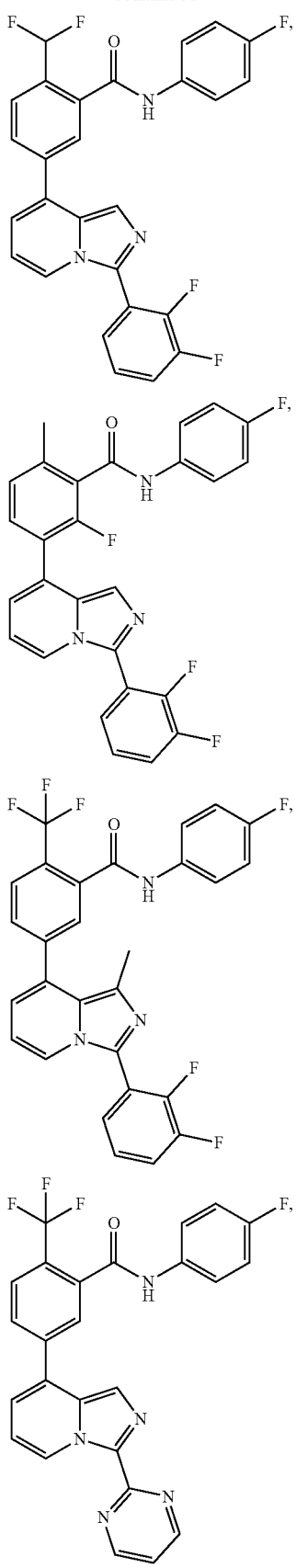
-continued
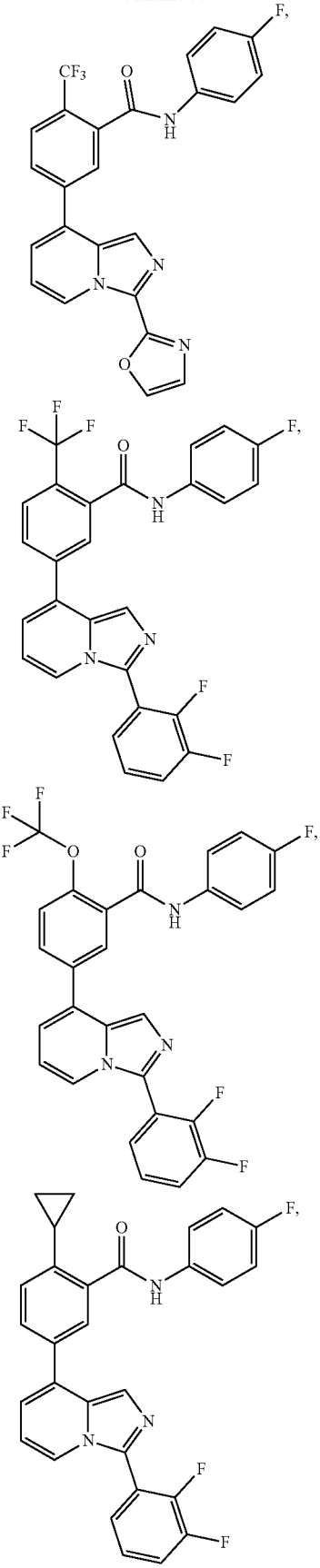

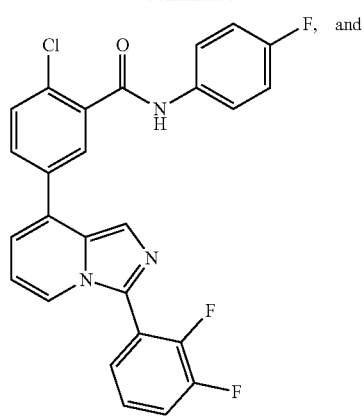
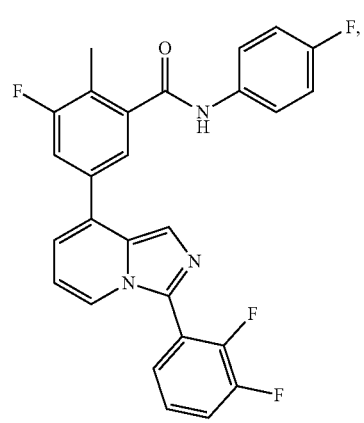
or a pharmaceutically acceptable salt thereof.
In one embodiment, the compound of the present disclosure is selected from the group consisting of:
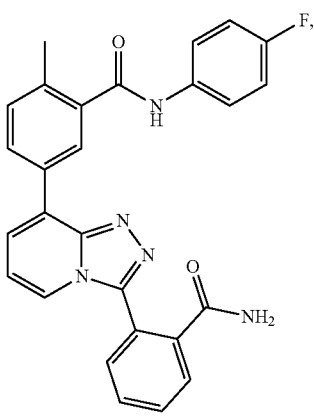
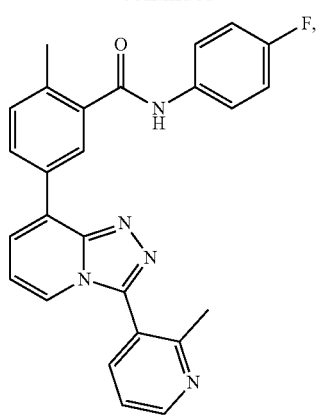
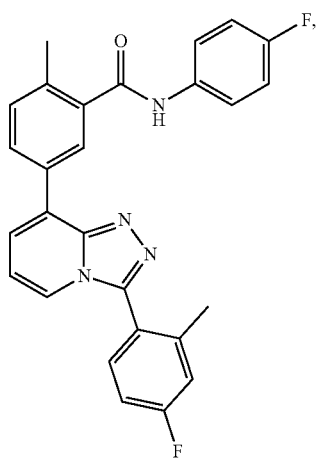
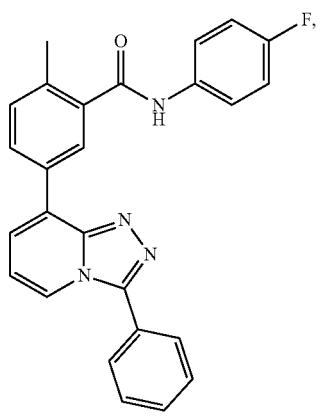
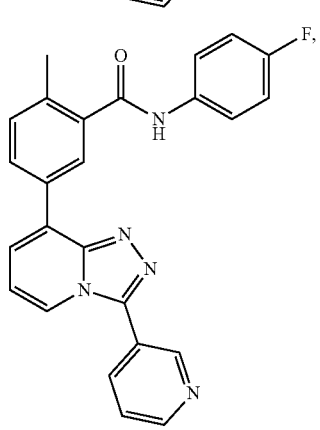

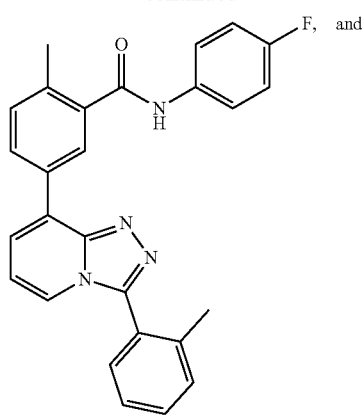
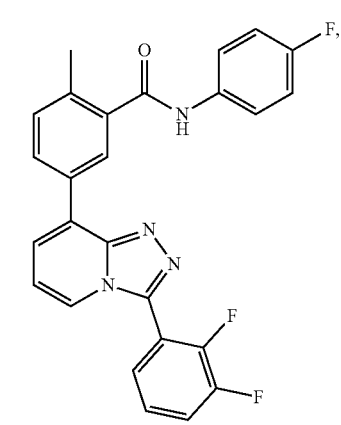
or a pharmaceutically acceptable salt thereof.
In one embodiment, the compound of the present disclosure is selected from the group consisting of:
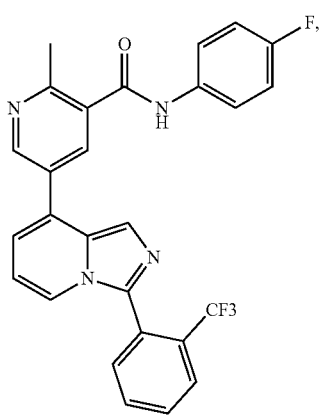
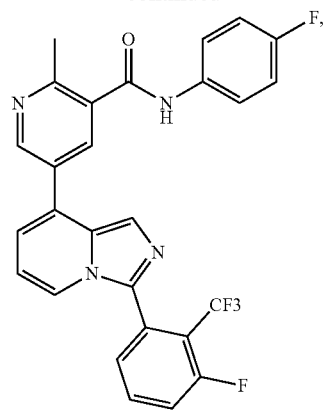
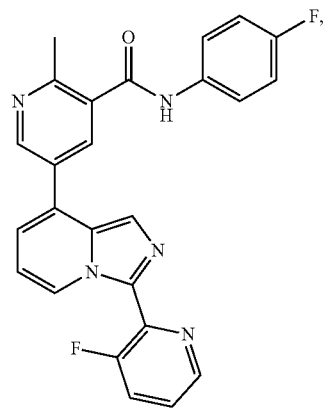
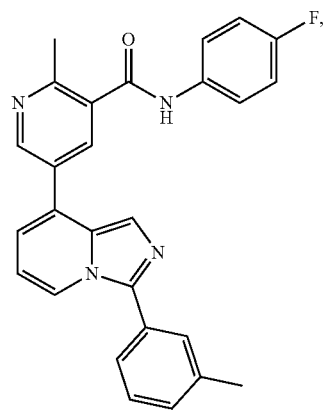
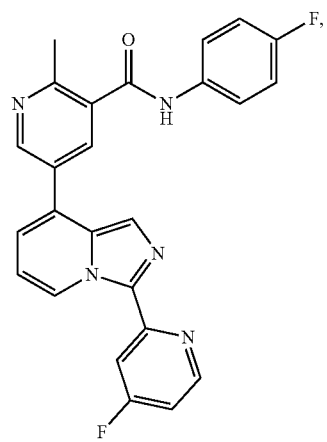

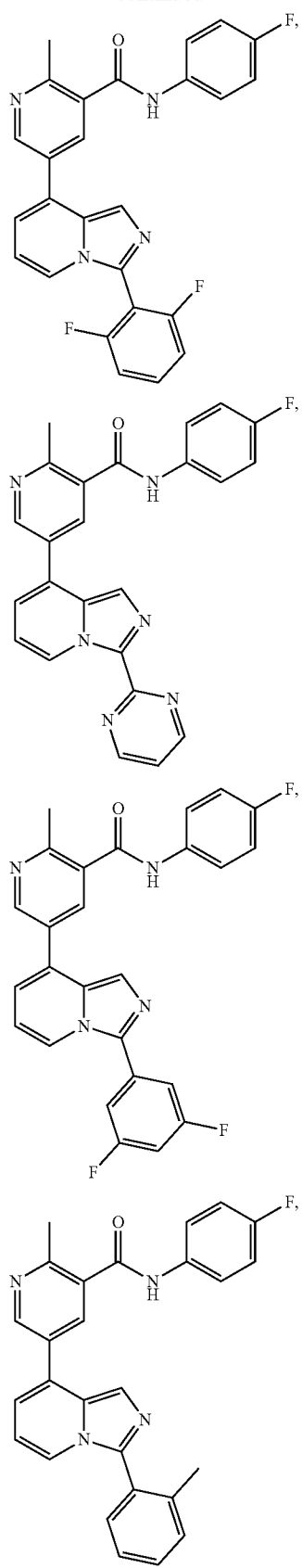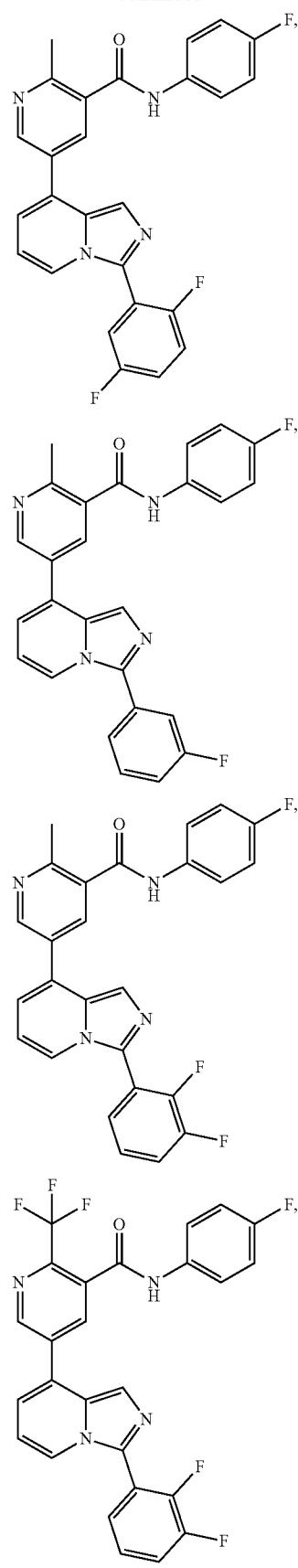

-continued
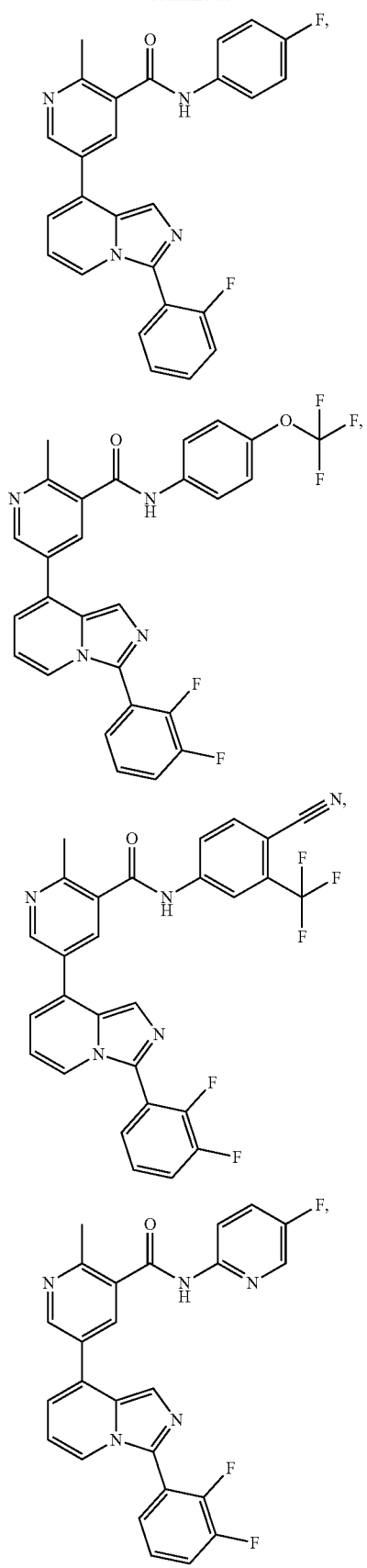
-continued
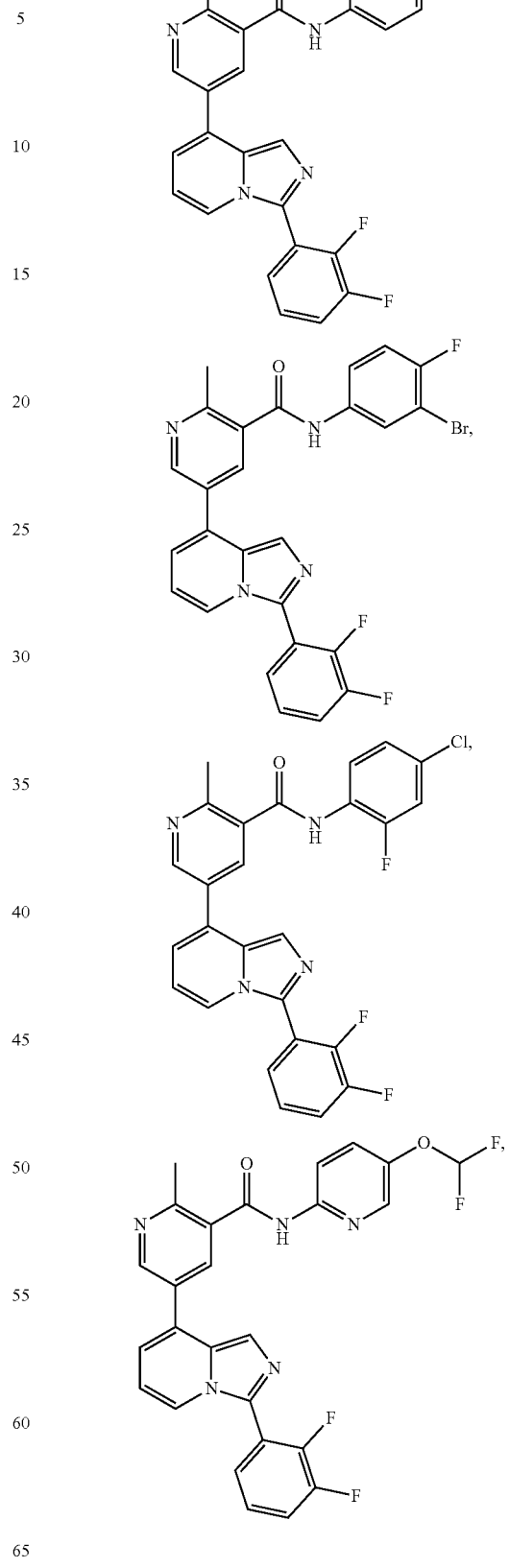

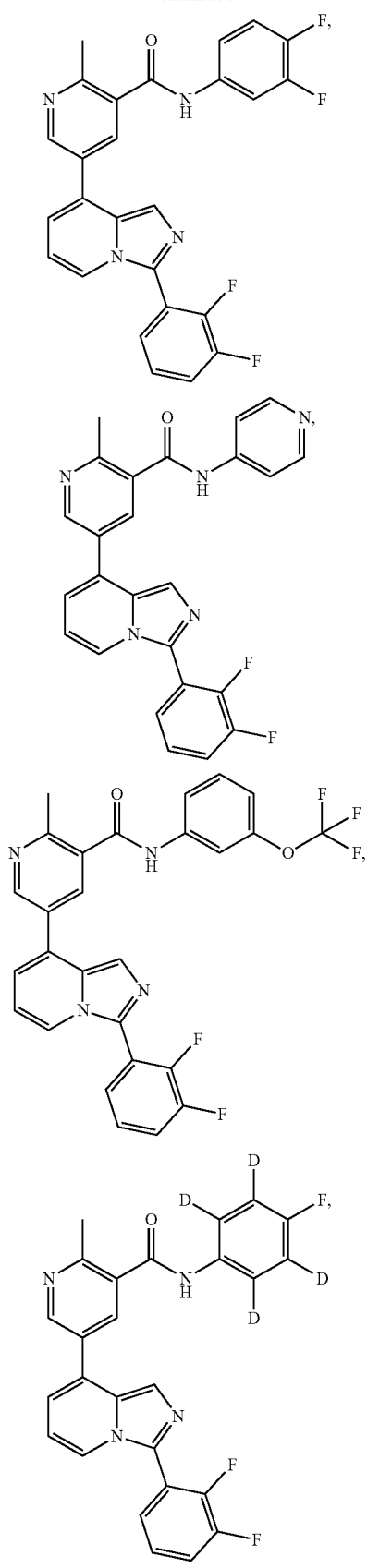
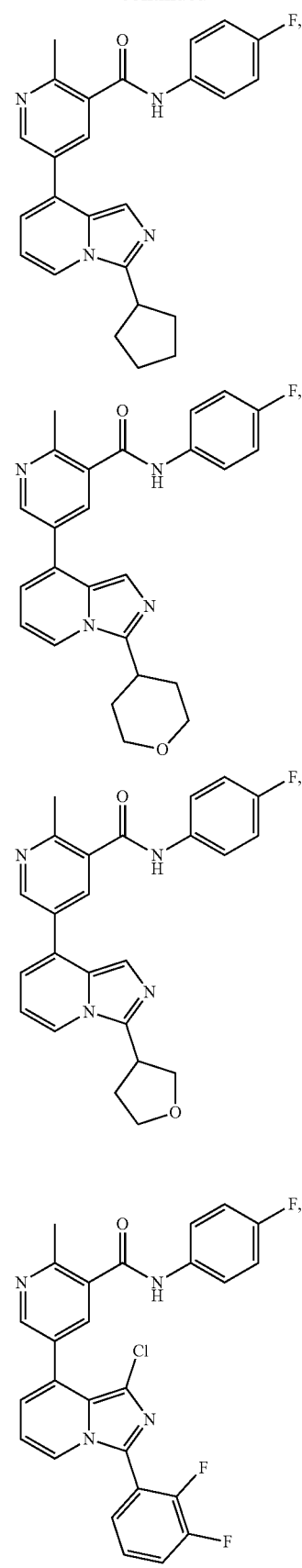

-continued
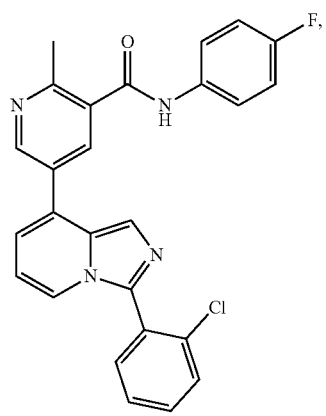
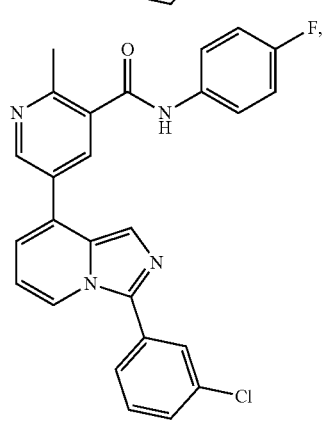
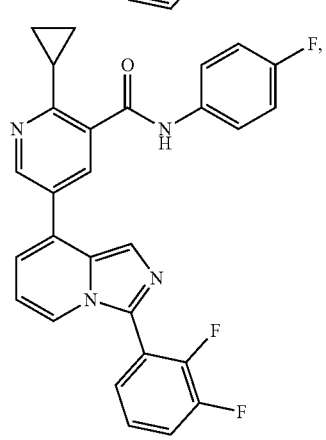
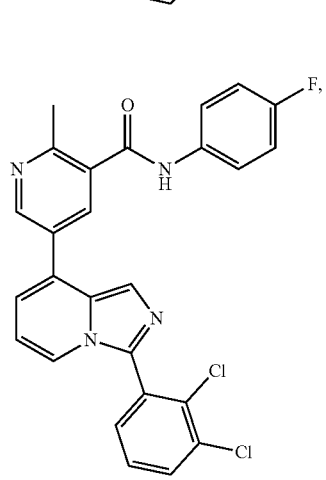
-continued
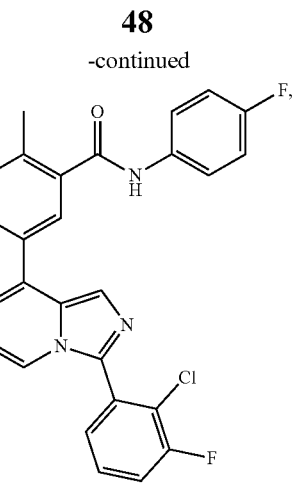
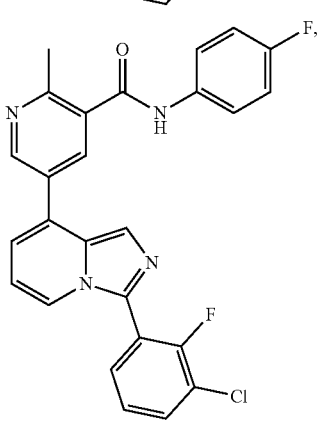
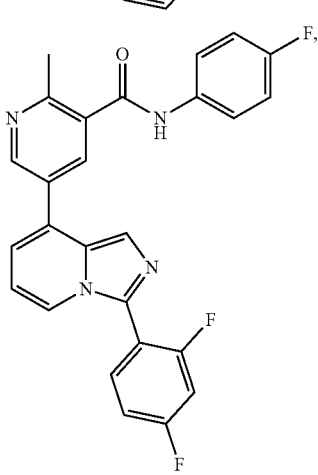
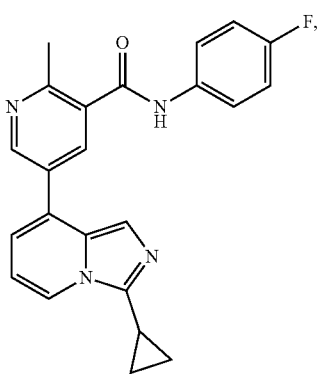

-continued
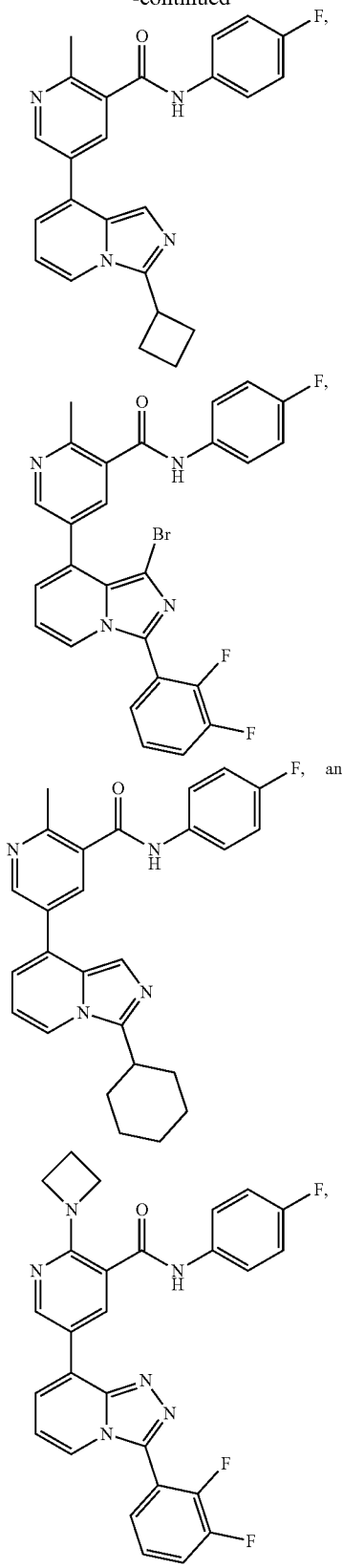
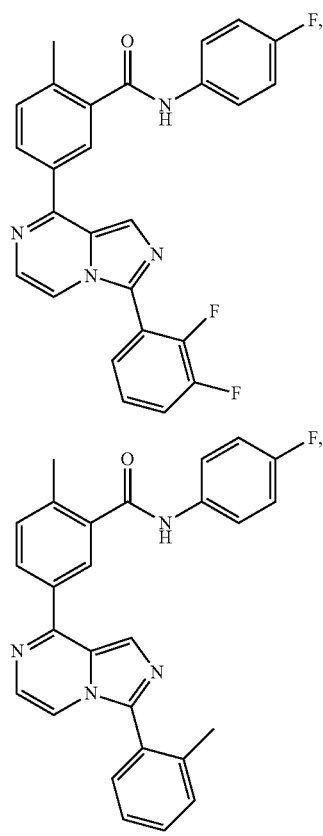
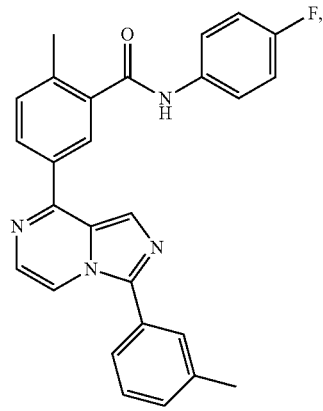 [SMILES: Cc1ccc(-c2nccn3c(-c4ccccn4)ncc23)cc1C(=O)Nc1ccc(F)cc1]
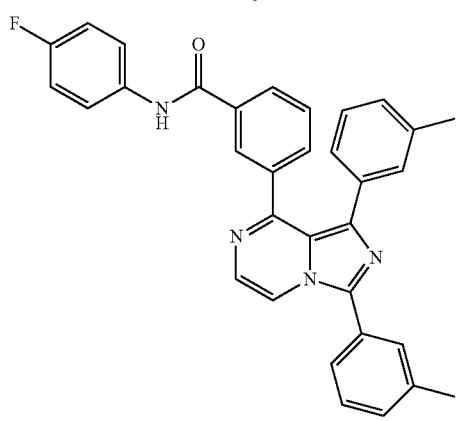
or a pharmaceutically acceptable salt thereof.
In one embodiment, the compound of the present disclosure is selected from the group consisting of:

51
-continued
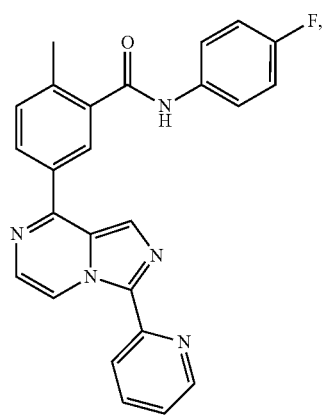
or a pharmaceutically acceptable salt thereof.
In one embodiment, the compound of the present disclosure is selected from the group consisting of:
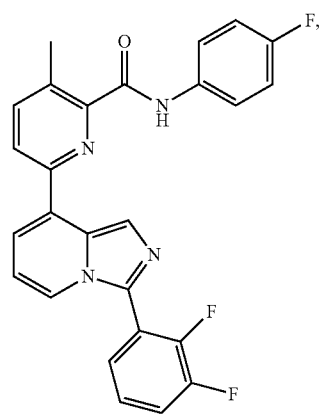
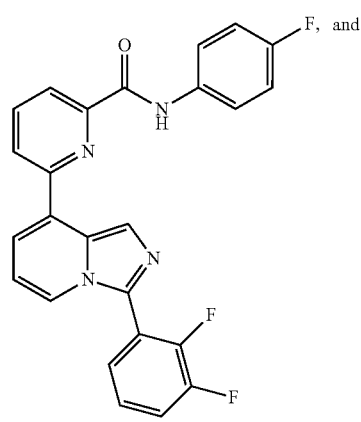
52
-continued
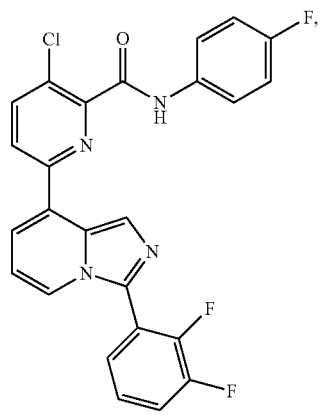
or a pharmaceutically acceptable salt thereof.
In one embodiment, the compound of the present disclosure is selected from the group consisting of:
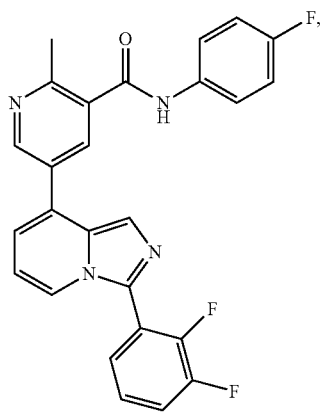
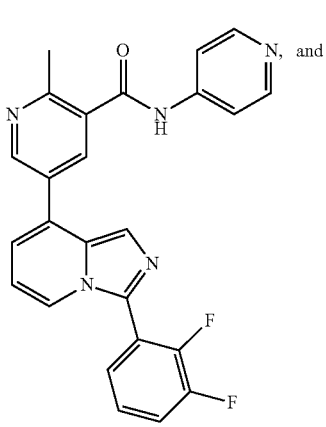

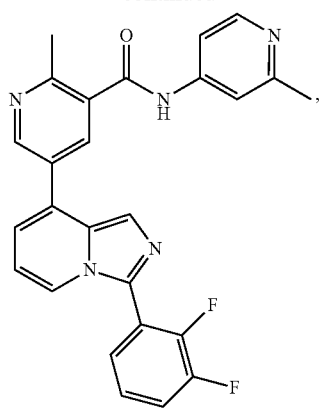
or a pharmaceutically acceptable salt thereof.
In one embodiment, the compound of the present disclosure is selected from the group consisting of:
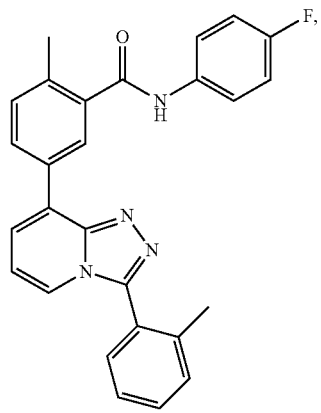
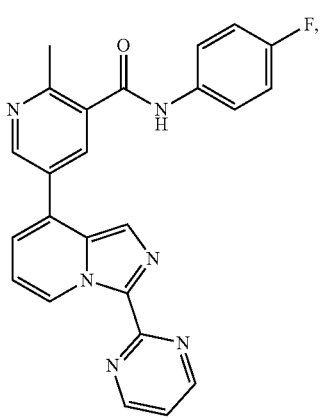
or a pharmaceutically acceptable salt thereof.
In one embodiment, the compound of the present disclosure is selected from the group consisting of:
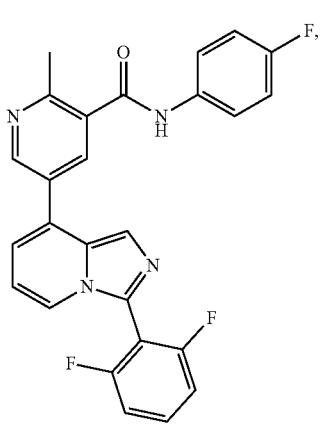

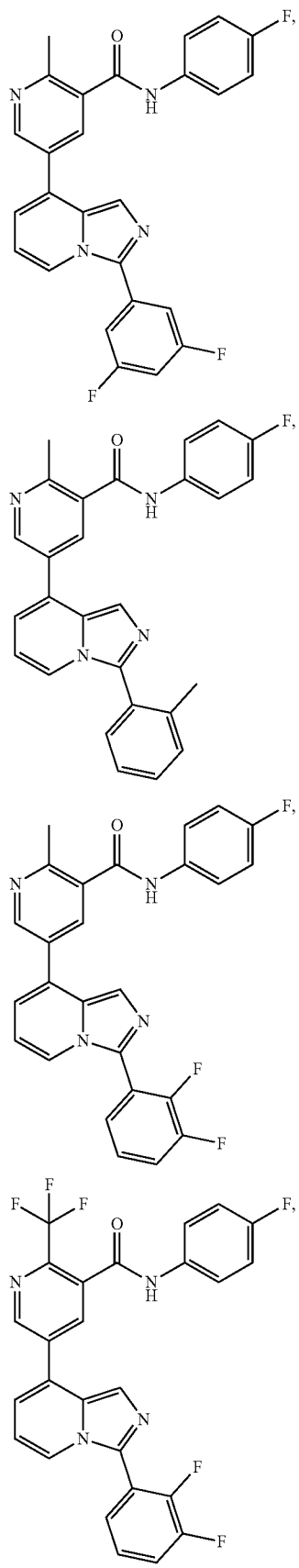
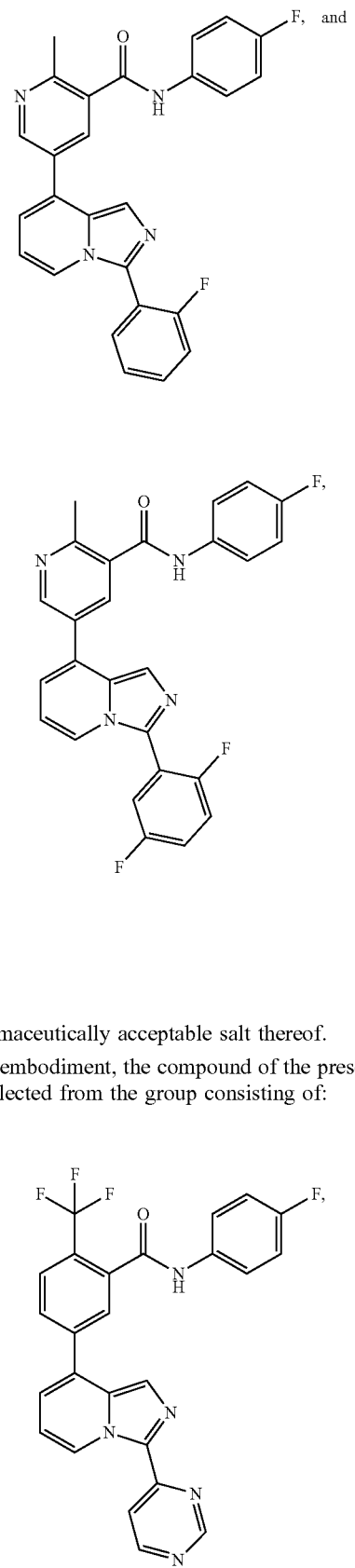
or a pharmaceutically acceptable salt thereof.
In one embodiment, the compound of the present disclosure is selected from the group consisting of:

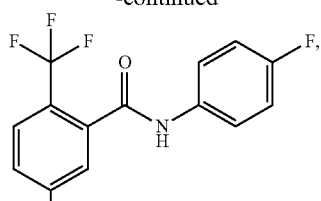
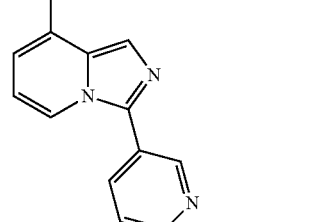
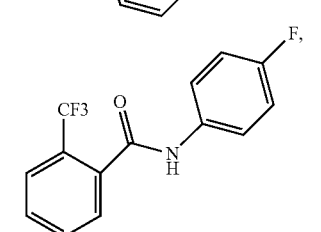

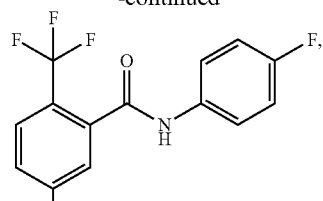
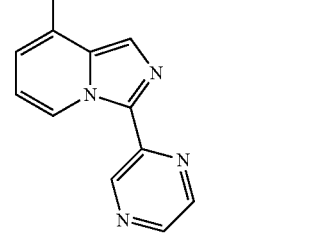
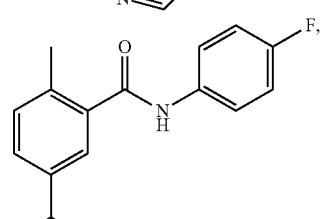
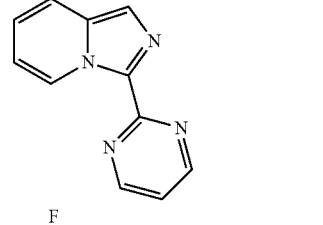

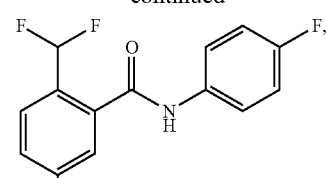
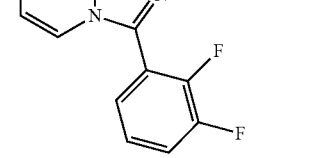
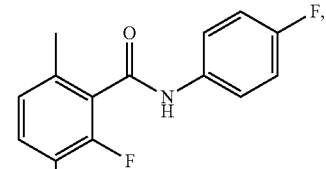
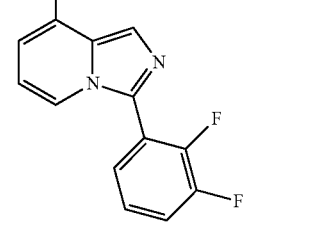
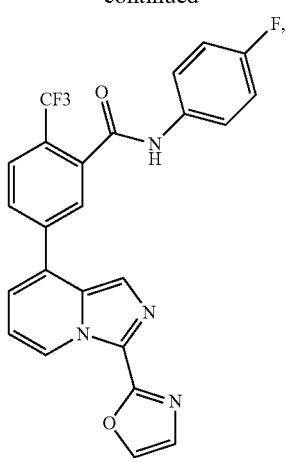
or a pharmaceutically acceptable salt thereof.
In one embodiment, the compound of the present disclosure is either
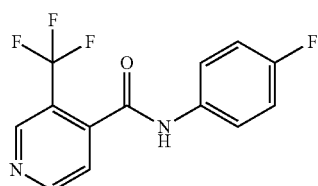
or
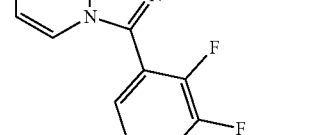
or a pharmaceutically acceptable salt thereof.
In some embodiments, provided herein is 5-(3-(2,3-difluorophenyl)imidazo[1,5-a]pyridin-8-yl)-N-(4-fluorophenyl)-2-(trifluoromethyl)benzamide, having the following structure:

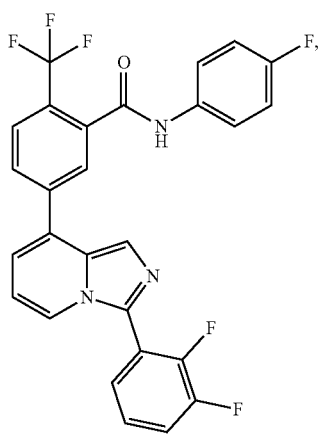

or a pharmaceutically acceptable salt thereof.

In some embodiments, provided herein is N-(4-fluorophenyl)-5-(3-(oxazol-2-yl)imidazo[1,5-a]pyridin-8-yl)-2-(trifluoromethyl)benzamide, having the following structure:

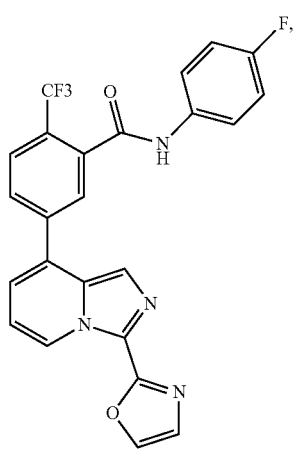 [SMILES: O=C(Nc1ccc(F)cc1)c1cc(-c2cccn3c(-c4ncco4)ncc23)ccc1C(F)(F)F]

or a pharmaceutically acceptable salt thereof.

In some embodiments, provided herein is N-(4-fluorophenyl)-5-(3-(pyrimidin-2-yl)imidazo[1,5-a]pyridin-8-yl)-2-(trifluoromethyl)benzamide, having the following structure

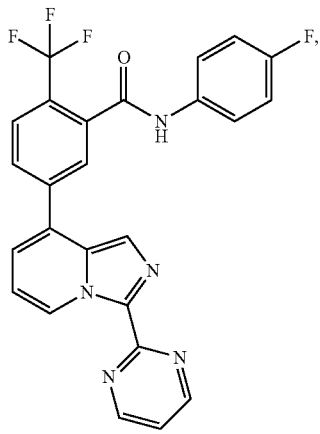 [SMILES: O=C(Nc1ccc(F)cc1)c1cc(-c2cccn3c(-c4ncccn4)ncc23)ccc1C(F)(F)F]

or a pharmaceutically acceptable salt thereof.

In some embodiments, provided herein is 5-(3-(2,3-difluorophenyl)-1-methylimidazo[1,5-a]pyridin-8-yl)-N-(4-fluorophenyl)-2-(trifluoromethyl)benzamide, having the following structure

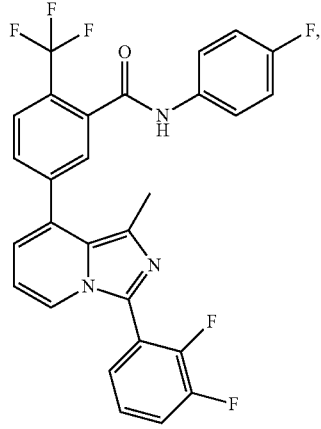 [SMILES: Cc1nc(-c2cccc(F)c2F)n2cccc(-c3ccc(C(F)(F)F)c(C(=O)Nc4ccc(F)cc4)c3)c12]

or a pharmaceutically acceptable salt thereof.

In some embodiments, provided herein is 2-(difluoromethyl)-5-(3-(2,3-difluorophenyl)imidazo[1,5-a]pyridin-8-yl)-N-(4-fluorophenyl)benzamide, having the following structure

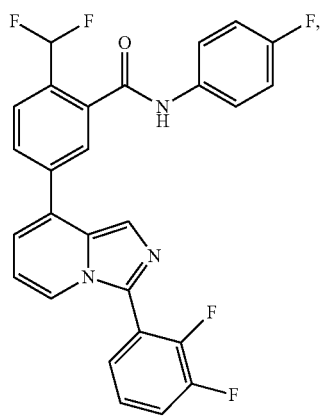 [SMILES: O=C(Nc1ccc(F)cc1)c1cc(-c2cccn3c(-c4cccc(F)c4F)ncc23)ccc1C(F)F]

or a pharmaceutically acceptable salt thereof.

In some embodiments, provided herein is 3-(3-(2,3-difluorophenyl)imidazo[1,5-a]pyridin-8-yl)-2-fluoro-N-(4-fluorophenyl)-6-methylbenzamide, having the following structure

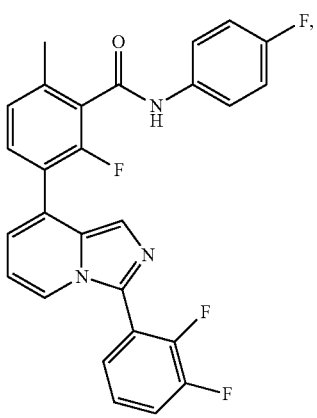 [SMILES: Cc1ccc(-c2cccn3c(-c4cccc(F)c4F)ncc23)c(F)c1C(=O)Nc1ccc(F)cc1]

or a pharmaceutically acceptable salt thereof.

In some embodiments, provided herein is N-(4-fluorophenyl)-5-(3-(2-fluorophenyl)imidazo[1,5-a]pyridin-8-yl)-2-methylnicotinamide, having the following structure

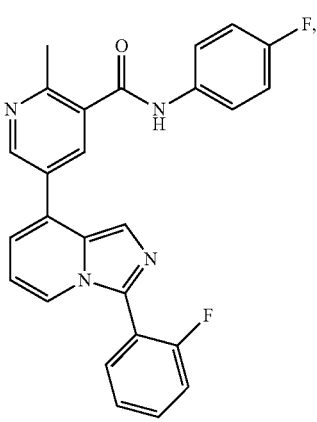

or a pharmaceutically acceptable salt thereof.

In some embodiments, provided herein is 5-(3-(2,3-difluorophenyl)imidazo[1,5-a]pyridin-8-yl)-N-(4-fluorophenyl)-2-(trifluoromethyl)nicotinamide, having the following structure

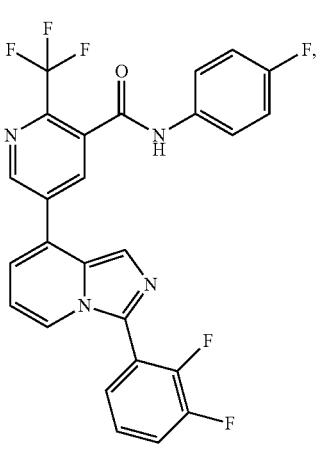

or a pharmaceutically acceptable salt thereof.

In some embodiments, provided herein is 5-(3-(2,3-difluorophenyl)imidazo[1,5-a]pyridin-8-yl)-N-(4-fluorophenyl)-2-methylnicotinamide, having the following structure

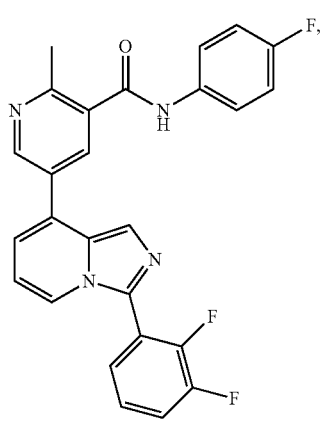 [SMILES: Cc1ncc(-c2cccn3c(-c4cccc(F)c4F)ncc23)cc1C(=O)Nc1ccc(F)cc1]

or a pharmaceutically acceptable salt thereof.

In some embodiments, provided herein is 6-(3-(2,3-difluorophenyl)imidazo[1,5-a]pyridin-8-yl)-N-(4-fluorophenyl)-3-(trifluoromethyl)picolinamide, having the structure

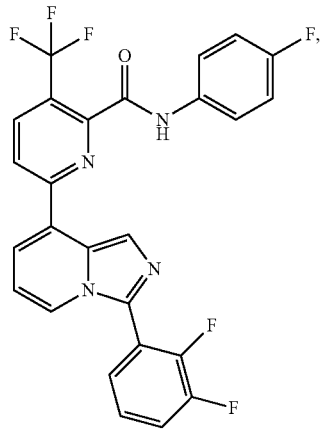

or a pharmaceutically acceptable salt thereof.

In some embodiments, provided herein is 2-(3-(2,3-difluorophenyl)imidazo[1,5-a]pyridin-8-yl)-N-(4-fluorophenyl)-5-(trifluoromethyl)isonicotinamide, having the structure

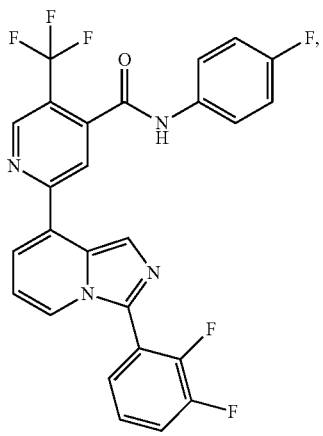 [SMILES: O=C(Nc1ccc(F)cc1)c1nc(-c2cccn3c(-c4cccc(F)c4F)ncc23)ccc1C(F)(F)F]

or a pharmaceutically acceptable salt thereof.

In some embodiments, provided herein is a compound having structure of Formula II:

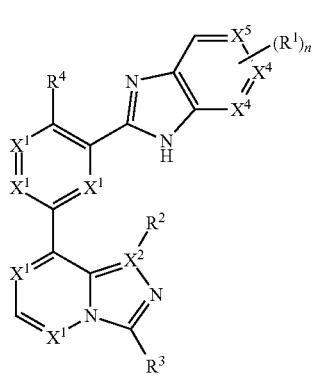

Formula II wherein
- $X^1$ at each location in Formula II is independently N, CH, or $CX^R$;
- $X^2$ is N or C, wherein $R^2$ is absent when $X^2$ is N;
- $X^4$ at each location in Formula II is independently N, CH, or $CR^1$;
- $X^5$ is CH, $CX^R$, or $CR^1$;
- $X^R$ is hydrogen, halogen, $C_{1-3}$ haloalkyl, or $C_{1-6}$ alkyl;
- $R^1$ is hydrogen, deuterium, halogen, —CN, —$OCF_3$, —$OCHF_2$, or —$CF_3$, wherein n is 0-4 and where if n is >1, $R^1$ can be independently the same or different from each other;
- $R^2$ is hydrogen, halogen, $C_{1-6}$ alkyl, or an unsubstituted or substituted aryl with one, two, or three substituents independently selected from halogen, —CN, $C_{1-6}$ haloalkyl, and $C_{1-6}$ alkyl;
- $R^3$ is $C_{3-6}$ cycloalkyl, $C_{3-6}$ heterocycle, mono or bicyclic aryl or heteroaryl, wherein each mono or bicyclic aryl or heteroaryl is unsubstituted or substituted with one, two, or three substituents independently selected from halogen, —CN, $C_{1-6}$ haloalkyl, and $C_{1-6}$ alkyl; and
- $R^4$ is halogen, $C_{1-6}$ alkyl, $C_{1-6}$ haloalkyl, —$OCF_3$, $C_{3-6}$ cycloalkyl, or a 4-12 membered heterocycle, or or a pharmaceutically acceptable salt thereof.

In some embodiments, compounds of formula II are compounds of formula IIa:

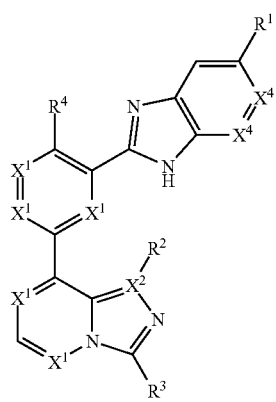

Formula IIa wherein
- $X^1$ at each location of Formula IIa is independently N, CH, or $CX^R$;
- $X^2$ is N or C, wherein $R^2$ is absent when $X^2$ is N;
- $X^4$ at each location of Formula IIa is independently N, CH, or $CR^1$;
- $X^R$ is hydrogen, halogen, $C_{1-3}$ haloalkyl, or $C_{1-6}$ alkyl;
- $R^1$ is hydrogen, deuterium, halogen, —CN, —$OCF_3$, —$OCHF_2$, or —$CF_3$, wherein $R^1$ can be independently the same or different from each other;
- $R^2$ is absent when $X^2$ is N; or $R^2$ is hydrogen, halogen, $C_{1-6}$ alkyl, or an unsubstituted or substituted aryl with one, two, or three substituents independently selected from halogen, —CN, $C_{1-6}$ haloalkyl, and $C_{1-6}$ alkyl;
- $R^3$ is $C_{3-6}$ cycloalkyl, $C_{3-6}$ heterocycle, mono or bicyclic aryl or heteroaryl, wherein each mono or bicyclic aryl or heteroaryl is unsubstituted or substituted with one, two, or three substituents independently selected from halogen, —CN, $C_{1-6}$ haloalkyl, and $C_{1-6}$ alkyl; and
- $R^4$ is halogen, $C_{1-6}$ alkyl, $C_{1-6}$ haloalkyl, —$OCF_3$, $C_{3-6}$ cycloalkyl, or a 4-12 membered heterocycle, or a pharmaceutically acceptable salt thereof.

In some embodiments, compounds of formula II are compounds of formula IIb:

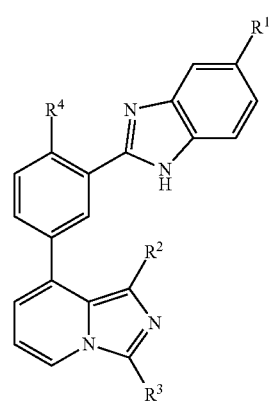

Formula IIb wherein
- $R^1$ is halogen or hydrogen;
- $R^2$ is hydrogen, $C_{1-3}$ alkyl, or an unsubstituted or substituted aryl with one, two, or three substituents independently selected from halogen, —CN, $C_{1-3}$ haloalkyl, and $C_{1-3}$ alkyl;

R³ is a C₃₋₆ cycloalkyl, C₃₋₆ heterocycle, mono or bicyclic aryl or heteroaryl, wherein each mono or bicyclic aryl or heteroaryl is unsubstituted or substituted with one, two, or three substituents independently selected from halogen, —CN, $C_{1-3}$ haloalkyl, and $C_{1-3}$ alkyl; and R⁴ is halogen, $C_{1-3}$ alkyl, $C_{1-3}$ haloalkyl, —OCF₃, $C_{3-6}$ cycloalkyl, or 4-12 membered heterocycle, or a pharmaceutically acceptable salt thereof.

In some embodiments, compounds of formula II are compounds of formula IIc:

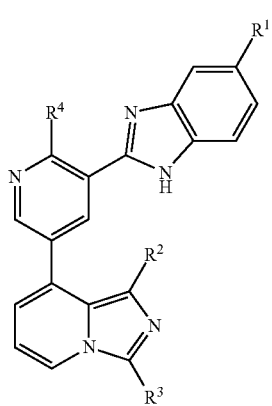

Formula IIc wherein
R¹ is halogen or hydrogen;
R² is hydrogen, $C_{1-3}$ alkyl, or an unsubstituted or substituted aryl with one, two, or three substituents independently selected from halogen, —CN, $C_{1-3}$ haloalkyl, and $C_{1-3}$ alkyl;
R³ is a $C_{3-6}$ cycloalkyl, $C_{3-6}$ heterocycle, mono or bicyclic aryl or heteroaryl, wherein each mono or bicyclic aryl or heteroaryl is unsubstituted or substituted with one, two, or three substituents independently selected from halogen, —CN, $C_{1-3}$ haloalkyl, and $C_{1-3}$ alkyl; and
R⁴ is halogen, $C_{1-3}$ alkyl, $C_{1-3}$ haloalkyl, —OCF₃, $C_{3-6}$ cycloalkyl, or 4-12 membered heterocycle, or a pharmaceutically acceptable salt thereof.

Specific values listed below are values for compounds of formula II as well as all related formulas (e.g., IIa, IIb, and IIc), or pharmaceutically acceptable salts thereof. It is to be understood that two or more values may combined. Thus, it is to be understood that any variable for compounds of formula II may be combined with any other variable for compounds of formula II the same as if each and every combination of variables were specifically and individually listed. For example, it is understood that any specific value of R¹ detailed herein for compounds of Formula II may be combined with any other specific value for one or more of the variables $X^1$, $X^2$, $X^4$, $X^5$, $X^6$, $X^R$, R², R³, or R⁴ the same as if each and every combination were specifically and individually listed.

In some embodiments, a group of compounds of formula II are compounds wherein $X^1$ is selected from nitrogen, methine (—CH), or a carbon further attached to a group denoted as $X^R$. The specific group of compounds of formula II are compounds where $X^R$ is selected from hydrogen, halogen, $C_{1-3}$ haloalkyl, or $C_{1-6}$ alkyl.

In some embodiments, a group of compounds of formula II are compounds wherein $X^1$ is either nitrogen or —CH group.

In some embodiments, a group of compound of formula II are compounds wherein $X^1$ is a carbon having a hydrogen, halogen, $C_{1-3}$ haloalkyl, or $C_{1-6}$ alkyl as a substituent.

In some embodiments, a group of compounds of formula II are compounds wherein $X^2$ is selected from nitrogen, —CH group, or a carbon further substituted with substituents denoted by R².

In some embodiments, a group of compounds of formula II are compounds wherein $X^2$ is a —CH group.

In some embodiments, a group of compounds of formula II are compounds wherein $X^2$ is carbon attached to R² where R² is hydrogen, halogen, $C_{1-6}$ alkyl, or an unsubstituted or substituted aryl with one, two, or three substituents independently selected from halogen, —CN, $C_{1-6}$ haloalkyl, and $C_{1-6}$ alkyl.

In some embodiments, a group of compounds of formula II are compounds wherein R² is hydrogen.

In some embodiments, a group of compounds of formula II are compounds wherein R² is bromo, chloro, or fluoro.

In some embodiments, a group of compounds of formula II are compounds wherein R² is methyl, ethyl, propyl, isopropyl, butyl, n-butyl, sec-butyl, isobutyl, t-butyl, pentyl, or hexyl.

In some embodiments, a group of compounds of formula II are compounds wherein $X^4$ is nitrogen, a —CH group, or a carbon substituted with $X^1$.

In some embodiments, a group of compounds of formula II are compounds wherein $X^4$ is a —CH group.

In some embodiments, a group of compounds of formula II are compounds wherein $X^4$ is a carbon substituted with a hydrogen or a carbon substituted with $X^R$, wherein $X^R$ is either hydrogen, halogen, $C_{1-3}$ haloalkyl, or $C_{1-6}$ alkyl.

In some embodiments, a group of compounds of formula II are compounds wherein $X^5$ is selected from nitrogen, —CH group, and carbon substituted with R¹.

In some embodiments, a group of compounds of formula II are compounds wherein $X^5$ is selected from a —CH group and carbon substituted with R¹.

In some embodiments, a group of compounds of formula II are compounds substituted with one R¹ group.

In some embodiments, a group of compounds of formula II are compounds that are substituted with more than one R¹ group, where the R¹ groups may be either the same or different from one another.

In some embodiments, a group of compounds of formula II are compounds where R¹ is hydrogen, deuterium, halogen, cyano (—CN), —OC(R⁷)₃, —OCH(R⁷)₂, or —C(R⁷)₃, wherein R⁷ is halogen and where when there is more than one R⁷ group attached, R⁷ may be the same or different from each other.

In some embodiments, a group of compounds of formula II are compounds wherein R¹ is hydrogen, fluoro, bromo, or chloro.

In some embodiments, a group of compounds of formula II are compounds wherein R¹ is hydrogen.

In some embodiments, a group of compounds of formula II are compounds wherein R¹ is fluoro.

In some embodiments, a group of compounds of formula II are compounds where R³ is $C_{3-6}$ cycloalkyl, $C_{3-6}$ heterocycle, mono or bicyclic aryl or heteroaryl, wherein each mono or bicyclic aryl or heteroaryl is unsubstituted or substituted with one, two, or three substituents independently selected from halogen, —CN, $C_{1-6}$ haloalkyl, $C_{1-6}$ alkyl, and —C(O)N(R⁵)(R⁶).

In some embodiments, a group of compounds of formula II are compounds wherein within R³, groups R⁵ and R⁶ together with the atoms they are bound to, join to form a $C_{3-6}$ cycloalkyl, where the $C_{3-6}$ cycloalkyl can be further substituted with $X^R$.

In some embodiments, a group of compounds of formula II are compounds wherein within $R^3$, $R^5$ and $R^6$, together with the atoms they are bound to, join to form a $C_{3-6}$ heterocycle, where the $C_{3-6}$ heterocycle can be further substituted with $X^R$.

In some embodiments, a group of compounds of formula II are compounds wherein $R^3$ is cyclopropyl, cyclobutyl, cyclopentyl, or cyclohexyl.

In some embodiments, a group of compounds of formula II are compounds wherein $R^3$ is phenyl, 1-3 halo substituted phenyl, $C_{1-3}$ alkyl substituted phenyl, or $C_{1-3}$ haloalkyl substituted phenyl.

In some embodiments, a group of compounds of formula II are compounds wherein $R^3$ is a dihalo substituted phenyl, where the halo atoms can be either the same or different.

In some embodiments, a group of compounds of formula II are compounds wherein $R^3$ is a phenyl substituted with one halo.

In some embodiments, a group of compounds of formula II are compounds wherein $R^3$ is pyridine, pyridazine, pyrimidine, or pyrazine.

In some embodiments, a group of compounds of formula II are compounds wherein $R^3$ is naphthyl or hetero-naphthyl.

In some embodiments, a group of compounds of formula II are compounds wherein $R^3$ is selected from:

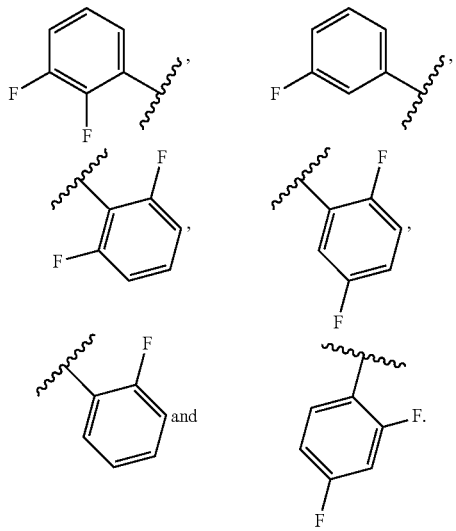

In some embodiments, a group of compounds of formula II are compounds wherein $R^3$ is selected from:

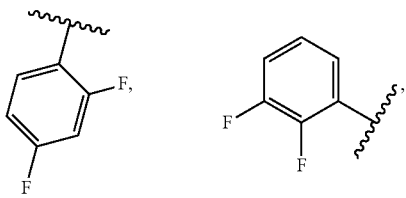

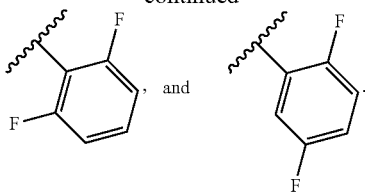

In some embodiments, a group of compounds of formula II are compounds wherein $R^4$ is halogen, $C_{1-6}$ alkyl, $C_{1-6}$ haloalkyl, $C_{1-3}$ haloalkoxy, $C_{3-6}$ cycloalkyl, or a 4-12 membered heterocycle.

In some embodiments, a group of compounds of formula II are compounds wherein $R^4$ is halogen, $C_{1-6}$ alkyl, or $C_{1-3}$ haloalkoxy.

In some embodiments, a group of compounds of formula II are compounds wherein $R^4$ is chloro, fluoro, or bromo.

In some embodiments, a group of compounds of formula II are compounds wherein $R^4$ is chloro.

In some embodiments, a group of compounds of formula II are compounds wherein $R^4$ is $C_{1-6}$ alkyl.

In some embodiments, a group of compounds of formula II are compounds wherein $R^4$ is $C_{1-3}$ alkyl.

In some embodiments, a group of compounds of formula II are compounds wherein $R^4$ is methyl or ethyl.

In some embodiments, a group of compounds of formula II are compounds wherein $R^4$ is trifluoro methyl, tribromo methyl, or trichloro methyl.

In some embodiments, a group of compounds of formula II are compounds wherein $R^4$ is trifluoro methyl.

In some embodiments, a group of compounds of formula II are compounds wherein $R^4$ is difluoro methyl, dichloro methyl, or dibromo methyl.

In some embodiments, a group of compounds of formula II are compounds wherein $R^4$ is fluoro methyl, chloro methyl, or bromo methyl.

In some embodiments, a group of compounds of formula II are compounds wherein $R^4$ is fluoro methoxy, difluoro methoxy, or trifluoro methoxy.

In some embodiments, a group of compounds of formula II are compounds wherein $R^4$ is cyclopropyl, cyclobutyl, cyclopentyl, or cyclohexyl.

In some embodiments, compounds of formula II are compounds wherein $R^4$ is absent.

In some embodiments, the compound of the present disclosure is selected from the group consisting of:

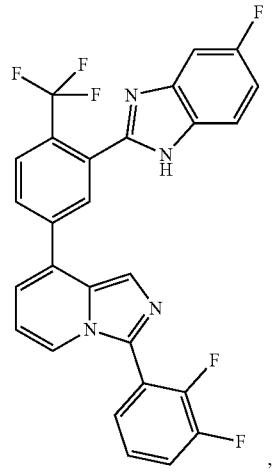 [SMILES: Fc1ccc2[nH]c(-c3cc(-c4cccn5c(-c6cccc(F)c6F)ncc45)ccc3C(F)(F)F)nc2c1]

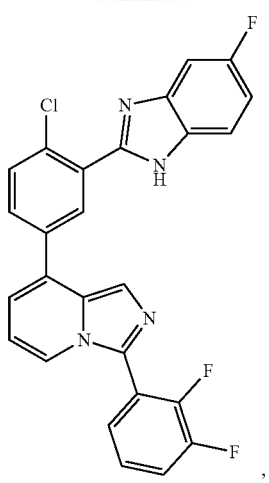 [SMILES: Fc1ccc2[nH]c(-c3cc(-c4cccn5c(-c6cccc(F)c6F)ncc45)ccc3Cl)nc2c1]

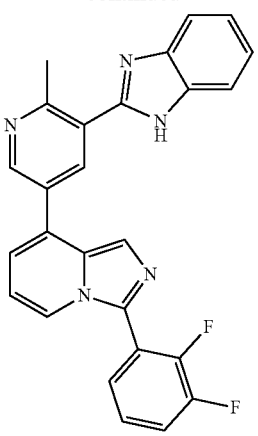

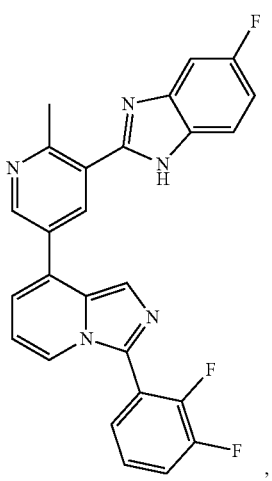 [SMILES: Cc1ncc(-c2cccn3c(-c4cccc(F)c4F)ncc23)cc1-c1nc2cc(F)ccc2[nH]1]

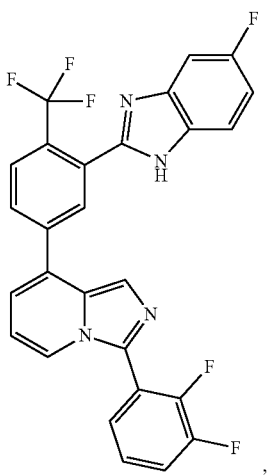

or a pharmaceutically acceptable salt thereof.

In some embodiments, provided herein is 2-(5-(3-(2,3-difluorophenyl)imidazo[1,5-a]pyridin-8-yl)-2-(trifluoromethyl)phenyl)-5-fluoro-1H-benzo[d]imidazole, having the structure:

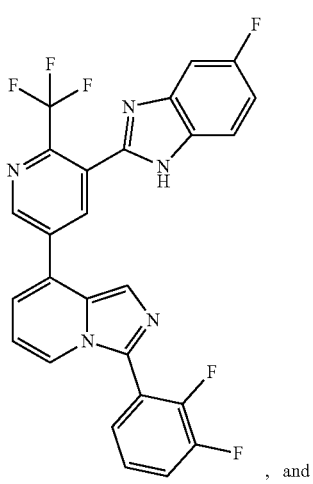

, and or a pharmaceutically acceptable salt thereof.

In some embodiments, provided herein is 2-(2-chloro-5-(3-(2,3-difluorophenyl)imidazo[1,5-a]pyridin-8-yl)phenyl)-5-fluoro-1H-benzo[d]imidazole, having the structure:

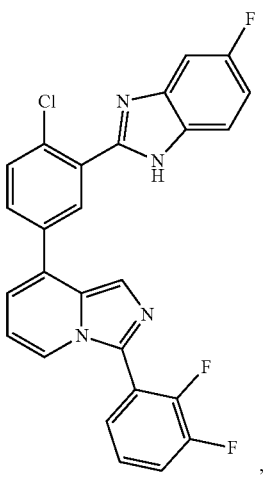

or a pharmaceutically acceptable salt thereof.

In some embodiments, provided herein is 2-(5-(3-(2,3-difluorophenyl)imidazo[1,5-a]pyridin-8-yl)-2-methylpyridin-3-yl)-5-fluoro-1H-benzo[d]imidazole, having the structure:

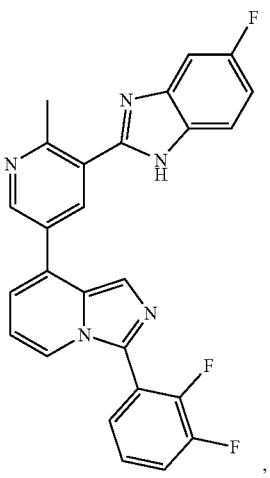

or a pharmaceutically acceptable salt thereof.

In some embodiments, provided herein is 2-(5-(3-(2,3-difluorophenyl)imidazo[1,5-a]pyridin-8-yl)-2-(trifluoromethyl)pyridin-3-yl)-5-fluoro-1H-benzo[d]imidazole, having the structure:

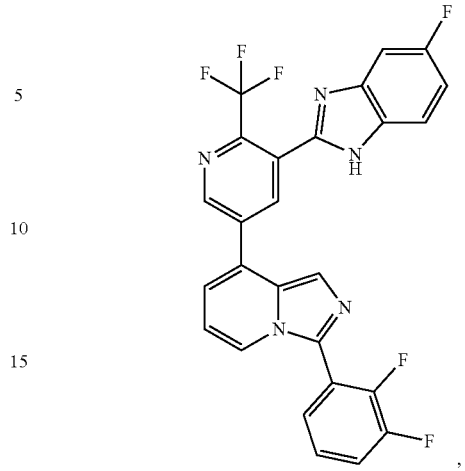

or a pharmaceutically acceptable salt thereof.

In some embodiments, provided herein is 2-(5-(3-(2,3-difluorophenyl)imidazo[1,5-a]pyridin-8-yl)-2-methylpyridin-3-yl)-1H-benzo[d]imidazole, having the structure:

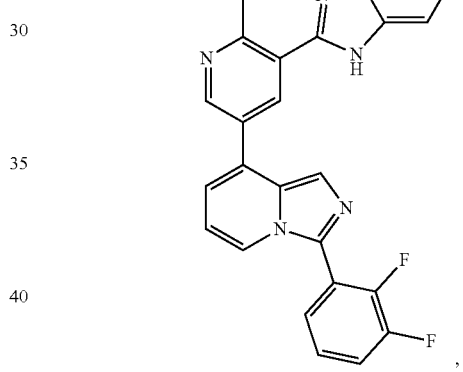

or a pharmaceutically acceptable salt thereof.

Provided are also compounds described herein or pharmaceutically acceptable salts, isomer, or a mixture thereof, in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds may increase resistance to metabolism, and thus may be useful for increasing the half-life of the compounds described herein or pharmaceutically acceptable salts, isomer, or a mixture thereof when administered to a mammal. See, e.g., Foster, "Deuterium Isotope Effects in Studies of Drug Metabolism", Trends Pharmacol. Sci., 5(12):524-527 (1984). Such compounds are synthesized by means well known in the art, for example by employing starting materials in which one or more hydrogen atoms have been replaced by deuterium.

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts.

A "solvate" is formed by the interaction of a solvent and a compound. Solvates of salts of the compounds described herein are also provided. Hydrates of the compounds described herein are also provided.

A "prodrug" is a biologically inactive derivative of a drug that upon administration to the human body is converted to the biologically active parent drug according to some chemical or enzymatic pathway.

In certain embodiments, provided are optical isomers, racemates, or other mixtures thereof of the compounds described herein or pharmaceutically acceptable salts or a mixture thereof. In those situations, the single enantiomer or diastereomer, i.e., optically active form, can be obtained by asymmetric synthesis or by resolution of the racemate. Resolution of racemates can be accomplished, for example, by conventional methods such as crystallization in the presence of a resolving agent, or chromatography, using, for example a chiral high pressure liquid chromatography (HPLC) column. In addition, provided are also Z- and E-forms (or cis- and trans-forms) of the hydroxyamidine compounds described herein. Specifically, Z- and E-forms are included even if only one designation is named for both carbon-carbon double bonds as well as the hydroxyamidine bond.

Where chirality is not specified but is present, it is understood that the embodiment is directed to either the specific diastereomerically or enantiomerically enriched form; or a racemic or scalemic mixture of such compound (s).

"Enantiomers" are a pair of stereoisomers that are non-superimposable mirror images of each other. A 1:1 mixture of a pair of enantiomers is a "racemic" mixture. A mixture of enantiomers at a ratio other than 1:1 is a "scalemic" mixture.

"Diastereoisomers" are stereoisomers that have at least two asymmetric atoms, but which are not mirror-images of each other.

Compositions provided herein that include a compound described herein or pharmaceutically acceptable salts, isomer, or a mixture thereof may include racemic mixtures, or mixtures containing an enantiomeric excess of one enantiomer or single diastereomers or diastereomeric mixtures. All such isomeric forms of these compounds are expressly included herein the same as if each and every isomeric form were specifically and individually listed.

In certain embodiments, provided herein are also crystalline and amorphous forms of the compounds described herein or pharmaceutically acceptable salts, isomer, or a mixture thereof.

In certain embodiments, provided are also chelates, non-covalent complexes, and mixtures thereof, of the compounds described herein or pharmaceutically acceptable salts, isomer, or a mixture thereof. A "chelate" is formed by the coordination of a compound to a metal ion at two (or more) points. A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding).

Therapeutic Uses of the Compounds

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. Exemplary tissue samples include tumors and biopsies thereof. In this context, the invention may be used for a variety of purposes, including therapeutic and experimental purposes. For example, the invention may be used ex vivo to determine the optimal schedule and/or dosing of administration of an IDO1 inhibitor for a given indication, cell type, individual, and other parameters. Information gleaned from such use may be used for experimental purposes or in the clinic to set protocols for in vivo treatment. Other ex vivo uses for which the invention may be suited are described below or will become apparent to those skilled in the art. The selected compounds may be further characterized to examine the safety or tolerance dosage in human or non-human subjects. Such properties may be examined using commonly known methods to those skilled in the art.

In some embodiments, the compounds described herein may be used to treat subjects who have or are suspected of having disease states, disorders, and conditions (also collectively referred to as "indications") responsive or believed to be responsive to the inhibition of IDO1 activity. In some embodiments, the compounds described herein may be used to inhibit the activity of an IDO1 polypeptide. In some embodiments, the compounds described herein may be used to inhibit excessive or destructive immune reactions or growth or a proliferation of a cell, such as a cancer cell, or inhibit immunosuppression.

Example indications suitable for treatment with compounds described here include, without limitation cancer, viral infection such as HIV infection, HBV infection, HCV infection, other infections (e.g., skin infections, GI infection, urinary tract infections, genito-urinary infections, and systemic infections), depression, neurodegenerative disorders such as Alzheimer's disease and Huntington's disease, trauma, age-related cataracts, organ transplantation (e.g., organ transplant rejection), and autoimmune diseases.

Examples of autoimmune diseases include, but are not limited to, asthma, collagen diseases such as rheumatoid arthritis, systemic lupus erythematosus. Sharp's syndrome, CREST syndrome (calcinosis, Raynaud's syndrome, esophageal dysmotility, sclerodactyly, telangiectasia), dermatomyositis, vasculitis (Morbus Wegener's) and Sjögren's syndrome, renal diseases such as Goodpasture's syndrome, rapidly-progressing glomerulonephritis and membrano-proliferative glomerulonephritis type II, endocrine diseases such as type-I diabetes, autoimmune polyendocrinopathy-candidiasis-ectodermal dystrophy (APECED), autoimmune parathyroidism, pernicious anemia, gonad insufficiency, idiopathic Morbus Addison's, hyperthyreosis, Hashimoto's thyroiditis and primary myxedema, skin diseases such as pemphigus vulgaris, bullous pemphigoid, herpes gestationis, epidermolysis bullosa and erythema multiforme major, liver diseases such as primary biliary cirrhosis, autoimmune cholangitis, autoimmune hepatitis type-1, autoimmune hepatitis type-2, primary sclerosing cholangitis, neuronal diseases such as multiple sclerosis, myasthenia gravis, myasthenic Lambert-Eaton syndrome, acquired neuromyotomy, Guillain-Barre syndrome (Muller-Fischer syndrome), stiff-man syndrome, cerebellar degeneration, ataxia, opsoclonus, sensoric neuropathy and achalasia, blood diseases such as autoimmune hemolytic anemia, idiopathic thrombocytopenic purpura (Morbus Werlhof), infectious diseases with associated autoimmune reactions such as AIDS, allergic inflammation, inflammatory bowel disease, psoriasis and systemic lupus erythematosusor, malaria and Chagas disease.

In some embodiments, the compounds described herein may be used for treating cancer, viral infection, depression, a neurodegenerative disorder, trauma, age-related cataracts, organ transplant rejection, or an autoimmune disease.

In other embodiments, the disease to be treated is a solid tumor. In particular embodiments, the solid tumor is from pancreatic cancer, bladder cancer, colorectal cancer, breast cancer, prostate cancer, renal cancer, hepatocellular cancer, lung cancer, ovarian cancer, cervical cancer, gastric cancer, esophageal cancer, head and neck cancer, melanoma, neuroendocrine cancers, CNS cancers, brain tumors (e.g., glioma, anaplastic oligodendroglioma, adult glioblastoma multiforme, and adult anaplastic astrocytoma), bone cancer, or soft tissue sarcoma. In some embodiments, the solid tumor is from non-small cell lung cancer, small-cell lung cancer, colon cancer, CNS cancer, melanoma, ovarian cancer, renal cancer, prostate cancer, or breast cancer.

In some embodiments, the disease to be treated is leukemia or lymphoma. In some embodiments, the disease to be treated is acute lymphoblastic leukemia (ALL), such as B-cell acute lymphoblastic leukemia (BALL), acute myeloid leukemia (AML), chronic lymphocytic leukemia (CLL), chronic myeloid leukemia (CML), or hairy cell leukemia (HCL).

In some embodiments, the disease is an autoimmune disease. In particular embodiments, the autoimmune disease is systemic lupus erythematosus (SLE), myestenia gravis, rheumatoid arthritis (RA), acute disseminated encephalomyelitis, idiopathic thrombocytopenic purpura, multiple sclerosis (MS), psoriasis, Sjoegren's syndrome, psoriasis, autoimmune hemolytic anemia, asthma, or chronic obstructive pulmonary disease (COPD). In other embodiments, the disease is inflammation. In yet other embodiments, the disease is excessive or destructive immune reactions, such as asthma, rheumatoid arthritis, multiple sclerosis, chronic obstructive pulmonary disease (COPD), and lupus.

Provided is a method for treating a subject, who has or is suspected of having a disease or condition responsive or believed to be responsive to the inhibition of IDO1 activity by administering to the subject the compound described herein or pharmaceutically acceptable salts, isomer, or a mixture thereof. Provided is also a method of inhibiting kinase activity of a IDO1 polypeptide by contacting the polypeptide with the compound described herein or pharmaceutically acceptable salts, isomer, or a mixture thereof. Provided is also a method of inhibiting a growth or a proliferation of cancer cells of hematopoietic origin comprising contacting the cancer cells with an effective amount of a compound described herein or pharmaceutically acceptable salts, isomer, or a mixture thereof.

In one embodiment, the compounds of the present application may be used in combination with one or more additional therapeutic agent that are being used and/or developed to treat cancers or inflammatory disorders. The one or more additional therapeutic agent may be a chemotherapeutic agent, an immunotherapeutic agent, a radiotherapeutic agent, an anti-neoplastic agent, an anti-cancer agent, an anti-proliferation agent, an anti-fibrotic agent, an anti-angiogenic agent, a therapeutic antibody, or any combination thereof.

The one or more additional therapeutic agent may be an inhibitor to PI3K such as PI3Kγ, PI3Kβ, PI3Kδ, and/or PI3Kα, Janus kinase (JAK) such as JAK1, JAK2 and/or JAK3, spleen tyrosine kinase (SYK), Bruton's tyrosine kinase (BTK), bromodomain containing protein inhibitor (BRD) such as BRD4, a lysyl oxidase protein (LOX), lysyl oxidase-like protein (LOXL) such as LOXL1-5, matrix metalloprotease (MMP) such as MMP 1-10, adenosine A2B receptor (A2B), isocitrate dehydrogenase (IDH) such as IDH1, apoptosis signal-regulating kinase (ASK) such as ASK1, serine/threonine kinase TPL2, discoidin domain receptor (DDR) such as DDR1 and DDR2, histone deacetylase (HDAC), protein kinase C (PKC), or any combination thereof.

The compounds described herein may be used or combined with one or more of a chemotherapeutic agent, an anti-cancer agent, an anti-angiogenic agent, an anti-fibrotic agent, an immunotherapeutic agent, a therapeutic antibody, a bispecific antibody and "antibody-like" therapeutic protein (such as DARTs®, Duobodies®, Bites®, XmAbs®, TandAbs®, Fab derivatives), an antibody-drug conjugate (ADC), a radiotherapeutic agent, an anti-neoplastic agent, an anti-proliferation agent, an oncolytic virus, gene modifiers or editors such as CRISPR (including CRISPR Cas9), zinc finger nucleases or synthetic nucleases (TALENs), a CAR (chimeric antigen receptor) T-cell immunotherapeutic agent, T-cell receptor (TCR) immunotherapeutic agent, an immune checkpoint inhibitor, an immune checkpoint stimulatory protein agonist, or any combination thereof. These therapeutic agents may be in the forms of compounds, antibodies, polypeptides, or polynucleotides. In one embodiment, the application provides a product comprising a compound described herein and an additional therapeutic agent as a combined preparation for simultaneous, separate, or sequential use in therapy.

In some embodiments, the compounds disclosed herein may be used or combined with one or more of a chemotherapeutic agent, an anti-cancer agent, an anti-angiogenic agent, an anti-fibrotic agent, an immunotherapeutic agent, a therapeutic antibody, a bispecific antibody and "antibody-like" therapeutic protein (such as DARTs®, Duobodies®, Bites®, XmAbs®, TandAbs®, Fab derivatives), an antibody-drug conjugate (ADC), a radiotherapeutic agent, an anti-neoplastic agent, an anti-proliferation agent, an oncolytic virus, gene modifiers or editors such as CRISPR (including CRISPR Cas9), zinc finger nucleases or synthetic nucleases (TALENs), a CAR (chimeric antigen receptor) T-cell immunotherapeutic agent, T-cell receptor (TCR) immunotherapeutic agent, or any combination thereof. These therapeutic agents may be in the forms of compounds, antibodies, polypeptides, live cells (e.g., cell therapy), or polynucleotides. In some embodiments, the application provides a product comprising a compound described herein and an additional therapeutic agent as a combined preparation for simultaneous, separate, or sequential use in therapy.

In some embodiments, the CAR (chimeric antigen receptor) T-cell immunotherapeutic agent is selected from YES-CARTA™ (axicabtagene ciloleucel) and KYMRIAH™ (tisagenlecleucel).

In some embodiments, the CAR (chimeric antigen receptor) T-cell immunotherapeutic agent is YESCARTA™ (axicabtagene ciloleucel).

In some embodiments, the compound is administered to the subject prior to, subsequent to, or simultaneous to administration of one or more additional therapeutic agents. In some embodiments, the compound is administered to the subject about 30 minutes or more, about 1 hour or more, about 2 hours or more, about 4 hours or more, about 6 hours or more, about 12 hours or more, about 24 hours or more, about 48 hours or more, or about 72 hour or more prior to or subsequent to administration of the one or more additional therapeutic agents. In some embodiments, the compound is administered to the subject about 30 minutes or less, about 1 hour or less, about 2 hours or less, about 4 hours or less, about 6 hours or less, about 12 hours or less, about 24 hours or less, about 48 hours or less, or about 72 hour or less prior to or subsequent to administration of the one or more additional therapeutic agents.

In some embodiments, a method of treating a disease in a subject comprises administering to the subject a therapeutically effective amount of any of the compounds described herein (e.g., a compound of Formula I or a compound of Formula II, or a pharmaceutically acceptable salt thereof) in combination with one or more additional therapeutic agents. In some embodiments, the one or more additional therapeutic agents includes an immunotherapeutic agent, such as an immune checkpoint inhibitor, an hematopoietic progenitor kinase 1 (HPK1) inhibitor, an immune checkpoint stimulatory protein agonist, or an engineered immune cell (for example a T cell with an chimeric antigen receptor (i.e., a CAR T cell) or a T cell with an engineered T cell receptor (TCR). In some embodiments, the compound is administered to the subject prior to, subsequent to, or simultaneous to administration of one or more immunotherapeutic agents. In some embodiments, the compound is administered to the subject about 30 minutes or more, about 1 hour or more, about 2 hours or more, about 4 hours or more, about 6 hours or more, about 12 hours or more, about 24 hours or more, about 48 hours or more, or about 72 hour or more prior to or subsequent to administration of the one or more immunotherapeutic agents. In some embodiments, the compound is administered to the subject about 30 minutes or less, about 1 hour or less, about 2 hours or less, about 4 hours or less, about 6 hours or less, about 12 hours or less, about 24 hours or less, about 48 hours or less, or about 72 hour or less prior to or subsequent to administration of the one or more immunotherapeutic agents.

In some embodiments, a method of treating a disease in a subject comprises administering to the subject a therapeutically effective amount of any of the compounds described herein (e.g., a compound of Formula I or a compound of Formula II, or a pharmaceutically acceptable salt thereof) in combination with a therapeutically effective amount of one or more immune checkpoint inhibitors. In some embodiments, the compound is administered to the subject prior to, subsequent to, or simultaneous to administration of the immune checkpoint inhibitor. In some embodiments, the immune checkpoint inhibitor is a small-molecule inhibitor. In some embodiments, the immune checkpoint inhibitor is an antibody or a fragment thereof. In some embodiments, the immune checkpoint inhibitor inhibits the Adenosine $A_{2A}$ Receptor (A2aR), B7-H3, V-Set Domain-Containing T-cell Activation Inhibitor 1 (VTCN1, also known as B7-H4), the B- and T-Lymphocyte Attenuator (BTLA), cytotoxic T-Lypmphocyte-Associated protein 4 (CTLA-4), Killer-cell Immunoglobulin-like Receptor (KIR), Lymphocyte Activation Gene 3 (LAG3), Programmed Death 1 (PD-1), Programmed Death Ligand 1 (PD-L1), Programmed Death Ligand 2 (PD-L2), T-cell Immunoreceptor with Ig and ITIM Domains (TIGIT), T-cell Immunoglobulin and Mucin-Domain Containing 3 (TIM-3), or V-Domain Ig Suppressor of T-cell Activation (VISTA). Exemplary immune checkpoint inhibitors include, but are not limited to, avelumab, atezolizumab, durvalumab, nivolumab, pembrolizumab, ipilimumab, PDR001, TSR-042, and BMS-986016.

In some embodiments, a method of treating a disease in a subject comprises administering to the subject a therapeutically effective amount of any of the compounds described herein (e.g., a compound of Formula I or a compound of Formula II, or a pharmaceutically acceptable salt thereof) in combination with a therapeutically effective amount of one or more immune checkpoint stimulatory protein agonists. In some embodiments, the compound is administered to the subject prior to, subsequent to, or simultaneous to administration of the immune checkpoint stimulatory protein agonist. In some embodiments, the immune checkpoint stimulatory protein agonist is an antibody or a fragment thereof. In some embodiments, the immune checkpoint stimulatory protein agonist is an agonist of CD27, CD28, CD40, CD122, 4-1BB, OX40, Glucocorticoid-Induced TNFR family related protein (GITR), or Inducible T-Cell Costimulator (ICOS).

In some embodiments, a method of treating a disease in a subject comprises administering to the subject a therapeutically effective amount of any of the compounds described herein (e.g., a compound of Formula I or a compound of Formula II, or a pharmaceutically acceptable salt thereof) in combination with a therapeutically effective amount of engineered immune cells, such as CART cells or T cells with an engineered TCR. In some embodiments, the compound is administered to the subject prior to, subsequent to, or simultaneous to administration of the engineered immune cells. In some embodiments, the engineered immune cells are heterologous engineered immune cells, such as heterologous engineered T cells (e.g., CAR T cells or T cells with an engineered TCR). In some embodiments, the engineered immune cells are autologous engineered immune cells, such as autologous engineered T cells (e.g., CAR T cells or T cells with an engineered TCR).

In some embodiments, a method of treating a disease in a subject comprises administering to the subject a therapeutically effective amount of any of the compounds described herein (e.g., a compound of Formula I or a compound of Formula II, or a pharmaceutically acceptable salt thereof) in combination with a therapeutically effective amount of axicabtagene ciloleucel, sold under the trade name YESCARTA™. In some embodiments, a method of treating a disease in a subject comprises administering to the subject a therapeutically effective amount of any of the compounds described herein (e.g., a compound of Formula I or a compound of Formula II, or a pharmaceutically acceptable salt thereof) in combination with a therapeutically effective amount of tisagenlecleucel, sold under the trade name KYMRIAH™.

In some embodiments, a method of treating a disease in a subject comprises administering to the subject a therapeutically effective amount of any of the compounds described herein (e.g., a compound of Formula I or a compound of Formula II, or a pharmaceutically acceptable salt thereof) in combination with (1) a therapeutically effective amount of engineered immune cells, such as CAR T cells or T cells with an engineered TCR, and (2) a therapeutically effective amount of an immune checkpoint inhibitor or an immune checkpoint stimulatory protein agonist.

In some embodiments, a method of treating cancer or a proliferative disorder in a subject comprises administering to the subject a therapeutically effective amount of any of the compounds described herein (e.g., a compound of Formula I or a compound of Formula II, or a pharmaceutically acceptable salt thereof) in combination with one or more additional therapeutic agents. In some embodiments, the one or more additional therapeutic agents includes an immunotherapeutic agent, such as an immune checkpoint inhibitor, an hematopoietic progenitor kinase 1 (HPK1) inhibitor, an immune checkpoint stimulatory protein agonist, or an engineered immune cell (for example a T cell with an chimeric antigen receptor (i.e., a CAR T cell) or a T cell with an engineered T cell receptor (TCR). In some embodiments, the compound is administered to the subject prior to, subsequent to, or simultaneous to administration of one or more immunotherapeutic agents. In some embodiments, the compound is administered to the subject about 30 minutes or more, about 1 hour or more, about 2 hours or more, about 4 hours or more, about 6 hours or more, about 12 hours or more, about 24 hours or more, about 48 hours or more, or about 72 hour or more prior to or subsequent to administration of the one or more immunotherapeutic agents. In some embodiments, the compound is administered to the subject about 30 minutes or less, about 1 hour or less, about 2 hours or less, about 4 hours or less, about 6 hours or less, about 12 hours or less, about 24 hours or less, about 48 hours or less, or about 72 hour or less Prior to or subsequent to administration of the one or more immunotherapeutic agents.

In some embodiments, a method of treating cancer or a proliferative disease in a subject comprises administering to the subject a therapeutically effective amount of any of the compounds described herein (e.g., a compound of Formula I or a compound of Formula II, or a pharmaceutically acceptable salt thereof) in combination with a therapeutically effective amount of one or more immune checkpoint inhibitors. In some embodiments, the compound is administered to the subject prior to, subsequent to, or simultaneous to administration of the immune checkpoint inhibitor. In some embodiments, the immune checkpoint inhibitor is a small-molecule inhibitor. In some embodiments, the immune checkpoint inhibitor is an antibody or a fragment thereof. In some embodiments, the immune checkpoint inhibitor inhibits the Adenosine $A_{2A}$ Receptor (A2aR), B7-H3, V-Set Domain-Containing T-cell Activation Inhibitor 1 (VTCN1, also known as B7-H4), the B- and T-Lymphocyte Attenuator (BTLA), cytotoxic T-Lypmphocyte-Associated protein 4 (CTLA-4), Killer-cell Immunoglobulin-like Receptor (KIR), Lymphocyte Activation Gene 3 (LAG3), Programmed Death 1 (PD-1), Programmed Death Ligand 1 (PD-L1), Programmed Death Ligand 2 (PD-L2), T-cell Immunoreceptor with Ig and ITIM Domains (TIGIT), T-cell Immunoglobulin and Mucin-Domain Containing 3 (TIM-3), or V-Domain Ig Suppressor of T-cell Activation (VISTA). Exemplary immune checkpoint inhibitors include, but are not limited to, avelumab, atezolizumab, durvalumab, nivolumab, pembrolizumab, ipilimumab, PDR001, TSR-042, and BMS-986016.

In some embodiments, a method of treating cancer or a proliferative disease in a subject comprises administering to the subject a therapeutically effective amount of any of the compounds described herein (e.g., a compound of Formula I or a compound of Formula II, or a pharmaceutically acceptable salt thereof) in combination with a therapeutically effective amount of one or more immune checkpoint stimulatory protein agonists. In some embodiments, the compound is administered to the subject prior to, subsequent to, or simultaneous to administration of the immune checkpoint stimulatory protein agonist. In some embodiments, the immune checkpoint stimulatory protein agonist is an antibody or a fragment thereof. In some embodiments, the immune checkpoint stimulatory protein agonist is an agonist of CD27, CD28, CD40, CD122, 4-1BB, OX40, Glucocorticoid-Induced TNFR family related protein (GITR), or Inducible T-Cell Costimulator (ICOS).

In some embodiments, a method of treating cancer or a proliferative disease in a subject comprises administering to the subject a therapeutically effective amount of any of the compounds described herein (e.g., a compound of Formula I or a compound of Formula II, or a pharmaceutically acceptable salt thereof) in combination with a therapeutically effective amount of engineered immune cells, such as CAR T cells or T cells with an engineered TCR. In some embodiments, the compound is administered to the subject prior to, subsequent to, or simultaneous to administration of the engineered immune cells. In some embodiments, the engineered immune cells are heterologous engineered immune cells, such as heterologous engineered T cells (e.g., CAR T cells or T cells with an engineered TCR). In some embodiments, the engineered immune cells are autologous engineered immune cells, such as autologous engineered T cells (e.g., CAR T cells or T cells with an engineered TCR). In some embodiments, the engineered immune cells (e.g., engineered T cells) target a tumor antigen. In some embodiments, the engineered immune cells (e.g., engineered T cells) target CD7, CD19, CD22, CD30, CD33, CD70, CD123, GD2, HER2, EpCAM, PSA, MUC1, CEA, B-cell maturation antigen (BCMA), glypican 3, mesothelin, or EGFRvIII.

In some embodiments, a method of treating cancer or a proliferative disease in a subject comprises administering to the subject a therapeutically effective amount of any of the compounds described herein (e.g., a compound of Formula I or a compound of Formula II, or a pharmaceutically acceptable salt thereof) in combination with a therapeutically effective amount of axicabtagene ciloleucel, sold under the trade name YESCARTA™. In some embodiments, a method of treating cancer or a proliferative disease in a subject comprises administering to the subject a therapeutically effective amount of any of the compounds described herein (e.g., a compound of Formula I or a compound of Formula II, or a pharmaceutically acceptable salt thereof) in combination with a therapeutically effective amount of tisagenlecleucel, sold under the trade name KYMRIAH™.

In some embodiments, a method of treating cancer or a proliferative disease in a subject comprises administering to the subject a therapeutically effective amount of any of the compounds described herein (e.g., a compound of Formula I or a compound of Formula II, or a pharmaceutically acceptable salt thereof) in combination with (1) a therapeutically effective amount of engineered immune cells, such as CAR T cells or T cells with an engineered TCR, and (2) a therapeutically effective amount of an immune checkpoint inhibitor or an immune checkpoint stimulatory protein agonist. In some embodiments, a method of treating cancer or a proliferative disease in a subject comprises administering to the subject a therapeutically effective amount of any of the compounds described herein (e.g., a compound of Formula I or a compound of Formula II, or a pharmaceutically acceptable salt thereof) in combination with (1) a therapeutically effective amount of engineered immune cells, such as CAR T cells or T cells with an engineered TCR, and (2) a therapeutically effective amount of a chemotherapeutic agent. In some embodiments, a method of treating cancer or a proliferative disease in a subject comprises administering to the subject a therapeutically effective amount of any of the compounds described herein (e.g., a compound of Formula I or a compound of Formula II, or a pharmaceutically acceptable salt thereof) in combination with (1) a therapeutically effective amount of an immune checkpoint inhibitor or an immune checkpoint stimulatory protein agonist, and (2) a therapeutically effective amount of a chemotherapeutic agent. In some embodiments, a method of treating cancer or a proliferative disease in a subject comprises administering to the subject a therapeutically effective amount of any of the compounds described herein (e.g., a compound of Formula I or a compound of Formula II, or a pharmaceutically acceptable salt thereof) in combination with (1) a therapeutically effective amount of engineered immune cells, such as CAR T cells or T cells with an engineered TCR, (2) a therapeutically effective amount of an immune checkpoint inhibitor or an immune checkpoint stimulatory protein agonist, and (3) a therapeutically effective amount of a chemotherapeutic agent.

A phosphoinositide 3-kinase inhibitor (PI3K inhibitor) functions by inhibiting one or more of the phosphoinositide 3-kinase enzymes, including but not limited to PI3Kγ, PI3Kβ, PI3Kδ, and PI3Kα. Non-limiting examples of PI3K inhibitors include wortmannin, demethoxyviridin, LY294002, idelalisib, perifosine, PX-866, IPI-145, BAY 80-6946, BEZ235, RP6530, TGR 1202, INK1117, GDC-0941, BKM120, XL147 (also known as SAR245408), XL765 (also known as SAR245409), Palomid 529, GSK1059615, ZSTK474, PWT33597, IC87114, CAL263, RP6503, PI-103, GNE-477, CUDC-907 and AEZS-136. In some embodiments, the PI3K inhibitor is a PI3Kδ inhibitors, such as idelalisib, IPI-145, RP6530, and RP6503, as well as those disclosed in U.S. Pat. No. 8,569,296, and PCT publications WO 2014/006,572 and WO 2015/001,491.

In some embodiments, the one or more additional therapeutic agent may be an MMP9 inhibitor, or an agent that inhibits the expression and/or activity of MMP9. A representative protein sequence for MMP9 is GenBank Accession No. NP_004985. The inhibitor can be small molecule or biologic. For instance, Gu et al., *The Journal of Neuroscience,* 25(27): 6401-6408 (2005) discloses a specific MMP9 inhibitor, SB-3CT (CAS 292605-14-2). Further, siRNA, antisense RNA and antibodies have also been demonstrated to inhibit the expression or activity of MMP9 and are within the scope of the present disclosure. In one embodiment, an MMP9 inhibitor is a monoclonal anti-MMP9 antibody. In some embodiment, the one or more additional therapeutic agent includes an MMP9 inhibitor and a nucleoside analog such as gemcitabine.

One, two, three, or more of the therapeutic agents (e.g. a PI3K inhibitor, a JAK inhibitor, a SYK inhibitor, a BTK inhibitor, a BRD4 inhibitor, a LOXL2 inhibitor, a MMP9 inhibitor, a A2B inhibitor, an IDH inhibitor, an ASK inhibitor, a TPL2 inhibitor, a DDR1 inhibitor, a TBK inhibitor, a HDAC inhibitor, a PKC inhibitor) may be further used or combined with a chemotherapeutic agent, an immunotherapeutic agent, a radiotherapeutic agent, an anti-neoplastic agent, an anti-cancer agent, an anti-fibrotic agent, an anti-angiogenic agent, a therapeutic antibody, or any combination thereof.

Chemotherapeutic agents may be categorized by their mechanism of action into, for example, the following groups: anti-metabolites/anti-cancer agents, such as pyrimidine analogs (floxuridine, capecitabine, and cytarabine); purine analogs, folate antagonists and related inhibitors, antiproliferative/antimitotic agents including natural products such as vinca alkaloid (vinblastine, vincristine) and microtubule such as taxane (paclitaxel, docetaxel), vinblastin, nocodazole, epothilones and navelbine, epipodophyllotoxins (etoposide, teniposide); DNA damaging agents (actinomycin, amsacrine, busulfan, carboplatin, chlorambucil, cisplatin, cyclophosphamide, Cytoxan, dactinomycin, daunorubicin, doxorubicin, epirubicin, iphosphamide, melphalan, mechlorethamine, mitomycin, mitoxantrone, nitrosourea, procarbazine, taxol, taxotere, teniposide, etoposide, triethiylenethiophosphoramide); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards cyclophosphamide and analogs, melphalan, chlorambucil), and (hexamethylmelamine and thiotepa), alkyl nitrosoureas (BCNU) and analogs, streptozocin), trazenes-dacarbazinine (DTIC); antiproliferative/antimitotic antimetabolites such as folic acid analogs (methotrexate); platinum coordination complexes (cisplatin, oxiloplatinim, carboplatin), procarbazine, hydroxyurea, mitotane, am inoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel; antimigratory agents; antisecretory agents (breveldin); immunosuppressives tacrolimus sirolimus azathioprine, mycophenolate; compounds (TNP-470, genistein) and growth factor inhibitors (vascular endothelial growth factor inhibitors, fibroblast growth factor inhibitors); angiotensin receptor blocker, nitric oxide donors; anti-sense oligonucleotides; antibodies (trastuzumab, rituximab); cell cycle inhibitors and differentiation inducers (tretinoin); inhibitors, topoisomerase inhibitors (doxorubicin (adriamycin), daunorubicin, dactinomycin, eniposide, epirubicin, etoposide, idarubicin, irinotecan and mitoxantrone, topotecan, irinotecan, camptothecin), corticosteroids (cortisone, dexamethasone, hydrocortisone, methylprednisolone, prednisone, and prednisolone); growth factor signal transduction kinase inhibitors; dysfunction inducers, toxins such as Cholera toxin, ricin, Pseudomonas exotoxin, Bordetella pertussis adenylate cyclase toxin, or diphtheria toxin, and caspase activators; and chromatin.

As used herein the term "chemotherapeutic agent" or "chemotherapeutic" (or "chemotherapy," in the case of treatment with a chemotherapeutic agent) is meant to encompass any non-proteinaceous (i.e., non-peptidic) chemical compound useful in the treatment of cancer. Examples of chemotherapeutic agents include alkylating agents such as thiotepa and cyclophosphamide (CYTOXAN); alkyl sulfonates such as busulfan, improsulfan and piposulfan; aziridines such as benzodopa, carboquone, meturedepa, and uredepa; emylerumines and memylamelamines including altretamine, triemylenemelamine, trietylenephosphoramide, triethiylenethiophosphoramide and trimemylolomelamine; acetogenins (especially bullatacin and bullatacinone); a camptothecin (including synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodyctin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, foremustine, lomustine, nimustine, ranimustine; antibiotics such as the enediyne antibiotics (e.g., calicheamicin, especially calicheamicin gammaII and calicheamicin phiI1, see, e.g., Agnew, Chem. Intl. Ed. Engl, 33:183-186 (1994); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carrninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrroline-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as demopterin, methotrexate, pteropterin, trimetrexate; purine analogs such as fludarabine, 6-mercaptopurine, thiamiprine, thioguanine; pyrimidine analogues such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; hestrabucil; bisantrene; edatraxate; defofamine; demecolcine; diaziquone; elformithine; elliptinium acetate; an epothilone; etoglucid; gallium nitrate; hydroxyurea; lentinan; leucovorin; lonidamine; maytansinoids such as maytansine and ansamitocins; mitoguazone; mitoxantrone; mopidamol; nitracrine; pentostatin; phenamet; pirarubicin; losoxantrone; fluoropyrimidine; folinic acid; podophyllinic acid; 2-ethylhydrazide; procarbazine; PSK(r); razoxane; rhizoxin; sizofiran; spirogermanium; tenuazonic acid; triaziquone; 2,2',2"-tricUorotriemylamine; trichothecenes (especially T-2 toxin, verracurin A, roridin A and anguidine); urethane; vindesine; dacarbazine; mannomustine; mitobronitol; mitolactol; pipobroman; gacytosine; arabinoside ("Ara-C"); cyclophosphamide; thiotepa; taxoids, e.g., paclitaxel (TAXOL(r) and docetaxel (TAXOTERE(r)); chlorambucil; gemcitabine (Gemzar(r)); 6-thioguanine; mercaptopurine; methotrexate; platinum analogs such as cisplatin and carboplatin; vinblastine; platinum; etoposide (VP-16); ifosfamide; mitoxantrone; vincristine; vinorelbine (Navelbine(r)); novantrone; teniposide; edatrexate; daunomycin; aminopterin; xeoloda; ibandronate; CPT-11; topoisomerase inhibitor RFS 2000; difluoromethylornithine (DMFO); retinoids such as retinoic acid; capecitabine; FOLFIRI (fluorouracil, leucovorin, and irinotecan) and pharmaceutically acceptable salts, acids or derivatives of any of the above. One or more chemotherapeutic agent are used or included in the present application. For example, gemcitabine, nab-paclitaxel, and gemcitabine/nab-paclitaxel are used with the JAK inhibitor and/or PI3Kδ inhibitor for treating hyperproliferative disorders.

Also included in the definition of "chemotherapeutic agent" are anti-hormonal agents that act to regulate or inhibit hormone action on tumors such as anti-estrogens and selective estrogen receptor modulators (SERMs), including, for example, tamoxifen (including Nolvadex™), raloxifene, droloxifene, 4-hydroxytamoxifen, trioxifene, keoxifene, LY117018, onapristone, and toremifene (Fareston(r)); inhibitors of the enzyme aromatase, which regulates estrogen production in the adrenal glands, such as, for example, 4(5)-imidazoles, aminoglutethimide, megestrol acetate (Megace(r)), exemestane, formestane, fadrozole, vorozole (Rivisnr(r)), letrozole (Femara(r)), and anastrozole (Arimidex(r)); and anti-androgens such as flutamide, nilutamide, bicalutamide, leuprohde, and goserelin; and pharmaceutically acceptable salts, acids or derivatives of any of the above.

The anti-angiogenic agents include, but are not limited to, retinoid acid and derivatives thereof, 2-methoxyestradiol, ANGIOSTATIN(r), ENDOSTATIN(r), suramin, squalamine, tissue inhibitor of metalloproteinase-1, tissue inhibitor of metalloproteinase-2, plasminogen activator inhibitor-1, plasminogen activator inhibitor-2, cartilage-derived inhibitor, paclitaxel (nab-paclitaxel), platelet factor 4, protamine sulphate (clupeine), sulfated chitin derivatives (prepared from queen crab shells), sulfated polysaccharide peptidoglycan complex (sp-pg), staurosporine, modulators of matrix metabolism, including for example, proline analogs ((1-azetidine-2-carboxylic acid (LACA), cishydroxyproline, D,L-3,4-dehydroproline, thiaproline, alpha-dipyridyl, beta-aminopropionitrile fumarate, 4-propyl-5-(4-pyridinyl)-2 (3H)-oxazolone; methotrexate, mitoxantrone, heparin, interferons, 2 macroglobulin-serum, chimp-3, chymostatin, beta-cyclodextrin tetradecasulfate, eponemycin; fumagillin, gold sodium thiomalate, d-penicillamine (CDPT), beta-1-anticollagenase-serum, alpba-2-antiplasmin, bisantrene, lobenzarit disodium, n-2-carboxyphenyl-4-chloroanthronilic acid disodium or "CCA", thalidomide; angiostatic steroid, carboxynaminolmidazole; metalloproteinase inhibitors such as BB94. Other anti-angiogenesis agents include antibodies, preferably monoclonal antibodies against these angiogenic growth factors: beta-FGF, alpha-FGF, FGF-5, VEGF isoforms, VEGF-C, HGF/SF and Ang-1/Ang-2. See Ferrara N. and Alitalo, K. "Clinical application of angiogenic growth factors and their inhibitors" (1999) Nature Medicine 5:1359-1364.

The anti-fibrotic agents include, but are not limited to, the compounds such as beta-aminopropionitrile (BAPN), as well as the compounds disclosed in U.S. Pat. No. 4,965,288 to Palfreyman, et al., issued Oct. 23, 1990, entitled "Inhibitors of lysyl oxidase," relating to inhibitors of lysyl oxidase and their use in the treatment of diseases and conditions associated with the abnormal deposition of collagen; U.S. Pat. No. 4,997,854 to Kagan, et al., issued Mar. 5, 1991, entitled "Anti-fibrotic agents and methods for inhibiting the activity of lysyl oxidase in situ using adjacently positioned diamine analogue substrate," relating to compounds which inhibit LOX for the treatment of various pathological fibrotic states, which are herein incorporated by reference. Further exemplary inhibitors are described in U.S. Pat. No. 4,943,593 to Palfreyman, et al., issued Jul. 24, 1990, entitled "Inhibitors of lysyl oxidase," relating to compounds such as 2-isobutyl-3-fluoro-, chloro-, or bromo-allylamine; as well as, e.g., U.S. Pat. Nos. 5,021,456; 5,5059,714; 5,120,764; 5,182,297; 5,252,608 (relating to 2-(1-naphthyloxymemyl)-3-fluoroallylamine); and U.S. Patent Application No. 2004/0248871, which are herein incorporated by reference. Exemplary anti-fibrotic agents also include the primary amines reacting with the carbonyl group of the active site of the lysyl oxidases, and more particularly those which produce, after binding with the carbonyl, a product stabilized by resonance, such as the following primary amines: emylenemamine, hydrazine, phenylhydrazine, and their derivatives, semicarbazide, and urea derivatives, aminonitriles, such as beta-aminopropionitrile (BAPN), or 2-nitroethylamine, unsaturated or saturated haloamines, such as 2-bromo-ethylamine, 2-chloroethylamine, 2-trifluoroethylamine, 3-bromopropylamine, p-halobenzylamines, selenohomocysteine lactone. Also, the anti-fibrotic agents are copper chelating agents, penetrating or not penetrating the cells. Exemplary compounds include indirect inhibitors such compounds blocking the aldehyde derivatives originating from the oxidative deamination of the lysyl and hydroxylysyl residues by the lysyl oxidases, such as the thiolamines, in particular D-penicillamine, or its analogues such as 2-amino-5-mercapto-5-methylhexanoic acid, D-2-amino-3-methyl-3-((2-acetamidoethyl)dithio)butanoic acid, p-2-amino-3-methyl-3-((2-aminoethyl)dithio)butanoic acid, sodium-4-((p-1-dimethyl-2-amino-2-carboxyethyl)dithio)butane sulphurate, 2-acetamidoethyl-2-acetamidoethanethiol sulphenate, sodium-4-mercaptobutanesulphinate trihydrate.

The immunotherapeutic agents include and are not limited to therapeutic antibodies suitable for treating patients; such as abagovomab, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, cetuximab, citatuzumab, cixutumumab, clivatuzumab, conatumumab, daratumumab, drozitumab, duligotumab, dusigitumab, detumomab, dacetuzumab, dalotuzumab, ecromeximab, elotuzumab, ensituximab, ertumaxomab, etaracizumab, farietuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab, iratumumab, labetuzumab, lexatumumab, lintuzumab, lorvotuzumab, lucatumumab, mapatumumab, matuzumab, milatuzumab, minretumomab, mitumomab, moxetumomab, namatumab, naptumomab, necitumumab nimotuzumab, nofetumomabn, ocaratuzumab, ofatumumab, olaratumab, onartuzumab, oportuzumab, oregovomab, panitumumab, parsatuzumab, patritumab, pemtumomab, pertuzumab, pintumomab, pritumumab, racotumomab, radretumab, rilotumumab, rituximab, robatumumab, satumomab, sibrotuzumab, siltuximab, simtuzumab, solitomab, tacatuzumab, taplitumomab, tenatumomab, teprotumumab, tigatuzumab, tositumomab, trastuzumab, tucotuzumab, ublituximab, veltuzumab, vorsetuzumab, votumumab, zalutumumab, CC49 and 3F8. The exemplified therapeutic antibodies may be further labeled or combined with a radioisotope particle, such as indium In 111, yttrium Y 90, iodine I-131.

The application also provides method for treating a subject who is undergoing one or more standard therapies, such as chemotherapy, radiotherapy, immunotherapy, surgery, or combination thereof. Accordingly, one or more therapeutic agent or inhibitors may be administered before, during, or after administration of chemotherapy, radiotherapy, immunotherapy, surgery or combination thereof.

In certain embodiments, the subject may be a human who is (i) substantially refractory to at least one chemotherapy treatment, or (ii) in relapse after treatment with chemotherapy, or both (i) and (ii). In some of embodiments, the subject is refractory to at least two, at least three, or at least four chemotherapy treatments (including standard or experimental chemotherapies).

In certain embodiments, the subject is refractory to at least one, at least two, at least three, or at least four chemotherapy treatment (including standard or experimental chemotherapy) selected from fludarabine, rituximab, obinutuzumab, alkylating agents, alemtuzumab and other chemotherapy treatments such as CHOP (cyclophosphamide, doxorubicin, vincristine, prednisone); R-CHOP (rituximab-CHOP); hyperCVAD (hyperfractionated cyclophosphamide, vincristine, doxorubicin, dexamethasone, methotrexate, cytarabine); R-hyperCVAD (rituximab-hyperCVAD); FCM (fludarabine, cyclophosphamide, mitoxantrone); R-FCM (rituximab, fludarabine, cyclophosphamide, mitoxantrone); bortezomib and rituximab; temsirolimus and rituximab; temsirolimus and Velcade®; Iodine-131 tositumomab (Bexxar®) and CHOP; CVP (cyclophosphamide, vincristine, prednisone); R-CVP (rituximab-CVP); ICE (iphosphamide, carboplatin, etoposide); R-ICE (rituximab-ICE); FCR (fludarabine, cyclophosphamide, rituximab); FR (fludarabine, rituximab); and D.T. PACE (dexamethasone, thalidomide, cisplatin, Adriamycin®, cyclophosphamide, etoposide).

Other examples of chemotherapy treatments (including standard or experimental chemotherapies) are described below. In addition, treatment of certain lymphomas is reviewed in Cheson, B. D., Leonard, J. P., "Monoclonal Antibody Therapy for B-Cell Non-Hodgkin's Lymphoma" *The New England Journal of Medicine* 2008, 359(6), p. 613-626; and Wierda, W. G., "Current and Investigational Therapies for Patients with CLL" *Hematology* 2006, p. 285-294. Lymphoma incidence patterns in the U.S. is profiled in Morton, L. M., et al. "Lymphoma Incidence Patterns by WHO Subtype in the U.S., 1992-2001" *Blood* 2006, 107(1), p. 265-276.

Examples of immunotherapeutic agents treating lymphoma or leukemia include, but are not limited to, rituximab (such as Rituxan), alemtuzumab (such as Campath, Mab-Campath), anti-CD19 antibodies, anti-CD20 antibodies, anti-MN-14 antibodies, anti-TRAIL, Anti-TRAIL DR4 and DR5 antibodies, anti-CD74 antibodies, apolizumab, bevacizumab, CHIR-12.12, epratuzumab (hLL2-anti-CD22 humanized antibody), galiximab, ha20, ibritumomab tiuxetan, lumiliximab, milatuzumab, ofatumumab, PRO131921, SGN-40, WT-1 analog peptide vaccine, WT1 126-134 peptide vaccine, tositumomab, autologous human tumor-derived HSPPC-96, and veltuzumab. Additional immunotherapy agents includes using cancer vaccines based upon the genetic makeup of an individual patient's tumor, such as lymphoma vaccine example is GTOP-99 (MyVax®).

Examples of chemotherapy agents for treating lymphoma or leukemia include aldesleukin, alvocidib, antineoplaston AS2-1, antineoplaston A10, anti-thymocyte globulin, amifostine trihydrate, aminocamptothecin, arsenic trioxide, beta alethine, Bcl-2 family protein inhibitor ABT-263, BMS-345541, bortezomib (Velcade®), bryostatin 1, busulfan, carboplatin, campath-1H, CC-5103, carmustine, caspofungin acetate, clofarabine, cisplatin, Cladribine (Leustarin), Chlorambucil (Leukeran), Curcumin, cyclosporine, Cyclophosphamide (Cyloxan, Endoxan, Endoxana, Cyclostin), cytarabine, denileukin diftitox, dexamethasone, DT PACE, docetaxel, dolastatin 10, Doxorubicin (Adriamycin®, Adriblastine), doxorubicin hydrochloride, enzastaurin, epoetin alfa, etoposide, Everolimus (RAD001), fenretinide, filgrastim, melphalan, mesna, Flavopiridol, Fludarabine (Fludara), Geldanamycin (17-AAG), ifosfamide, irinotecan hydrochloride, ixabepilone, Lenalidomide (Revlimid®, CC-5013), lymphokine-activated killer cells, melphalan, methotrexate, mitoxantrone hydrochloride, motexafin gadolinium, mycophenolate mofetil, nelarabine, oblimersen (Genasense) Obatoclax (GX15-070), oblimersen, octreotide acetate, omega-3 fatty acids, oxaliplatin, paclitaxel, PD0332991, PEGylated liposomal doxorubicin hydrochloride, pegfilgrastim, Pentstatin (Nipent), perifosine, Prednisolone, Prednisone, R-roscovitine (Selicilib, CYC202), recombinant interferon alfa, recombinant interleukin-12, recombinant interleukin-11, recombinant flt3 ligand, recombinant human thrombopoietin, rituximab, sargramostim, sildenafil citrate, simvastatin, sirolimus, Styryl sulphones, tacrolimus, tanespimycin, Temsirolimus (CC1-779), Thalidomide, therapeutic allogeneic lymphocytes, thiotepa, tipifarnib, Velcade® (bortezomib or PS-341), Vincristine (Oncovin), vincristine sulfate, vinorelbine ditartrate, Vorinostat (SAHA), vorinostat, and FR (fludarabine, rituximab), CHOP (cyclophosphamide, doxorubicin, vincristine, prednisone), CVP (cyclophosphamide, vincristine and prednisone), FCM (fludarabine, cyclophosphamide, mitoxantrone), FCR (fludarabine, cyclophosphamide, rituximab), hyperCVAD (hyperfractionated cyclophosphamide, vincristine, doxorubicin, dexamethasone, methotrexate, cytarabine), ICE (iphosphamide, carboplatin and etoposide), MCP (mitoxantrone, chlorambucil, and prednisolone), R-CHOP (rituximab plus CHOP), R-CVP (rituximab plus CVP), R-FCM (rituximab plus FCM), R-ICE (rituximab-ICE), and R-MCP (Rituximab-MCP).

In some embodiments, the cancer is melanoma. Suitable agents for use in combination with the compounds described herein include, without limitation, dacarbazine (DTIC), optionally, along with other chemotherapy drugs such as carmustine (BCNU) and cisplatin; the "Dartmouth regimen", which consists of DTIC, BCNU, cisplatin and tamoxifen; a combination of cisplatin, vinblastine, and DTIC, temozolomide or YERVOY™ Compounds according to the invention may also be combined with immunotherapy drugs, including cytokines such as interferon alpha, interleukin 2, and tumor necrosis factor (TNF) in the treatment of melanoma.

Compounds described here may also be used in combination with vaccine therapy in the treatment of melanoma. Anti-melanoma vaccines are, in some ways, similar to the anti-virus vaccines which are used to prevent diseases caused by viruses such as polio, measles, and mumps. Weakened melanoma cells or parts of melanoma cells called antigens may be injected into a patient to stimulate the body's immune system to destroy melanoma cells.

Melanomas that are confined to the arms or legs may also be treated with a combination of agents including one or more compounds described herein, using a hyperthermic isolated limb perfusion technique. This treatment protocol temporarily separates the circulation of the involved limb from the rest of the body and injects high doses of chemotherapy into the artery feeding the limb, thus providing high doses to the area of the tumor without exposing internal organs to these doses that might otherwise cause severe side effects. Usually the fluid is warmed to 102° to 104° F. Melphalan is the drug most often used in this chemotherapy procedure. This can be given with another agent called tumor necrosis factor (TNF).

The therapeutic treatments can be supplemented or combined with any of the abovementioned therapies with stem cell transplantation or treatment. One example of modified approach is radioimmunotherapy, wherein a monoclonal antibody is combined with a radioisotope particle, such as indium In 111, yttrium Y 90, iodine 1-131. Examples of combination therapies include, but are not limited to, Iodine-131 tositumomab (Bexxar®), Yttrium-90 ibritumomab tiuxetan (Zevalin®), Bexxar® with CHOP.

Other therapeutic procedures include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, pharmacological study, low-LET cobalt-60 gamma ray therapy, bleomycin, conventional surgery, radiation therapy, and nonmyeloablative allogeneic hematopoietic stem cell transplantation.

Anti-HBV Combination Therapy

In certain embodiments, a method for treating or preventing an HBV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, four, one or two, or one to three, or one to four) additional therapeutic agents. In one embodiment, a method for treating an HBV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, four, one or two, or one to three, or one to four) additional therapeutic agents.

In certain embodiments, the present disclosure provides a method for treating an HBV infection, comprising administering to a patient in need thereof a therapeutically effective amount of a compound disclosed herein, or a pharmaceutically acceptable salt thereof, in combination with a therapeutically effective amount of one or more additional therapeutic agents which are suitable for treating an HBV infection.

In one embodiment, pharmaceutical compositions comprising a compound disclosed herein, or a pharmaceutically acceptable salt thereof, in combination with one or more (e.g., one, two, three, four, one or two, or one to three, or one to four) additional therapeutic agents, and a pharmaceutically acceptable carrier, diluent or excipient are provided.

In one embodiment, kits comprising a compound disclosed herein, or a pharmaceutically acceptable salt thereof, in combination with one or more (e.g., one, two, three, four, one or two, or one to three, or one to four) additional therapeutic agents are provided.

In the above embodiments, the additional therapeutic agent may be an anti-HBV agent. For example, in some embodiments, the additional therapeutic agent is selected from the group consisting of HBV combination drugs, HBV DNA polymerase inhibitors, immunomodulators, toll-like receptor modulators (modulators of tlr1, tlr2, tlr3, tlr4, tlr5, tlr6, tlr7, tlr8, tlr9, tlr10, tlr11, tlr12 and tlr13), interferon alpha receptor ligands, hyaluronidase inhibitors, recombinant IL-7, hepatitis B surface antigen (HBsAg) inhibitors, compounds targeting hepatitis B core antigen (HbcAg), cyclophilin inhibitors, HBV therapeutic vaccines, HBV prophylactic vaccines, HBV viral entry inhibitors, NTCP (Na+-taurocholate cotransporting polypeptide) inhibitors, antisense oligonucleotide targeting viral mRNA, short interfering RNAs (siRNA), miRNA gene therapy agents, endonuclease modulators, inhibitors of ribonucleotide reductase, hepatitis B virus E antigen inhibitors, recombinant scavenger receptor A (SRA) proteins, Src kinase inhibitors, HBx inhibitors, cccDNA inhibitors, short synthetic hairpin RNAs (sshRNAs), HBV antibodies including HBV antibodies targeting the surface antigens of the hepatitis B virus and bispecific antibodies and "antibody-like" therapeutic proteins (such as DARTs®, Duobodies®, Bites®, XmAbs®, TandAbs®, Fab derivatives), CCR2 chemokine antagonists, thymosin agonists, cytokines, nucleoprotein inhibitors (HBV core or capsid protein inhibitors), stimulators of retinoic acid-inducible gene 1, stimulators of NOD2, stimulators of NOD1, Arginase-1 inhibitors, STING agonists, PI3K inhibitors, lymphotoxin beta receptor activators, Natural Killer Cell Receptor 2B4 inhibitors, Lymphocyte-activation gene 3 inhibitors, CD160 inhibitors, cytotoxic T-lymphocyte-associated protein 4 inhibitors, CD137 inhibitors, Killer cell lectin-like receptor subfamily G member 1 inhibitors, TIM-3 inhibitors, B- and T-lymphocyte attenuator inhibitors, CD305 inhibitors, PD-1 inhibitors, PD-L1 inhibitors, PEG-Interferon Lambda, recombinant thymosin alpha-1, BTK inhibitors, modulators of TIGIT, modulators of CD47, modulators of SIRPalpha, modulators of ICOS, modulators of CD27, modulators of CD70, modulators of OX40, modulators of NKG2D, modulators of Tim-4, modulators of B7-H4, modulators of B7-H3, modulators of NKG2A, modulators of GITR, modulators of CD160, modulators of HEVEM, modulators of CD161, modulators of Axl, modulators of Mer, modulators of Tyro, gene modifiers or editors such as CRISPR (including CRISPR Cas9), zinc finger nucleases or synthetic nucleases (TALENs), Hepatitis B virus replication inhibitors compounds such as those disclosed in US20100143301 (Gilead Sciences), US20110098248 (Gilead Sciences), US20090047249 (Gilead Sciences), U.S. Pat. No. 8,722,054 (Gilead Sciences), US20140045849 (Janssen), US20140073642 (Janssen), WO2014/056,953 (Janssen), WO2014/076,221 (Janssen), WO2014/128,189 (Janssen), US20140350031 (Janssen), WO2014/023,813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (VentirxPharma), US20140275167 (Novira therapeutics), US20130251673 (Novira therapeutics), U.S. Pat. No. 8,513,184 (Gilead Sciences), US20140030221 (Gilead Sciences), US20130344030 (Gilead Sciences), US20130344029 (Gilead Sciences), US20140343032 (Roche), WO2014037480 (Roche), US20130267517 (Rothe), WO2014131847 (Janssen), WO2014033176 (Janssen), WO2014033170 (Janssen), WO2014033167 (Janssen), US20140330015 (Ono pharmaceutical), US20130079327 (Ono pharmaceutical), US20130217880 (Ono pharmaceutical), and other drugs for treating HBV, and combinations thereof.

In certain embodiments, the one or more additional therapeutic agents include a Toll-like receptor 8 (TLR8) modulator. In some embodiments, the Toll-like receptor 8 (TLR8) modulator is a Toll-like receptor 8 (TLR8) agonist. In some embodiments, the Toll-like receptor 8 (TLR8) agonist is a compound disclosed in U.S. Pat. No. 9,670,205, which is incorporated herein by reference in its entirety and specifically with respect to the compounds disclosed (such as, but not limited to, compounds of Examples 59, 61, 62, 63, 65, 66, 80, 98, 101, 114, and 116, or a pharmaceutically acceptable salt thereof) and methods of making and using the same. In some embodiments, the Toll-like receptor 8 (TLR8) agonist is selected from the group consisting of:

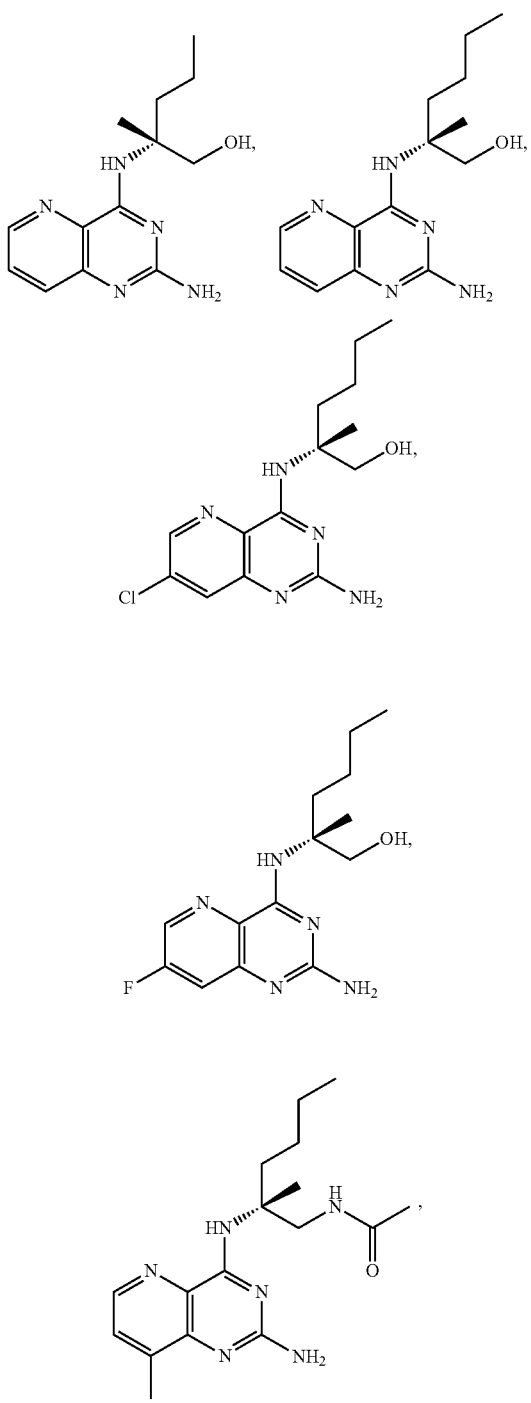

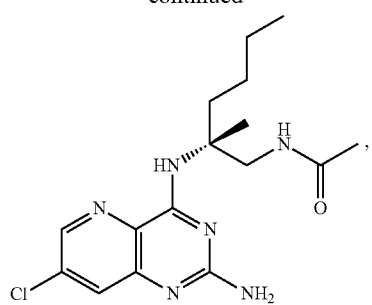
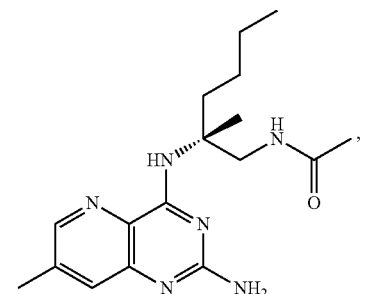
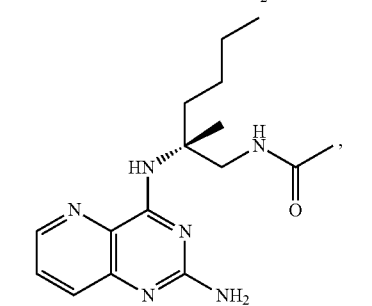
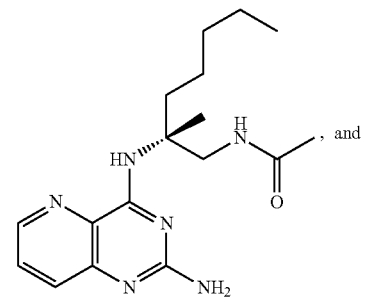
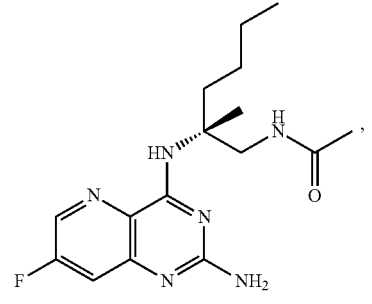
pharmaceutically acceptable salt thereof. In some embodiments, the Toll-like receptor 8 (TLR8) agonist is selected from the group consisting of:
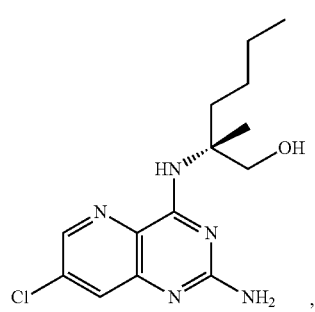
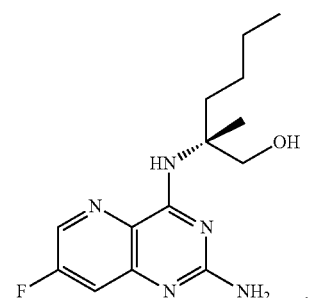
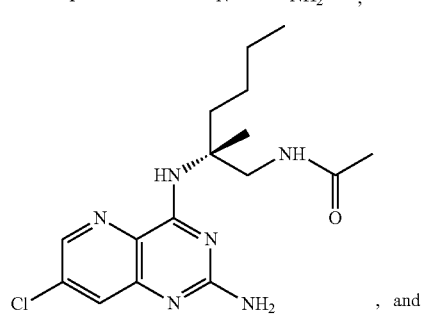
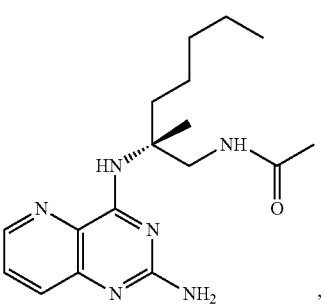
or a pharmaceutically acceptable salt thereof.
In some embodiments, the Toll-like receptor 8 (TLR8) agonist is selected from the group consisting of:
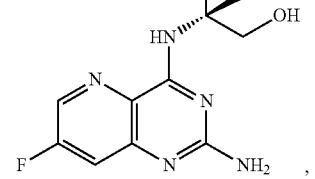

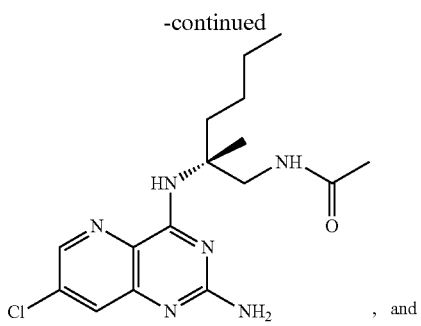

, and

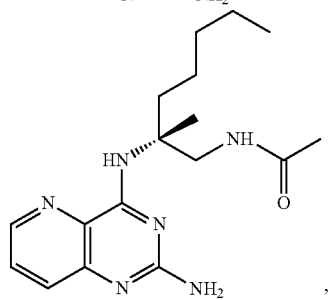

, or a pharmaceutically acceptable salt thereof.

In some embodiments, the Toll-like receptor 8 (TLR8) agonist is:

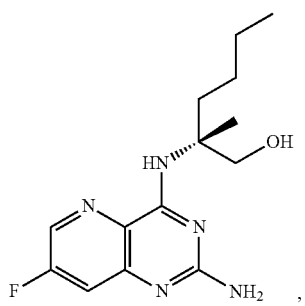

, or a pharmaceutically acceptable salt thereof.

In some embodiments, the Toll-like receptor 8 (TLR8) agonist is:

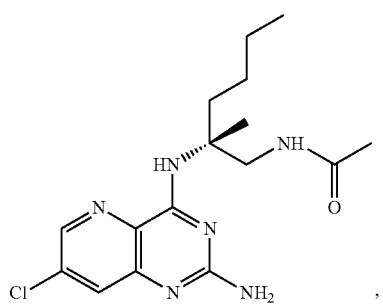

, or a pharmaceutically acceptable salt thereof.

In some embodiments, the Toll-like receptor 8 (TLR8) agonist is:

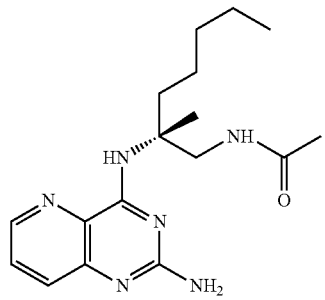

, or a pharmaceutically acceptable salt thereof.

In some embodiments, the one or more additional therapeutic agents further include a Programmed Death 1 (PD-1) inhibitor and/or a Programmed Death Ligand 1 (PD-L1) inhibitor. In some embodiments, the Programmed Death 1 (PD-1) inhibitor is selected from the group consisting of nivolumab, lambrolizumab, pembrolizumab, pidilizumab, PDR001, and TSR-001, or a pharmaceutically acceptable salt or solvate of any of the forgoing. In some embodiments, the Programmed Death Ligand 1 (PD-L1) inhibitor is selected from the group consisting of atezolizumab, durvalumab, or avelumab, or a pharmaceutically acceptable salt or solvate of any of the forgoing.

In certain embodiments, a method for treating an HBV infection in a human having the infection is provided, comprising administering to the human:

(i) a therapeutically effective amount of a compound disclosed herein, which is selected from the group consisting of:

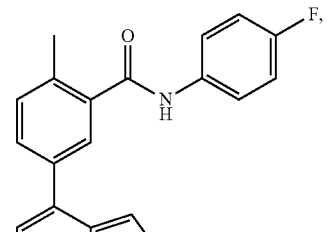

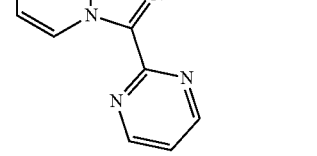

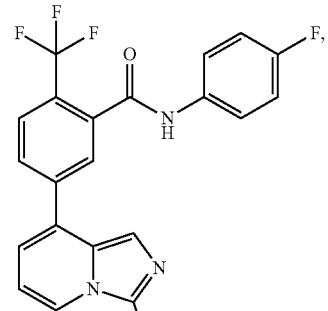

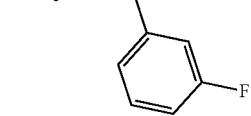

97
-continued
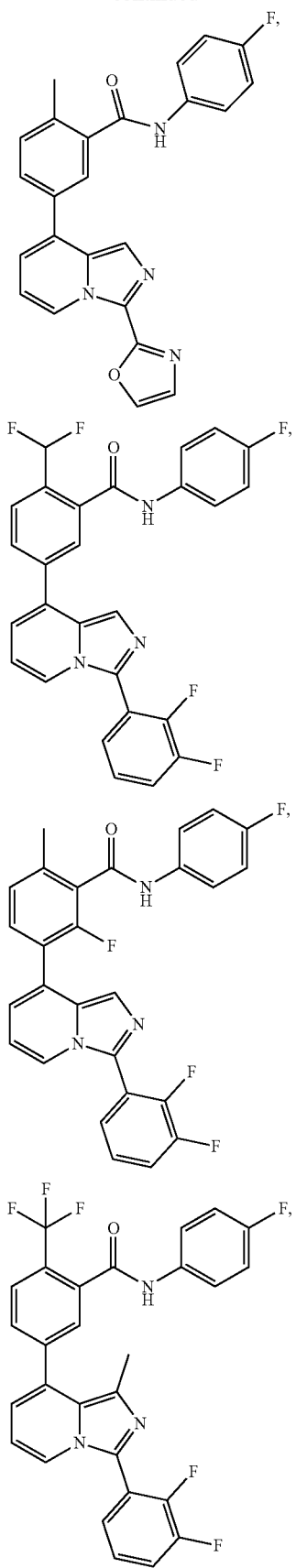
98
-continued
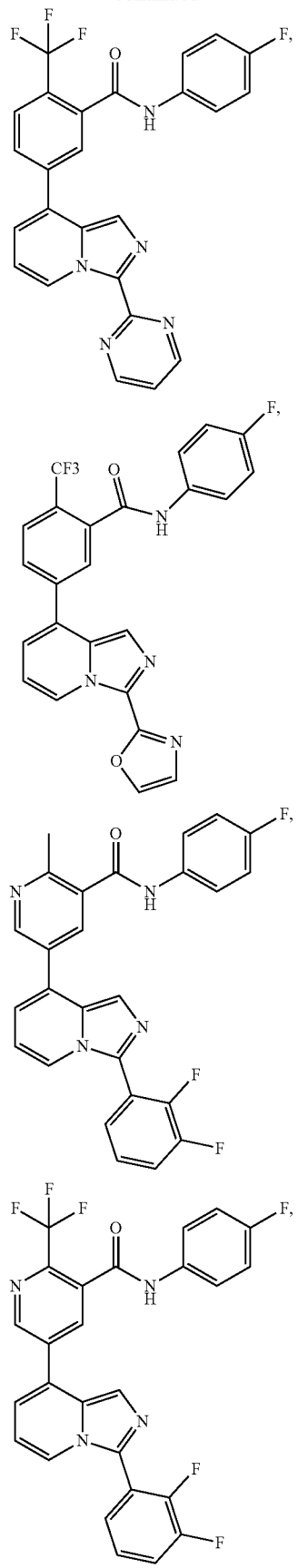

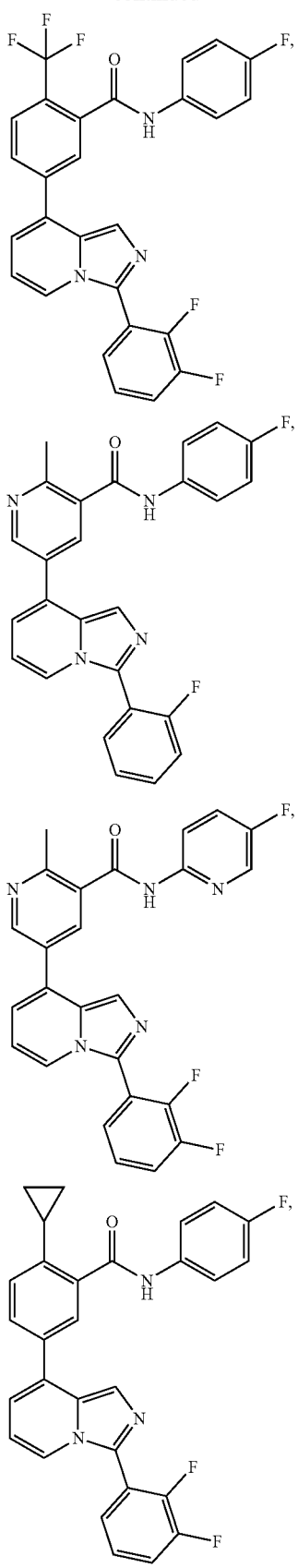
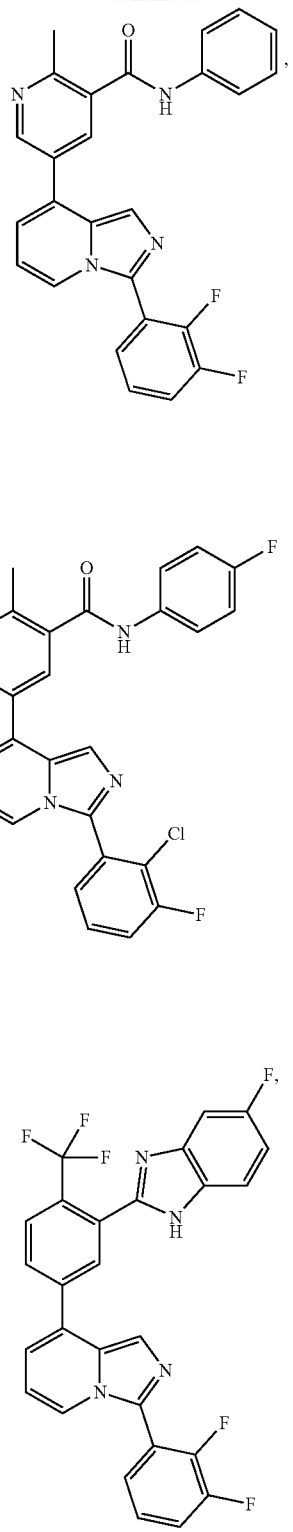
or a pharmaceutically acceptable salt thereof; in combination with
(ii) a therapeutically effective amount of a Toll-like receptor 8 (TLR8) agonist which is selected from the group consisting of:

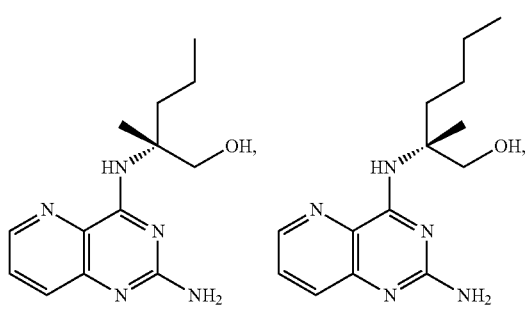
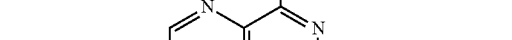
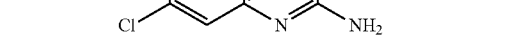
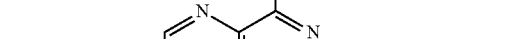
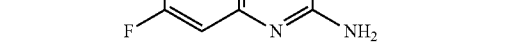
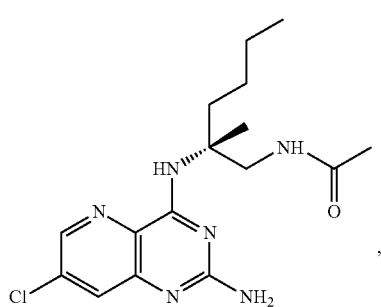
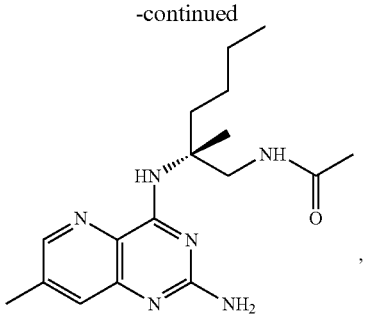
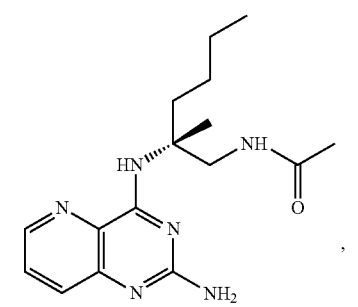
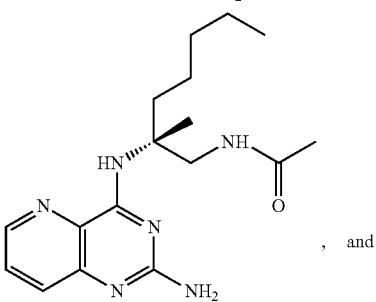
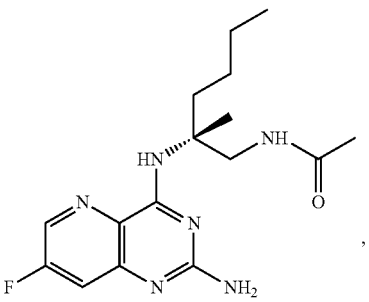

pharmaceutically acceptable salt thereof, and (iii) optionally, a PD-1 inhibitor and/or a PD-L1 inhibitor. In one such method, the optional PD-1 inhibitor and/or a PD-L1 inhibitor is not administered. In another such method, the optional PD-1 inhibitor and/or PD-L1 inhibitor is administered. In one such method, a PD-1 inhibitor is administered. In another such method, a PD-L1 inhibitor is administered. In another such method, a PD-1 inhibitor and a PD-L1 inhibitor are administered.

In certain embodiments, a method for treating an HBV infection in a human having the infection is provided, comprising administering to the human:

(i) a therapeutically effective amount of a compound which is selected from the group consisting of:

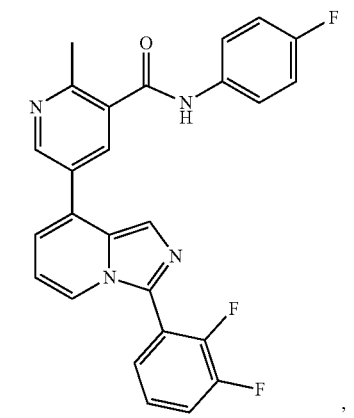

,

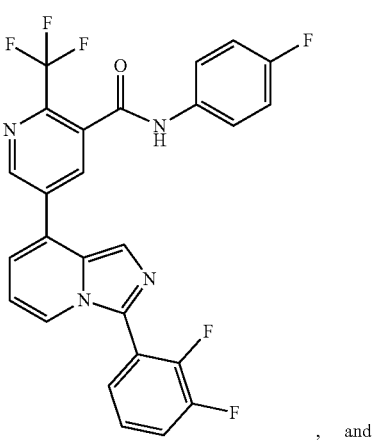

, and

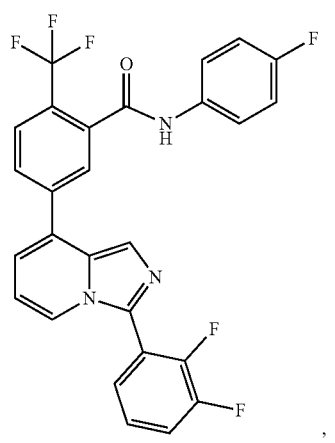

, or a pharmaceutically acceptable salt thereof; in combination with (ii) a therapeutically effective amount of a Toll-like receptor 8 (TLR8) agonist which is selected from the group consisting of:

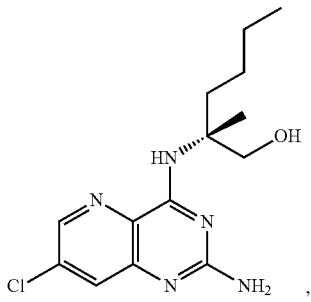

,

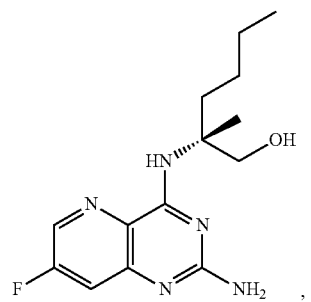

,

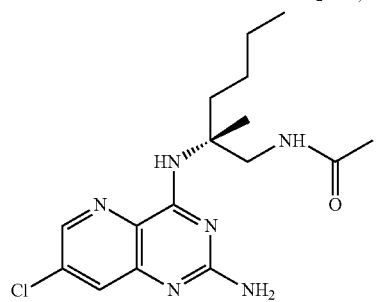

, and

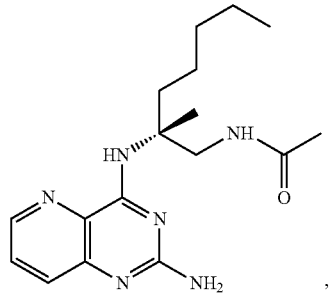

, or a pharmaceutically acceptable salt thereof; and (iii) optionally, a PD-1 inhibitor and/or a PD-L1 inhibitor. In one such method, the optional PD-1 inhibitor and/or a PD-L1 inhibitor is not administered. In another such method, the optional PD-1 inhibitor and/or PD-L1 inhibitor is administered. In one such method, a PD-1 inhibitor is administered. In another such method, a PD-L1 inhibitor is administered. In another such method, a PD-1 inhibitor and a PD-L1 inhibitor are administered.

In certain embodiments, a method for treating an HBV infection in a human having the infection is provided, comprising administering to the human:

(i) a therapeutically effective amount of a compound which is selected from the group consisting of:

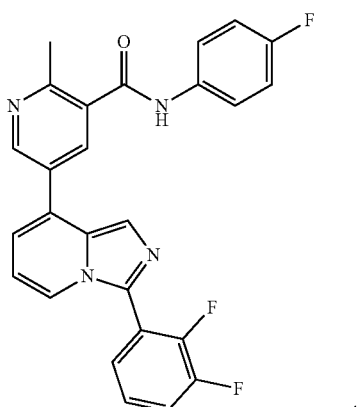

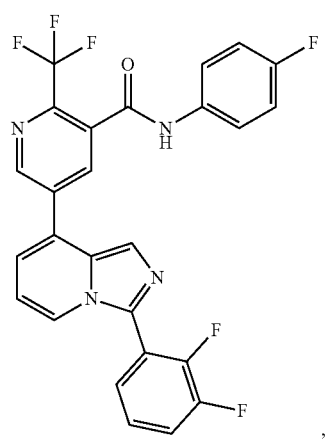

and or a pharmaceutically acceptable salt thereof; in combination with (ii) a therapeutically effective amount of a Toll-like receptor 8 (TLR8) agonist which is selected from the group consisting of:

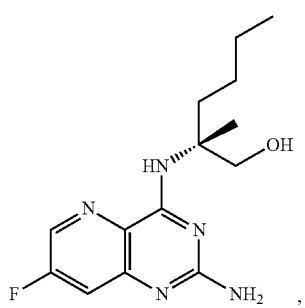

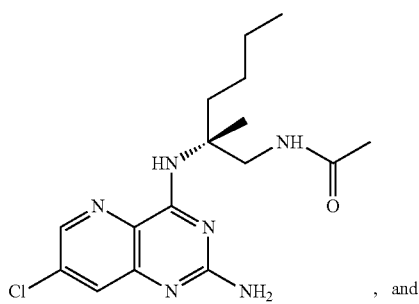

, and

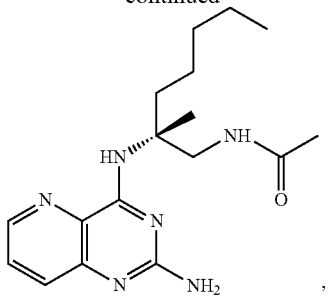

, or a pharmaceutically acceptable salt thereof; and
(iii) optionally, a PD-1 inhibitor and/or a PD-L1 inhibitor. In one such method, the optional PD-1 inhibitor and/or a PD-L1 inhibitor is not administered. In another such method, the optional PD-1 inhibitor and/or PD-L1 inhibitor is administered. In one such method, a PD-1 inhibitor is administered. In another such method, a PD-L1 inhibitor is administered. In another such method, a PD-1 inhibitor and a PD-L1 inhibitor are administered.

In certain embodiments, a method for treating an HBV infection in a human having the infection is provided, comprising administering to the human:
(i) a therapeutically effective amount of a compound which is:

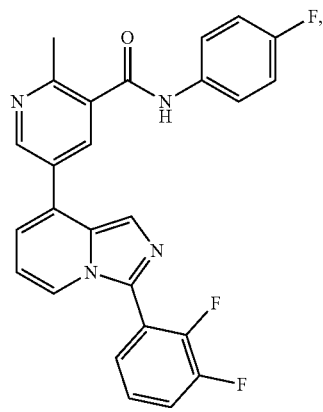 [SMILES: Cc1ncc(-c2cccn3c(-c4cccc(F)c4F)ncc23)cc1C(=O)Nc1ccc(F)cc1]

or a pharmaceutically acceptable salt thereof; in combination with
(ii) a therapeutically effective amount of a Toll-like receptor 8 (TLR8) agonist which is:

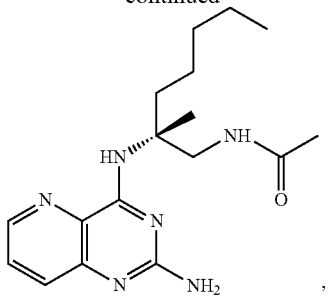

or a pharmaceutically acceptable salt thereof; and
(ii) optionally, a PD-1 inhibitor and/or a PD-L1 inhibitor. In one such method, the optional PD-1 inhibitor and/or a PD-L1 inhibitor is not administered. In another such method, the optional PD-1 inhibitor and/or PD-L1 inhibitor is administered. In one such method, a PD-1 inhibitor is administered. In another such method, a PD-L1 inhibitor is administered. In another such method, a PD-1 inhibitor and a PD-L1 inhibitor are administered.

In certain embodiments, a method for treating an HBV infection in a human having the infection is provided, comprising administering to the human:

(iii) a therapeutically effective amount of a compound which is:

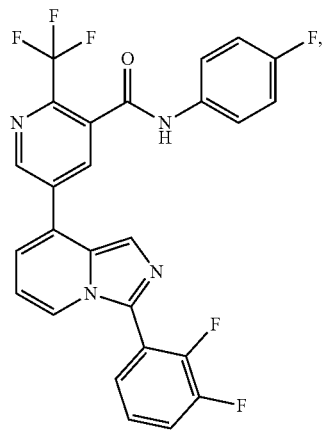

or a pharmaceutically acceptable salt thereof; in combination with (ii) a therapeutically effective amount of a Toll-like receptor 8 (TLR8) agonist which is:

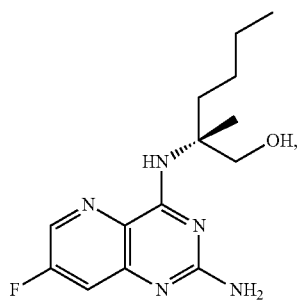

or a pharmaceutically acceptable salt thereof; and (iii) optionally, a PD-1 inhibitor and/or a PD-L1 inhibitor. In one such method, the optional PD-1 inhibitor and/or a PD-L1 inhibitor is not administered. In another such method, the optional PD-1 inhibitor and/or PD-L1 inhibitor is administered. In one such method, a PD-1 inhibitor is administered. In another such method, a PD-L1 inhibitor is administered. In another such method, a PD-1 inhibitor and a PD-L1 inhibitor are administered.

Compositions and kits for combination therapy are also provided. In some embodiments, provided herein is a composition comprising:

(i) a compound disclosed herein, which is selected from the group consisting of:

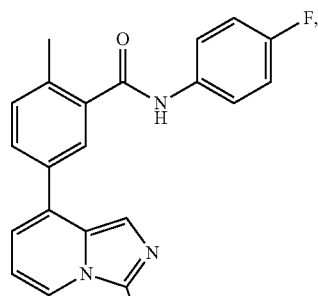

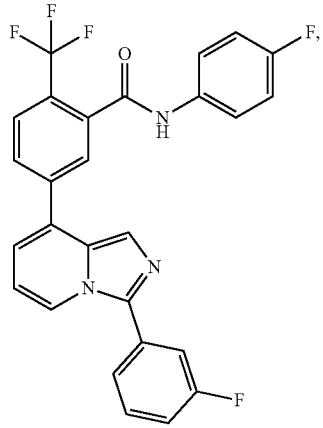

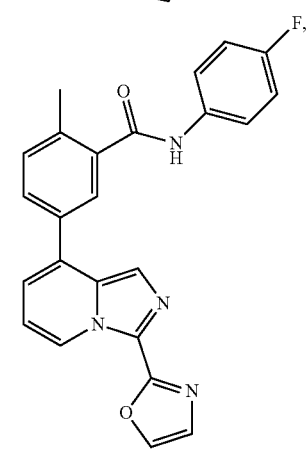

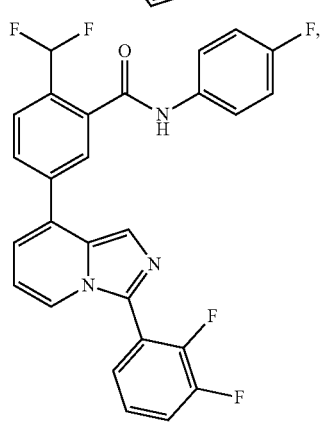

109
-continued
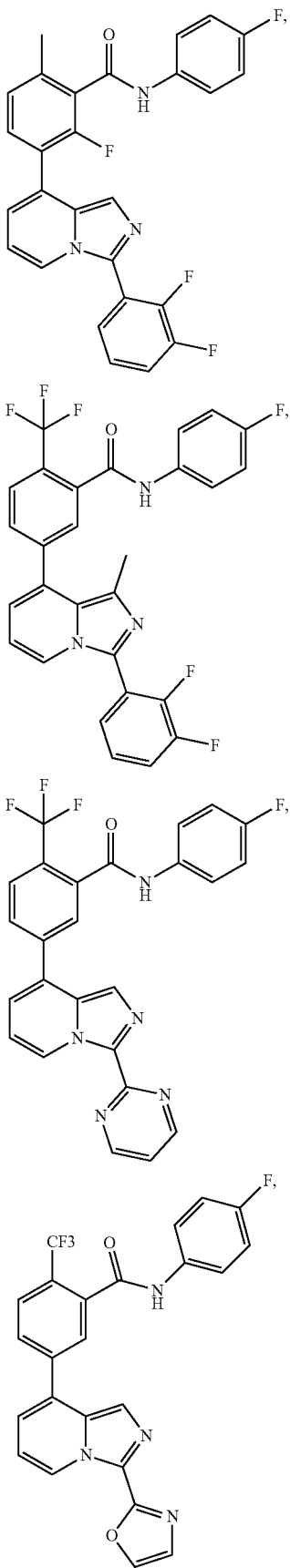
110
-continued
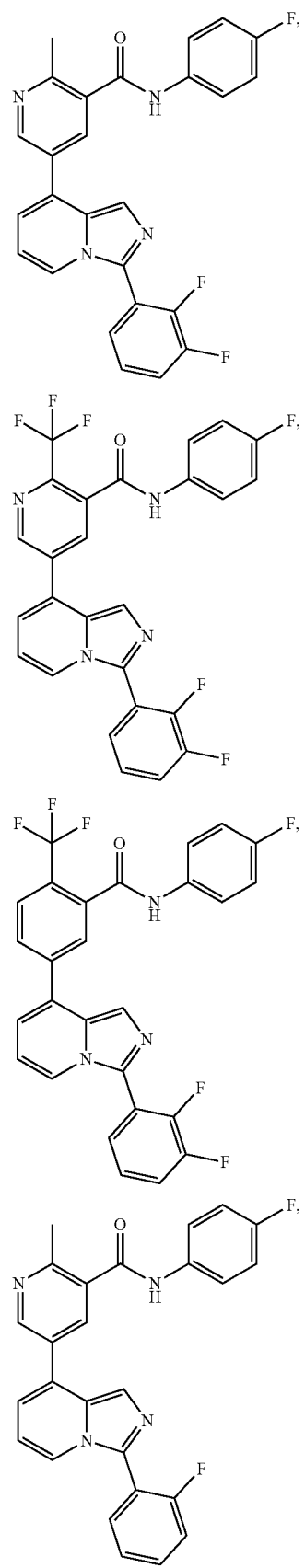

-continued
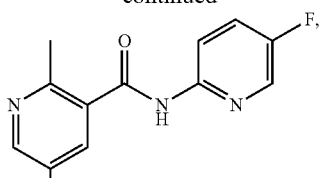
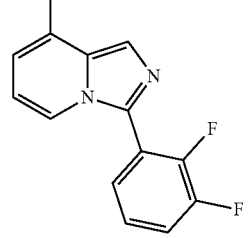
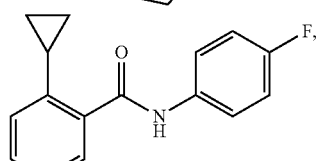
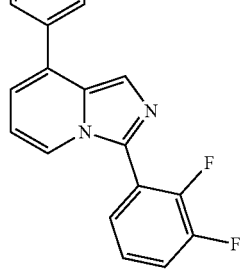
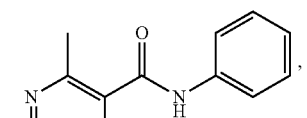
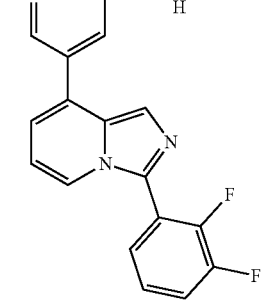 and
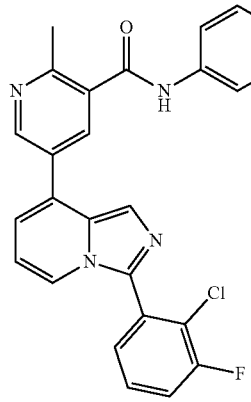
-continued
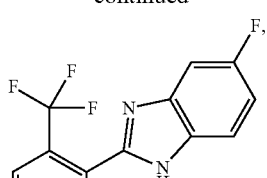
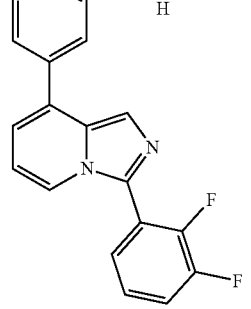
or a pharmaceutically acceptable salt thereof; and
(ii) a Toll-like receptor 8 (TLR8) agonist which is selected from the group consisting of:
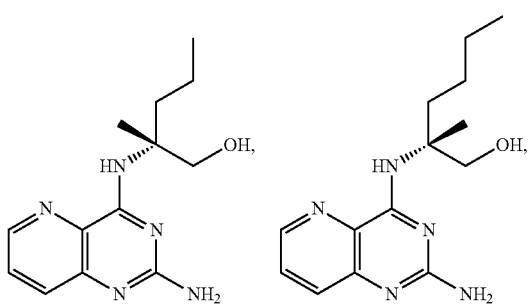
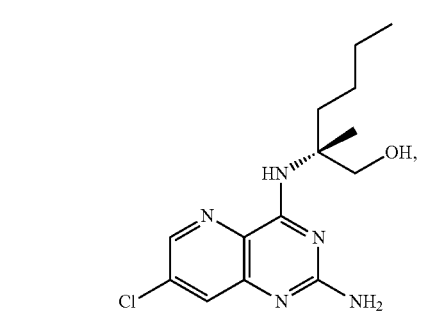
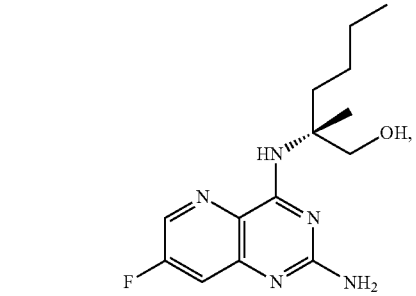

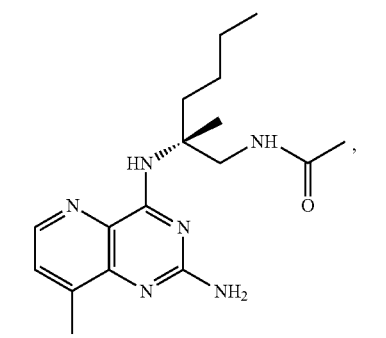
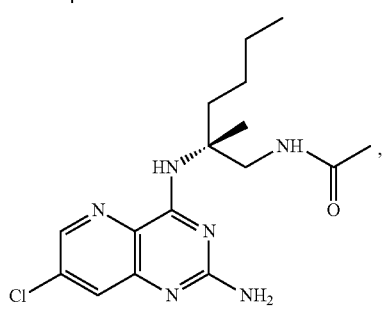
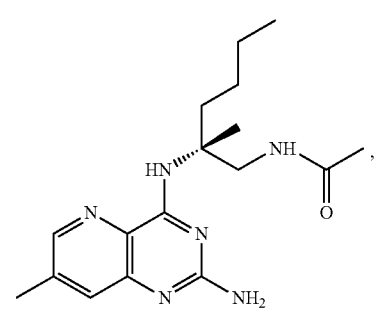
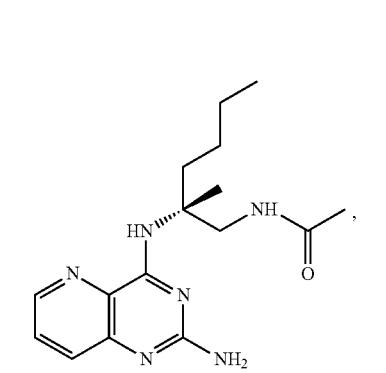
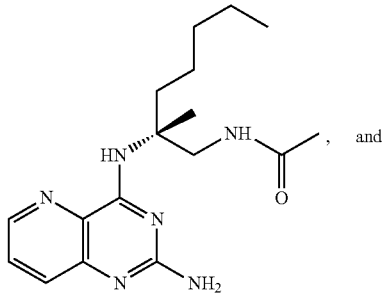
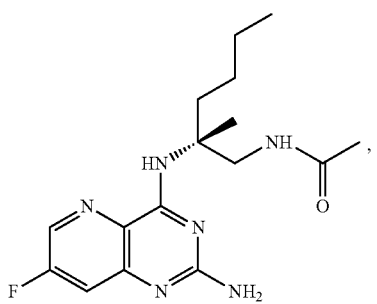
or a pharmaceutically acceptable salt thereof. In some embodiments, the composition further comprises a PD-1 inhibitor and/or a PD-L1 inhibitor.
In certain embodiments, a composition is provided, comprising:
(i) a compound disclosed herein, which is selected from the group consisting of:
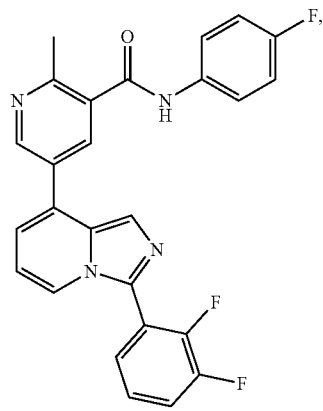 [SMILES: Cc1ncc(-c2cccn3c(-c4cccc(F)c4F)ncc23)cc1C(=O)Nc1ccc(F)cc1]
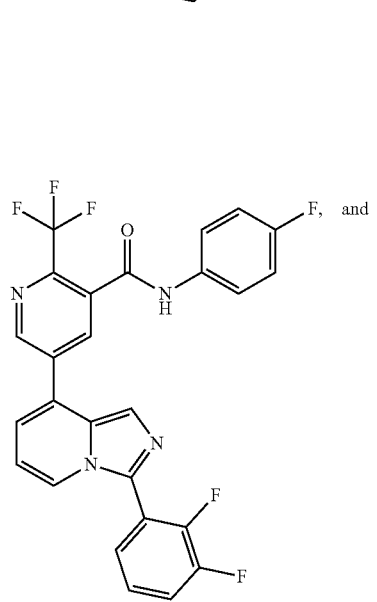

-continued

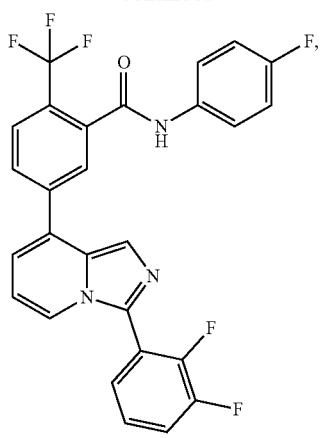

or a pharmaceutically acceptable salt thereof; and
(ii) a Toll-like receptor 8 (TLR8) agonist which is selected from the group consisting of:

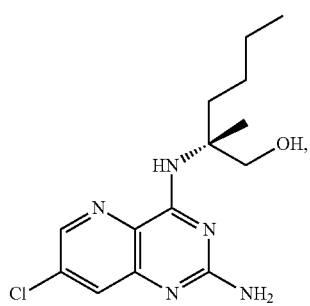

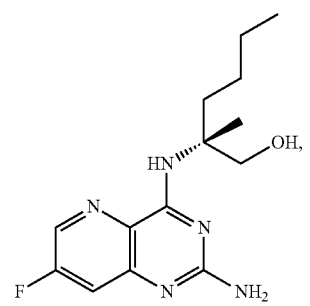

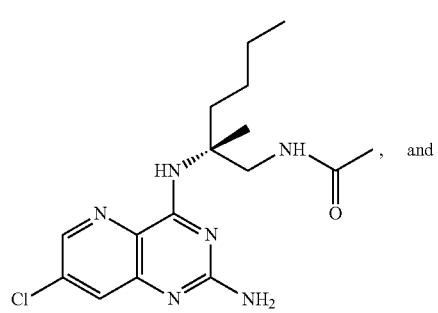

-continued

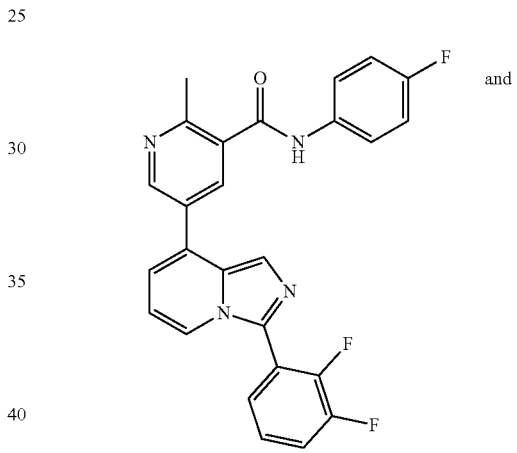

or a pharmaceutically acceptable salt thereof. In some embodiments, the composition further comprises a PD-1 inhibitor and/or a PD-L1 inhibitor.

In some embodiments, a composition is provided, comprising:
(i) a compound disclosed herein, which is selected from the group consisting of:

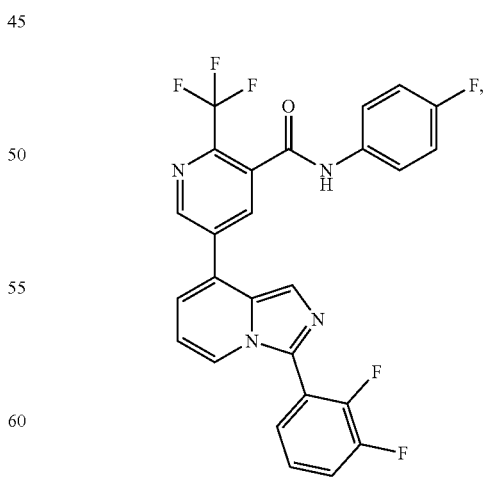

or a pharmaceutically acceptable salt thereof; and
(ii) a Toll-like receptor 8 (TLR8) agonist which is selected from the group consisting of:

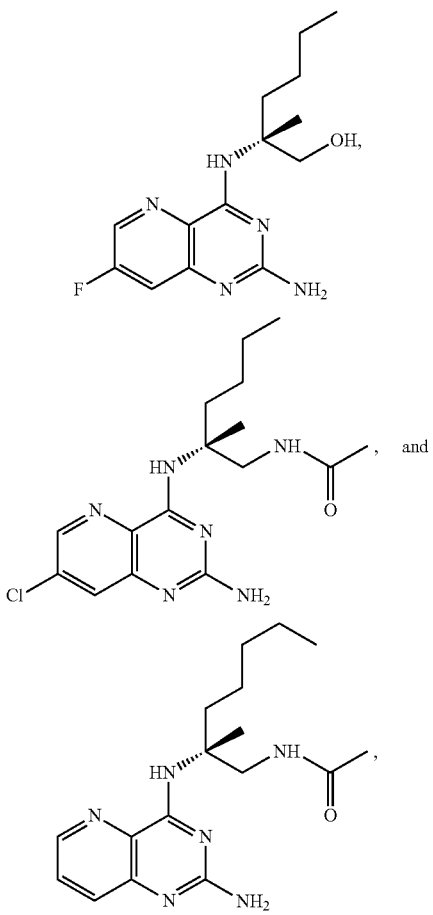

or a pharmaceutically acceptable salt thereof. In some embodiments, the composition further comprises a PD-1 inhibitor and/or a PD-L1 inhibitor.

In certain embodiments, a composition is provided, comprising:

(i) a compound disclosed herein, which is:

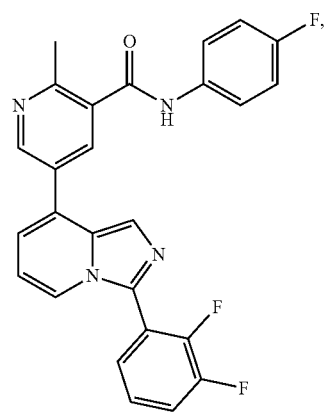

or a pharmaceutically acceptable salt thereof; and
(ii) a Toll-like receptor 8 (TLR8) agonist which is selected from the group consisting of:

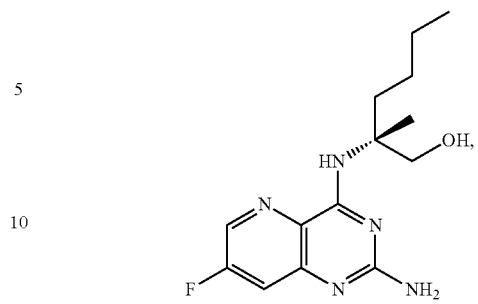

or a pharmaceutically acceptable salt thereof. In some embodiments, the composition further comprises a PD-1 inhibitor and/or a PD-L1 inhibitor.

In certain embodiments, a composition is provided, comprising:

(i) a compound disclosed herein, which is:

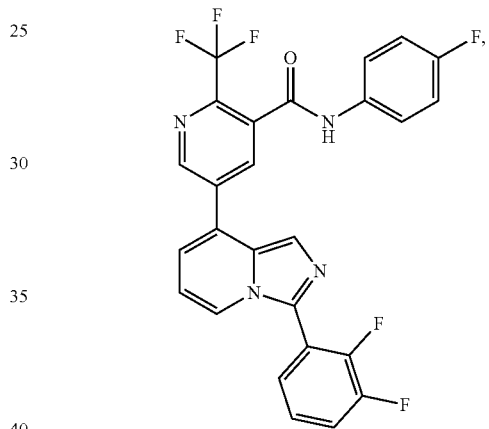

or a pharmaceutically acceptable salt thereof; and
(ii) a Toll-like receptor 8 (TLR8) agonist which is:

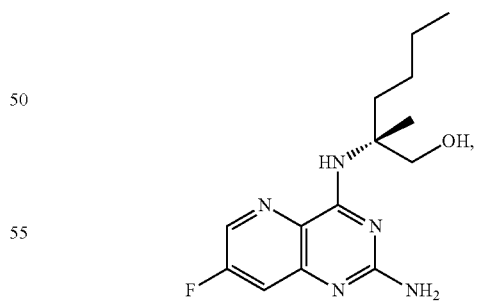

or a pharmaceutically acceptable salt thereof. In some embodiments, the composition further comprises a PD-1 inhibitor and/or a PD-L1 inhibitor.

In some embodiments, provided herein is a kit comprising:

(i) a compound disclosed herein, which is selected from the group consisting of:

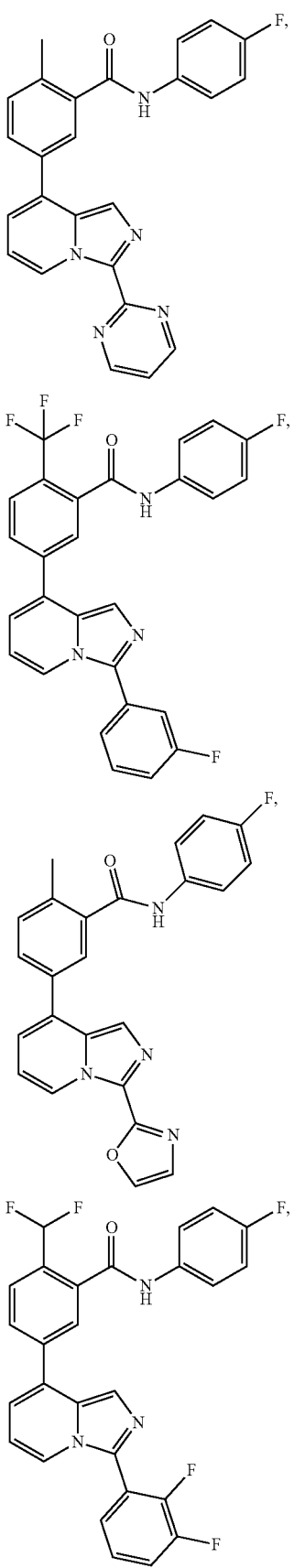
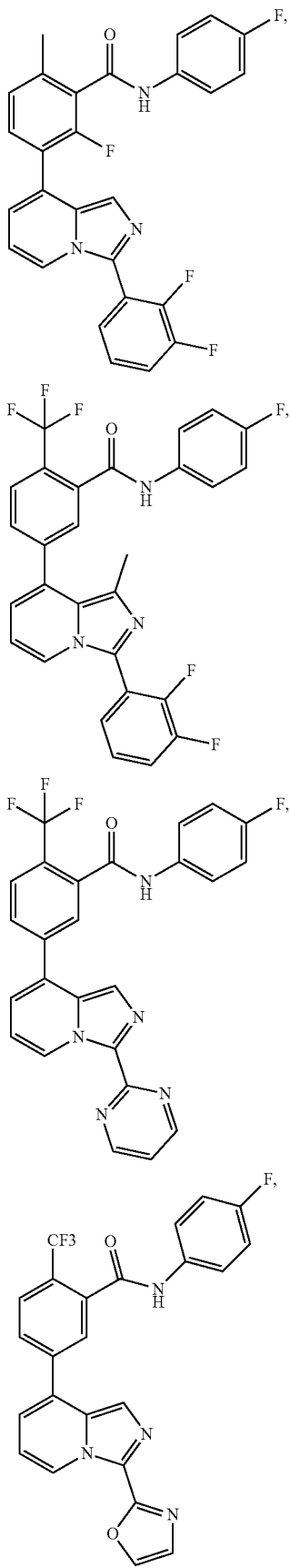

121
-continued
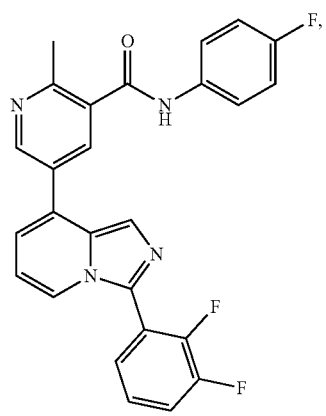
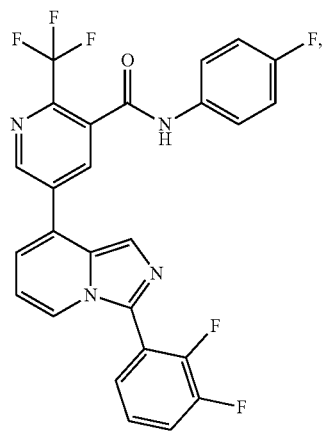
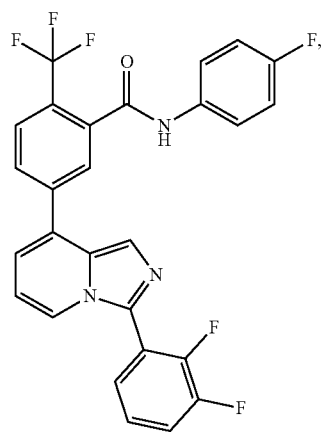
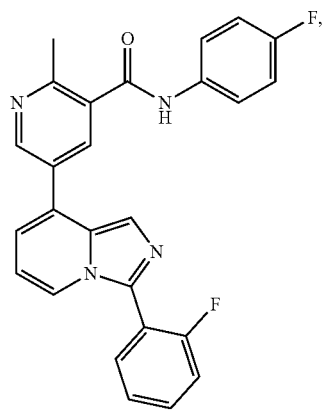
122
-continued
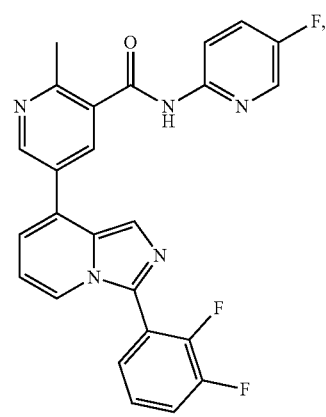
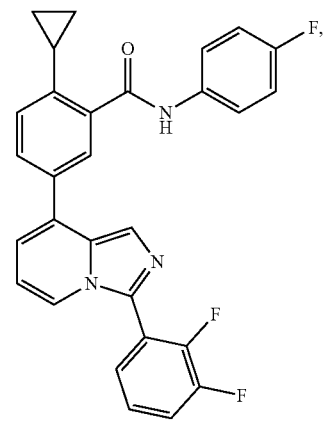
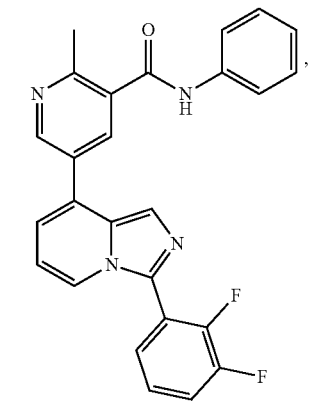
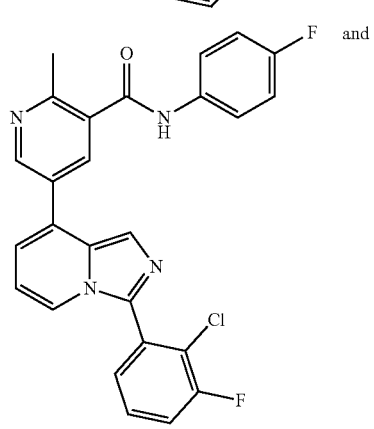

-continued
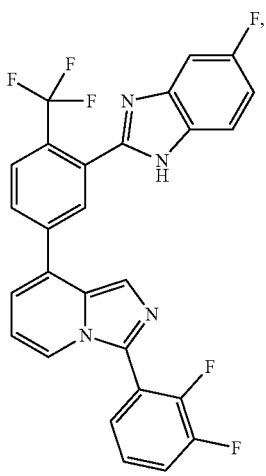
or a pharmaceutically acceptable salt thereof; and
(ii) a Toll-like receptor 8 (TLR8) agonist which is selected from the group consisting of:
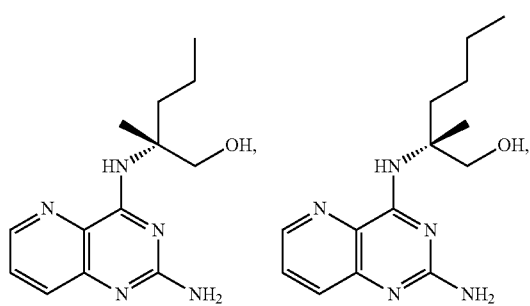
-continued
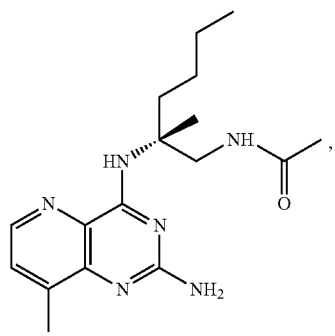
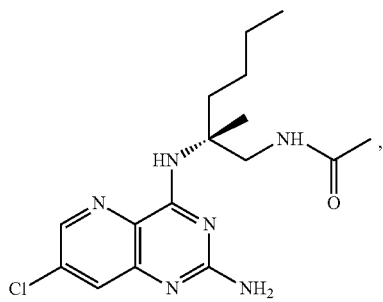
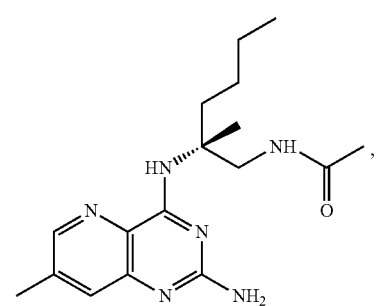
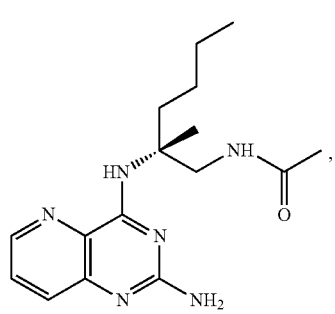
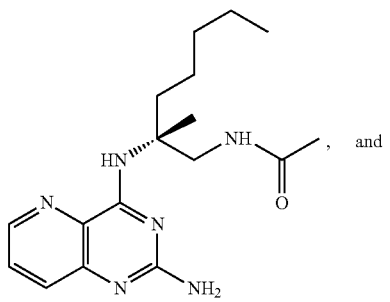

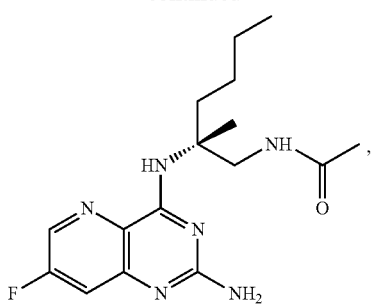

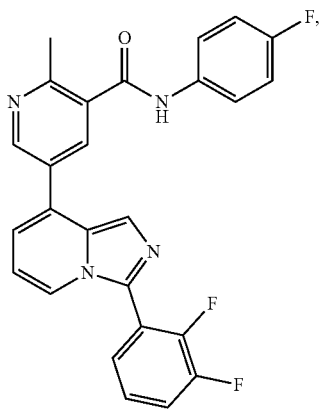

or a pharmaceutically acceptable salt thereof. In some embodiments, the kit further comprises a PD-1 inhibitor and/or a PD-L1 inhibitor. In some embodiments, the kit further comprises instructions for use in the treatment of an HBV infection in a human.

In certain embodiments, a kit is provided, comprising:

(i) a compound disclosed herein, which is selected from the group consisting of:

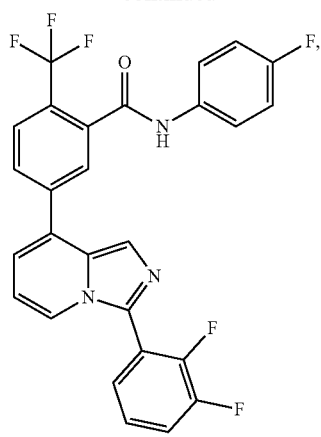

or a pharmaceutically acceptable salt thereof; and (ii) a Toll-like receptor 8 (TLR8) agonist which is selected from the group consisting of:

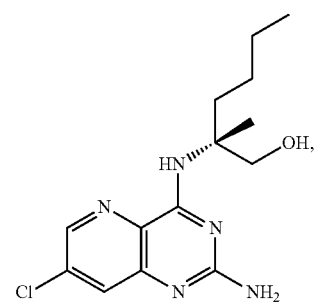

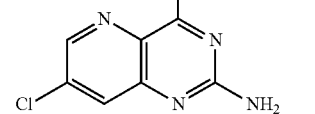

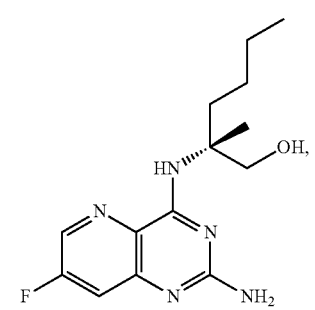

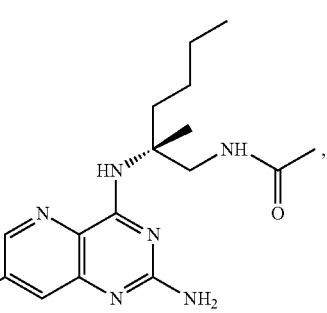

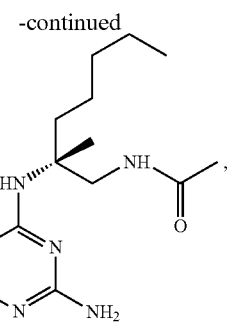

or a pharmaceutically acceptable salt thereof. In some embodiments, the kit further comprises a PD-1 inhibitor and/or a PD-L1 inhibitor. In some embodiments, the kit further comprises instructions for use in the treatment of an HBV infection in a human.

In certain embodiments, the additional therapeutic is selected from the group consisting of HBV combination drugs, HBV DNA polymerase inhibitors, toll-like receptor 7 modulators, toll-like receptor 8 modulators, Toll-like receptor 7 and 8 modulators, Toll-like receptor 3 modulators, interferon alpha receptor ligands, HBsAg inhibitors, compounds targeting HbcAg, cyclophilin inhibitors, HBV therapeutic vaccines, HBV prophylactic vaccines, HBV viral entry inhibitors, NTCP inhibitors, antisense oligonucleotide targeting viral mRNA, short interfering RNAs (siRNA), hepatitis B virus E antigen inhibitors, HBx inhibitors, cccDNA inhibitors, HBV antibodies including HBV antibodies targeting the surface antigens of the hepatitis B virus, thymosin agonists, cytokines, nucleoprotein inhibitors (HBV core or capsid protein inhibitors), stimulators of retinoic acid-inducible gene 1, stimulators of NOD2, stimulators of NOD1, recombinant thymosin alpha-1, BTK inhibitors, and hepatitis B virus replication inhibitors, and combinations thereof.

In certain embodiments a compound disclosed herein is formulated as a tablet, which may optionally contain one or more other compounds useful for treating HBV. In certain embodiments, the tablet can contain another active ingredient for treating HBV, such as HBV DNA polymerase inhibitors, immunomodulators, toll-like receptor modulators (modulators of tlr1, tlr2, tlr3, tlr4, tlr5, tlr6, tlr7, tlr8, tlr9, tlr10, tlr11, tlr12 and tlr13), modulators of tlr7, modulators of tlr8, modulators of tlr7 and tlr8, interferon alpha receptor ligands, hyaluronidase inhibitors, hepatitis B surface antigen (HBsAg) inhibitors, compounds targeting hepatitis B core antigen (HbcAg), cyclophilin inhibitors, HBV viral entry inhibitors, NTCP (Na+-taurocholate cotransporting polypeptide) inhibitors, endonuclease modulators, inhibitors of ribonucleotide reductase, hepatitis B virus E antigen inhibitors, Src kinase inhibitors, HBx inhibitors, cccDNA inhibitors, CCR2 chemokine antagonists, thymosin agonists, nucleoprotein inhibitors (HBV core or capsid protein inhibitors), stimulators of retinoic acid-inducible gene 1, stimulators of NOD2, stimulators of NOD1, Arginase-1 inhibitors, STING agonists, PI3K inhibitors, lymphotoxin beta receptor activators, Natural Killer Cell Receptor 2B4 inhibitors, Lymphocyte-activation gene 3 inhibitors, CD160 inhibitors, cytotoxic T-lymphocyte-associated protein 4 inhibitors, CD137 inhibitors, Killer cell lectin-like receptor subfamily G member 1 inhibitors, TIM-3 inhibitors, B- and T-lymphocyte attenuator inhibitors, CD305 inhibitors, PD-1 inhibitors, PD-L1 inhibitors, BTK inhibitors, modulators of TIGIT, modulators of CD47, modulators of SIRP alpha, modulators of ICOS, modulators of CD27, modulators of CD70, modulators of OX40, modulators of NKG2D, modulators of Tim-4, modulators of B7-H4, modulators of B7-H3, modulators of NKG2A, modulators of GITR, modulators of CD160, modulators of HEVEM, modulators of CD161, modulators of Axl, modulators of Mer, modulators of Tyro, and Hepatitis B virus replication inhibitors, and combinations thereof.

In some embodiments, a method of treating HBV in a subject comprises administering to the subject a therapeutically effective amount of any of the compounds described herein (e.g., a compound of Formula I or a compound of Formula II, or a pharmaceutically acceptable salt thereof) in combination with an immunotherapeutic agent, such as an immune checkpoint inhibitor, an hematopoietic progenitor kinase 1 (HPK1) inhibitor, an immune checkpoint stimulatory protein agonist, or an engineered immune cell (for example a T cell with an chimeric antigen receptor (i.e., a CAR T cell) or a T cell with an engineered T cell receptor (TCR). In some embodiments, the compound is administered to the subject prior to, subsequent to, or simultaneous to administration of one or more immunotherapeutic agents. In some embodiments, the compound is administered to the subject about 30 minutes or more, about 1 hour or more, about 2 hours or more, about 4 hours or more, about 6 hours or more, about 12 hours or more, about 24 hours or more, about 48 hours or more, or about 72 hour or more prior to or subsequent to administration of the one or more immunotherapeutic agents. In some embodiments, the compound is administered to the subject about 30 minutes or less, about 1 hour or less, about 2 hours or less, about 4 hours or less, about 6 hours or less, about 12 hours or less, about 24 hours or less, about 48 hours or less, or about 72 hour or less prior to or subsequent to administration of the one or more immunotherapeutic agents.

In some embodiments, a method of treating HBV in a subject comprises administering to the subject a therapeutically effective amount of any of the compounds described herein (e.g., a compound of Formula I or a compound of Formula II, or a pharmaceutically acceptable salt thereof) in combination with a therapeutically effective amount of one or more immune checkpoint inhibitors. In some embodiments, the compound is administered to the subject prior to, subsequent to, or simultaneous to administration of the immune checkpoint inhibitor. In some embodiments, the immune checkpoint inhibitor is a small-molecule inhibitor. In some embodiments, the immune checkpoint inhibitor is an antibody or a fragment thereof. In some embodiments, the immune checkpoint inhibitor inhibits the Adenosine $A_{2A}$ Receptor (A2aR), B7-H3, V-Set Domain-Containing T-cell Activation Inhibitor 1 (VTCN1, also known as B7-H4), the B- and T-Lymphocyte Attenuator (BTLA), cytotoxic T-Lypmphocyte-Associated protein 4 (CTLA-4), Killer-cell Immunoglobulin-like Receptor (KIR), Lymphocyte Activation Gene 3 (LAG3), Programmed Death 1 (PD-1), Programmed Death Ligand 1 (PD-L1), Programmed Death Ligand 2 (PD-L2), T-cell Immunoreceptor with Ig and ITIM Domains (TIGIT), T-cell Immunoglobulin and Mucin-Domain Containing 3 (TIM-3), or V-Domain Ig Suppressor of T-cell Activation (VISTA). Exemplary immune checkpoint inhibitors include, but are not limited to, avelumab, atezolizumab, durvalumab, nivolumab, pembrolizumab, ipilimumab, PDR001, TSR-042, and BMS-986016.

In some embodiments, a method of treating HBV in a subject comprises administering to the subject a therapeutically effective amount of any of the compounds described herein (e.g., a compound of Formula I or a compound of Formula II, or a pharmaceutically acceptable salt thereof) in combination with a therapeutically effective amount of one or more immune checkpoint stimulatory protein agonists. In some embodiments, the compound is administered to the subject prior to, subsequent to, or simultaneous to administration of the immune checkpoint stimulatory protein agonist. In some embodiments, the immune checkpoint stimulatory protein agonist is an antibody or a fragment thereof. In some embodiments, the immune checkpoint stimulatory protein agonist is an agonist of CD27, CD28, CD40, CD122, 4-1BB, OX40, Glucocorticoid-Induced TNFR family related protein (GITR), or Inducible T-Cell Costimulator (ICOS).

In some embodiments, a method of treating HBV in a subject comprises administering to the subject a therapeutically effective amount of any of the compounds described herein (e.g., a compound of Formula I or a compound of Formula II, or a pharmaceutically acceptable salt thereof) in combination with a therapeutically effective amount of engineered immune cells, such as CAR T cells or T cells with an engineered TCR. In some embodiments, the compound is administered to the subject prior to, subsequent to, or simultaneous to administration of the engineered immune cells. In some embodiments, the engineered immune cells are heterologous engineered immune cells, such as heterologous engineered T cells (e.g., CAR T cells or T cells with an engineered TCR). In some embodiments, the engineered immune cells are autologous engineered immune cells, such as autologous engineered T cells (e.g., CAR T cells or T cells with an engineered TCR). In some embodiments, the engineered immune cells (e.g., engineered T cells) target an HBV antigen, such as a hepatitis B surface antigen (HBsAg) or hepatitis B core antigen (HBcAg).

In some embodiments, a method of treating HBV in a subject comprises administering to the subject a therapeutically effective amount of any of the compounds described herein (e.g., a compound of Formula I or a compound of Formula II, or a pharmaceutically acceptable salt thereof) in combination with (1) a therapeutically effective amount of engineered immune cells, such as CAR T cells or T cells with an engineered TCR, and (2) a therapeutically effective amount of an immune checkpoint inhibitor or an immune checkpoint stimulatory protein agonist. In some embodiments, a method of treating HBV in a subject comprises administering to the subject a therapeutically effective amount of any of the compounds described herein (e.g., a compound of Formula I or a compound of Formula II, or a pharmaceutically acceptable salt thereof) in combination with (1) a therapeutically effective amount of engineered immune cells, such as CAR T cells or T cells with an engineered TCR, and (2) a therapeutically effective amount of an antiviral agent (such as an anti-HBV agent). In some embodiments, a method of treating HBV in a subject comprises administering to the subject a therapeutically effective amount of any of the compounds described herein (e.g., a compound of Formula I or a compound of Formula II, or a pharmaceutically acceptable salt thereof) in combination with (1) a therapeutically effective amount of an immune checkpoint inhibitor or an immune checkpoint stimulatory protein agonist, and (2) a therapeutically effective amount of an antiviral agent (such as an anti-HBV agent). In some embodiments, a method of treating HBV in a subject comprises administering to the subject a therapeutically effective amount of any of the compounds described herein (e.g., a compound of Formula I or a compound of Formula II, or a pharmaceutically acceptable salt thereof) in combination with (1) a therapeutically effective amount of engineered immune cells, such as CAR T cells or T cells with an engineered TCR, (2) a therapeutically effective amount of an immune checkpoint inhibitor or an immune checkpoint stimulatory protein agonist, and (3) a therapeutically effective amount of an antiviral agent (such as an anti-HBV agent).

In certain embodiments, such tablets are suitable for once daily dosing.

In certain embodiments, the additional therapeutic agent is selected from one or more of:

(1) Combination drugs selected from the group consisting of tenofovir disoproxil fumarate+emtricitabine (TRU-VADA®); adefovir+clevudine, ABX-203+lamivudine+PEG-IFNalpha, ABX-203+adefovir+PEG-IFNalpha and GBV-015;

(2) HBV DNA polymerase inhibitors selected from the group consisting of besifovir, entecavir (Baraclude®), adefovir (Hepsera®), tenofovir disoproxil fumarate (Viread®), tenofovir alafenamide, tenofovir, tenofovir disoproxil, tenofovir alafenamide fumarate, tenofovir alafenamide hemifumarate, tenofovir dipivoxil, tenofovir dipivoxil fumarate, tenofovir octadecyloxyethyl ester, telbivudine (Tyzeka®), pradefovir, Clevudine, emtricitabine (Emtriva®), ribavirin, lamivudine (Epivir-HBV®), phosphazide, famciclovir, SNC-019754, FMCA, fusolin, AGX-1009 and metacavir;

(3) Immunomodulators selected from the group consisting of rintatolimod, imidol hydrochloride, ingaron, dermaVir, plaquenil (hydroxychloroquine), proleukin, hydroxyurea, mycophenolate mofetil (MPA) and its ester derivative mycophenolate mofetil (MMF), WF-10, ribavirin, IL-12, polymer polyethyleneimine (PEI), Gepon, VGV-1, MOR-22, BMS-936559 and IR-103;

(4) Toll-like receptor 7 modulators selected from the group consisting of GS-9620, GSK-2245035, imiquimod, resiquimod, DSR-6434, DSP-3025, IMO-4200, MCT-465, 3M-051, SB-9922, 3M-052, Limtop, TMX-30X, TMX-202 RG-7863 and RG-7795;

(5) Toll-like receptor 8 modulators selected from the group consisting of motolimod, resiquimod, 3M-051, 3M-052, MCT-465, IMO-4200, VTX-763, VTX-1463;

(6) Toll-like receptor 3 modulators selected from the group consisting of rintatolimod, poly-ICLC, MCT-465, MCT-475, Riboxxon, Riboxxim and ND-1.1;

(7) Interferon alpha receptor ligands selected from the group consisting of interferon alpha-2b (Intron A®), pegylated interferon alpha-2a (Pegasys®), interferon alpha 1b (Hapgen®), Veldona, Infradure, Roferon-A, YPEG-interferon alfa-2a (YPEG-rhIFNalpha-2a), P-1101, Algeron, Alfarona, Ingaron (interferon gamma), rSIFN-co (recombinant super compound interferon), Ypeginterferon alfa-2b (YPEG-rhIFNalpha-2b), MOR-22, peginterferon alfa-2b (PEG-Intron®), Bioferon, Novaferon, Inmutag (Inferon), Multiferon®, interferon alfa-n1(Humoferon®), interferon beta-1a (Avonex®), Shaferon, interferon alfa-2b (AXXO), Alfaferone, interferon alfa-2b (BioGeneric Pharma), interferon-alpha 2 (CJ), Laferonum, VIPEG, BLAUFERON-B, BLAUFERON-A, Intermax Alpha, Realdiron, Lanstion, Pegaferon, PDferon-B PDferon-B, interferon alfa-2b (IFN, Laboratorios Bioprofarma), alfainterferona 2b, Kalferon, Pegnano, Feronsure, Pegi-Hep, interferon alfa 2b (Zydus-Cadila), Optipeg A, Realfa 2B, Reliferon, interferon alfa-2b (Amega), interferon alfa-2b (Virchow), peginterferon alfa-2b (Amega), Reaferon-EC, Proquiferon, Uniferon, Urifron, interferon alfa-2b (Changchun Institute of Biological Products), Anterferon, Shanferon, Layfferon, Shang Sheng Lei Tai, INTEFEN, SINOGEN, Fukangtai, Pegstat, rHSA-IFN alpha-2b and Interapo (Interapa);
(8) Hyaluronidase inhibitors selected from the group consisting of astodrimer;
(9) Modulators of IL-10;
(10) HBsAg inhibitors selected from the group consisting of HBF-0259, PBHBV-001, PBHBV-2-15, PBHBV-2-1, REP 9AC, REP-9C and REP 9AC';
(11) Toll like receptor 9 modulators selected from CYT003;
(12) Cyclophilin inhibitors selected from the group consisting of OCB-030, SCY-635 and NVP-018;
(13) HBV Prophylactic vaccines selected from the group consisting of Hexaxim, Heplisav, Mosquirix, DTwP-HBV vaccine, Bio-Hep-B, D/T/P/HBV/M (LBVP-0101; LBVW-0101), DTwP-Hepb-Hib-IPV vaccine, Heberpenta L, DTwP-HepB-Hib, V-419, CVI-HBV-001, Tetrabhay, hepatitis B prophylactic vaccine (Advax Super D), Hepatrol-07, GSK-223192A, Engerix B®, recombinant hepatitis B vaccine (intramuscular, Kangtai Biological Products), recombinant hepatitis B vaccine (Hansenual polymorpha yeast, intramuscular, Hualan Biological Engineering), Bimmugen, Euforavac, Eutravac, anrix-DTaP-IPV-Hep B, Infanrix-DTaP-IPV-Hep B-Hib, Pentabio Vaksin DTP-HB-Hib, Comvac 4, Twinrix, Euvax-B, Tritanrix HB, Infanrix Hep B, Comvax, DTP-Hib-HBV vaccine, DTP-HBV vaccine, Yi Tai, Heberbiovac HB, Trivac HB, GerVax, DTwP-Hep B-Hib vaccine, Bilive, Hepavax-Gene, SUPERVAX, Comvac5, Shanvac-B, Hebsulin, Recombivax HB, Revac B mcf, Revac B+, Fendrix, DTwP-HepB-Hib, DNA-001, Shan6, rhHBsAG vaccine, and DTaP-rHB-Hib vaccine;
(14) HBV Therapeutic vaccines selected from the group consisting of HBsAG-HBIG complex, Bio-Hep-B, NASVAC, abi-HB (intravenous), ABX-203, Tetrabhay, GX-110E, GS-4774, peptide vaccine (epsilonPA-44), Hepatrol-07, NASVAC (NASTERAP), IMP-321, BEVAC, Revac B mcf, Revac B+, MGN-1333, KW-2, CVI-HBV-002, AltraHepB, VGX-6200, FP-02, TG-1050, NU-500, HBVax, im/TriGrid/antigen vaccine, Mega-CD40L-adjuvanted vaccine, HepB-v, NO-1800, recombinant VLP-based therapeutic vaccine (HBV infection, VLP Biotech), AdTG-17909, AdTG-17910 AdTG-18202, ChronVac-B, and Lm HBV;
(15) HBV viral entry inhibitor selected from the group consisting of Myrcludex B;
(16) Antisense oligonucleotide targeting viral mRNA selected from the group consisting of ISIS-HBVRx;
(17) Short interfering RNAs (siRNA) selected from the group consisting of TKM-HBV (TKM-HepB), ALN-HBV, SR-008, ddRNAi and ARC-520;
(18) Endonuclease modulators selected from the group consisting of PGN-514;
(19) Inhibitors of ribonucleotide reductase selected from the group consisting of Trimidox;
(20) Hepatitis B virus E antigen inhibitors selected from the group consisting of wogonin;
(21) HBV antibodies targeting the surface antigens of the hepatitis B virus selected from the group consisting of GC-1102, XTL-17, XTL-19, XTL-001, KN-003 and fully human monoclonal antibody therapy (hepatitis B virus infection, Humabs BioMed);
(22) HBV antibodies including monoclonal antibodies and polyclonal antibodies selected from the group consisting of Zutectra, Shang Sheng Gan Di, Uman Big (Hepatitis B Hyperimmune), Omri-Hep-B, Nabi-HB, Hepatect CP, HepaGam B, igantibe, Niuliva, CT-P24, hepatitis B immunoglobulin (intravenous, pH4, HBV infection, Shanghai RAAS Blood Products) and Fovepta (BT-088);
(23) CCR2 chemokine antagonists selected from the group consisting of propagermanium;
(24) Thymosin agonists selected from the group consisting of Thymalfasin;
(25) Cytokines selected from the group consisting of recombinant IL-7, CYT-107, interleukin-2 (IL-2, Immunex); recombinant human interleukin-2 (Shenzhen Neptunus) and celmoleukin;
(26) Nucleoprotein inhibitors (HBV core or capsid protein inhibitors) selected from the group consisting of NVR-1221, NVR-3778, BAY 41-4109, morphothiadine mesilate and DVR-23;
(27) Stimulators of retinoic acid-inducible gene 1 selected from the group consisting of SB-9200, SB-40, SB-44, ORI-7246, ORI-9350, ORI-7537, ORI-9020, ORI-9198 and ORI-7170;
(28) Stimulators of NOD2 selected from the group consisting of SB-9200;
(29) Recombinant thymosin alpha-1 selected from the group consisting of NL-004 and PEGylated thymosin alpha 1;
(30) Hepatitis B virus replication inhibitors selected from the group consisting of isothiafludine, IQP-HBV, RM-5038 and Xingantie;
(31) PI3K inhibitors selected from the group consisting of idelalisib, AZD-8186, buparlisib, CLR-457, pictilisib, neratinib, rigosertib, rigosertib sodium, EN-3342, TGR-1202, alpelisib, duvelisib, UCB-5857, taselisib, XL-765, gedatolisib, VS-5584, copanlisib, CAI orotate, perifosine, RG-7666, GSK-2636771, DS-7423, panulisib, GSK-2269557, GSK-2126458, CUDC-907, PQR-309, INCB-040093, pilaralisib, BAY-1082439, puquitinib mesylate, SAR-245409, AMG-319, RP-6530, ZSTK-474, MLN-1117, SF-1126, RV-1729, sonolisib, LY-3023414, SAR-260301 and CLR-1401;
(32) cccDNA inhibitors selected from the group consisting of BSBI-25;
(33) PD-L1 inhibitors selected from the group consisting of MEDI-0680, RG-7446, durvalumab, KY-1003, KD-033, MSB-0010718C, TSR-042, ALN-PDL, STI-A1014 and BMS-936559;
(34) PD-1 inhibitors selected from the group consisting of nivolumab, pembrolizumab, pidilizumab, BGB-108 and mDX-400;
(35) BTK inhibitors selected from the group consisting of ACP-196, dasatinib, ibrutinib, PRN-1008, SNS-062, ONO-4059, BGB-3111, MSC-2364447, X-022, spebrutinib, TP-4207, HM-71224, KBP-7536 and AC-0025;
(36) Other drugs for treating HBV selected from the group consisting of gentiopicrin (gentiopicroside), nitazoxanide, birinapant, NOV-205 (Molixan; BAM-205), Oligotide, Mivotilate, Feron, levamisole, Ka Shu Ning, Alloferon, WS-007, Y-101 (Ti Fen Tai), rSIFN-co, PEG-IIFNm, KW-3, BP-Inter-014, oleanolic acid, HepB-nRNA, cTP-5 (rTP-5), HSK-II-2, HEISCO-106-1, HEISCO-106, Hepbarna, IBPB-006IA, Hepuyinfen, DasKloster 0014-01, Jiangantai (Ganxikang), picroside, GA5 NM-HBV, DasKloster-0039, hepulantai, IMB-2613, TCM-800B, reduced glutathione and ZH-2N; and
(37) The compounds disclosed in US20100143301 (Gilead Sciences), US20110098248 (Gilead Sciences), US20090047249 (Gilead Sciences), U.S. Pat. No. 8,722,054 (Gilead Sciences), US20140045849 (Janssen), US20140073642 (Janssen), WO2014/056,953 (Janssen), WO2014/076,221 (Janssen), WO2014/128,189 (Janssen), US20140350031 (Janssen), WO2014/023,813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (VentirxPharma), US20140275167 (Novira therapeutics), US20130251673 (Novira therapeutics), U.S. Pat. No. 8,513,184 (Gilead Sciences), US20140030221 (Gilead Sciences), US20130344030 (Gilead Sciences), US20130344029 (Gilead Sciences), US20140343032 (Roche), WO2014037480 (Roche), US20130267517 (Roche), WO2014131847 (Janssen), WO2014033176 (Janssen), WO2014033170 (Janssen), WO2014033167 (Janssen), US20140330015 (Ono pharmaceutical), US20130079327 (Ono pharmaceutical), and US20130217880 (Ono pharmaceutical).

In certain embodiments, a compound disclosed herein, or a pharmaceutically acceptable salt thereof, is combined with one, two, three, four or more additional therapeutic agents. In certain embodiments, a compound disclosed herein, or a pharmaceutically acceptable salt thereof, is combined with two additional therapeutic agents. In other embodiments, a compound disclosed herein, or a pharmaceutically acceptable salt thereof, is combined with three additional therapeutic agents. In further embodiments, a compound disclosed herein, or a pharmaceutically acceptable salt thereof, is combined with four additional therapeutic agents. The one, two, three, four or more additional therapeutic agents can be different therapeutic agents selected, from the same class of therapeutic agents, and/or they can be selected from different classes of therapeutic agents.

In a specific embodiment, a compound disclosed herein, or a pharmaceutically acceptable salt thereof, is combined with an HBV DNA polymerase inhibitor. In another specific embodiment, a compound disclosed herein, or a pharmaceutically acceptable salt thereof, is combined with an HBV DNA polymerase inhibitor and at least one additional therapeutic agent selected from the group consisting of: immunomodulators, toll-like receptor modulators (modulators of tlr1, tlr2, tlr3, tlr4, tlr5, tlr6, tlr7, tlr8, tlr9, tlr10, tlr11, tlr12 and tlr13), interferon alpha receptor ligands, hyaluronidase inhibitors, recombinant IL-7, HBsAg inhibitors, compounds targeting HbcAg, cyclophilin inhibitors, HBV therapeutic vaccines, HBV prophylactic vaccines HBV viral entry inhibitors, NTCP inhibitors, antisense oligonucleotide targeting viral mRNA, short interfering RNAs (siRNA), miRNA gene therapy agents, endonuclease modulators, inhibitors of ribonucleotide reductase, Hepatitis B virus E antigen inhibitors, recombinant scavenger receptor A (SRA) proteins, src kinase inhibitors, HBx inhibitors, cccDNA inhibitors, short synthetic hairpin RNAs (sshRNAs), HBV antibodies including HBV antibodies targeting the surface antigens of the hepatitis B virus and bispecific antibodies and "antibody-like" therapeutic proteins (such as DARTs®, Duobodies®, Bites®, XmAbs®, TandAbs®, Fab derivatives), CCR2 chemokine antagonists, thymosin agonists, cytokines, nucleoprotein inhibitors (HBV core or capsid protein inhibitors), stimulators of retinoic acid-inducible gene 1, stimulators of NOD2, stimulators of NOD1, Arginase-1 inhibitors, STING agonists, PI3K inhibitors, lymphotoxin beta receptor activators, Natural Killer Cell Receptor 2B4 inhibitors, Lymphocyte-activation gene 3 inhibitors, CD160 inhibitors, cytotoxic T-lymphocyte-associated protein 4 inhibitors, CD137 inhibitors, Killer cell lectin-like receptor subfamily G member 1 inhibitors, TIM-3 inhibitors, B- and T-lymphocyte attenuator inhibitors, CD305 inhibitors, PD-1 inhibitors, PD-L1 inhibitors, PEG-Interferon Lambda, recombinant thymosin alpha-1, BTK inhibitors, modulators of TIGIT, modulators of CD47, modulators of SIRPalpha, modulators of ICOS, modulators of CD27, modulators of CD70, modulators of OX40, modulators of NKG2D, modulators of Tim-4, modulators of B7-H4, modulators of B7-H3, modulators of NKG2A, modulators of GITR, modulators of CD160, modulators of HEVEM, modulators of CD161, modulators of Axl, modulators of Mer, modulators of Tyro, gene modifiers or editors such as CRISPR (including CRISPR Cas9), zinc finger nucleases or synthetic nucleases (TALENs), and Hepatitis B virus replication inhibitors.

In another specific embodiment, a compound disclosed herein, or a pharmaceutically acceptable salt thereof, is combined with an HBV DNA polymerase inhibitor and at least a second additional therapeutic agent selected from the group consisting of: immunomodulators, toll-like receptor modulators (modulators of tlr1, tlr2, tlr3, tlr4, tlr5, tlr6, tlr7, tlr8, tlr9, tlr10, tlr11, tlr12 and tlr13), HBsAg inhibitors, HBV therapeutic vaccines, HBV antibodies including HBV antibodies targeting the surface antigens of the hepatitis B virus and bispecific antibodies and "antibody-like" therapeutic proteins (such as DARTs®, Duobodies®, Bites®, XmAbs®, TandAbs®, Fab derivatives), cyclophilin inhibitors, stimulators of retinoic acid-inducible gene 1, PD-1 inhibitors, PD-L1 inhibitors, Arginase-1 inhibitors, PI3K inhibitors and stimulators of NOD2.

In another specific embodiment, a compound disclosed herein, or a pharmaceutically acceptable salt thereof, is combined with an HBV DNA polymerase inhibitor and at least a second additional therapeutic agent selected from the group consisting of: HBV viral entry inhibitors, NTCP inhibitors, HBx inhibitors, cccDNA inhibitors, HBV antibodies targeting the surface antigens of the hepatitis B virus, short interfering RNAs (siRNA), miRNA gene therapy agents, short synthetic hairpin RNAs (sshRNAs), and nucleoprotein inhibitors (HBV core or capsid protein inhibitors).

In another specific embodiment, a compound disclosed herein, or a pharmaceutically acceptable salt thereof, is combined with an HBV DNA polymerase inhibitor, one or two additional therapeutic agents selected from the group consisting of: immunomodulators, toll-like receptor modulators (modulators of tlr1, tlr2, tlr3, tlr4, tlr5, tlr6, tlr7, tlr8, tlr9, tlr10, tlr11, tlr12 and tlr13), HBsAg inhibitors, HBV therapeutic vaccines, HBV antibodies including HBV antibodies targeting the surface antigens of the hepatitis B virus and bispecific antibodies and "antibody-like" therapeutic proteins (such as DARTs®, Duobodies®, Bites®, XmAbs®, TandAbs®, Fab derivatives), cyclophilin inhibitors, stimulators of retinoic acid-inducible gene 1, PD-1 inhibitors, PD-L1 inhibitors, Arginase-1 inhibitors, PI3K inhibitors and stimulators of NOD2, and one or two additional therapeutic agents selected from the group consisting of: HBV viral entry inhibitors, NTCP inhibitors, HBx inhibitors, cccDNA inhibitors, HBV antibodies targeting the surface antigens of the hepatitis B virus, short interfering RNAs (siRNA), miRNA gene therapy agents, short synthetic hairpin RNAs (sshRNAs), and nucleoprotein inhibitors (HBV core or capsid protein inhibitors).

In a particular embodiment, a compound disclosed herein, or a pharmaceutically acceptable salt thereof, is combined with one, two, three, four or more additional therapeutic agents selected from adefovir (Hepsera®), tenofovir disoproxil fumarate+emtricitabine (TRUVADA®), tenofovir disoproxil fumarate (Viread®), entecavir (Baraclude®), lamivudine (Epivir-HBV®), tenofovir alafenamide, tenofovir, tenofovir disoproxil, tenofovir alafenamide fumarate, tenofovir alafenamide hemifumarate, telbivudine (Tyzeka®), Clevudine®, emtricitabine (Emtriva®), peginterferon alfa-2b (PEG-Intron®), Multiferon®, interferon alpha 1b (Hapgen®), interferon alpha-2b (Intron A®), pegylated interferon alpha-2a (Pegasys®), interferon alfa-n1 (Humoferon®), ribavirin, interferon beta-1a (Avonex®), Bioferon, Ingaron, Inmutag (Inferon), Algeron, Roferon-A, Oligotide, Zutectra, Shaferon, interferon alfa-2b (AXXO), Alfaferone, interferon alfa-2b (BioGeneric Pharma), Feron, interferon-alpha 2 (CJ), BEVAC, Laferonum, VIPEG, BLAUFERON-B, BLAUFERON-A, Intermax Alpha, Realdiron, Lanstion, Pegaferon, PDferon-B, interferon alfa-2b (IFN, Laboratorios Bioprofarma), alfainterferona 2b, Kalferon, Pegnano, Feronsure, PegiHep, interferon alfa 2b (Zydus-Cadila), Optipeg A, Realfa 2B, Reliferon, interferon alfa-2b (Amega), interferon alfa-2b (Virchow), peginterferon alfa-2b (Amega), Reaferon-EC, Proquiferon, Uniferon, Urifron, interferon alfa-2b (Changchun Institute of Biological Products), Anterferon, Shanferon, MOR-22, interleukin-2 (IL-2, Immunex), recombinant human interleukin-2 (Shenzhen Neptunus), Layfferon, Ka Shu Ning, Shang Sheng Lei Tai, INTEFEN, SINOGEN, Fukangtai, Alloferon and celmoleukin;

In a particular embodiment, a compound disclosed herein, or a pharmaceutically acceptable salt thereof, is combined with entecavir (Baraclude®), adefovir (Hepsera®), tenofovir disoproxil fumarate (Viread®), tenofovir alafenamide, tenofovir, tenofovir disoproxil, tenofovir alafenamide fumarate, tenofovir alafenamide hemifumarate, telbivudine (Tyzeka®) or lamivudine (Epivir-HBV®).

In a particular embodiment, a compound disclosed herein, or a pharmaceutically acceptable salt thereof, is combined with entecavir (Baraclude®), adefovir (Hepsera®), tenofovir disoproxil fumarate (Viread®), tenofovir alafenamide hemifumarate, telbivudine (Tyzeka®) or lamivudine (Epivir-HBV®).

In a particular embodiment, a compound disclosed herein, or a pharmaceutically acceptable salt thereof, is combined with a first additional therapeutic agent selected from the group consisting of: entecavir (Baraclude®), adefovir (Hepscra®), tenofovir disoproxil fumarate (Viread®), tenofovir alafenamide, tenofovir, tenofovir disoproxil, tenofovir alafenamide fumarate, tenofovir alafenamide hemifumarate, telbivudine (Tyzeka®) or lamivudine (Epivir-HBV®) and at least a second additional therapeutic agent selected from the group consisting of immunomodulators, toll-like receptor modulators (modulators of tlr1, tlr2, tlr3, tlr4, tlr5, tlr6, tlr7, tlr8, tlr9, tlr10, tlr11, tlr12 and tlr13), interferon alpha receptor ligands, hyaluronidase inhibitors, recombinant IL-7, HBsAg inhibitors, compounds targeting HbcAg, cyclophilin inhibitors, HBV Therapeutic vaccines, HBV prophylactic vaccines, HBV viral entry inhibitors, NTCP inhibitors, antisense oligonucleotide targeting viral mRNA, short interfering RNAs (siRNA), miRNA gene therapy agents, endonuclease modulators, inhibitors of ribonucleotide reductase, Hepatitis B virus E antigen inhibitors, recombinant scavenger receptor A (SRA) proteins, src kinase inhibitors, HBx inhibitors, cccDNA inhibitors, short synthetic hairpin RNAs (sshRNAs), HBV antibodies including HBV antibodies targeting the surface antigens of the hepatitis B virus and bispecific antibodies and "antibody-like" therapeutic proteins (such as DARTs®, Duobodies®, Bites®, XmAbs®, TandAbs®, Fab derivatives), CCR2 chemokine antagonists, thymosin agonists, cytokines, nucleoprotein inhibitors (HBV core or capsid protein inhibitors), stimulators of retinoic acid-inducible gene 1, stimulators of NOD2, stimulators of NOD1, recombinant thymosin alpha-1, Arginase-1 inhibitors, STING agonists, PI3K inhibitors, lymphotoxin beta receptor activators, Natural Killer Cell Receptor 2B4 inhibitors, Lymphocyte-activation gene 3 inhibitors, CD160 inhibitors, cytotoxic T-lymphocyte-associated protein 4 inhibitors, CD137 inhibitors, Killer cell lectin-like receptor subfamily G member 1 inhibitors, TIM-3 inhibitors, B- and T-lymphocyte attenuator inhibitors, CD305 inhibitors, PD-1 inhibitors, PD-L1 inhibitors, PEG-Interferon Lambd, BTK inhibitors, modulators of TIGIT, modulators of CD47, modulators of SIRPalpha, modulators of ICOS, modulators of CD27, modulators of CD70, modulators of OX40, modulators of NKG2D, modulators of Tim-4, modulators of B7-H4, modulators of B7-H3, modulators of NKG2A, modulators of GITR, modulators of CD160, modulators of HEVEM, modulators of CD161, modulators of Axl, modulators of Mer, modulators of Tyro, gene modifiers or editors such as CRISPR (including CRISPR Cas9), zinc finger nucleases or synthetic nucleases (TALENs), a and Hepatitis B virus replication inhibitors.

In a particular embodiment, a compound disclosed herein, or a pharmaceutically acceptable salt thereof, is combined with a first additional therapeutic agent selected from the group consisting of: entecavir (Baraclude®), adefovir (Hepsera®), tenofovir disoproxil fumarate (Viread®), tenofovir alafenamide, tenofovir, tenofovir disoproxil, tenofovir alafenamide fumarate, tenofovir alafenamide hemifumarate, telbivudine (Tyzeka®) or lamivudine (Epivir-HBV®) and at least a second additional therapeutic agent selected from the group consisting of peginterferon alfa-2b (PEG-Intron®), Multiferon®, interferon alpha 1b (Hapgen®), interferon alpha-2b (Intron A®), pegylated interferon alpha-2a (Pegasys®), interferon alfa-n1 (Humoferon®), ribavirin, interferon beta-1a (Avonex®), Bioferon, Ingaron, Inmutag (Inferon), Algeron, Roferon-A, Oligotide, Zutectra, Shaferon, interferon alfa-2b (AXXO), Alfaferone, interferon alfa-2b (BioGeneric Pharma), Feron, interferon-alpha 2 (CJ), BEVAC, Laferonum, VIPEG, BLAUFERON-B, BLAUFERON-A, Intermax Alpha, Realdiron, Lanstion, Pegaferon, PDferon-B, interferon alfa-2b (IFN, Laboratorios Bioprofarma), alfainterferona 2b, Kalferon, Pegnano, Feronsure, PegiHep, interferon alfa 2b (Zydus-Cadila), Optipeg A, Realfa 2B, Reliferon, interferon alfa-2b (Amega), interferon alfa-2b (Virchow), peginterferon alfa-2b (Amega), Reaferon-EC, Proquiferon, Uniferon, Urifron, interferon alfa-2b (Changchun Institute of Biological Products), Anterferon, Shanferon, MOR-22, interleukin-2 (IL-2, Immunex), recombinant human interleukin-2 (Shenzhen Neptunus), Layfferon, Ka Shu Ning, Shang Sheng Lei Tai, INTEFEN, SINOGEN, Fukangtai, Alloferon and celmoleukin;

In a particular embodiment, a compound disclosed herein, or a pharmaceutically acceptable salt thereof, is combined with a first additional therapeutic agent selected from the group consisting of: entecavir (Baraclude®), adefovir (Hepsera®), tenofovir disoproxil fumarate (Viread®), tenofovir alafenamide, tenofovir, tenofovir disoproxil, tenofovir alafenamide fumarate, tenofovir alafenamide hemifumarate, telbivudine (Tyzeka®) or lamivudine (Epivir-HBV®) and at least a second additional therapeutic agent selected from the group consisting of immunomodulators, toll-like receptor modulators (modulators of tlr1, tlr2, tlr3, tlr4, tlr5, tlr6, tlr7, tlr8, tlr9, tlr10, tlr11, tlr12 and tlr13), HBsAg inhibitors, HBV therapeutic vaccines, HBV antibodies including HBV antibodies targeting the surface antigens of the hepatitis B virus and bispecific antibodies and "antibody-like" therapeutic proteins (such as DARTs®, Duobodies®, Bites®, XmAbs®, TandAbs®, Fab derivatives), cyclophilin inhibitors, stimulators of retinoic acid-inducible gene 1, Arginase-1 inhibitors, PI3K inhibitors, PD-1 inhibitors, PD-L1 inhibitors and stimulators of NOD2.

In a particular embodiment, a compound disclosed herein, or a pharmaceutically acceptable salt thereof, is combined with a first additional therapeutic agent selected from the group consisting of: entecavir (Baraclude®), adefovir (Hepsera®), tenofovir disoproxil fumarate (Viread®), tenofovir alafenamide, tenofovir, tenofovir disoproxil, tenofovir alafenamide fumarate, tenofovir alafenamide hemifumarate, telbivudine (Tyzeka®) or lamivudine (Epivir-HBV®) and at least a second additional therapeutic agent selected from the group consisting of HBV viral entry inhibitors, NTCP inhibitors, HBx inhibitors, cccDNA inhibitors, HBV antibodies targeting the surface antigens of the hepatitis B virus, short interfering RNAs (siRNA), miRNA gene therapy agents, short synthetic hairpin RNAs (sshRNAs), and nucleoprotein inhibitors (HBV core or capsid protein inhibitors).

In a particular embodiment, a compound disclosed herein, or a pharmaceutically acceptable salt thereof, is combined with a first additional therapeutic agent selected from the group consisting of: entecavir (Baraclude®), adefovir (Hepsera®), tenofovir disoproxil fumarate (Viread®), tenofovir alafenamide, tenofovir, tenofovir disoproxil, tenofovir alafenamide fumarate, tenofovir alafenamide hemifumarate, telbivudine (Tyzeka®) or lamivudine (Epivir-HBV®), one or two additional therapeutic agents selected from the group consisting of: immunomodulators, toll-like receptor modulators (modulators of tlr1, tlr2, tlr3, tlr4, tlr5, tlr6, tlr7, tlr8, tlr9, tlr10, tlr11, tlr12 and tlr13), HBsAg inhibitors, HBV therapeutic vaccines, HBV antibodies including HBV antibodies targeting the surface antigens of the hepatitis B virus and bispecific antibodies and "antibody-like" therapeutic proteins (such as DARTs®, Duobodies®, Bites®, XmAbs®, TandAbs®, Fab derivatives), cyclophilin inhibitors, stimulators of retinoic acid-inducible gene 1, PD-1 inhibitors, PD-L1 inhibitors, Arginase-1 inhibitors, PI3K inhibitors and stimulators of NOD2, and one or two additional therapeutic agents selected from the group consisting of: HBV viral entry inhibitors, NTCP inhibitors, HBx inhibitors, cccDNA inhibitors, HBV antibodies targeting the surface antigens of the hepatitis B virus, short interfering RNAs (siRNA), miRNA gene therapy agents, short synthetic hairpin RNAs (sshRNAs), and nucleoprotein inhibitors (HBV core or capsid protein inhibitors).

In certain embodiments, a compound disclosed herein, or a pharmaceutically acceptable salt thereof, is combined with 5-30 mg tenofovir alafenamide fumarate, tenofovir alafenamide hemifumarate, or tenofovir alafenamide. In certain embodiments, a compound disclosed herein, or a pharmaceutically acceptable salt thereof, is combined with 5-10; 5-15; 5-20; 5-7.5; 25-30; 20-30; 15-30; or 10-30 mg tenofovir alafenamide fumarate, tenofovir alafenamide hemifumarate, or tenofovir alafenamide. In certain embodiments, a compound disclosed herein, or a pharmaceutically acceptable salt thereof, is combined with 10 mg tenofovir alafenamide fumarate, tenofovir alafenamide hemifumarate, or tenofovir alafenamide. In certain embodiments, a compound disclosed herein, or a pharmaceutically acceptable salt thereof, is combined with 25 mg tenofovir alafenamide fumarate, tenofovir alafenamide hemifumarate, or tenofovir alafenamide. A compound as disclosed herein (e.g., a compound of formula (I) and/or a compound of formula (II)) may be combined with the agents provided herein in any dosage amount of the compound (e.g., from 50 mg to 500 mg of compound) the same as if each combination of dosages were specifically and individually listed.

In certain embodiments, a compound disclosed herein, or a pharmaceutically acceptable salt thereof, is combined with 100-400 mg tenofovir disoproxil fumarate, tenofovir disoproxil hemifumarate, or tenofovir disoproxil. In certain embodiments, a compound disclosed herein, or a pharmaceutically acceptable salt thereof, is combined with 100-150; 100-200, 100-250; 100-300; 100-350; 150-200; 150-250; 150-300; 150-350; 150-400; 200-250; 200-300; 200-350; 200-400; 250-350; 250-400; 350-400 or 300-400 mg tenofovir disoproxil fumarate, tenofovir disoproxil hemifumarate, or tenofovir disoproxil. In certain embodiments, a compound disclosed herein, or a pharmaceutically acceptable salt thereof, is combined with 300 mg tenofovir disoproxil fumarate, tenofovir disoproxil hemifumarate, or tenofovir disoproxil. In certain embodiments, a compound disclosed herein, or a pharmaceutically acceptable salt thereof, is combined with 250 mg tenofovir disoproxil fumarate, tenofovir disoproxil hemifumarate, or tenofovir disoproxil. In certain embodiments, a compound disclosed herein, or a pharmaceutically acceptable salt thereof, is combined with 150 mg tenofovir disoproxil fumarate, tenofovir disoproxil hemifumarate, or tenofovir disoproxil. A compound as disclosed herein (e.g., a compound of formula (I) and/or a compound of formula (II)) may be combined with the agents provided herein in any dosage amount of the compound (e.g., from 50 mg to 500 mg of compound) the same as if each combination of dosages were specifically and individually listed.

In certain embodiments, when a compound disclosed herein is combined with one or more additional therapeutic agents as described above, the components of the composition are administered as a simultaneous or sequential regimen. When administered sequentially, the combination may be administered in two or more administrations.

In certain embodiments, a compound disclosed herein is combined with one or more additional therapeutic agents in a unitary dosage form for simultaneous administration to a patient, for example as a solid dosage form for oral administration.

In certain embodiments, a compound disclosed herein is administered with one or more additional therapeutic agents. Co-administration of a compound disclosed herein with one or more additional therapeutic agents generally refers to simultaneous or sequential administration of a compound disclosed herein and one or more additional therapeutic agents, such that therapeutically effective amounts of the compound disclosed herein and one or more additional therapeutic agents are both present in the body of the patient.

Co-administration includes administration of unit dosages of the compounds disclosed herein before or after administration of unit dosages of one or more additional therapeutic agents, for example, administration of the compound disclosed herein within seconds, minutes, or hours of the administration of one or more additional therapeutic agents. For example, in some embodiments, a unit dose of a compound disclosed herein is administered first, followed within seconds or minutes by administration of a unit dose of one or more additional therapeutic agents. Alternatively, in other embodiments, a unit dose of one or more additional therapeutic agents is administered first, followed by administration of a unit dose of a compound disclosed herein within seconds or minutes. In some embodiments, a unit dose of a compound disclosed herein is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound disclosed herein.

Anti-HIV Combination Therapy

In certain embodiments, a method for treating or preventing an HIV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, four, one or two, or one to three, or one to four) additional therapeutic agents. In one embodiment, a method for treating an HIV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, four, one or two, or one to three, or one to four) additional therapeutic agents.

In certain embodiments, the present disclosure provides a method for treating an HIV infection, comprising administering to a patient in need thereof a therapeutically effective amount of a compound disclosed herein, or a pharmaceutically acceptable salt thereof, in combination with a therapeutically effective amount of one or more additional therapeutic agents which are suitable for treating an HIV infection.

In one embodiment, pharmaceutical compositions comprising a compound disclosed herein, or a pharmaceutically acceptable salt thereof, in combination with one or more (e.g., one, two, three, four, one or two, or one to three, or one to four) additional therapeutic agents, and a pharmaceutically acceptable carrier, diluent or excipient are provided.

In one embodiment, kits comprising a compound disclosed herein, or a pharmaceutically acceptable salt thereof, in combination with one or more (e.g., one, two, three, four, one or two, or one to three, or one to four) additional therapeutic agents are provided.

In the above embodiments, the additional therapeutic agent may be an anti-HIV agent. For example, in some embodiments, the additional therapeutic agent is selected from the group consisting of HIV protease inhibitors, HIV non-nucleoside inhibitors of reverse transcriptase, HIV nucleoside or nucleotide inhibitors of reverse transcriptase, HIV integrase inhibitors, HIV non-catalytic site (or allosteric) integrase inhibitors, entry inhibitors (e.g., CCR5 inhibitors, gp41 inhibitors (i.e., fusion inhibitors) and CD4 attachment inhibitors), CXCR4 inhibitors, gp120 inhibitors, G6PD and NADH-oxidase inhibitors, compounds that target the HIV capsid ("capsid inhibitors"; e.g., capsid polymerization inhibitors or capsid disrupting compounds such as those disclosed in WO 2013/006,738 (Gilead Sciences), US 2013/0165489 (University of Pennsylvania), and WO 2013/006,792 (Pharma Resources), pharmacokinetic enhancers, and other drugs for treating HIV, and combinations thereof.

In further embodiments, the additional therapeutic agent is selected from one or more of:

(1) HIV protease inhibitors selected from the group consisting of amprenavir, atazanavir, fosamprenavir, indinavir, lopinavir, ritonavir, nelfmavir, saquinavir, tipranavir, brecanavir, darunavir, TMC-126, TMC-114, mozenavir (DMP-450), JE-2147 (AG1776), L-756423, R00334649, KNI-272, DPC-681, DPC-684, GW640385X, DG17, PPL-100, DG35, and AG 1859;

(2) HIV non-nucleoside or non-nucleotide inhibitors of reverse transcriptase selected from the group consisting of capravirine, emivirine, delaviridine, efavirenz, nevirapine, (+) calanolide A, etravirine, GW5634, DPC-083, DPC-961, DPC-963, MIV-150, TMC-120, rilpivirene, BILR 355 BS, VRX 840773, lersivirine (UK-453061), RDEA806, KM023 and MK-1439;

(3) HIV nucleoside or nucleotide inhibitors of reverse transcriptase selected from the group consisting of zidovudine, emtricitabine, didanosine, stavudine, zalcitabine, lamivudine, abacavir, abavavir sulfate, amdoxovir, elvucitabine, alovudine, MIV-210, ±-FTC, D-d4FC, emtricitabine, phosphazide, fozivudine tidoxil, apricitibine (AVX754), KP-1461, GS-9131 (Gilead Sciences) and fosalvudine tidoxil (formerly HDP 99.0003), tenofovir, tenofovir disoproxil fumarate, tenofovir alafenamide (Gilead Sciences), tenofovir alafenamide hemifumarate (Gilead Sciences), GS-9148 (Gilead Sciences), adefovir, adefovir dipivoxil, CMX-001 (Chimerix) or CMX-157 (Chimerix);

(4) HIV integrase inhibitors selected from the group consisting of curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, AR-177, L-870812, and L-870810, raltegravir, BMS-538158, GSK364735C, BMS-707035, MK-2048, BA 011, elvitegravir, dolutegravir and GSK-744;

(5) HIV non-catalytic site, or allosteric, integrase inhibitors (NCINI) including, but not limited to, BI-224436, CX0516, CX05045, CX14442, compounds disclosed in WO 2009/062,285 (Boehringer Ingelheim), WO 2010/130,034 (Boehringer Ingelheim), WO 2013/159,064 (Gilead Sciences), WO 2012/145,728 (Gilead Sciences), WO 2012/003,497 (Gilead Sciences), WO 2012/003,498 (Gilead Sciences) each of which is incorporated by references in its entirety herein;

(6) gp41 inhibitors selected from the group consisting of enfuvirtide, sifuvirtide, albuvirtide, FB006M, and TRI-1144;

(7) the CXCR4 inhibitor AMD-070;

(8) the entry inhibitor SP01A;

(9) the gp120 inhibitor BMS-488043;

(10) the G6PD and NADH-oxidase inhibitor immunitin;

(11) CCR5 inhibitors selected from the group consisting of aplaviroc, vicriviroc, maraviroc, cenicriviroc, PRO-140, INCB15050, PF-232798 (Pfizer), and CCR5mAb004;

(12) CD4 attachment inhibitors selected from the group consisting of ibalizumab (TMB-355) and BMS-068 (BMS-663068);

(13) pharmacokinetic enhancers selected from the group consisting of cobicistat and SPI-452; and

(14) other drugs for treating HIV selected from the group consisting of BAS-100, SPI-452, REP 9, SP-01A, TNX-355, DES6, ODN-93, ODN-112, VGV-1, PA-457 (bevirimat), HRG214, VGX-410, KD-247, AMZ 0026, CYT 99007A-221 HIV, DEBIO-025, BAY 50-4798, MDX010 (ipilimumab), PBS 119, ALG 889, and PA-1050040 (PA-040), and combinations thereof.

In certain embodiments, the additional therapeutic agent is a Toll-like receptor 8 modulator selected from the group consisting of motolimod, resiquimod, 3M-051, 3M-052, MCT-465, IMO-4200, VTX-763, VTX-1463 and those disclosed in US20140045849 (Janssen), US20140073642

(Janssen), WO2014/056,953 (Janssen), WO2014/076,221 (Janssen), WO2014/128,189 (Janssen), US20140350031 (Janssen), WO2014/023,813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (VentirxPharma), US20140275167 (Novira therapeutics), US20130251673 (Novira therapeutics), U.S. Pat. No. 9,670,205 (Gilead Sciences Inc.), US20160289229 (Gilead Sciences Inc.), U.S. patent application Ser. No. 15/692,161 (Gilead Sciences Inc.), and U.S. patent application Ser. No. 15/692,093 (Gilead Sciences Inc.).

In certain embodiments, the one or more additional therapeutic agents include a Toll-like receptor 8 (TLR8) modulator. In some embodiments, the Toll-like receptor 8 (TLR8) modulator is a Toll-like receptor 8 (TLR8) agonist. In some embodiments, the Toll-like receptor 8 (TLR8) agonist is a compound disclosed in U.S. Pat. No. 9,670,205, or a pharmaceutically acceptable salt thereof.

In certain embodiments, a compound disclosed herein, or a pharmaceutically acceptable salt thereof, is combined with one, two, three, four or more additional therapeutic agents. In certain embodiments, a compound disclosed herein, or a pharmaceutically acceptable salt thereof, is combined with two additional therapeutic agents. In other embodiments, a compound disclosed herein, or a pharmaceutically acceptable salt thereof, is combined with three additional therapeutic agents. In further embodiments, a compound disclosed herein, or a pharmaceutically acceptable salt thereof, is combined with four additional therapeutic agents. The two, three, four or more additional therapeutic agents can be different therapeutic agents selected from the same class of therapeutic agents, or they can be selected from different classes of therapeutic agents. In a specific embodiment, a compound disclosed herein, or a pharmaceutically acceptable salt thereof, is combined with an HIV nucleoside or nucleotide inhibitor of reverse transcriptase and an HIV non-nucleoside inhibitor of reverse transcriptase. In another specific embodiment, a compound disclosed herein, or a pharmaceutically acceptable salt thereof, is combined with an HIV nucleoside or nucleotide inhibitor of reverse transcriptase, and an HIV protease inhibiting compound. In a further embodiment, a compound disclosed herein, or a pharmaceutically acceptable salt thereof, is combined with an HIV nucleoside or nucleotide inhibitor of reverse transcriptase, an HIV non-nucleoside inhibitor of reverse transcriptase, and an HIV protease inhibiting compound. In an additional embodiment, a compound disclosed herein, or a pharmaceutically acceptable salt thereof, is combined with an HIV nucleoside or nucleotide inhibitor of reverse transcriptase, an HIV non-nucleoside inhibitor of reverse transcriptase, and a pharmacokinetic enhancer. In another embodiment, a compound disclosed herein, or a pharmaceutically acceptable salt thereof, is combined with two HIV nucleoside or nucleotide inhibitor of reverse transcriptase.

In a particular embodiment, a compound disclosed herein, or a pharmaceutically acceptable salt thereof, is combined with abacavir sulfate, tenofovir, tenofovir disoproxil fumarate, tenofovir alafenamide, or tenofovir alafenamide hemifumarate.

In a particular embodiment, a compound disclosed herein, or a pharmaceutically acceptable salt thereof, is combined with tenofovir, tenofovir disoproxil fumarate, tenofovir alafenamide, or tenofovir alafenamide hemifumarate.

In a particular embodiment, a compound disclosed herein, or a pharmaceutically acceptable salt thereof, is combined with a first additional therapeutic agent selected from the group consisting of: abacavir sulfate, tenofovir, tenofovir disoproxil fumarate, tenofovir alafenamide, and tenofovir alafenamide hemifumarate and a second additional therapeutic agent selected from the group consisting of emtricitibine and lamivudine. In a particular embodiment, a compound disclosed herein, or a pharmaceutically acceptable salt thereof, is combined with a first additional therapeutic agent selected from the group consisting of: tenofovir, tenofovir disoproxil fumarate, tenofovir alafenamide, and tenofovir alafenamide hemifumarate and a second additional therapeutic agent, wherein the second additional therapeutic agent is emtricitibine.

In some embodiments, a method of treating HIV in a subject comprises administering to the subject a therapeutically effective amount of any of the compounds described herein (e.g., a compound of Formula I or a compound of Formula II, or a pharmaceutically acceptable salt thereof) in combination with an immunotherapeutic agent, such as an immune checkpoint inhibitor, an hematopoietic progenitor kinase 1 (HPK1) inhibitor, an immune checkpoint stimulatory protein agonist, or an engineered immune cell (for example a T cell with an chimeric antigen receptor (i.e., a CAR T cell) or a T cell with an engineered T cell receptor (TCR), In some embodiments, the compound is administered to the subject prior to, subsequent to, or simultaneous to administration of one or more immunotherapeutic agents. In some embodiments, the compound is administered to the subject about 30 minutes or more, about 1 hour or more, about 2 hours or more, about 4 hours or more, about 6 hours or more, about 12 hours or more, about 24 hours or more, about 48 hours or more, or about 72 hour or more prior to or subsequent to administration of the one or more immunotherapeutic agents. In some embodiments, the compound is administered to the subject about 30 minutes or less, about 1 hour or less, about 2 hours or less, about 4 hours or less, about 6 hours or less, about 12 hours or less, about 24 hours or less, about 48 hours or less, or about 72 hour or less prior to or subsequent to administration of the one or more immunotherapeutic agents.

In some embodiments, a method of treating HIV in a subject comprises administering to the subject a therapeutically effective amount of any of the compounds described herein (e.g., a compound of Formula I or a compound of Formula II, or a pharmaceutically acceptable salt thereof) in combination with a therapeutically effective amount of one or more immune checkpoint inhibitors. In some embodiments, the compound is administered to the subject prior to, subsequent to, or simultaneous to administration of the immune checkpoint inhibitor. In some embodiments, the immune checkpoint inhibitor is a small-molecule inhibitor. In some embodiments, the immune checkpoint inhibitor is an antibody or a fragment thereof. In some embodiments, the immune checkpoint inhibitor inhibits the Adenosine $A_{2A}$ Receptor (A2aR), B7-H3, V-Set Domain-Containing T-cell Activation Inhibitor 1 (VTCN1, also known as B7-H4), the B- and T-Lymphocyte Attenuator (BTLA), cytotoxic T-Lypmphocyte-Associated protein 4 (CTLA-4), Killer-cell Immunoglobulin-like Receptor (KIR), Lymphocyte Activation Gene 3 (LAG3), Programmed Death 1 (PD-1), Programmed Death Ligand 1 (PD-L1), Programmed Death Ligand 2 (PD-L2), T-cell Immunoreceptor with Ig and ITIM Domains (TIGIT), T-cell Immunoglobulin and Mucin-Domain Containing 3 (TIM-3), or V-Domain Ig Suppressor of T-cell Activation (VISTA). Exemplary immune checkpoint inhibitors include, but are not limited to, avelumab, atezolizumab, durvalumab, nivolumab, pembrolizumab, ipilimumab, PDR001, TSR-042, and BMS-986016.

In some embodiments, a method of treating HIV in a subject comprises administering to the subject a therapeutically effective amount of any of the compounds described herein (e.g., a compound of Formula I or a compound of Formula II, or a pharmaceutically acceptable salt thereof) in combination with a therapeutically effective amount of one or more immune checkpoint stimulatory protein agonists. In some embodiments, the compound is administered to the subject prior to, subsequent to, or simultaneous to administration of the immune checkpoint stimulatory protein agonist. In some embodiments, the immune checkpoint stimulatory protein agonist is an antibody or a fragment thereof. In some embodiments, the immune checkpoint stimulatory protein agonist is an agonist of CD27, CD28, CD40, CD122, 4-1BB, OX40, Glucocorticoid-Induced TNFR family related protein (GITR), or Inducible T-Cell Costimulator (ICOS).

In some embodiments, a method of treating HIV in a subject comprises administering to the subject a therapeutically effective amount of any of the compounds described herein (e.g., a compound of Formula I or a compound of Formula II, or a pharmaceutically acceptable salt thereof) in combination with a therapeutically effective amount of engineered immune cells, such as CAR T cells or T cells with an engineered TCR. In some embodiments, the compound is administered to the subject prior to, subsequent to, or simultaneous to administration of the engineered immune cells. In some embodiments, the engineered immune cells are heterologous engineered immune cells, such as heterologous engineered T cells (e.g., CAR T cells or T cells with an engineered TCR). In some embodiments, the engineered immune cells are autologous engineered immune cells, such as autologous engineered T cells (e.g., CAR T cells or T cells with an engineered TCR).

In some embodiments, a method of treating HIV in a subject comprises administering to the subject a therapeutically effective amount of any of the compounds described herein (e.g., a compound of Formula I or a compound of Formula II, or a pharmaceutically acceptable salt thereof) in combination with (1) a therapeutically effective amount of engineered immune cells, such as CAR T cells or T cells with an engineered TCR, and (2) a therapeutically effective amount of an immune checkpoint inhibitor or an immune checkpoint stimulatory protein agonist. In some embodiments, a method of treating HIV in a subject comprises administering to the subject a therapeutically effective amount of any of the compounds described herein (e.g., a compound of Formula I or a compound of Formula II, or a pharmaceutically acceptable salt thereof) in combination with (1) a therapeutically effective amount of engineered immune cells, such as CAR T cells or T cells with an engineered TCR, and (2) a therapeutically effective amount of an antiviral agent (such as an anti-HIV agent). In some embodiments, a method of treating HIV in a subject comprises administering to the subject a therapeutically effective amount of any of the compounds described herein (e.g., a compound of Formula I or a compound of Formula II, or a pharmaceutically acceptable salt thereof) in combination with (1) a therapeutically effective amount of an immune checkpoint inhibitor or an immune checkpoint stimulatory protein agonist, and (2) a therapeutically effective amount of an antiviral agent (such as an anti-HIV agent). In some embodiments, a method of treating HIV in a subject comprises administering to the subject a therapeutically effective amount of any of the compounds described herein (e.g., a compound of Formula I or a compound of Formula II, or a pharmaceutically acceptable salt thereof) in combination with (1) a therapeutically effective amount of engineered immune cells, such as CAR T cells or T cells with an engineered TCR, (2) a therapeutically effective amount of an immune checkpoint inhibitor or an immune checkpoint stimulatory protein agonist, and (3) a therapeutically effective amount of an antiviral agent (such as an anti-HIV agent).

In certain embodiments, when a compound disclosed herein is combined with one or more additional therapeutic agents as described above, the components of the composition are administered as a simultaneous or sequential regimen. When administered sequentially, the combination may be administered in two or more administrations.

In certain embodiments, a compound disclosed herein is combined with one or more additional therapeutic agents in a unitary dosage form for simultaneous administration to a patient, for example as a solid dosage form for oral administration.

In certain embodiments, a compound disclosed herein is administered with one or more additional therapeutic agents. Co-administration of a compound disclosed herein with one or more additional therapeutic agents generally refers to simultaneous or sequential administration of a compound disclosed herein and one or more additional therapeutic agents, such that therapeutically effective amounts of the compound disclosed herein and one or more additional therapeutic agents are both present in the body of the patient.

Co-administration includes administration of unit dosages of the compounds disclosed herein before or after administration of unit dosages of one or more additional therapeutic agents, for example, administration of the compound disclosed herein within seconds, minutes, or hours of the administration of one or more additional therapeutic agents. For example, in some embodiments, a unit dose of a compound disclosed herein is administered first, followed within seconds or minutes by administration of a unit dose of one or more additional therapeutic agents. Alternatively, in other embodiments, a unit dose of one or more additional therapeutic agents is administered first, followed by administration of a unit dose of a compound disclosed herein within seconds or minutes. In some embodiments, a unit dose of a compound disclosed herein is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound disclosed herein.

Kits

Provided herein are also kits that include a compound of Formula I, or a pharmaceutically acceptable salt, stereoisomer, prodrug, or solvate thereof, and suitable packaging. In one embodiment, a kit further includes instructions for use. In one aspect, a kit includes a compound of Formula I, or a pharmaceutically acceptable salt, stereoisomer, prodrug, or solvate thereof, and a label and/or instructions for use of the compounds in the treatment of the indications, including the diseases or conditions, described herein.

Also provided herein are also kits that include a compound of Formula II, or a pharmaceutically acceptable salt, stereoisomer, prodrug, or solvate thereof; and suitable packaging. In one embodiment, a kit further includes instructions for use. In one aspect, a kit includes a compound of Formula II, or a pharmaceutically acceptable salt, stereoisomer, prodrug, or solvate thereof, and a label and/or instructions for use of the compounds in the treatment of the indications, including the diseases or conditions, described herein.

Provided herein are also articles of manufacture that include a compound described herein or pharmaceutically acceptable salts, isomer, or a mixture thereof in a suitable container. The container may be a vial, jar, ampoule, preloaded syringe, and intravenous bag.

Pharmaceutical Compositions and Modes of Administration

Compounds provided herein are usually administered in the form of pharmaceutical compositions. Thus, provides herein are also pharmaceutical compositions that contain one or more of the compounds described herein or pharmaceutically acceptable salts, isomer, or a mixture thereof and one or more pharmaceutically acceptable vehicles selected from carriers, adjuvants and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

The pharmaceutical compositions may be administered in either single or multiple doses. The pharmaceutical composition may be administered by various methods including, for example, rectal, buccal, intranasal and transdermal routes. In certain embodiments, the pharmaceutical composition may be administered by intra-arterial injection, intravenously, intraperitoneally, parenterally, intramuscularly, subcutaneously, orally, topically, or as an inhalant.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds described herein. Administration may be via, for example, capsule or enteric coated tablets. In making the pharmaceutical compositions that include at least one compound described herein or pharmaceutically acceptable salts, isomer, or a mixture thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one compound described herein or pharmaceutically acceptable salts, isomer, or a mixture thereof can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds described herein in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound described herein or pharmaceutically acceptable salts, isomer, or a mixture thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

Dosing

The specific dose level of a compound of the present application for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound described herein per kilogram of the subject's body weight (mg/kg). Dosages of between about 0.1 and 150 mg/kg may be appropriate. In some embodiments, about 0.1 and 100 mg/kg may be appropriate. In other embodiments a dosage of between 0.5 and 60 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

The daily dosage may also be described as a total amount of a compound described herein administered per dose or per day. Daily dosage of a compound of Formula I or a compound of Formula II, or a pharmaceutically acceptable salt thereof, may be between about 1 mg and 4,000 mg, between about 2,000 to 4,000 mg/day, between about 1 to 2,000 mg/day, between about 1 to 1,000 mg/day, between about 10 to 500 mg/day, between about 20 to 500 mg/day, between about 50 to 300 mg/day, between about 75 to 200 mg/day, or between about 15 to 150 mg/day.

When administered orally, the total daily dosage for a human subject may be between 1 mg and 1,000 mg, between about 10-500 mg/day, between about 50-300 mg/day, between about 75-200 mg/day, or between about 100-150 mg/day.

In some embodiments, daily dosage (which may be an oral dosage) of a compound of Formula I or a compound of Formula II, or a pharmaceutically acceptable salt thereof, is between about 40 mg/day and about 120 mg/day, between about 60 mg/day and about 100 mg/day, or about 80 mg/day.

The compounds of the present application or the compositions thereof may be administered once, twice, three, or four times daily, using any suitable mode described above. Also, administration or treatment with the compounds may be continued for a number of days; for example, commonly treatment would continue for at least 7 days, 14 days, or 28 days, for one cycle of treatment. Treatment cycles are well known in cancer chemotherapy, and are frequently alternated with resting periods of about 1 to 28 days, commonly about 7 days or about 14 days, between cycles. The treatment cycles, in other embodiments, may also be continuous.

In a particular embodiment, the method comprises administering to the subject an initial daily dose of about 1 to 500 mg of a compound described herein and increasing the dose by increments until clinical efficacy is achieved. Increments of about 5, 10, 25, 50, or 100 mg can be used to increase the dose. The dosage can be increased daily, every other day, twice per week, or once per week.

Synthesis of the Compounds of Formula I and Formula II

The compounds may be prepared using the methods disclosed herein and routine modifications thereof, which will be apparent given the disclosure herein and methods well known in the art. Conventional and well-known synthetic methods may be used in addition to the teachings herein. The synthesis of typical compounds described herein may be accomplished as described in the following examples. If available, reagents may be purchased commercially, e.g., from Sigma Aldrich or other chemical suppliers.

General Synthesis

Typical embodiments of compounds described herein may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments described in the present disclosure, inspection of the structure of the compound to be synthesized will provide the identity of each substituent group. The identity of the final product will generally render apparent the identity of the necessary starting materials by a simple process of inspection, given the examples herein. In general, compounds described herein are typically stable and isolatable at room temperature and pressure.

Synthetic Reaction Parameters

The compounds of this disclosure can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts (1999) Protecting Groups in Organic Synthesis, 3rd Edition, Wiley, New York, and references cited therein.

Furthermore, the compounds of this disclosure may contain one or more chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

The terms "solvent", "inert organic solvent", or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, and the like). Unless specified to the contrary, the solvents used in the reactions of the present invention are inert organic solvents, and the reactions are carried out under an inert gas, preferably nitrogen.

The term "q.s." means adding a quantity sufficient to achieve a stated function, e.g., to bring a solution to the desired volume (i.e., 100%).

Compounds of Formula I and Formula II

The compounds of Formula I and/or Formula II may prepared by the schemes shown below.

Each of the intermediates in the below schemes may be isolated and/or purified prior to the subsequent step, or used in the next step without purification and/or isolation. It will also be appreciated that the addition of any substituent may result in the production of a number of isomeric products any or all of which may be isolated and purified using conventional techniques.

EXAMPLES

The following examples are included to demonstrate specific embodiments of the disclosure. It should be appreciated by those of skill in the art that the techniques disclosed in the examples which follow represent techniques discovered by the inventor to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

List of Abbreviations and Acronyms

| Abbreviation | Meaning |
| --- | --- |
| % | Percent |
| ° C. | Degree Celsius |
| A2B | Adenosine A2B receptor |
| Ac | Acetyl |
| ACN/CH$_3$CN/MeCN | Acetonitrile |
| ADME | Absorption, distribution, metabolism and excretion |
| APECED | Autoimmune polyendocrinopathy-candidiasis-ectodermal dystrophy |
| ASK | Apoptosis signal-regulating kinase |
| BAPN | Beta-aminoproprionitrile |
| BCNU | Carmustine |
| bicarb | Bicarbonate |
| br | Broad |
| BRD | Bromodomain containing protein inhibitor |
| BTK | Bruton's tyrosine kinase |
| CAS | Chemical Abstract Service |
| CD | Cluster of differentiation |
| CHOP | Cyclophosphamide |
| CNS | Central nervous system |
| COPD | Chronic obstructive pulmonary disease |
| CREST | Calcinosis, Raynaud's syndrome, esophageal dysmotility, sclerodactyly and telangiectasia |
| CRISPR | Clustered regularly interspaced short palindromic repeats |
| CVP | Cyclophosphamide, vincristine, prednisone |
| d | Doublet |
| D | Deuterium |
| D.T. PACE | Dexamethasone, thalidomide, cisplatin, Adriamycin ®, cyclophosphamide, etoposide |
| D/d | Deuterium |
| DABCO ® | 1,4-Diazabicyclo[2.2.2]octane |
| DCE | Dichloroethane |
| DCM/CH$_2$Cl$_2$ | Dichloromethane/methylene chloride |
| dd | Doublet of doublets |
| DDR | Discoidin domain receptor |
| DIPEA/DIEA | N,N-Diisopropylethylamine |
| DMF | Dimethylformamide |
| DMFO | Difluoromethylornithine |
| DMPK | Drug metabolism and pharmacokinetics |
| DMSO | Dimethylsulfoxide |
| DTIC | Dacarbazine |
| EC$_{50}$ | The half maximal effective concentration |
| equiv/eq | Equivalents |
| Et | Ethyl |
| EtOAc/AcOEt | Ethylacetate |
| EtOH | Ethanol |
| F | Fahrenheit |
| Fab | Fragment antigen-binding |
| FBS | Fetal bovine serum |
| FCM | Fludarabine, cyclophosphamide, mitoxantrone |
| FCR | Fludarabine, cyclophosphamide, rituximab |
| FOLFIRI | Fluorouracil, leucovorin, and irinotecan |
| FR | Fludarabine, rituximab |
| g | Grams |
| GITR | Glucocorticoid-induced TNFR-related protein |
| Gp | Glycoprotein |
| h/hr | Hours |
| HATU | (1-[Bis(dimethylamino)methylene]-1H-1,2,3-triazolo[4,5-b]pyridinium 3-oxid hexafluorophosphate) |
| HbcAg | Hepatitis B core antigen |
| HBsAg | Hepatitis B surface antigen |
| HBV | Hepatitis B virus |
| HBx | Hepatitis B viral protein |
| HDAC | Histone deacetylase |
| hex | Hexanes |
| HPLC | High pressure liquid chromatography |
| hyperCVAD | Hyperfractionated cyclophosphamide, vincristine, doxorubicin, dexamethasone, methotrexate, cytarabine |
| Hz | Hertz |
| ICE | Iphosphamide, carboplatin, etoposide |
| ICOS | Inducible T-cell COStimulator |
| IDH | Isocitrate dehydrogenase |
| IDO1 | Indoleamine 2,3-dioxygenase 1 |
| IL | Interleukin |
| INCB24360 | Epacadostat |
| IUPAC | International Union of Pure and Applied Chemistry |
| J | Coupling constant (MHz) |
| JAK | Janus kinase |
| Kg/kg | Kilogram |
| LACA | 1-Azetidine-2-carboxylic acid |
| LCMS/LC-MS | Liquid chromatography-mass spectrometry |
| LOX | Lysyl oxidase protein |
| LOXL | Lysyl oxidase-like protein |
| M | Molar |
| m | multiplet |
| M+ | Mass peak |
| M + H | Mass peak plus hydrogen |
| MCP | Mitoxantrone, chlorambucil, and prednisolone |
| Me | Methyl |
| mg | Milligram |
| MHz | Megahertz |
| min/m | Minute |
| miRNA | MicroRNA |
| ml/mL | Milliliter |
| mM | Millimolar |

151
-continued

| Abbreviation | Meaning |
|---|---|
| MMF | Ester derivative mycophenolate mofetil |
| mmol | Millimole |
| MMP | Matrix metalloprotease |
| mol | Mole |
| MS | Mass spectroscopy |
| MS | Multiple sclerosis |
| N | Normal |
| NADH | Nicotinamide adenine dinucleotide in reduced form |
| NCINI | Non-catalytic site, or allosteric, integrase inhibitors |
| ng | Nanograms |
| nM | NanoMolar |
| NMR | Nuclear magnetic resonance |
| NTCP | $Na^+$-taurocholate cotransporting polypeptide |
| PD-L | Programmed death-ligand |
| PEG | Polyethylene glycol |
| PEI | Polymer polyethyleneimine |
| PET | Positron emission tomography |
| Ph | Phenyl |
| PI3K | Phosphoinositide 3-kinase |
| PKC | Protein kinase C |
| prep | Preparative |
| q.s. | Quantity sufficient to achieve a stated function |
| RA | Rheumatoid arthritis |
| R-CHOP | Rituximab-CHOP (Rituximab plus CHOP) |
| R-CVP | Rituximab-CVP (Rituximab plus CVP) |
| Rf | Retention factor |
| R-FCM | Rituximab plus FCM |
| R-hyperCVAD | Rituximab-hyperCVAD |
| R-ICE | Rituximab-ICE |
| R-MCP | Rituximab-MCP |
| RPM | Revolutions per minute |
| rSIFN-co | Recombinant super compound interferon |
| RT/rt | Room temperature |
| s | Second |
| s | Singlet |
| SAHA | Vorinostat |
| sat. | Saturated |
| SERMs | Selective estrogen receptor modulators |
| siRNA | Short interfering RNAs |
| SIRP | Signal-regulatory protein |
| SLE | Systemic lupus erythematosus |
| SPECT | Single-photon emission computed tomography |
| SRA | Scavenger receptor A |
| Src | Proto-oncogene tyrosine-protein kinase |
| sshRNAs | Short synthetic hairpin RNAs |
| STING | Sequence To and withIN Graphics |
| SYK | Spleen tyrosine kinase |
| t | Triplet |
| TALENs | Transcription activator-like effector nucleases |
| TCA | Trichloroacetic acid |
| TEA | Triethylamine |
| temp. | Temperature |
| TFA | Trifluoroacetic acid |
| THF | Tetrahydrofuran |
| TIGIT | T cell immunoreceptor with Ig and ITIM domains |
| TIM | T-cell immunoglobulin and mucin domain |
| TKM-HBV | TKM-HepB |
| Tlr | Toll-like receptor modulators |
| TNF | Tumor necrosis factor |
| TPL2 | Serine/threonine kinase |
| Vac | Vacuum |
| w/v | Weight/volume |
| w/w | Weight/weight |
| YPEG-rhIFNalpha-2a | PEG-interferon alfa-2a |
| YPEG-rhIFNalpha-2b | Ypeginterferon alfa-2b |
| δ | Chemical shift (ppm) |
| μg | Microgram |
| μL/μl | Microliter |
| μM | Micromolar |
| μm | Micrometer |
| μmol | Micromole |

152
General Synthetic Sequence of Formula I

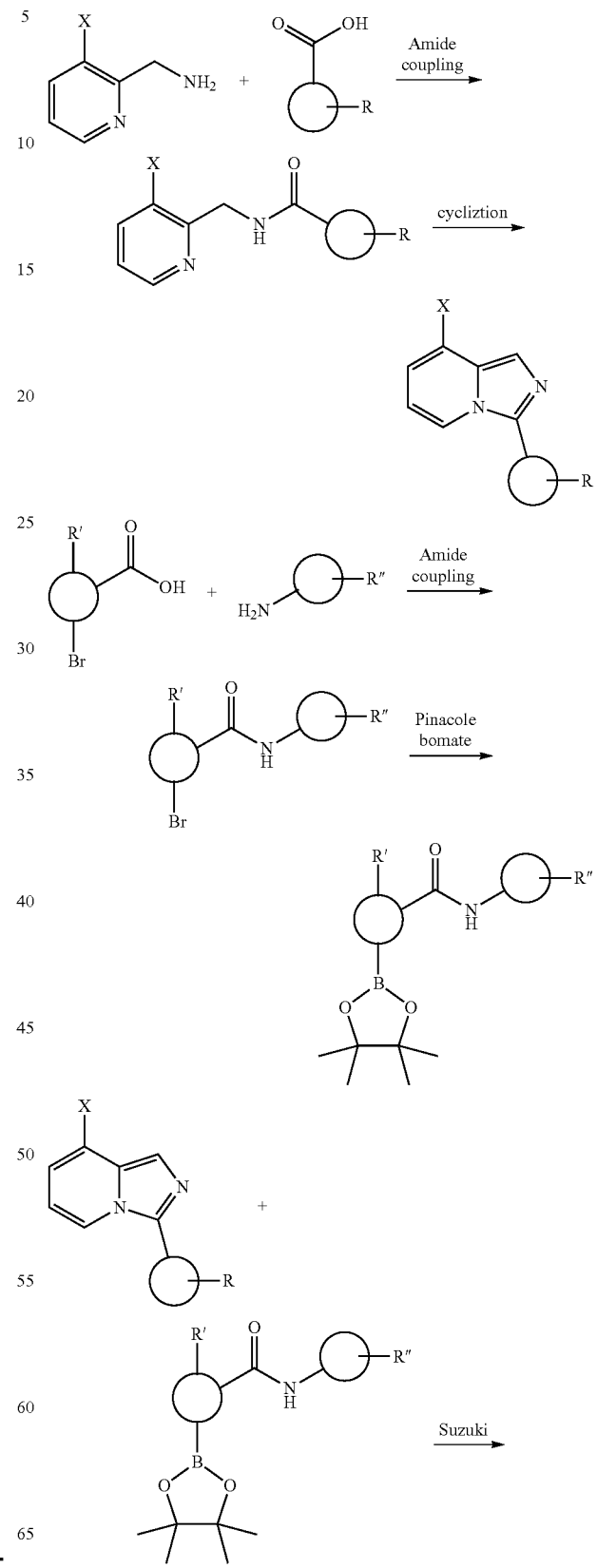

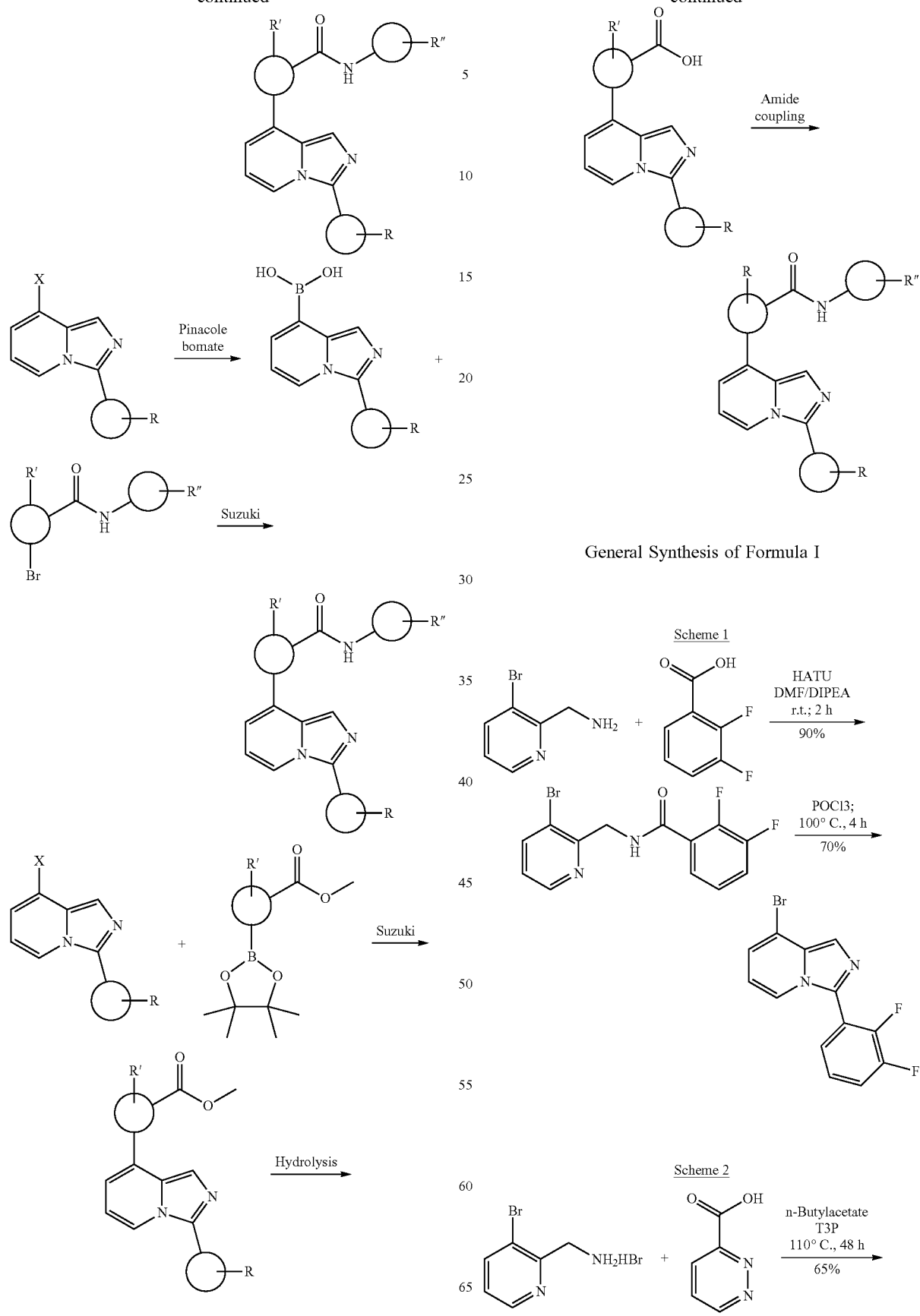

155
-continued
156
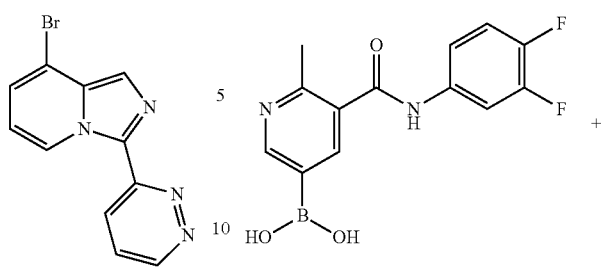
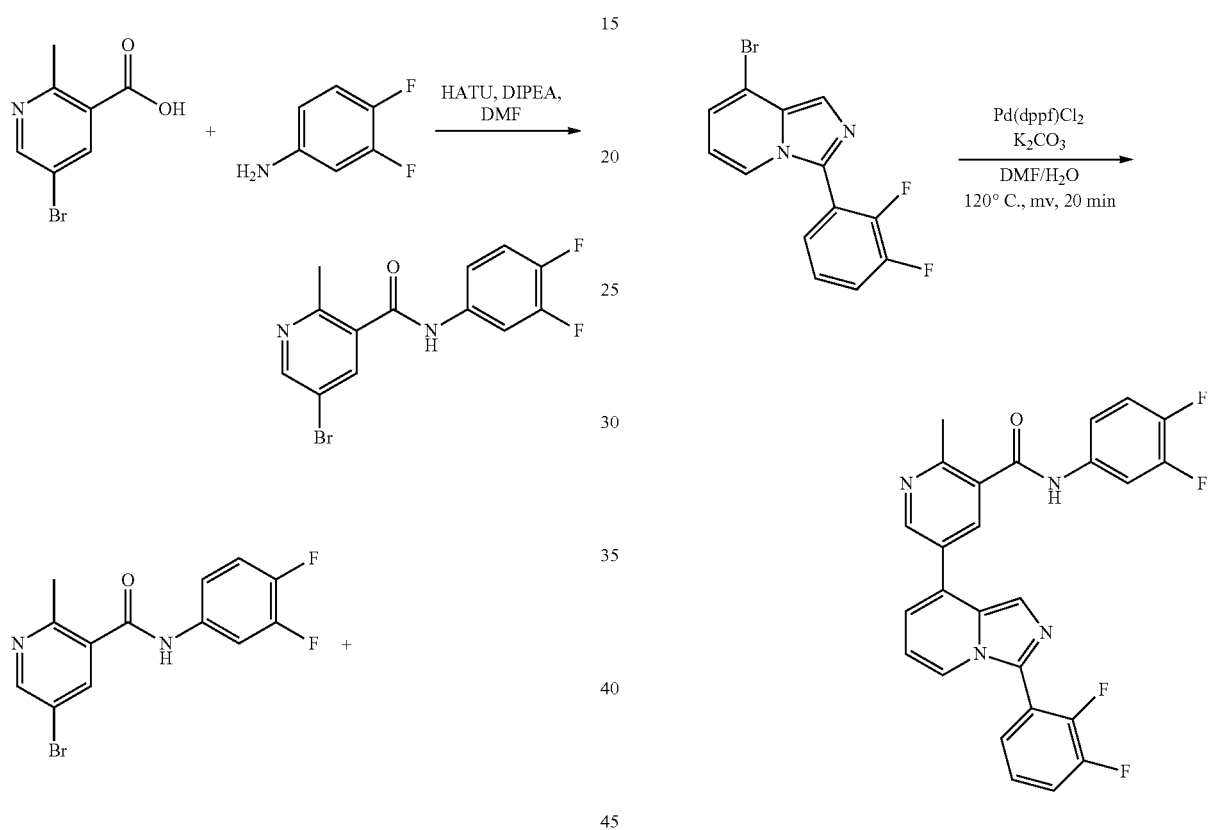
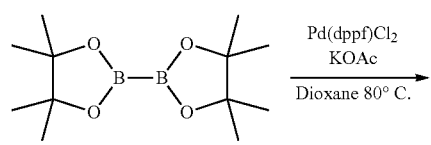
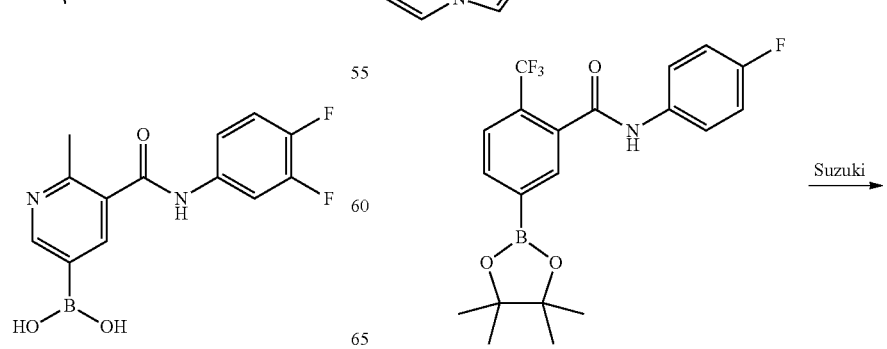

-continued

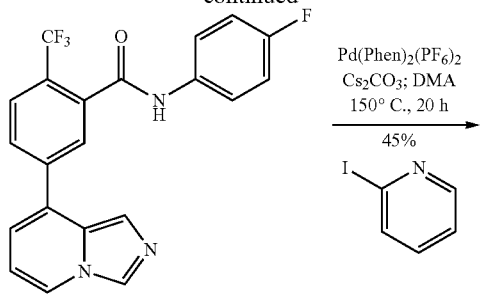

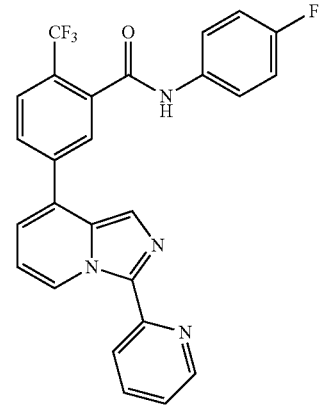

Example 1

5-(3-(2-carbamoylphenyl)-[1,2,4]triazolo[4,3-a]pyridin-8-yl)-N-(4-fluorophenyl)-2-methylbenzamide

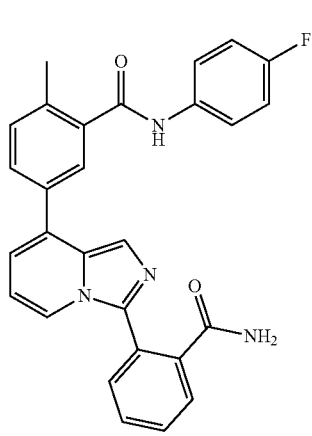 [SMILES: Cc1ccc(-c2cccn3c(-c4ccccc4C(N)=O)ncc23)cc1C(=O)Nc1ccc(F)cc1]

Example 1 was synthesized following the procedure explained for the synthesis of Example 9; using (2-cyanophenyl)boronic acid instead of phenyl boronic acid. Under the Suzuki conditions, the nitrile was converted to the amide. C27H20FN5O2; 466.1 (M+1); 1H NMR (400 MHz, Methanol-d4) δ 8.22 (d, J=1.9 Hz, 1H), 8.01-7.90 (m, 3H), 7.83-7.71 (m, 5H), 7.66 (dd, J=7.0, 1.0 Hz, 1H), 7.53 (d, J=8.0 Hz, 1H), 7.24-7.00 (m, 3H), 2.58 (s, 3H), 1.30 (s, 3H).

Example 2

N-(4-fluorophenyl)-2-methyl-5-(3-(5-methyl-1,3,4-oxadiazol-2-yl)imidazo[1,5-a]pyridin-8-yl)benzamide

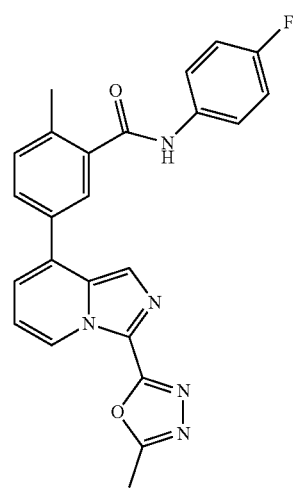 [SMILES: Cc1nnc(-c2ncc3c(-c4ccc(C)c(C(=O)Nc5ccc(F)cc5)c4)cccn23)o1]

This compound was synthesized in a manner similar to that employed in the synthesis of Example 48 using 5-methyl-1,3,4-oxadiazole-2-carboxylic acid. MS m/z 428.2 (M+H)

Example 3

N-(4-fluorophenyl)-2-methyl-5-(3-(1-methyl-1H-1,2,3-triazol-5-yl)imidazo[1,5-a]pyridin-8-yl)benzamide

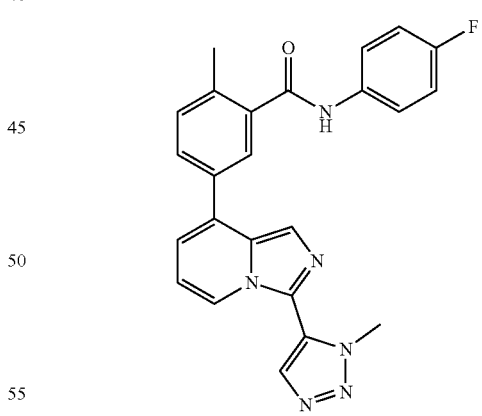

This compound was synthesized in a manner similar to that employed in the synthesis of Example 17 using 1-methyl-1H-1,2,3-triazole-5-carboxylic acid instead of pyridazine-3-carboxylic acid and performing Suzuki with N-(4-fluorophenyl)-2-methyl-5-(4,4,5,5-tetramethyl-1,3,2-dioxaborolan-2-yl)benzamide. C24H19FN6O. 427.1 (M+H). ¹H NMR (400 MHz, Chloroform-d) δ 8.21 (s, 1H), 8.07 (d, J=6.9 Hz, 1H), 7.93 (s, 1H), 7.78 (s, 1H), 7.74-7.51 (m, 4H), 7.47 (d, J=8.0 Hz, 1H), 7.14-6.89 (m, 4H), 4.32 (s, 3H), 2.60 (s, 3H).

Example 4

N-(4-fluorophenyl)-2-methyl-5-(3-(2-methylpyridin-3-yl)-[1,2,4]triazolo[4,3-a]pyridin-8-yl)benzamide

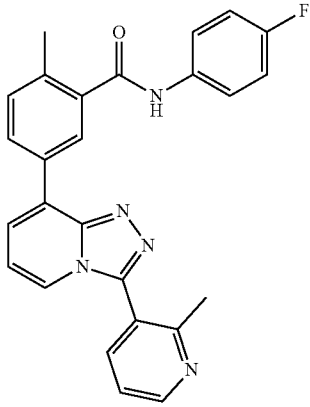 [SMILES: Cc1ccc(-c2cccn3c(-c4cccnc4C)nnc23)cc1C(=O)Nc1ccc(F)cc1]

Example 4 was synthesized following the procedure explained for the synthesis of Example 9; using (2-methylpyridin-3-yl)boronic acid instead of phenyl boronic acid. C26H20FN5O; 438.1 (M+1); 1H NMR (400 MHz, DMSO-d6) δ 10.49 (s, 1H), 8.72 (dd, J=4.9, 1.7 Hz, 1H), 8.35 (dt, J=4.5, 2.0 Hz, 2H), 8.16 (d, J=6.8 Hz, 1H), 8.05 (dd, J=7.8, 1.8 Hz, 1H), 7.92-7.72 (m, 3H), 7.62-7.41 (m, 2H), 7.20 (t, J=8.9 Hz, 2H), 7.13 (t, J=7.0 Hz. 1H). 2.48 (s, 3H), 2.41 (s, 3H).

Example 5

5-(3-(4-fluoro-2-methylphenyl)-[1,2,4]triazolo[4,3-a]pyridin-8-yl)-N-(4-fluorophenyl)-2-methylbenzamide

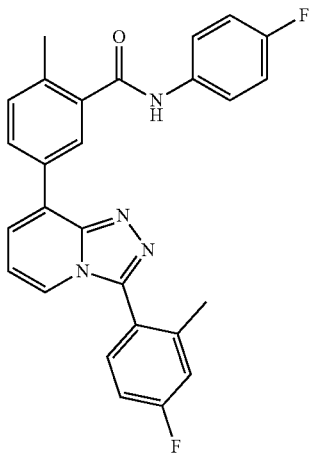 [SMILES: Cc1ccc(-c2cccn3c(-c4ccc(F)cc4C)nnc23)cc1C(=O)Nc1ccc(F)cc1]

Example 5 was synthesized following the procedure explained for the synthesis of Example 9; using (4-fluoro-2-methylphenyl)boronic acid instead of phenyl boronic acid. C27H20F2N4O; 455.1 (M+1); 1H NMR (400 MHz, DMSO-d6) δ 10.48 (s, 1H), 8.33 (d, J=7.6 Hz, 2H), 8.07 (d, J=6.9 Hz, 1H), 7.89-7.72 (m, 3H), 7.69-7.60 (m, 1H), 7.51 (d, J=7.8 Hz, 1H), 7.40 (dd, J=10.2, 2.6 Hz, 1H), 7.29 (td, J=8.6, 2.7 Hz, 1H), 7.20 (t, J=8.9 Hz, 2H), 7.11 (t, J=6.9 Hz, 1H), 2.48 (s, 3H), 2.20 (s, 3H).

Example 6

2-(8-(3-((4-fluorophenyl)carbamoyl)-4-(trifluoromethyl)phenyl)imidazo[1,5-a]pyridin-3-yl)isonicotinamide

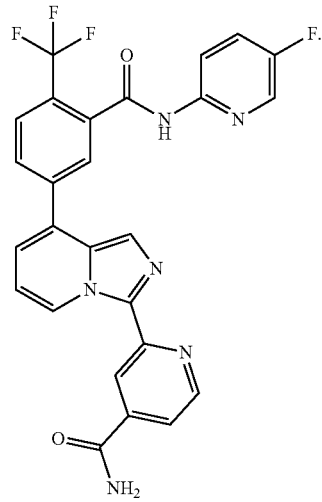 [SMILES: NC(=O)c1ccnc(-c2ncc3c(-c4ccc(C(F)(F)F)c(C(=O)Nc5ccc(F)cn5)c4)cccn23)c1]

Example 6 was synthesized following the procedure explained for the synthesis of Example 17 using 3-cyanobenzoic acid instead of pyridazine-3-carboxylic acid. Under the Suzuki conditions, the nitrile was converted to the amide. C27H17F4N5O2. 520.1 (M+1). 1H NMR (400 MHz, DMSO-d6) δ 10.73 (s, 1H), 9.98 (d, J=7.2 Hz, 1H), 8.89-8.78 (m, 1H), 8.70 (d, J=1.4 Hz, 1H), 8.40 (s, 1H), 8.11 (d, J=8.3 Hz, 1H), 8.08-7.97 (m, 2H), 7.90 (d, J=0.9 Hz, 1H), 7.80-7.63 (m, 3H), 7.28 (d, J=6.8 Hz, 1H), 7.19 (t, J=8.9 Hz, 2H), 7.11 (t, J=7.0 Hz, 1H), 5.73 (s, 1H).

Example 7

5-(3-(1,2,3-oxadiazol-5-yl)imidazo[1,5-a]pyridin-8-yl)-N-(4-fluorophenyl)-2-methylbenzamide

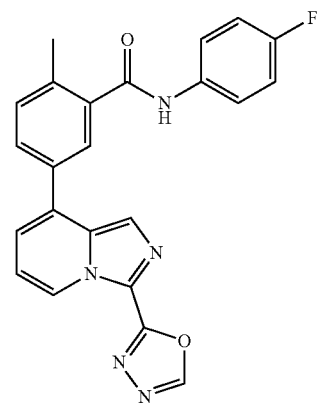 [SMILES: Cc1ccc(-c2cccn3c(-c4nnco4)ncc23)cc1C(=O)Nc1ccc(F)cc1]

This compound was synthesized in a manner similar to that employed in the synthesis of Example 17 using 1,3,4-oxadiazole-2-carboxylic acid instead of pyridazine-3-carboxylic acid and performing Suzuki with N-(4-fluorophenyl)-2-methyl-5-(4,4,5,5-tetramethyl-1,3,2-dioxaborolan-2-yl)benzamide. C23H16FN5O2. 414.1 (M+H). ¹H NMR (400 MHz, Chloroform-d) δ 8.57 (s, 1H), 7.93 (s, 1H), 7.78 (s, 1H), 7.37 (t, J=7.4 Hz, 3H), 7.21-6.98 (m, 7H), 2.60 (s, 3H).

Example 8

N-(4-fluorophenyl)-5-(3-(1-methyl-1H-1,2,3-triazol-5-yl)imidazo[1,5-a]pyridin-8-yl)-2-(trifluoromethyl)benzamide

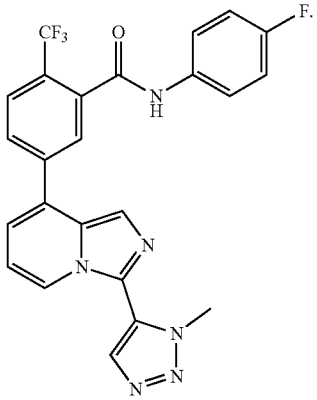 [SMILES: Cn1nncc1-c1ncc2c(-c3ccc(C(F)(F)F)c(C(=O)Nc4ccc(F)cc4)c3)cccn12]

This compound was synthesized in a manner similar to that employed in the synthesis of Example 17 using 1-methyl-1H-1,2,3-triazole-5-carboxylic acid instead of pyridazine-3-carboxylic acid. C24H16F4N6O. 481.1 (M+H). 1H NMR (400 MHz, Chloroform-d) δ8.23 (s, 1H), 8.13 (d, J=7.1 Hz, 1H), 8.03-7.84 (m, 4H), 7.64-7.52 (m, 3H), 7.16-6.93 (m, 4H), 4.34 (s, 3H).

Example 9

N-(4-fluorophenyl)-2-methyl-5-(3-phenyl-[1,2,4]triazolo[4,3-a]pyridin-8-yl)benzamide

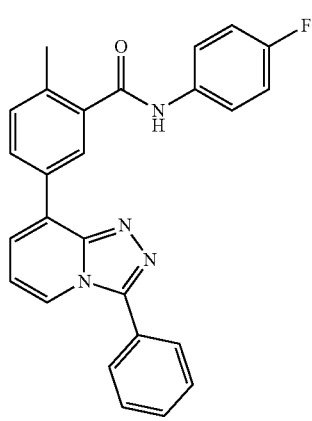 [SMILES: Cc1ccc(-c2cccn3c(-c4ccccc4)nnc23)cc1C(=O)Nc1ccc(F)cc1]

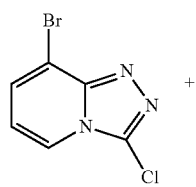 +

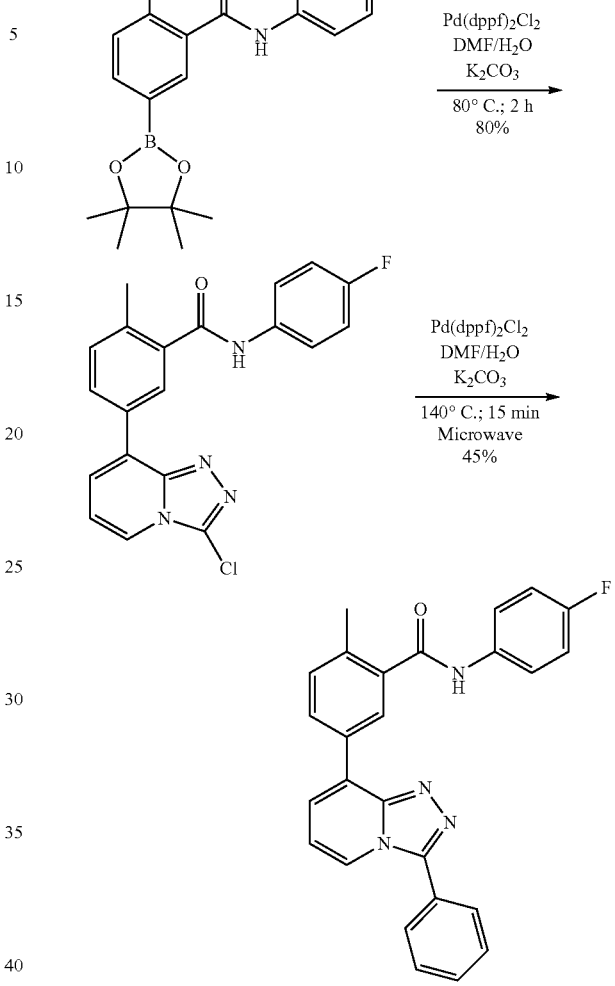

To a suspension of 8-bromo-3-chloro-[1,2,4]triazolo[4,3-a]pyridine (50 mg, 0.18 mmol), N-(4-fluorophenyl)-2-methyl-5-(4,4,5,5-tetramethyl-1,3,2-dioxaborolan-2-yl)benzamide (51 mg, 0.22 mmol) and potassium carbonate (26 mg, 0.18 mmol) in DMF/Water (9:1) palladium catalyst (5 mol %) was added. The reaction mixture was heated at about 80° C. for about 2 h. The reaction was diluted with ethyl acetate, filtered through celite. The filtrate was washed with water, brine, and dried over MgSO4, filtered and concentrated in vacuo. The residue was used without further purification for the next step.

To a suspension of 5-(3-chloro-[1,2,4]triazolo[4,3-a]pyridin-8-yl)-N-(4-fluorophenyl)-2-methylbenzamide (30 mg, 0.08 mmol), phenyl boronic acid (14 mg, 0.12 mmol), potassium carbonate (11 mg, 0.08 mmol)) in DMF/Water (9:1) palladium catalyst (5 mol %) was added. The reaction mixture was subjected to microwave irradiation at about 140° C. for about 15 min. The reaction was diluted with ethyl acetate, filtered through celite and concentrated. The residue was purified by prep HPLC using Gilson reverse phase eluting with ACN and water with 0.1% TFA using Luna column, to give the title compound (14 mg, 45% yield). C26H19FN4O; 423.1 (M+1); 1H NMR (400 MHz, DMSO-d6) δ 10.49 (s, 1H), 8.56 (d, J=6.9 Hz, 1H), 8.39-8.19 (m, 2H), 7.96-7.89 (m, 2H), 7.85-7.74 (m, 3H), 7.64

(dd, J=8.5, 6.9 Hz, 3H), 7.52 (d, J=8.6 Hz, 1H), 7.20 (t, J=8.8 Hz, 2H), 7.15 (t, J=7.0 Hz, 1H), 2.48 (s, 3H).

Example 10

5-(3-(4-cyanopyridin-2-yl)imidazo[1,5-a]pyridin-8-yl)-N-(4-fluorophenyl)-2-(trifluoromethyl)benzamide

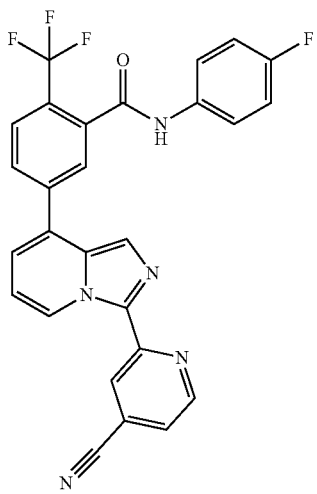 [SMILES: N#Cc1ccnc(-c2ncc3c(-c4ccc(C(F)(F)F)c(C(=O)Nc5ccc(F)cc5)c4)cccn23)c1]

Example 10 was synthesized following the procedure explained for the synthesis of Example 33 using 2-iodoisonicotinonitrile instead of 2-iodopyridine. C27H15F4N5O. 502.1 (M+1). 1H NMR (400 MHz, DMSO-d6) δ10.76 (s, 1H), 9.92 (d, J=7.3 Hz, 1H), 8.95 (d, J=5.1 Hz, 1H), 8.59 (t, J=1.2 Hz, 1H), 8.13 (d, J=8.2 Hz, 1H), 8.08 (s, 1H), 8.04 (d, J=8.2 Hz, 1H), 7.96 (s, 1H), 7.81 (dd, J=5.2, 1.6 Hz, 1H), 7.78-7.67 (m, 3H), 7.35 (d, J=6.7 Hz, 1H), 7.25-7.14 (m, 3H).

Example 11

N-(4-fluorophenyl)-2-methyl-5-(3-(pyridin-3-yl)-[1,2,4]triazolo[4,3-a]pyridin-8-yl)benzamide

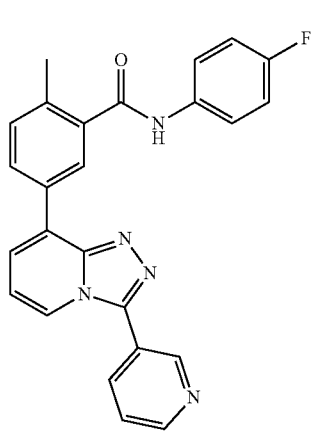 [SMILES: Cc1ccc(-c2cccn3c(-c4cccnc4)nnc23)cc1C(=O)Nc1ccc(F)cc1]

Example 11 was synthesized following the procedure explained for the synthesis of Example 9; using pyridin-3-ylboronic acid instead of phenyl boronic acid. C25H18FN5O; 424.1 (M+1); 1H NMR (400 MHz, DMSO-d6) δ 10.50 (s, 1H), 9.13 (d, J=2.2 Hz, 1H), 8.82 (dd, J=4.9, 1.6 Hz, 1H), 8.62 (d, J=7.0 Hz, 1H), 8.39 (dt, J=8.0, 2.0 Hz, 1H), 8.32 (d, J=7.8 Hz, 2H), 7.84 (d, J=7.0 Hz, 7.82-7.75 (m, 2H), 7.71 (dd, J=7.9, 4.9 Hz, 1H), 7.52 (d, J=7.8 Hz, 1H), 7.26-7.12 (m, 3H), 2.48 (s, 3H).

Example 12

N-(4-fluorophenyl)-2-methyl-5-(3-(o-tolyl)-[1,2,4]triazolo[4,3-a]pyridin-8-yl)benzamide

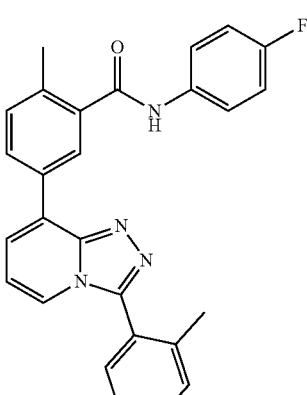

Example 12 was synthesized following the procedure explained for the synthesis of Example 9; using o-tolylboronic acid instead of phenyl boronic acid. C27H21FN4O; 437.1 (M+1); 1H NMR (400 MHz, DMSO-d6) δ 10.49 (s, 1H), 8.34 (d, J=8.0 Hz, 2H), 8.05 (dd, J=6.9, 0.9 Hz, 1H), 7.89-7.72 (m, 3H), 7.60-7.49 (m, 4H), 7.45 (td, J=7.4, 1.6 Hz, 1H), 7.20 (t, J=8.9 Hz, 2H), 7.11 (t, J=6.9 Hz, 1H), 2.48 (s, 3H), 2.21 (s, 3H).

Example 13

N-(4-fluorophenyl)-5-(3-(1-methyl-1H-imidazol-4-yl)imidazo[1,5-a]pyridin-8-yl)-2-(trifluoromethyl)benzamide

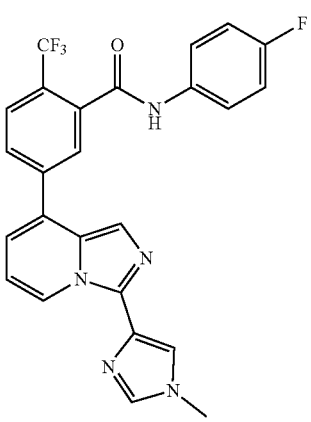 [SMILES: Cn1cnc(-c2ncc3c(-c4ccc(C(F)(F)F)c(C(=O)Nc5ccc(F)cc5)c4)cccn23)c1]

This compound was synthesized in a manner similar to that employed in the synthesis of Example 17 using 1-methyl-1H-imidazole-4-carboxylic acid instead of pyridazine-3-carboxylic acid. C25H17F4N5O. 480.1 (M+H). 1H NMR (400 MHz, Methanol-d4) δ 11.51 (s, 1H), 10.09 (s, 1H), 9.09-8.58 (m, 7H), 8.57-8.44 (m, 2H), 8.10-7.75 (m, 5H), 4.63 (s, 3H).

Example 14

N-(4-fluorophenyl)-2-methyl-5-(3-(1-methyl-1H-imidazol-4-yl)imidazo[1,5-a]pyridin-8-yl)benzamide

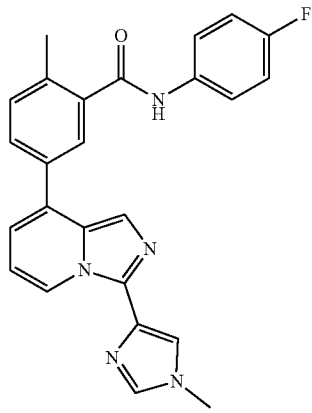 [SMILES: Cc1ccc(-c2cccn3c(-c4cn(C)cn4)ncc23)cc1C(=O)Nc1ccc(F)cc1]

This compound was synthesized in a manner similar to that employed in the synthesis of Example 17 using 1-methyl-1H-imidazole-4-carboxylic acid instead of pyridazine-3-carboxylic acid and performing Suzuki with N-(4-fluorophenyl)-2-methyl-5-(4,4,5,5-tetramethyl-1,3,2-dioxaborolan-2-yl)benzamide. C25H20FN5O. 426.1 (M+H). 1H NMR (400 MHz, Chloroform-d) δ 9.67 (d, J=6.6 Hz, 1H), 8.36 (s, 1H), 7.97 (d, J=7.0 Hz, 2H), 7.81-7.36 (m, 6H), 7.17-6.93 (m, 4H), 3.86 (s, 3H), 2.59 (s, 3H).

Example 15

5-(3-(3-cyanopyridin-2-yl)imidazo[1,5-a]pyridin-8-yl)-N-(4-fluorophenyl)-2-(trifluoromethyl)benzamide

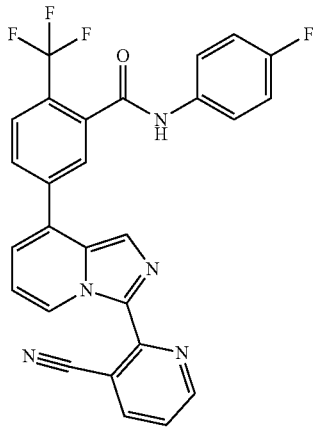 [SMILES: N#Cc1cccnc1-c1ncc2c(-c3ccc(C(F)(F)F)c(C(=O)Nc4ccc(F)cc4)c3)cccn12]

Example 15 was synthesized following the procedure explained for the synthesis of Example 33 using 2-iodonicotinonitrile instead of 2-iodopyridine. C27H15F4N5O. 502.1 (M+1).

Example 16

N-(4-fluorophenyl)-2-methyl-5-(3-(2-(trifluoromethyl)phenyl)imidazo[1,5-a]pyridin-8-yl)nicotinamide

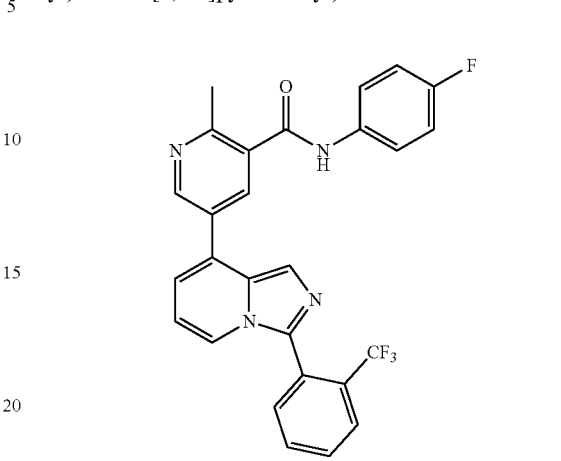

Example 16 was made analogously to Example 24 (5-(3-(2,6-difluorophenyl)imidazo[1,5-a]pyridin-8-yl)-N-(4-fluorophenyl)-2-methylnicotinamide) using 2-(trifluoromethyl)benzoic acid in place of 2,6-difluorobenzoic acid. C27H18F4N4O. 492.2 (M+1). 1H NMR (400 MHz, DMSO-d6) δ 10.62 (s, 1H), 8.99 (d, J=2.2 Hz, 1H), 8.30 (d, J=2.2 Hz, 1H), 8.02 (dd, J=7.8, 1.4 Hz, 1H), 7.95-7.81 (m, 4H), 7.78 (ddt, J=7.7, 4.8, 2.4 Hz, 3H), 7.27-7.18 (m, 2H), 7.15 (d, J=6.7 Hz, 1H), 6.84 (t, J=6.9 Hz, 1H), 2.68 (s, 3H).

Example 17

N-(4-fluorophenyl)-5-(3-(pyridazin-3-yl)imidazo[1,5-a]pyridin-8-yl)-2-(trifluoromethyl)benzamide

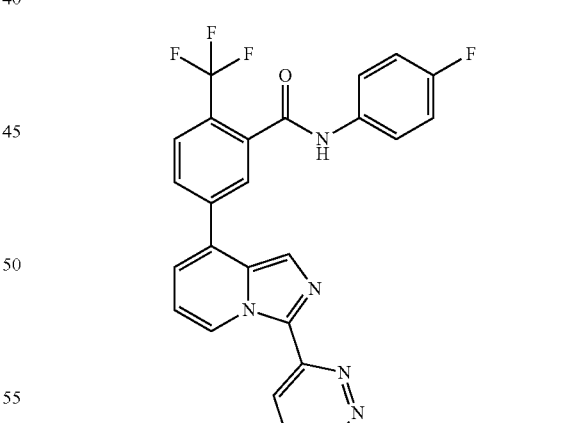

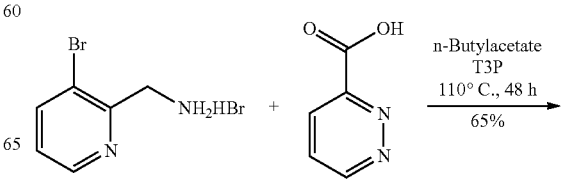

-continued

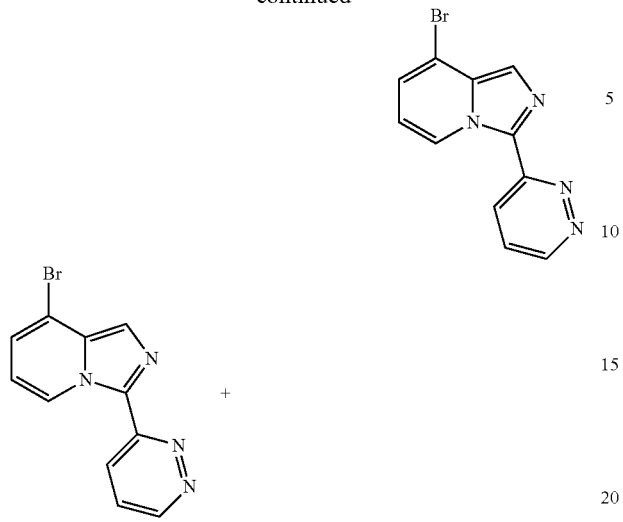

To a suspension of (3-bromopyridin-2-yl)methanamine hydrobromide (100 mg, 0.37 mmol) and the pyridazine-3-carboxylic acid (60 mg, 0.49 mmol) in n-butyl acetate (5 mL), T3P (propylphosphonic anhydride. 50% wt. in ethyl acetate; 2 mL) was added and stirred at room temperature for about 30 min. The reaction mixture was heated at about 100° C. for about 48 h. The reaction mixture was cooled, diluted with ethyl acetate, washed with sodium bicarbonate, water, brine and dried over sodium sulphate and concentrated. The residue was purified by prep HPLC using Gilson reverse phase eluting with ACN and water with 0.1% TFA using Luna column, to get the cyclized compound 8-bromo-3-(pyridazin-3-yl)imidazo[1,5-a]pyridine (65 mg, 64% yield). 275.1 (M+1).

To a suspension of 8-bromo-3-(pyridazin-3-yl)imidazo[1,5-a]pyridine (65 mg, 0.23 mmol), N-(4-fluorophenyl)-5-(4,4,5,5-tetramethyl-1,3,2-dioxaborolan-2-yl)-2-(trifluoromethyl)benzamide (97 mg, 0.0.23 mmol), potassium carbonate (12 mg, 0.08 mmol)) in DMF/Water (9:1) palladium catalyst (5 mol %) was added. The reaction mixture was subjected to microwave irradiation at about 120° C. for about 20 min. The reaction was diluted with ethyl acetate, filtered through celite and concentrated. The residue was purified by prep HPLC using Gilson reverse phase column eluting with ACN and water with 0.1% TFA using Luna column, to give the title compound (70 mg, 62% yield). C25H15F4N5O. 478.1 (M+1). 1H NMR (400 MHz, DMSO-d6) δ 10.76 (s, 1H), 9.99 (dt, J=7.2, 0.9 Hz, 1H), 9.23 (dd, J=4.9, 1.6 Hz, 1H), 8.50 (dd, J=8.7, 1.6 Hz, 1H), 8.14 (d, J=8.3 Hz, 1H), 8.10 (d, J=1.7 Hz, 1H), 8.05 (d, J=8.2 Hz, 1H), 7.99 (d, J=0.9 Hz, 1H), 7.86 (dd, J=8.7, 4.9 Hz, 1H), 7.78-7.69 (m, 2H), 7.37 (dd, J=6.9, 0.9 Hz, 1H), 7.32-7.08 (m, 3H).

Example 18

5-(3-(3-fluoro-2-(trifluoromethyl)phenyl)imidazo[1,5-a]pyridin-8-yl)-N-(4-fluorophenyl)-2-methylnicotinamide

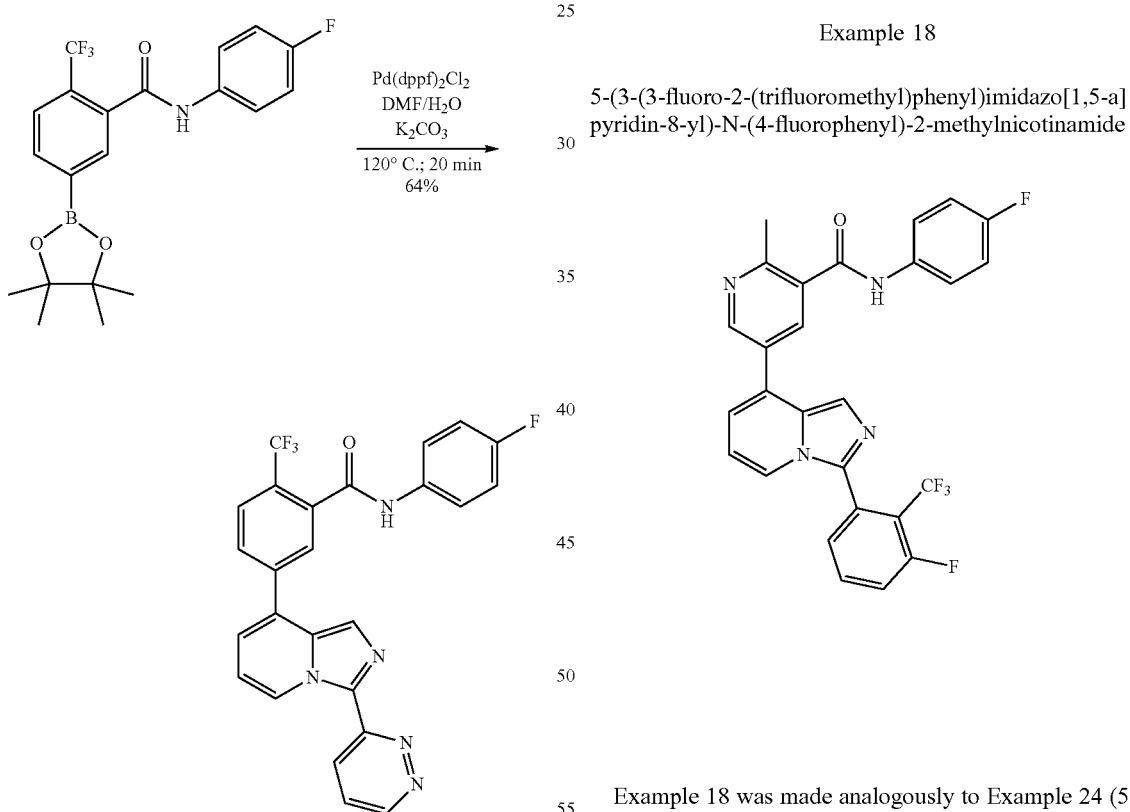

Example 18 was made analogously to Example 24 (5-(3-(2,6-difluorophenyl)imidazo[1,5-a]pyridin-8-yl)-N-(4-fluorophenyl)-2-methylnicotinamide) using 3-fluoro-2-(trifluoromethyl)benzoic acid in place of 2,6-difluorobenzoic acid and N-(4-fluorophenyl)-2-methyl-5-(4,4,5,5-tetramethyl-1,3,2-dioxaborolan-2-yl)nicotinamide in place of (5-((4-fluorophenyl)carbamoyl)-6-methylpyridin-3-yl)boronic acid. C27H17F5N4O. 459.3 (M+1). 1H NMR (400 MHz, DMSO-d6) δ 10.62 (s, 1H), 8.98 (d, J=2.3 Hz, 1H), 8.28 (d, J=2.3 Hz, 1H), 7.96 (dd, J=11.4, 6.4 Hz, 2H), 7.85 (s, 1H), 7.77 (ddt, J=8.8, 6.1, 2.9 Hz, 1H), 7.56 (d, J=7.7 Hz, 1H), 7.26-7.18 (m, 2H), 7.14 (d, J=6.7 Hz, 1H), 6.85 (t, J=6.9 Hz, 1H), 2.68 (s, 3H).

Example 19

N-(4-fluorophenyl)-5-(3-(3-fluoropyridin-2-yl)imidazo[1,5-a]pyridin-8-yl)-2-methylnicotinamide

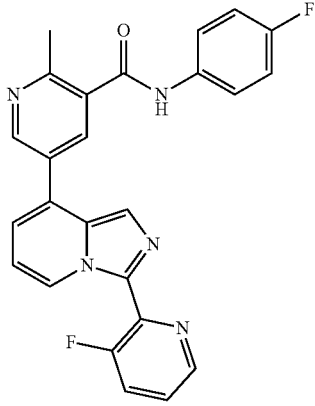

Example 19 was synthesized following the procedure explained for the synthesis of Example 17 using 3-fluoropicolinic acid instead of pyridazine-3-carboxylic acid, and replacing N-(4-fluorophenyl)-5-(4,4,5,5-tetramethyl-1,3,2-dioxaborolan-2-yl)-2-(trifluoromethyl)benzamide with N-(4-fluorophenyl)-2-methyl-5-(4,4,5,5-tetramethyl-1,3,2-dioxaborolan-2-yl)nicotinamide. C25H17F2N5O. 442.1 (M+1). 1H NMR (400 MHz, DMSO-d6) δ 10.64 (s, 1H), 9.44 (d, J=7.2 Hz, 1H), 8.98 (d, J=2.3 Hz, 1H), 8.63 (dt, J=4.6, 1.5 Hz, 1H), 8.30 (d, J=2.3 Hz, 1H), 7.93 (s, 1H), 7.86-7.65 (m, 2H), 7.57 (dt, J=8.2, 4.0 Hz, 1H), 7.35-7.12 (m, 3H), 7.05 (t, J=7.0 Hz, 1H), 2.68 (s, 3H).

Example 20

5-(3-(2,3-difluorophenyl)-[1,2,4]triazolo[4,3-a]pyridin-8-yl)-N-(4-fluorophenyl)-2-methylbenzamide

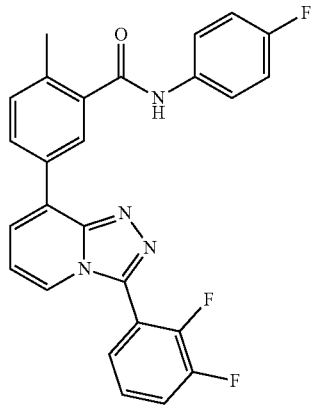 [SMILES: Cc1ccc(-c2cccn3c(-c4cccc(F)c4F)nnc23)cc1C(=O)Nc1ccc(F)cc1]

Example 20 was synthesized following the procedure explained for the synthesis of Example 9; using (2,3-difluorophenyl)boronic acid instead of phenyl boronic acid. C26H17F3N4O; 459.1 (M+1); 1H NMR (400 MHz, DMSO-d6) δ 10.49 (s, 1H), 8.40 (dd, J=7.0, 3.0 Hz, 1H), 8.36-8.29 (m, 2H), 7.86 (d, J=7.0 Hz, 1H), 7.84-7.71 (m, 3H), 7.70-7:62 (m, 1H), 7.52 (dd, J=8.7, 5.0 Hz, 2H), 7.25-7.10 (m, 3H), 2.48 (s, 2H).

Example 21

N-(4-fluorophenyl)-5-(3-(quinolin-4-yl)imidazo[1,5-a]pyridin-8-yl)-2-(trifluoromethyl)benzamide

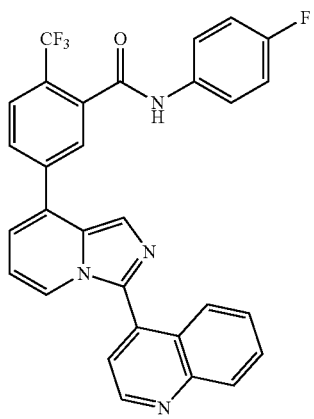 [SMILES: O=C(Nc1ccc(F)cc1)c1cc(-c2cccn3c(-c4ccnc5ccccc45)ncc23)ccc1C(F)(F)F]

This compound was synthesized in a manner similar to that employed in the synthesis of Example 17 using quinoline-4-carboxylic acid instead of pyridazine-3-carboxylic acid. C30H18F4N4O. 427.1 (M+H). 1H NMR (400 MHz, Chloroform-d) δ9.34 (d, J=5.5 Hz, 1H), 9.22 (d, J=5.0 Hz, 1H), 8.52 (dd, J=8.5, 3.3 Hz, 2H), 8.38 (d, J=8.6 Hz, 1H), 8.29-8.20 (m, 2H), 8.11-7.78 (m, 11H).

Example 22

N-(4-fluorophenyl)-2-methyl-5-(3-(m-tolyl)imidazo[1,5-a]pyridin-8-yl)nicotinamide

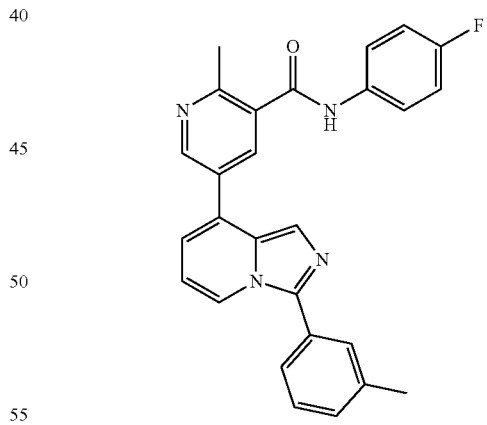

Example 22 was made analogously to Example 24 (5-(3-(2,6-difluorophenyl)imidazo[1,5-a]pyridin-8-yl)-N-(4-fluorophenyl)-2-methylnicotinamide) using 3-methylbenzoic acid in place of 2,6-difluorobenzoic acid. C27H21FN4O. 438.1 (M+1). 1H NMR (400 MHz, DMSO-d6) δ 10.64 (s, 1H), 8.96 (d, J=2.2 Hz, 1H), 8.53 (d, J=7.2 Hz, 1H), 8.27 (d, J=2.3 Hz, 1H), 8.01 (d, J=4.5 Hz, 1H), 7.84-7.72 (m, 2H); 7.67 (d, J=11.5 Hz, 2H), 7.51 (t, J=7.6 Hz, 1H), 7.38 (d, J=7.6 Hz, 1H), 7.29-7.16 (m, 3H), 6.98 (t, J=7.0 Hz, 1H), 2.68 (s, 3H), 2.44 (s, 3H).

Example 23

N-(4-fluorophenyl)-5-(3-(4-fluoropyridin-2-yl)imidazo[1,5-a]pyridin-8-yl)-2-methylnicotinamide

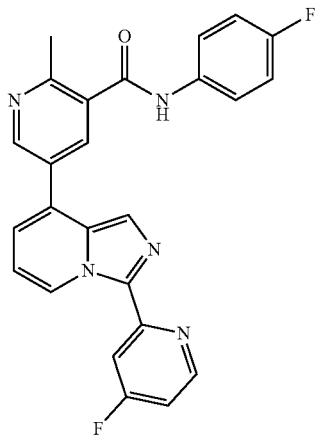

Example 23 was synthesized following the procedure explained for the synthesis of Example 17 using 4-fluoropicolinic acid instead of pyridazine-3-carboxylic acid, and replacing N-(4-fluorophenyl)-5-(4,4,5,5-tetramethyl-1,3,2-dioxaborolan-2-yl)-2-(trifluoromethyl)benzamide with N-(4-fluorophenyl)-2-methyl-5-(4,4,5,5-tetramethyl-1,3,2-dioxaborolan-2-yl)nicotinamide. C25H17F2N5O. 442.1 (M+1). 1H NMR (400 MHz, DMSO-d6) δ 10.64 (s, 1H), 9.97 (d, J=7.2 Hz, 1H), 8.97 (d, J=2.3 Hz, 1H), 8.77 (dd, J=8.8, 5.7 Hz, 1H), 8.29 (d, J=2.3 Hz, 1H), 8.05 (dd, J=10.6, 2.6 Hz, 1H), 7.93 (d, J=0.9 Hz, 1H), 7.84-7.70 (m, 2H), 7.35 (ddd, J=8.5, 5.7, 2.6 Hz, 1H), 7.29 (d, J=6.7 Hz, 1H), 7.22 (t, J=8.9 Hz, 2H), 7.13 (t, J=7.0 Hz, 1H), 2.68 (s, 3H).

Example 24

5-(3-(2,6-difluorophenyl)imidazo[1,5-a]pyridin-8-yl)-N-(4-fluorophenyl)-2-methylnicotinamide

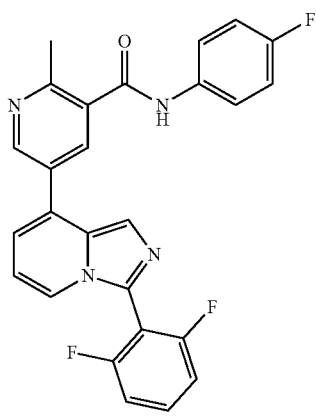

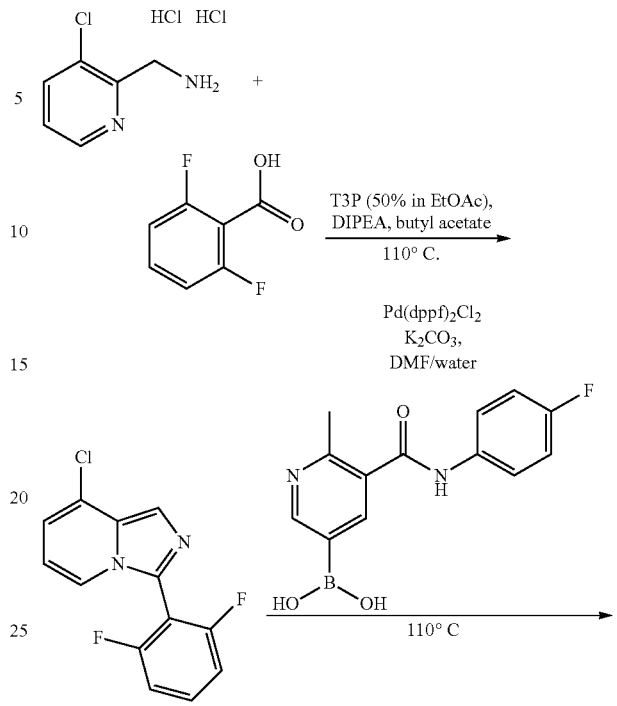

(3-chloropyridin-2-yl)methanamine dihydrochloride (200 mg, 0.928 mmol), 2,6-difluorobenzoic acid (1.3 eq), polyphosphonic anhydride (50% solution in EtOAc) (5.0 eq), and DIPEA (0.2 mL) were dissolved in butyl acetate (2.0 mL) and heated overnight at about 110° C. The reaction was cooled to room temperature, diluted with water (5.0 mL) and extracted with EtOAc (3×4 mL). Combined organic layers were concentrated under reduced pressure and purified by silica gel column chromatography (Rf 40% EtOAc/hexanes: 0.4) to give 8-chloro-3-(2,6-difluorophenyl)imidazo[1,5-a]pyridine. 8-chloro-3-(2,6-difluorophenyl)imidazo[1,5-a]pyridine (55 mg, 0.208 mmol), (5-((4-fluorophenyl)carbamoyl)-6-methylpyridin-3-yl)boronic acid (1.0 eq), Pd(dppf)Cl2 (0.1 eq), and K2CO3 (1.0 eq) were dissolved in degassed DMF (2.0 mL) and water (1.0 mL) and heated for about 4 hours at about 110° C. The reaction was cooled to room temperature, diluted with water (5 mL), and extracted with EtOAc (3×4 mL). Combined organic layers were washed with water (1×5 mL), concentrated under reduced pressure, and purified by reverse-phase prep HPLC to give 5-(3-(2,6-difluorophenyl)imidazo[1,5-a]pyridin-8-yl)-N-(4-fluorophenyl)-2-methylnicotinamide. C26H17F3N4). 460.1

(M+1). 1H NMR (400 MHz, DMSO-d6) δ 10.64 (s, 1H), 9.00 (d, J=2.2 Hz, 1H), 8.33 (d, J=2.2 Hz, 1H), 8.02 (d, J=7.1 Hz, 1H), 7.93 (d, J=1.0 Hz, 1H), 7.83-7.69 (m, 3H), 7.39 (t, J=8.2 Hz, 2H), 7.27-7.16 (m, 3H), 6.94 (t, J=6.9 Hz, 1H), 2.69 (s, 3H).

Example 25

N-(4-fluorophenyl)-2-methyl-5-(3-(pyrimidin-2-yl)imidazo[1,5-a]pyridin-8-yl)nicotinamide

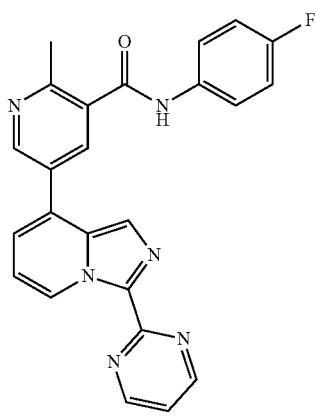 [SMILES: Cc1ncc(-c2cccn3c(-c4ncccn4)ncc23)cc1C(=O)Nc1ccc(F)cc1]

Example 25 was synthesized following the procedure explained for the synthesis of Example 34 using pyrimidine-2-carboxylic acid instead of 2,3-difluorobenzoic acid and using N-(4-fluorophenyl)-2-methyl-5-(4,4,5,5-tetramethyl-1,3,2-dioxaborolan-2-yl)nicotinamide instead of N-(4-fluorophenyl)-2-methyl-5-(4,4,5,5-tetramethyl-1,3,2-dioxaborolan-2-yl)benzamide. C24H17FN6O. 425.1 (M+1). 1H NMR (400 MHz, DMSO-d6) δ 10.66 (s, 1H), 9.90 (d, J=7.3 Hz, 1H), 9.02 (d, J=4.9 Hz, 2H), 8.98 (d, J=2.3 Hz, 1H), 8.31 (d, J=2.3 Hz, 1H), 8.10 (s, 1H), 7.88-7.66 (m, 2H), 7.53 (t, J=4.9 Hz, 1H), 7.38 (d, J=6.8 Hz, 1H), 7.28-7.15 (m, 3H), 2.69 (s, 3H).

Example 26

N-(4-fluorophenyl)-5-(3-(pyrimidin-4-yl)imidazo[1,5-a]pyridin-8-yl)-2-(trifluoromethyl)benzamide

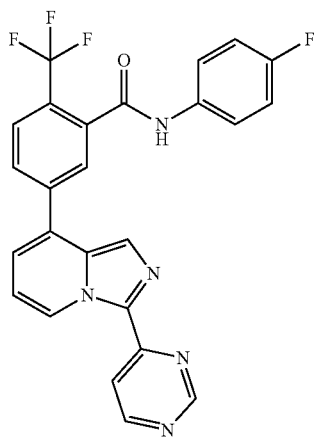 [SMILES: O=C(Nc1ccc(F)cc1)c1cc(-c2cccn3c(-c4ccncn4)ncc23)ccc1C(F)(F)F]

Example 26 was synthesized following the procedure explained for the synthesis of Example 17 using pyrimidine-4-carboxylic acid instead of pyridazine-3-carboxylic acid. C25H15F4N5O. 478.1 (M+1). 1H NMR (400 MHz, DMSO-d6) δ 10.75 (s, 1H), 10.05 (dd, J=7.2, 0.9 Hz, 1H), 9.29 (d, J=1.4 Hz, 1H), 8.86 (d, J=5.4 Hz, 1H), 8.24 (dd, J=5.4, 1.4 Hz, 1H), 8.15-8.07 (m, 2H), 8.04 (d, J=8.2 Hz, 1H), 8.00 (d, J=0.9 Hz, 1H), 7.79-7.67 (m, 2H), 7.41 (dd, J=6.9, 0.9 Hz, 1H), 7.29-7.17 (m, 3H).

Example 27

5-(3-(3,5-difluorophenyl)imidazo[1,5-a]pyridin-8-yl)-N-(4-fluorophenyl)-2-methylnicotinamide

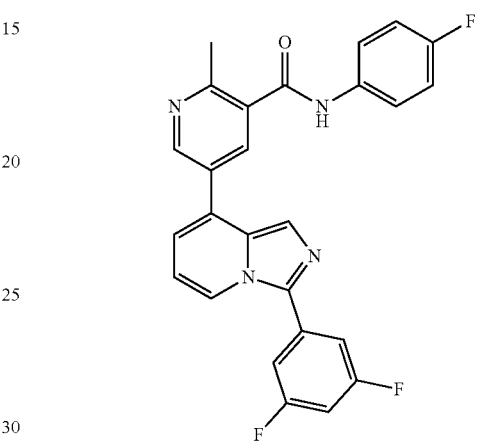

Example 27 was made analogously to Example 24 (5-(3-(2,6-difluorophenyl)imidazo[1,5-a]pyridin-8-yl)-N-(4-fluorophenyl)-2-methylnicotinamide) using 3,5-difluorobenzoic acid in place of 2,6-difluorobenzoic acid. C26H17F3N4O. 460.1 (M+1). 1H NMR (400 MHz, DMSO-d6) δ 10.64 (s, 1H), 8.95 (d, J=2.2 Hz, 1H), 8.65 (d, J=7.1 Hz, 1H), 8.26 (d, J=2.2 Hz, 1H), 7.88 (s, 1H), 7.81-7.74 (m, 2H), 7.69-7.56 (m, 2H), 7.44-7.36 (m, 1H), 7.27-7.14 (m, 3H), 6.96 (t, J=7.0 Hz, 1H), 2.67 (s, 3H).

Example 28

2-(3-(2,3-difluorophenyl)imidazo[1,5-a]pyridin-8-yl)-N-(4-fluorophenyl)-5-(trifluoromethyl)isonicotinamide

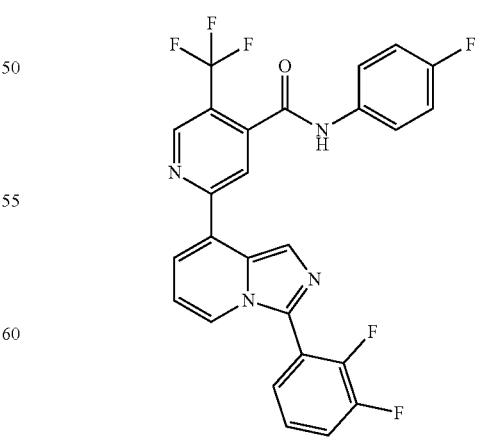

Example 28 was synthesized following the procedure explained for the synthesis of Example 42 using 2-bromo- N-(4-fluorophenyl)-5-(trifluoromethyl)isonicotinamide instead of 3-bromo-2-fluoro-N-(4-fluorophenyl)-6-methylbenzamide. C26H14F6N4O. 513.1 (M+1). 1H NMR (400 MHz, DMSO-d6) δ 10.91 (s, 1H), 9.30 (s, 1H), 8.53 (s, 1H), 8.39 (d, J=0.9 Hz, 1H), 8.34 (dd, J=7.2, 3.4 Hz, 1H), 7.88 (d, J=6.9 Hz, 1H), 7.77-7.70 (m, 2H), 7.71-7.62 (m, 1H), 7.62-7.55 (m, 1H), 7.45 (td, J=8.1, 4.0 Hz, 1H), 7.25 (t, J=8.9 Hz, 2H), 7.00 (t, J=7.0 Hz, 1H).

Example 29

N-(4-fluorophenyl)-2-methyl-5-(3-(o-tolyl)imidazo[1,5-a]pyridin-8-yl)nicotinamide

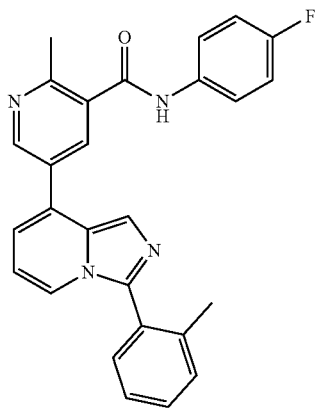 [SMILES: Cc1ccccc1-c1ncc2c(-c3cnc(C)c(C(=O)Nc4ccc(F)cc4)c3)cccn12]

Example 29 was made analogously to Example 24 (5-(3-(2,6-difluorophenyl)imidazo[1,5-a]pyridin-8-yl)-N-(4-fluorophenyl)-2-methylnicotinamide) using 2-methylbenzoic acid in place of 2,6-difluorobenzoic acid. C27H21FN4O. 438.1 (M+1). 1H NMR (400 MHz, DMSO-d6) δ 10.64 (s, 1H), 8.99 (d, J=2.3 Hz, 1H), 8.30 (d, J=2.3 Hz, 1H), 8.15 (s, 1H), 7.95 (d, J=7.1 Hz, 1H), 7.82-7.72 (m, 2H), 7.60-7.41 (m, 4H), 7.30-7.18 (m, 3H), 6.99 (t, J=7.0 Hz, 1H), 2.69 (s, 3H), 2.20 (s, 3H).

Example 30

5-(3-(2,5-difluorophenyl)imidazo[1,5-a]pyridin-8-yl)-N-(4-fluorophenyl)-2-methylnicotinamide

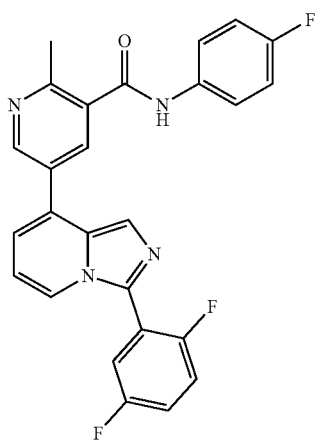 [SMILES: Cc1ncc(-c2cccn3c(-c4cc(F)ccc4F)ncc23)cc1C(=O)Nc1ccc(F)cc1]

Example 30 was made analogously to Example 24 (5-(3-(2,6-difluorophenyl)imidazo[1,5-a]pyridin-8-yl)-N-(4-fluorophenyl)-2-methylnicotinamide) using 2,5-difluorobenzoic acid in place of 2,6-difluorobenzoic acid. C26H17F3N4O. 460.1 (M+1). 1H NMR (400 MHz, DMSO-d6) δ 10.63 (s, 1H), 8.97 (d, J=2.2 Hz, 1H), 8.27 (d, J=2.3 Hz, 1H), 8.11 (dd, J=7.2, 3.9 Hz, 1H), 7.90 (s, 1H), 7.82-7.71 (m, 2H), 7.62-7.46 (m, 3H), 7.28-7.14 (m, 3H), 6.94 (t, J=6.9 Hz, 1H), 2.67 (s, 3H).

Example 31

N-(4-fluorophenyl)-5-(3-(pyridin-3-yl)imidazo[1,5-a]pyridin-8-yl)-2-(trifluoromethyl)benzamide

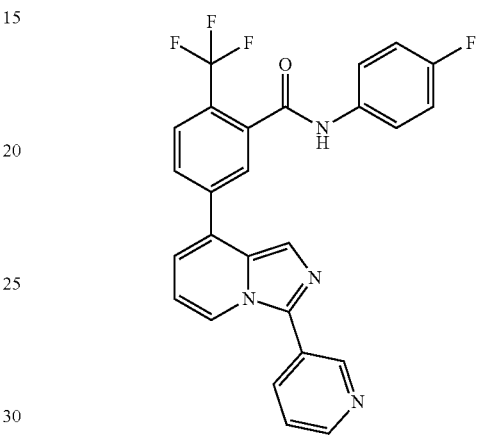

Example 31 was synthesized following the procedure explained for the synthesis of Example 33 using 3-iodopyridine instead of 2-iodopyridine. C26H16F4N4O. 477.1 (M+1). 1H NMR (400 MHz, DMSO-d6) δ 10.76 (s, 1H), 9.11 (d, J=2.2 Hz, 1H), 8.73 (dd, J=4.9, 1.6 Hz, 1H), 8.62 (d, J=7.1 Hz, 1H), 8.38 (dt, J=8.0, 1.9 Hz, 1H), 8.12 (d, J=8.1 Hz, 1H), 8.09-7.99 (m, 2H), 7.89 (s, 1H), 7.80-7.61 (m, 3H), 7.29-7.13 (m, 3H), 6.96 (t, J=7.0 Hz, 1H).

Example 32

5-(3-(1H-pyrazol-3-yl)imidazo[1,5-a]pyridin-8-yl)-N-(4-fluorophenyl)-2-(trifluoromethyl)benzamide

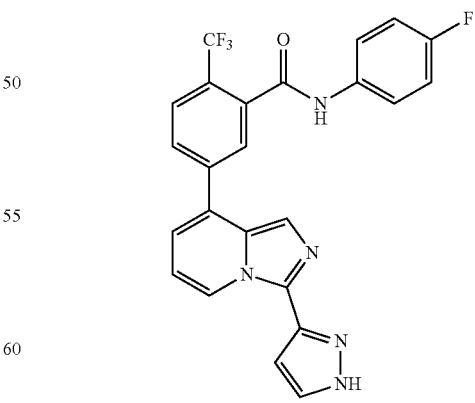

This compound was synthesized in a manner similar to that employed in the synthesis of Example 17 using 1H-pyrazole-3-carboxylic acid instead of pyridazine-3-carboxylic acid. C24H15F4N5O. 466.1 (M+H). 1H NMR (400

MHz, Chloroform-d) δ 9.81 (s, 1H), S 8.21 (s, 1H), 8.07 (d, J=6.9 Hz, 1H), 7.93 (s, 1H), 7.78 (s, 1H), 7.74-7.51 (m, 4H), 7.47 (d, J=8.0 Hz, 1H), 7.14-6.89 (m, 4H), 4.32 (s, 3H), 2.60 (s, 3H).

Example 33

N-(4-fluorophenyl)-5-(3-(pyridin-2-yl)imidazo[1,5-a]pyridin-8-yl)-2-(trifluoromethyl)benzamide

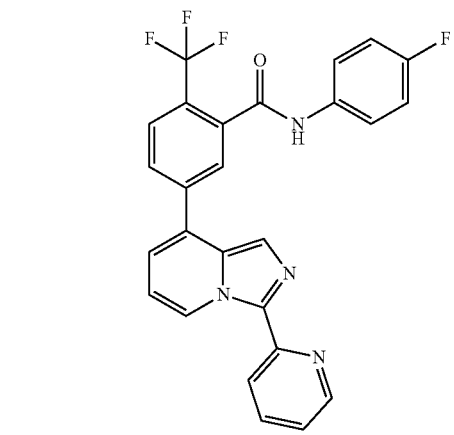 [SMILES: O=C(Nc1ccc(F)cc1)c1cc(-c2cccn3c(-c4ccccn4)ncc23)ccc1C(F)(F)F]

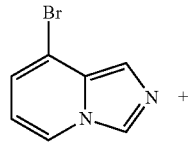
+
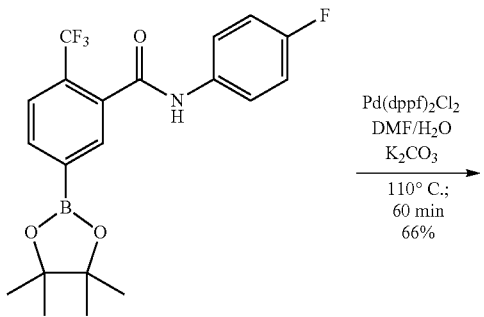

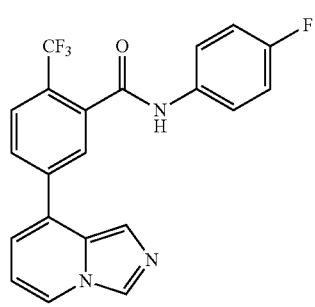

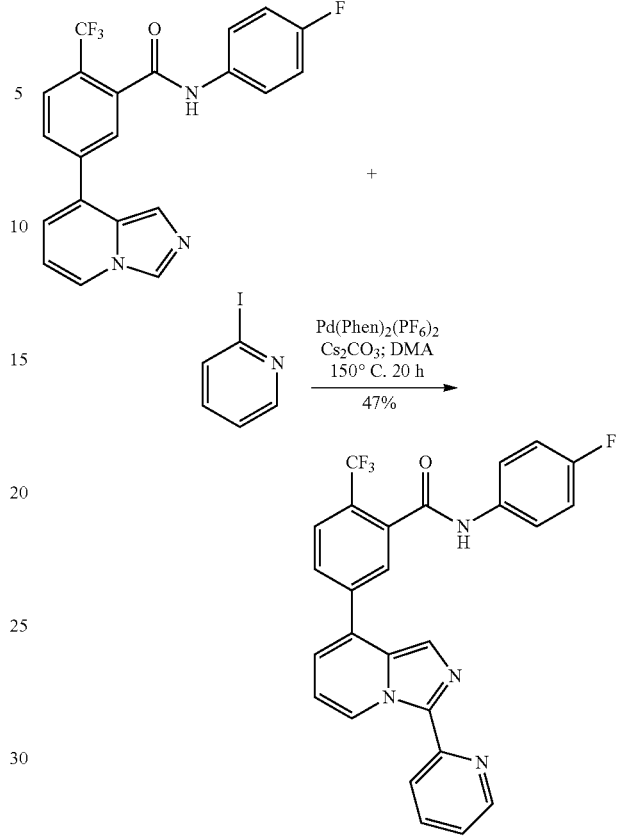

To a suspension of 8-bromoimidazole[1,5-a]pyridine[1,5-a]pyridine (290 mg, 1.5 mmol), N-(4-fluorophenyl)-5-(4,4,5,5-tetramethyl-1,3,2-dioxaborolan-2-yl)-2-(trifluoromethyl)benzamide (500 mg, 1.2 mmol), potassium carbonate (170 mg, 1.2 mmol) in DMF/Water (9:1) palladium catalyst (5 mol %) was added. The reaction mixture was heated at about 110° C. for about 60 min. The reaction was diluted with ethyl acetate, filtered through celite, washed with water, brine and concentrated. The residue was purified by prep HPLC using Gilson reverse phase eluting with ACN and water with 0.1% TFA using Luna column to get the N-(4-fluorophenyl)-5-(imidazo[1,5-a]pyridin-8-yl)-2-(trifluoromethyl)benzamide (490 mg, 66% yield). 400.1 (M+1). 1H NMR (400 MHz, DMSO-d6) δ 10.74 (s, 1H), 9.08 (s, 1H), 8.54 (d, J=7.0 Hz, 1H), 8.12-7.99 (m, 3H), 7.95 (s, 1H), 7.76-7.68 (m, 2H), 7.27 (d, J=6.8 Hz, 1H), 7.21 (t, J=8.9 Hz, 2H), 7.04 (t, J=7.0 Hz, 1H).

To a microwave vial the reagents N-(4-fluorophenyl)-5-(imidazo[1,5-a]pyridin-8-yl)-2-(trifluoromethyl)benzamide (50 mg, 0.12 mmol), 2-iodopyridine (28 mg, 0.13 mmol), Cesium carbonate (45 mg, 0.14 mmol) and the palladium complex Pd(phen)2(PF6)2 Bis(1,10-phenanthroline)palladium Hexafluorophosphate (5 mg, 5 mol %) were added in dimethyl acetamide (2 mL) and heated at about 150° C. for about 20 h. The reaction mixture was purified by prep HPLC using Gilson reverse phase eluting with ACN and water with 0.1% TFA using Luna column to get the title compound N-(4-fluorophenyl)-5-(3-(pyridin-2-yl)imidazo[1,5-a]pyridin-8-yl)-2-(trifluoromethyl)benzamide as a TFA salt (28 mg, 47% yield). C26H16F4N4O. 477.1 (M+1). 1H NMR (400 MHz, DMSO-d6) δ 10.75 (s, 1H), 10.00 (d, J=7.3 Hz, 1H), 8.79-8.67 (m, 1H), 8.31 (d, J=8.1 Hz, 1H), 8.16-8.09

(m, 1H), 8.07 (d, J=1.7 Hz, 1H), 8.03 (d, J=8.2 Hz, 1H), 7.97 (td, J=7.8, 1.8 Hz, 1H), 7.87 (s, 1H), 7.79-7.67 (m, 2H), 7.41 (ddd, J=7.5, 4.9, 1.2 Hz, 1H), 7.27 (d, J=6.8 Hz, 1H), 7.21 (t, J=8.9 Hz, 2H), 7.10 (t, J=7.0 Hz, 1H).

Example 34

5-(3-(2,3-difluorophenyl)imidazo[1,5-a]pyridin-8-yl)-N-(4-fluorophenyl)-2-methylbenzamide

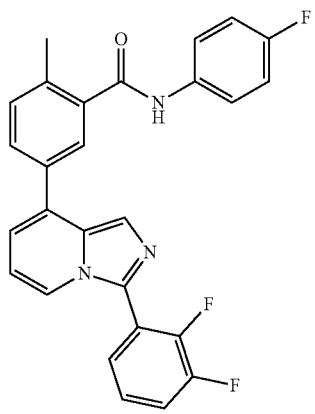 [SMILES: Cc1ccc(-c2cccn3c(-c4cccc(F)c4F)ncc23)cc1C(=O)Nc1ccc(F)cc1]

To a solution of the 2,3-difluorobenzoic acid (500 mg, 3.16 mmol) and HATU (1322 mg, 3.5 mmol) in DMF (2 mL), (3-chloropyridin-2-yl)methanamine (500 mg, 3.5 mmol) and DIPEA were added and stirred at room temperature for about 2 h. To the reaction mixture, water (50 mL) was added, stirred for about 30 min, and the product N-((3-chloropyridin-2-yl)methyl)-2,3-difluorobenzamide was filtered, washed with hexanes and dried (520 mg, 59% yield). 283.0 (M+1).

A solution of N-((3-chloropyridin-2-yl)methyl)-2,3-difluorobenzamide (520 mg, 1.8 mmol) in POCl₃ (5 mL) was heated at 100° C. for about 3 h. The reaction mixture was cooled, and slowly poured into an ice bath and stirred for about 45 min. No product precipitated out. The aqueous portion was extracted twice with dichloromethane (50 mL each). The organics were washed with water, brine, dried over sodium sulphate and concentrated to get the cyclized product 8-chloro-3-(2,3-difluorophenyl)imidazo[1,5-a]pyridine (355 mg, 73% yield) and used for the next step. 265.0 (M+1).

To a suspension of 8-chloro-3-(2,3-difluorophenyl)imidazo[1,5-a]pyridine (23 mg, 0.09 mmol), N-(4-fluorophenyl)-2-methyl-5-(4,4,5,5-tetramethyl-1,3,2-dioxaborolan-2-yl)benzamide (20 mg, 0.8 mmol), potassium carbonate (11 mg, 0.08 mmol)) in DMF/Water (9:1) palladium catalyst (5 mol %) was added. The reaction mixture was subjected to microwave irradiation at about 140° C. for about 15 min. The reaction was diluted with ethyl acetate, filtered through celite and concentrated. The residue was purified by prep HPLC using Gilson reverse phase eluting with acetonitrile (ACN) and water with 0.1% TFA using Luna column, to

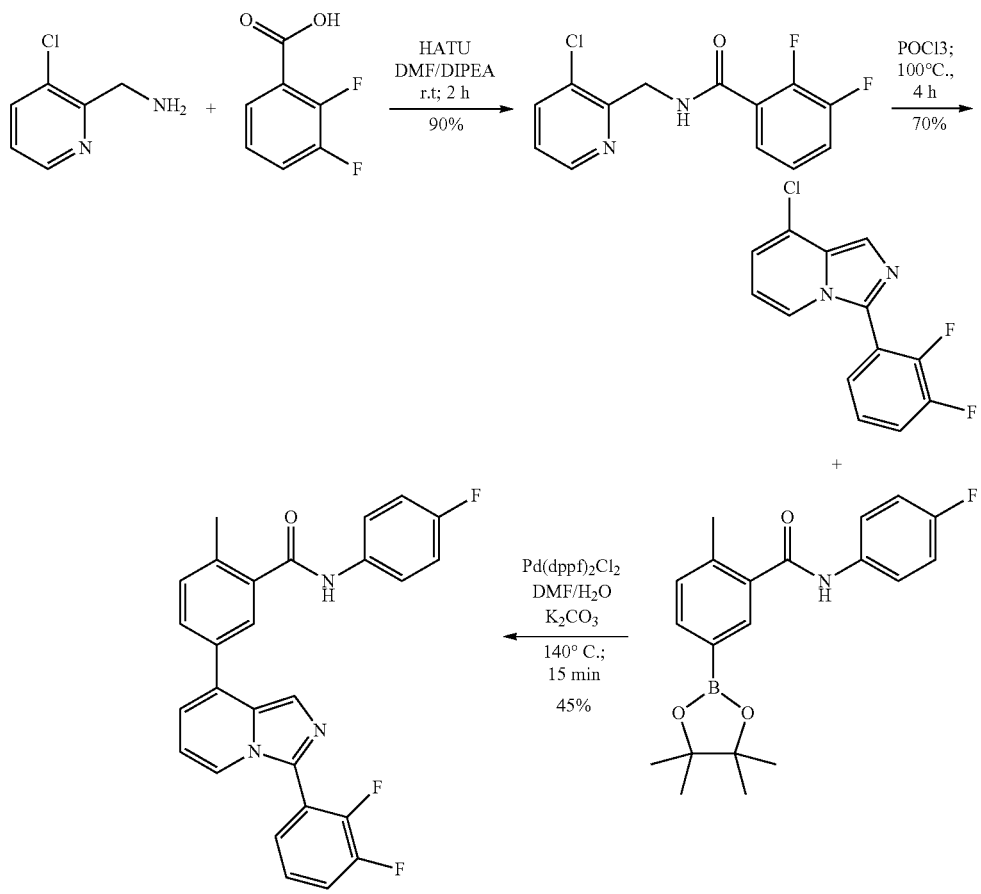

give the title compound as a TFA salt (15 mg, 45% yield). C27H18F3N3O. 458.1 (M+1). $^1$H NMR (400 MHz, DMSO-d6) δ 10.48 (s, 1H), 8.15 (dd, J=7.2, 3.6 Hz, 1H), 7.87-7.73 (m, 5H), 7.70-7.59 (m, 1H), 7.59-7.53 (m, 1H), 7.51 (d, J=8.4 Hz, 1H), 7.43 (td, J=8.2, 4.3 Hz, 1H), 7.20 (t, J=8.9 Hz, 2H), 7.09 (d, J=6.7 Hz, 1H), 6.91 (t, J=6.9 Hz, 1H), 2.48 (s, 3H).

Example 35

N-(4-fluorophenyl)-5-(3-(3-fluorophenyl)imidazo[1,5-a]pyridin-8-yl)-2-methylnicotinamide

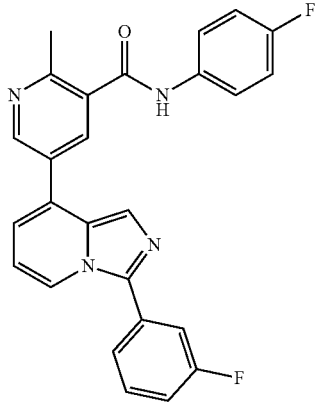 [SMILES: Cc1ncc(-c2cccn3c(-c4cccc(F)c4)ncc23)cc1C(=O)Nc1ccc(F)cc1]

Example 35 was synthesized following the procedure explained for the synthesis of Example 17 using 3-fluorobenzoic acid instead of pyridazine-3-carboxylic acid, and replacing N-(4-fluorophenyl)-5-(4,4,5,5-tetramethyl-1,3,2-dioxaborolan-2-yl)-2-(trifluoromethyl)benzamide with N-(4-fluorophenyl)-2-methyl-5-(4,4,5,5-tetramethyl-1,3,2-dioxaborolan-2-yl)nicotinamide. C26H18F2N4O. 441.1 (M+1). 1H NMR (400 MHz, Chloroform-d) δ 9.50 (s, 1H), 8.74 (d, J=2.2 Hz, 1H), 8.17 (d, J=7.0 Hz, 1H), 7.97 (d, J=2.2 Hz, 1H), 7.61 (dd, J=8.7, 4.9 Hz, 2H), 7.44 (dd, J=6.7, 4.3 Hz, 2H), 7.33 (dd, J=10.0, 2.6 Hz, 1H), 7.14 (ddd, J=10.2, 5.0, 2.8 Hz, 1H), 7.00 (t, J=8.6 Hz, 2H), 6.80-6.61 (m, 2H), 2.71 (s, 3H).

Example 36

N-(4-fluorophenyl)-5-(3-(pyrazin-2-yl)imidazo[1,5-a]pyridin-8-yl)-2-(trifluoromethyl)nicotinamide

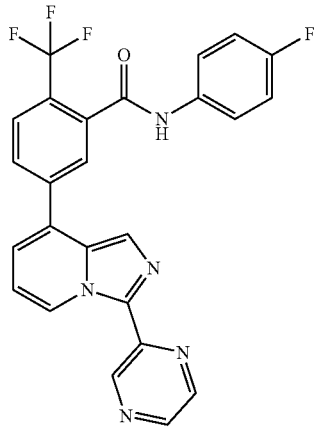 [SMILES: O=C(Nc1ccc(F)cc1)c1cc(-c2cccn3c(-c4cnccn4)ncc23)ccc1C(F)(F)F]

Example 36 was synthesized following the procedure explained for the synthesis of Example 17 using pyrazine-2-carboxylic acid instead of pyridazine-3-carboxylic acid. C25H15F4N5O. 478.1 (M+1). 1H NMR (400 MHz, DMSO-d6) δ 10.75 (s, 1H), 9.82 (d, J=7.2 Hz, 1H), 9.50 (d, J=1.4 Hz, 1H), 8.75 (dd, J=2.7, 1.4 Hz, 1H), 8.61 (dd, J=2.6, 1.1 Hz, 1H), 8.13 (d, J=8.3 Hz, 1H), 8.10-8.01 (m, 2H), 7.96 (s, 1H), 7.80-7.68 (m, 2H), 7.35 (d, J=6.8 Hz, 1H), 7.29-7.09 (m, 3H).

Example 37

N-(4-fluorophenyl)-2-methyl-5-(3-(pyrimidin-2-yl)imidazo[1,5-a]pyridin-8-yl)benzamide

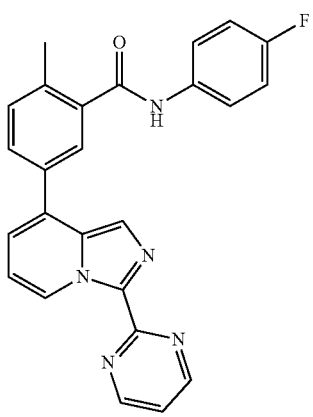 [SMILES: Cc1ccc(-c2cccn3c(-c4ncccn4)ncc23)cc1C(=O)Nc1ccc(F)cc1]

Example 37 was synthesized following the procedure explained for the synthesis of Example 34 using pyrimidine-2-carboxylic acid instead of 2,3-difluorobenzoic acid. C25H18FN5O. 424.1 (M+1). 1H NMR (400 MHz, DMSO-d6) δ 10.51 (s, 1H), 9.87 (d, J=7.2 Hz, 1H), 9.01 (d, J=4.9 Hz, 2H), 8.01 (s, 1H), 7.83 (s, 1H), 7.83-7.76 (m, 3H), 7.58-7.45 (m, 2H), 7.30 (d, J=6.8 Hz, 1H), 7.26-7.13 (m, 3H), 2.48 (s, 3H).

Example 38

6-(3-(2,3-difluorophenyl)imidazo[1,5-a]pyridin-8-yl)-N-(4-fluorophenyl)-3-(trifluoromethyl)picolinamide

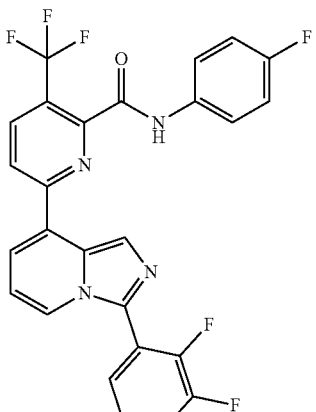

Example 38 was synthesized following the procedure explained for the synthesis of Example 42 using 6-bromo- N-(4-fluorophenyl)-3-(trifluoromethyl)picolinamide instead of 3-bromo-2-fluoro-N-(4-fluorophenyl)-6-methylbenzamide. C26H14F6N4O. 513.1 (M+1). 1H NMR (400 MHz, DMSO-d6) δ 10.93 (s, 1H), 8.53 (d, J=8.5 Hz, 1H), 8.46 (d, J=8.5 Hz, 1H), 8.33 (dd, J=7.3, 3.2 Hz, 1H), 8.30 (d, J=0.9 Hz, 1H), 7.89-7.73 (m, 3H), 7.66 (dtd, J=9.9, 8.3, 1.7 Hz, 1H), 7.56 (ddd, J=8.1, 4.7, 1.7 Hz, 1H), 7.44 (td, J=8.2, 3.8 Hz, 1H), 7.25 (t, J=8.9 Hz, 2H), 7.01 (t, J=7.0 Hz, 1H).

Example 39

N-(4-fluorophenyl)-5-(3-(3-fluorophenyl)imidazo[1,5-a]pyridin-8-yl)-2-(trifluoromethyl)benzamide

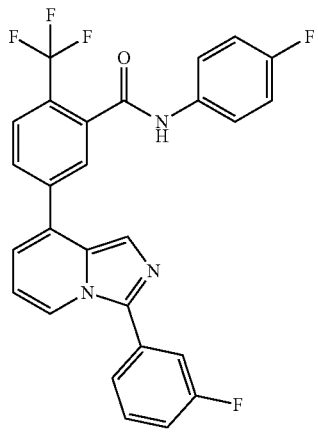 [SMILES: O=C(Nc1ccc(F)cc1)c1cc(-c2cccn3c(-c4cccc(F)c4)ncc23)ccc1C(F)(F)F]

Example 39 was synthesized following the procedure explained for the synthesis of Example 17 using 3-fluorobenzoic acid instead of pyridazine-3-carboxylic acid. C27H16F5N3O. 494.1 (M+1). 1H NMR (400 MHz, DMSO-d6) δ 10.75 (s, 1H), 8.60 (d, J=7.2 Hz, 1H), 8.11 (d, J=8.0 Hz, 1H), 8.08-7.96 (m, 2H), 7.81 (d, J=0.9 Hz, 1H), 7.78-7.56 (m, 5H), 7.35 (td, J=8.6, 2.3 Hz, 1H), 7.29-7.13 (m, 3H), 6.93 (t, J=7.0 Hz, 1H).

Example 40

N-(4-fluorophenyl)-2-methyl-5-(3-(oxazol-2-yl)imidazo[1,5-a]pyridin-8-yl)benzamide

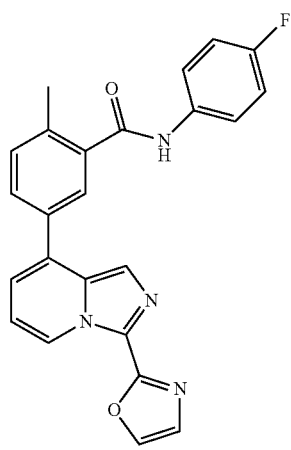 [SMILES: Cc1ccc(-c2cccn3c(-c4ncco4)ncc23)cc1C(=O)Nc1ccc(F)cc1]

This compound was synthesized in a manner similar to that employed in the synthesis of Example 17 using oxazole-2-carboxylic acid instead of pyridazine-3-carboxylic acid and performing Suzuki with N-(4-fluorophenyl)-2-methyl-5-(4,4,5,5-tetramethyl-1,3,2-dioxaborolan-2-yl)benzamide. C24H17FN4O2. 428.2 (M+H). 1H NMR (400 MHz, Chloroform-d) δ 9.61-9.34 (m, 1H), 8.03 (s, 1H), 7.89 (s, 1H), 7.76 (s, 2H), 7.66 (d, J=7.9 Hz, 3H), 7.53-7.32 (m, 2H), 7.19-6.93 (m, 4H), 2.59 (s, 3H).

Example 41

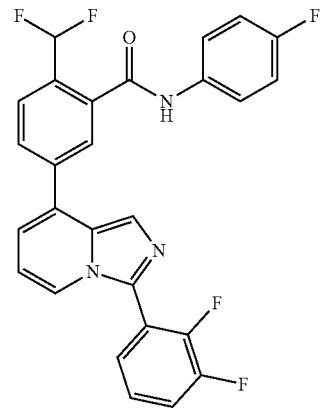 [SMILES: O=C(Nc1ccc(F)cc1)c1cc(-c2cccn3c(-c4cccc(F)c4F)ncc23)ccc1C(F)F]

2-(difluoromethyl)-5-(3-(2,3-difluorophenyl)imidazo[1,5-a]pyridin-8-yl)-N-(4-fluorophenyl)benzamide Example 41 was synthesized following the procedure explained for the synthesis of Example 48 using 2-(difluoromethyl)-N-(4-fluorophenyl)-5-(4,4,5,5-tetramethyl-1,3,2-dioxaborolan-2-yl)benzamide instead of N-(4-fluorophenyl)-5-(4,4,5,5-tetramethyl-1,3,2-dioxaborolan-2-yl)-2-(trifluoromethyl)benzamide. C27H16F5N3O. 494.1 (M+1). 1H NMR (400 MHz, DMSO-d6) δ 10.72 (s, 1H), 8.22 (dd, J=7.2, 3.3 Hz, 1H), 8.11 (dd, J=6.1, 2.1 Hz, 2H), 7.94 (t, J=4.4 Hz, 2H), 7.84-7.71 (m, 2H), 7.66 (dtd, J=10.0, 8.3, 1.7 Hz, 1H), 7.61-7.51 (m, 1H), 7.51-7.35 (m, 2H), 7.32-7.14 (m, 3H), 6.96 (t, J=6.9 Hz, 1H).

Example 42

3-(3-(2,3-difluorophenyl)imidazo[1,5-a]pyridin-8-yl)-2-fluoro-N-(4-fluorophenyl)-6-methylbenzamide

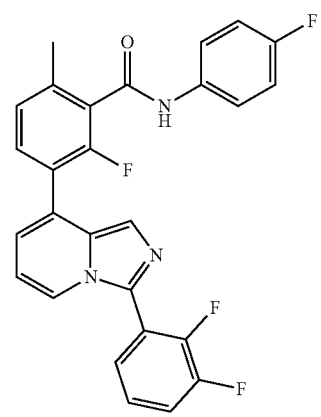 [SMILES: Cc1ccc(-c2cccn3c(-c4cccc(F)c4F)ncc23)c(F)c1C(=O)Nc1ccc(F)cc1]

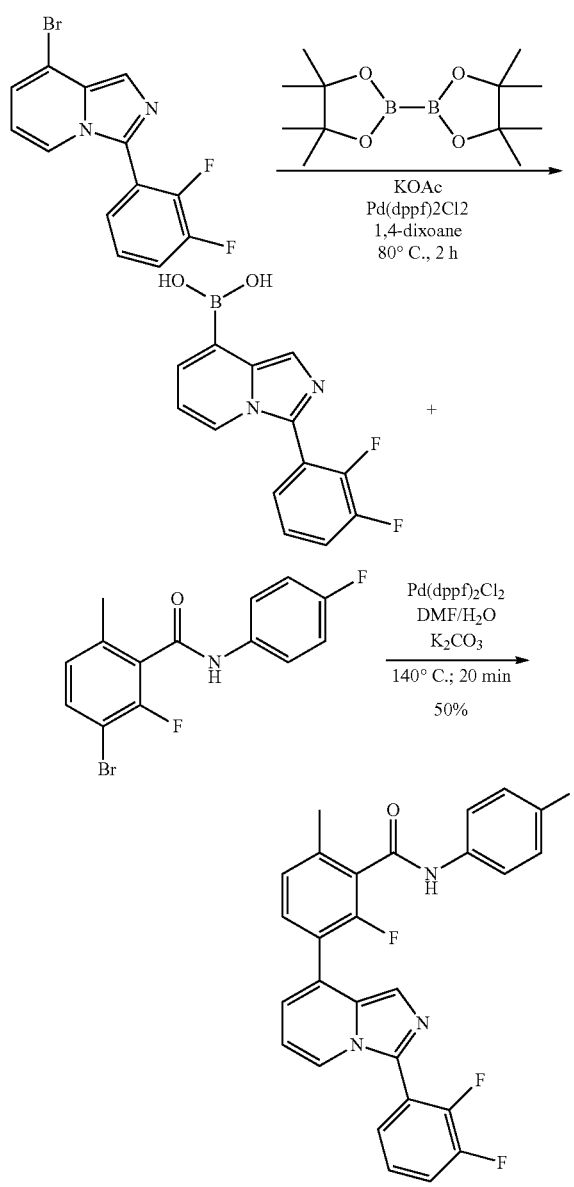

To a microwave tube 8-bromo-3-(2,3-difluorophenyl)imidazo[1,5-a]pyridine (300 mg, 0.97 mmol), bis(pinacolato)diboron (394 mg, 1.5 mmol), dichloro 1,1-bis(diphenylphosphino)ferrocene palladium(II) (100 mol %), and potassium acetate (285 mg, 2.9 mmol) were added, followed by anhydrous dioxane (5 mL). The tube was flushed with Ar, then sealed and heated to reflux for about 2 h. After the completion of the reaction, the reaction mixture was diluted with ethyl acetate, filtered through celite, concentrated. The resulting boronic acid obtained (220 mg, 80% yield) was used for the next step. 275.0 (M+1).

To a suspension of 3-bromo-2-fluoro-N-(4-fluorophenyl)-6-methylbenzamide (46 mg, 0.14 mmol), (3-(2,3-difluorophenyl)imidazo[1,5-a]pyridin-8-yl)boronic acid (30 mg, 0.11 mmol), potassium carbonate (12 mg, 0.08 mmol)) in DMF/Water (9:1), palladium catalyst (5 mol %) was added. The reaction mixture was subjected to microwave irradiation at about 140° C. for about 20 min. The reaction was diluted with ethyl acetate, filtered through celite and concentrated. The residue was purified by prep HPLC using Gilson reverse phase column eluting with ACN and water with 0.1% TFA using Luna column, to give the title compound as a TFA salt (26 mg, 50% yield). C27H17F4N3O. 476.1 (M+1). 1H NMR (400 MHz, DMSO-d6) δ 10.80 (s, 1H), 8.21 (dd, J=7.2, 3.6 Hz, 1H), 7.80-7.73 (m, 2H), 7.69 (s, 1H), 7.61-7.53 (m, 3H), 7.44 (tt, J=8.2, 4.3 Hz, 1H), 7.35 (d, J=8.0 Hz, 1H), 7.22 (t, J=8.9 Hz, 2H), 7.03 (d, J=6.7 Hz, 1H), 6.93 (t, J=6.9 Hz, 1H), 2.43 (s, 3H).

Example 43

5-(3-(2,3-difluorophenyl)imidazo[1,5-a]pyridin-8-yl)-N-(4-fluorophenyl)-2-methylnicotinamide

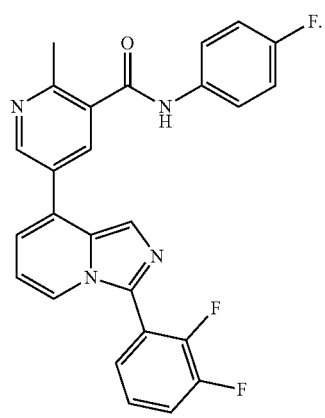 [SMILES: Cc1ncc(-c2cccn3c(-c4cccc(F)c4F)ncc23)cc1C(=O)Nc1ccc(F)cc1]

Example 43 was synthesized following the procedure explained for the synthesis of Example 42 using 5-bromo-N-(4-fluorophenyl)-2-methylnicotinamide instead of 3-bromo-2-fluoro-N-(4-fluorophenyl)-6-methylbenzamide. C26H17F3N4O. 459.1 (M+1). 1H NMR (400 MHz, DMSO-d6) δ 10.62 (s, 1H), 8.96 (d, J=2.2 Hz, 1H), 8.26 (d, J=2.3 Hz, 1H), 8.19 (dd, J=6.9, 3.0 Hz, 1H), 7.88 (d, J=1.0 Hz, 1H), 7.82-7.74 (m, 1H), 7.72-7.60 (m, 1H), 7.56 (ddd, J=8.2, 4.6, 1.7 Hz, 1H), 7.43 (td, J=8.2, 3.8 Hz, 1H), 7.22 (t, J=8.9 Hz, 2H), 7.16 (d, J=6.7 Hz, 1H), 6.93 (t, J=7.0 Hz, 1H), 2.67 (s, 3H).

Example 44

5-(3-(2,3-difluorophenyl)-1-methylimidazo[1,5-a]pyridin-8-yl)-N-(4-fluorophenyl)-2-(trifluoromethyl)benzamide

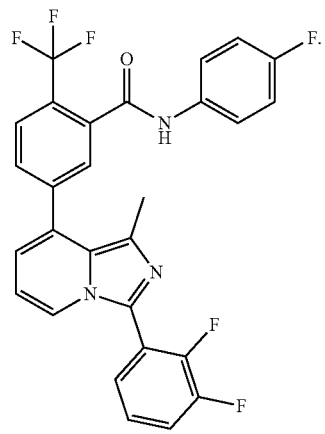 [SMILES: Cc1nc(-c2cccc(F)c2F)n2cccc(-c3ccc(C(F)(F)F)c(C(=O)Nc4ccc(F)cc4)c3)c12]

Example 44 was synthesized following the procedure explained for the synthesis of Example 48 using 1-(3-chloropyridin-2-yl)ethan-1-amine instead of (3-bromopyridin-2-yl)methanamine. C28H17F6N3O. 526.1 (M+1). 1H NMR (400 MHz, DMSO-d6) δ 10.64 (s, 1H), 8.12 (ddd, J=6.1, 4.1, 1.8 Hz, 1H), 7.98 (d, J=8.7 Hz, 1H), 7.84 (d, J=7.0 Hz, 2H), 7.74-7.66 (m, 2H), 7.66-7.58 (m, 1H), 7.53 (tt, J=5.9, 1.5 Hz, 1H), 7.48-7.37 (m, 1H), 7.20 (t, J=8.9 Hz, 2H), 6.95-6.71 (m, 2H), 2.11 (s, 3H).

Example 45

5-(3-(2,3-difluorophenyl)-1-methylimidazo[1,5-a]pyridin-8-yl)-N-(4-fluorophenyl)-2-(trifluoromethyl)benzamide

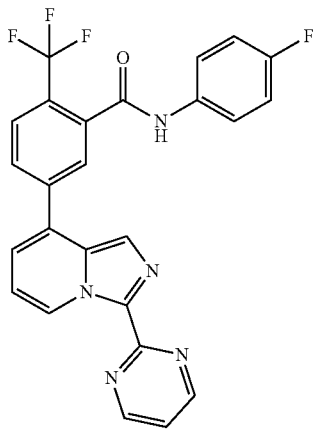 [SMILES: O=C(Nc1ccc(F)cc1)c1cc(-c2cccn3c(-c4ncccn4)ncc23)ccc1C(F)(F)F]

Example 45 was synthesized following the procedure explained for the synthesis of Example 48 using pyrimidine-2-carboxylic acid instead of 2,3-difluorobenzoic acid. C25H15F4N5O. 478.1 (M+1). 1H NMR (400 MHz, DMSO-d6) δ 10.77 (s, 1H), 9.91 (d, J=7.3 Hz, 1H), 9.02 (d, J=4.9 Hz, 2H), 8.22-7.97 (m, 4H), 7.82-7.66 (m, 2H), 7.52 (t, J=4.9 Hz, 1H), 7.45-7.34 (m, 1H), 7.30-7.14 (m, 3H).

Example 46

N-(4-fluorophenyl)-5-(3-(oxazol-2-yl)imidazo[1,5-a]pyridin-8-yl)-2-(trifluoromethyl)benzamide

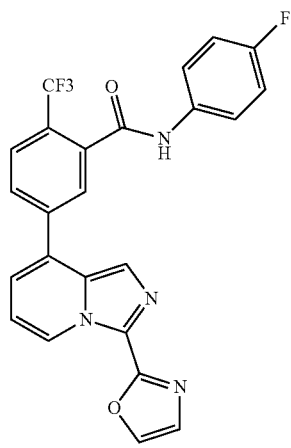 [SMILES: O=C(Nc1ccc(F)cc1)c1cc(-c2cccn3c(-c4ncco4)ncc23)ccc1C(F)(F)F]

This compound was synthesized in a manner similar to that employed in the synthesis of Example 17 using oxazole-2-carboxylic acid instead of pyridazine-3-carboxylic acid. C24H14F4N4O2. 426.1 (M+H). 1H NMR (400 MHz, Chloroform-d) δ 9.56 (d, J=6.9 Hz, 1H), 7.94 (d, J=8.9 Hz, 3H), 7.89-7.79 (m, 2H), 7.71-7.50 (m, 3H), 7.39 (d, J=0.8 Hz, 1H), 7.14-6.98 (m, 4H).

Example 47

5-(3-(2,3-difluorophenyl)imidazo[1,5-a]pyridin-8-yl)-N-(4-fluorophenyl)-2-(trifluoromethyl)nicotinamide

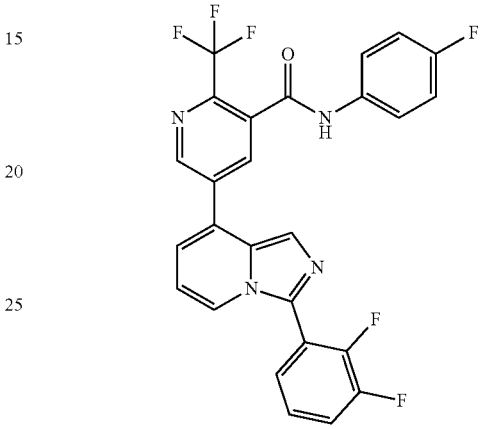

Example 47 was synthesized following the procedure explained for the synthesis of Example 42 using 5-bromo-N-(4-fluorophenyl)-2-(trifluoromethyl)nicotinamide instead of 3-bromo-2-fluoro-N-(4-fluorophenyl)-6-methylbenzamide. C26H14F6N4O. 513.0 (M+1). 1H NMR (400 MHz, DMSO-d6) δ 10.86 (s, 1H), 9.26 (d, J=2.0 Hz, 1H), 8.64 (d, J=2.1 Hz, 1H), 8.33-8.22 (m, 1H), 7.94 (d, J=1.0 Hz, 1H), 7.74-7.69 (m, 2H), 7.68-7.62 (m, 1H), 7.56 (ddd, J=8.2, 4.3, 1.7 Hz, 1H), 7.44 (td, J=8.2, 3.4 Hz, 1H), 7.30 (d, J=6.7 Hz, 1H), 7.23 (t, J=8.9 Hz, 2H), 6.98 (t, J=7.0 Hz, 1H).

Example 48

5-(3-(2,3-difluorophenyl)imidazo[1,5-a]pyridin-8-yl)-N-(4-fluorophenyl)-2-(trifluoromethyl)benzamide

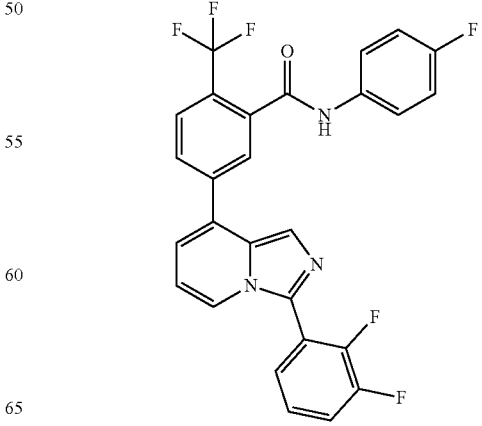

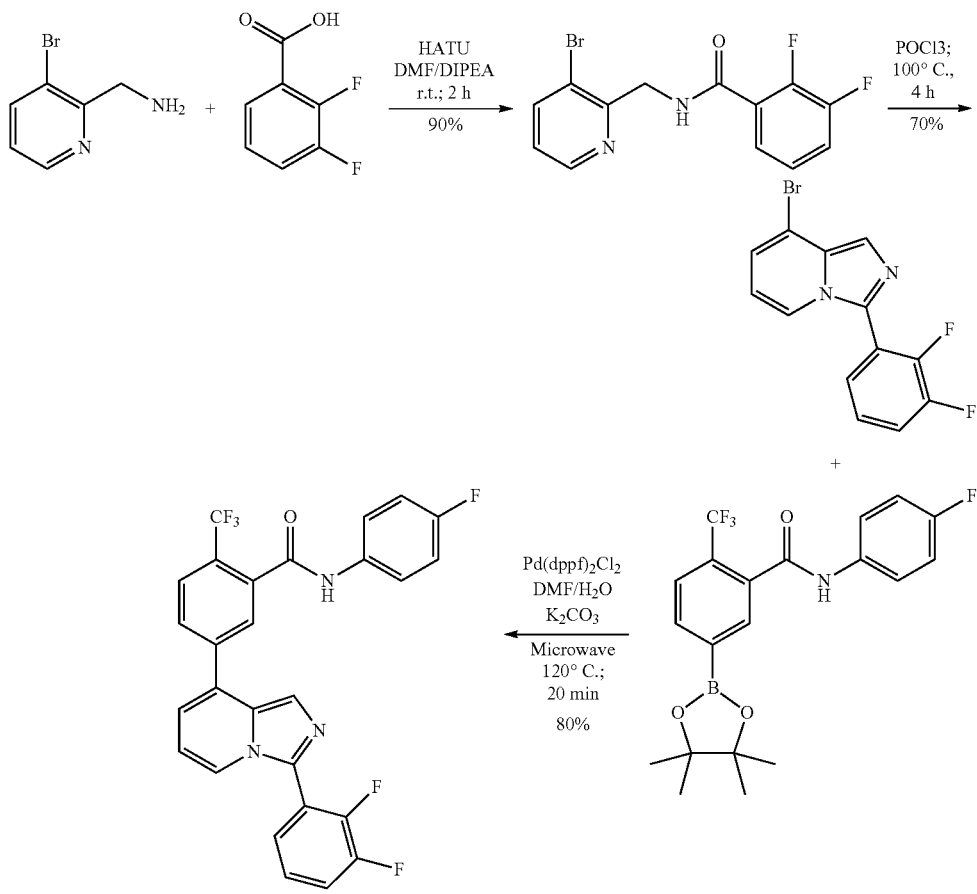

To a solution of the 2,3-difluorobenzoic acid (708 mg, 4.5 mmol) and HATU (1419 mg, 3.73 mmol) in DMF (3 mL), (3-bromopyridin-2-yl)methanamine hydrogen bromide (1000 mg, 3.7 mmol) and DIPEA (0.5 mL) were added and stirred at room temperature for about 2 h. To the reaction mixture, water (50 mL) was added, stirred for about 30 min, and the product N-((3-bromopyridin-2-yl)methyl)-2,3-difluorobenzamide was filtered, washed with hexanes and dried (1100 mg, 90% yield). 329.0 (M+1).

A solution of N-((3-bromopyridin-2-yl)methyl)-2,3-difluorobenzamide (1100 mg, 1.8 mmol) in POCl₃ (5 mL) was heated at 100° C. for about 3 h. The reaction mixture was cooled, and slowly poured in to an ice bath and stirred for about 45 min. No product precipitated out. The aqueous portion was extracted twice with dichloromethane (50 mL each). The organics were washed with water, brine, dried over sodium sulphate and concentrated to get the cyclized 8-bromo-3-(2,3-difluorophenyl)imidazo[1,5-a]pyridine (1020 mg, 88% yield) and used for the next step. 310.9 (M+1).

To a suspension of 8-bromo-3-(2,3-difluorophenyl)imidazo[1,5-a]pyridine (30 mg, 0.09 mmol), N-(4-fluorophenyl)-5-(4,4,5,5-tetramethyl-1,3,2-dioxaborolan-2-yl)-2-(trifluoromethyl)benzamide (50 mg, 0.12 mmol), potassium carbonate (11 mg, 0.08 mmol)) in DMF/Water (9:1) palladium catalyst (5 mol %) was added. The reaction mixture was subjected to microwave irradiation at about 120° C. for about 20 min. The reaction was diluted with ethyl acetate, filtered through celite and concentrated. The residue was purified by prep HPLC using Gilson reverse phase eluting with ACN and water with 0.1% TFA using Luna column, to give the title compound as a TFA salt (50 mg, 80% yield). C27H15F6N3O. 512.1 (M+1). 1H NMR (400 MHz, DMSO-d6) δ 10.75 (s, 1H), 8.24 (dd, J=7.3, 3.6 Hz, 1H), 8.16-8.10 (m, 1H), 8.08 (d, J=1.7 Hz, 1H), 8.03 (d, J=8.3 Hz, 1H), 7.92 (d, J=1.0 Hz, 1H), 7.73 (dd, J=9.1, 5.0 Hz, 2H), 7.66 (dtd, J=9.8, 8.1, 1.6 Hz, 1H), 7.57 (ddd, J=7.9, 4.9, 1.4 Hz, 1H), 7.44 (td, J=8.1, 4.6 Hz, 1H), 7.22 (dd, J=10.1, 7.7 Hz, 3H), 6.97 (t, J=7.0 Hz, 1H).

Example 49

N-(4-fluorophenyl)-5-(3-(2-fluorophenyl)imidazo[1,5-a]pyridin-8-yl)-2-methylnicotinamide

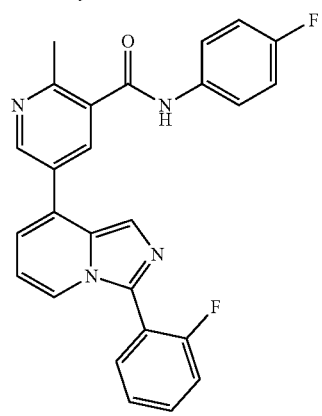

Example 49 was synthesized following the procedure explained for the synthesis of Example 17 using 2-fluorobenzoic acid instead of pyridazine-3-carboxylic acid, and replacing N-(4-fluorophenyl)-5-(4,4,5,5-tetramethyl-1,3,2-dioxaborolan-2-yl)-2-(trifluoromethyl)benzamide with N-(4-fluorophenyl)-2-methyl-5-(4,4,5,5-tetramethyl-1,3,2-dioxaborolan-2-yl)nicotinamide. C26H18F2N4O. 441.1 (M+1). 1H NMR (400 MHz, DMSO-d6) δ 10.62 (s, 1H), 8.97 (d, J=2.2 Hz, 1H), 8.28 (d, J=2.3 Hz, 1H), 8.05 (dd, J=7.1, 3.9 Hz, 1H), 7.91 (s, 1H), 7.84-7.69 (m, 3H), 7.70-7.58 (m, 1H), 7.57-7.35 (m, 2H), 7.22 (t, J=8.9 Hz, 2H), 7.16 (d, J=6.7 Hz, 1H), 6.93 (t, J=6.9 Hz, 1H), 2.67 (s, 3H).

Example 50

5-(3-(2,3-difluorophenyl)-[1,2,4]triazolo[4,3-b]pyridazin-8-yl)-N-(4-fluorophenyl)-2-methylnicotinamide

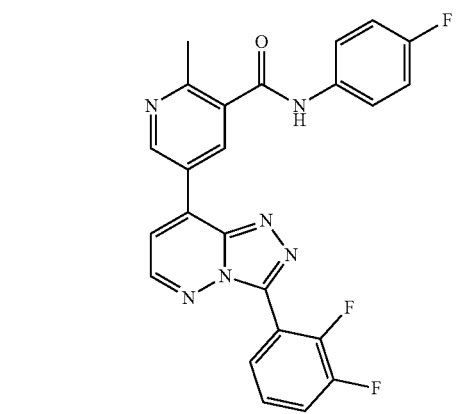 [SMILES: Cc1ncc(-c2ccnn3c(-c4cccc(F)c4F)nnc23)cc1C(=O)Nc1ccc(F)cc1]

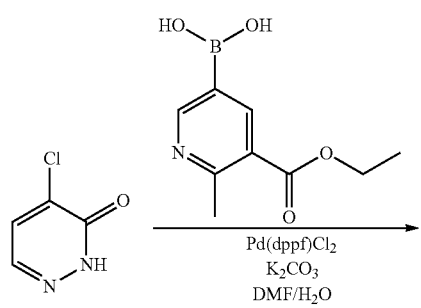

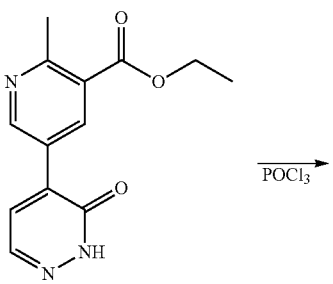

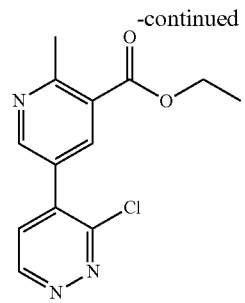

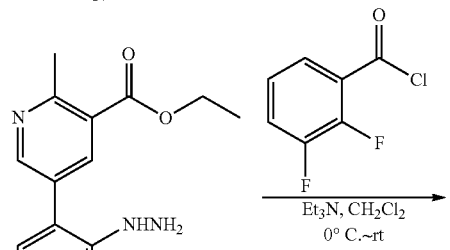

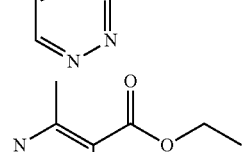

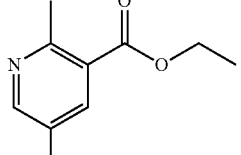

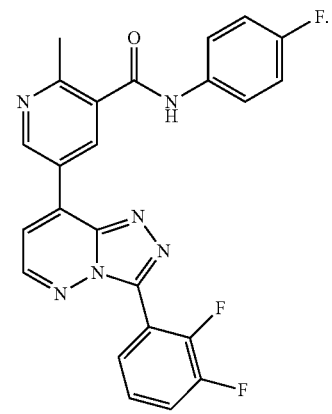

4-chloropyridazin-3(2H)-one (200.0 mg, 1.532 mmol), (5-(ethoxycarbonyl)-6-methylpyridin-3-yl)boronic acid (535.3 mg, 1.839 mmol), Pd(dppf)2Cl2 (125.1 mg, 0.153 mmol), and K2CO3 (635.3 mg, 4.597 mmol) in DMF (6 mL) and H2O (1 mL) were put onto microwave at 120° C. for 20 min. Diluted the reaction mixture with EtOAc, filtered through celite and washed with EtOAc. The filtrate was concentrated and purified by prep-HPLC to afford ethyl 2-methyl-5-(3-oxo-2,3-dihydropyridazin-4-yl)nicotinate (296 mg).

Ethyl 2-methyl-5-(3-oxo-2,3-dihydropyridazin-4-yl)nicotinate (296 mg, 1.142 mmol) was stirred in POCl3 (4 mL) at about 90° C. for about 2 h and concentrated. To the residue was added H2O and MeOH and purified by prep-HPLC to afford ethyl 5-(3-chloropyridazin-4-yl)-2-methylnicotinate (210 mg).

Ethyl 5-(3-chloropyridazin-4-yl)-2-methylnicotinate (90 mg, 0.324 mmol) was stirred in dioxane (5 mL) and hydrazine monohydrate (1 mL) at 100° C. for 2 h and concentrated. The crude ethyl 5-(3-hydrazinylpyridazin-4-yl)-2-methylnicotinate was used directly for next step.

To a stirred solution of ethyl 5-(3-chloropyridazin-4-yl)-2-methylnicotinate (88.6 mg, 0.324 mmol) in CH2Cl2 (10 mL) was added Et3N (163.9 mg, 1.62 mmol) in an ice bath, followed by 2,3-difluorobenzoyl chloride (114.4 mg, 0.648 mmol). The resulting mixture was stirred at rt for about 0.5 h. Poured the reaction mixture into H2O and extracted with CH2Cl2. The organic layer was concentrated and purified by prep-HPLC to afford ethyl 5-(3-(2-(2,3-difluorobenzoyl)hydrazinyl)pyridazin-4-yl)-2-methylnicotinate (25 mg).

Ethyl 5-(3-(2-(2,3-difluorobenzoyl)hydrazinyl)pyridazin-4-yl)-2-methylnicotinate (25 mg, 0.06 mmol) in acetic acid (3 mL) was put onto microwave at 140° C. for 30 min and concentrated. The residue was purified by prep-HPLC to afford 5-(3-(2,3-difluorophenyl)-[1,2,4]triazolo[4,3-b]pyridazin-8-yl)-N-(4-fluorophenyl)-2-methylnicotinamide (5 mg).

Example 51

5-(3-(2,3-difluorophenyl)imidazo[1,5-a]pyrazin-8-yl)-N-(4-fluorophenyl)-2-methylbenzamide

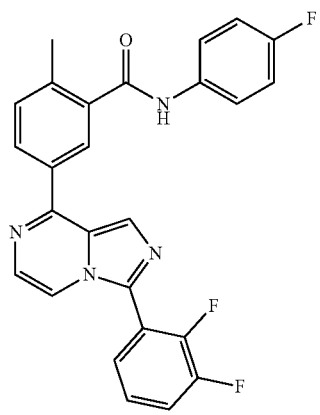 [SMILES: Cc1ccc(-c2nccn3c(-c4cccc(F)c4F)ncc23)cc1C(=O)Nc1ccc(F)cc1]

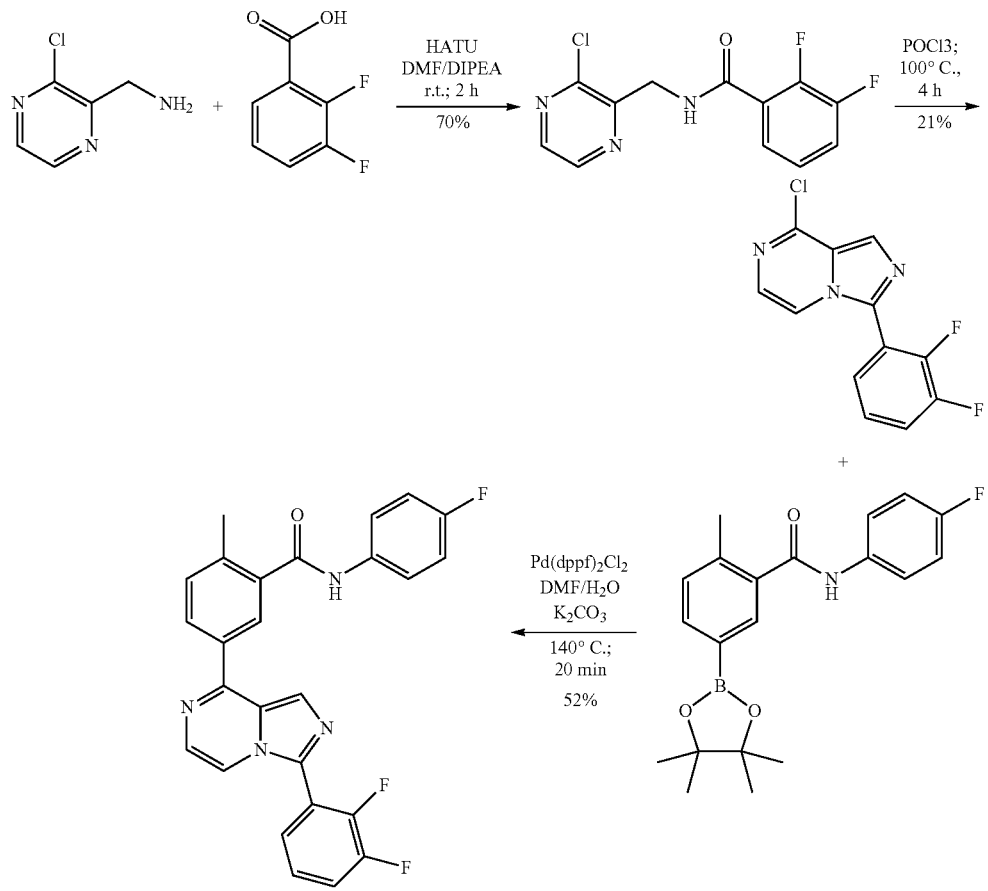

To a solution of the 2,3-difluorobenzoic acid (200 mg, 1.3 mmol) and HATU (530 mg, 1.3 mmol) in DMF (2 mL), (3-chloropyrazin-2-yl)methanamine (200 mg, 1.4 mmol) and DIPEA (0.5 mL) were added and stirred at room temperature for about 2 h. To the reaction mixture, water (50 mL) was added, stirred for about 30 min, and the product N-((3-chloropyrazin-2-yl)methyl)-2,3-difluorobenzamide was filtered, washed with hexanes and dried (250 mg, 70% yield). 284.0 (M+1).

A solution of N-((3-chloropyrazin-2-yl)methyl)-2,3-difluorobenzamide (250 mg, 0.9 mmol) in POCl3 (4 mL) was heated at about 100° C. for about 3 h. The reaction mixture was cooled, and slowly poured in to an ice bath and stirred for about 45 min. No product precipitated out. The aqueous portion was extracted twice with dichloromethane (50 mL each). The organics were washed with water, brine, dried over sodium sulphate and concentrated to get the cyclized 8-chloro-3-(2,3-difluorophenyl)imidazo[1,5-a]pyrazine (50 mg, 21% yield) and used for the next step. 266.0 (M+1).

To a suspension of 8-chloro-3-(2,3-difluorophenyl)imidazo[1,5-a]pyrazine (50 mg, 0.2 mmol), N-(4-fluorophenyl)-2-methyl-5-(4,4,5,5-tetramethyl-1,3,2-dioxaborolan-2-yl)benzamide (66 mg, 0.25 mmol), potassium carbonate (22 mg, 0.16 mmol)) in DMF/Water (9:1) palladium catalyst (5 mol %) was added. The reaction mixture was subjected to microwave irradiation at about 140° C. for about 15 min. The reaction was diluted with ethyl acetate, filtered through celite and concentrated. The residue was purified by prep HPLC using Gilson reverse phase eluting with ACN and water with 0.1% TFA using Luna column, to give the title compound 5-(3-(2,3-difluorophenyl)imidazo[1,5-a]pyrazin-8-yl)-N-(4-fluorophenyl)-2-methylbenzamide as a TFA salt (50 mg, 80% yield). C26H17F3N4O; 459.1 (M+1); 1H NMR (400 MHz, DMSO-d6) δ 10.52 (s, 1H), 8.33 (d, J=1.0 Hz, 1H), 8.16 (t, J=4.1 Hz, 1H), 8.11 (d, J=7.8 Hz, 2H), 7.82-7.74 (m, 3H), 7.73-7.62 (m, 1H), 7.59 (ddd, J=7.6, 4.5, 1.6 Hz, 1H), 7.54 (d, J=7.8 Hz, 1H), 7.44 (td, J=8.2, 3.6 Hz, 1H), 7.18 (t, J=8.9 Hz, 2H), 2.47 (s, 3H).

Example 52

N-(4-fluorophenyl)-2-methyl-5-(3-(o-tolyl)imidazo[1,5-a]pyrazin-8-yl)benzamide

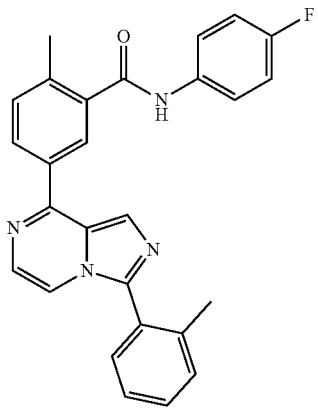 [SMILES: Cc1ccc(-c2nccn3c(-c4ccccc4C)ncc23)cc1C(=O)Nc1ccc(F)cc1]

Example 52 was synthesized following the procedure explained for the synthesis of Example 55 using 1-iodo-2-methylbenzene instead of 2-iodopyridine. C27H21FN4O; 437.1 (M+1); 1H NMR (400 MHz, DMSO-d6) δ 10.53 (s, 1H), 8.31 (s, 1H), 8.13 (d, J=7.9 Hz, 2H), 7.84 (dd, J=5.0, 1.1 Hz, 1H), 7.82-7.74 (m, 2H), 7.68 (d, J=5.0 Hz, 1H), 7.60-7.45 (m, 4H), 7.41 (td, J=7.3, 2.0 Hz, 1H), 7.20 (t, J=8.9 Hz, 2H), 2.49 (s, 3H), 2.20 (s, 3H).

Example 53

N-(4-fluorophenyl)-2-methyl-5-(3-(m-tolyl)imidazo[1,5-a]pyrazin-8-yl)benzamide

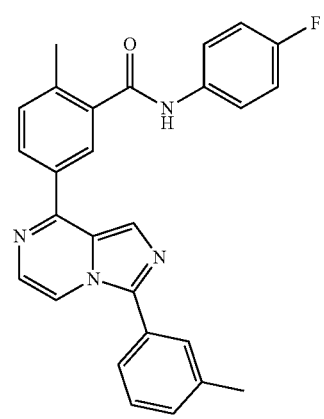 [SMILES: Cc1cccc(-c2ncc3c(-c4ccc(C)c(C(=O)Nc5ccc(F)cc5)c4)nccn23)c1]

Example 53 was synthesized following the procedure explained for the synthesis of Example 60 using 1-iodo-3-methylbenzene instead of 2-iodopyridine. C27H21FN4O; 437.1 (M+1); 1H NMR (400 MHz, DMSO-d6) δ 10.55 (s, 1H), 8.43 (dd, J=5.0, 1.0 Hz, 1H), 8.27 (s, 1H), 8.11 (d, J=7.3 Hz, 2H), 7.86-7.76 (m, 2H), 7.76-7.67 (m, 3H), 7.56 (d, J=7.9 Hz, 1H), 7.50 (t, J=7.6 Hz, 1H), 7.37 (d, J=7.6 Hz, 1H), 7.20 (t, J=8.9 Hz, 2H), 2.49 (s, 3H), 2.44 (s, 3H).

Example 54

N-(4-fluorophenyl)-2-methyl-5-(3-(pyridin-2-yl)imidazo[1,5-a]pyrazin-8-yl)benzamide

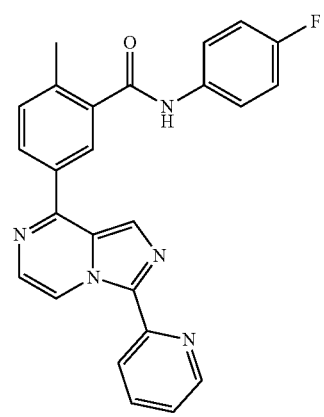 [SMILES: Cc1ccc(-c2nccn3c(-c4ccccn4)ncc23)cc1C(=O)Nc1ccc(F)cc1]

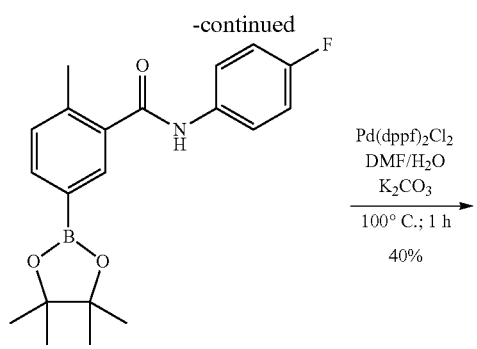

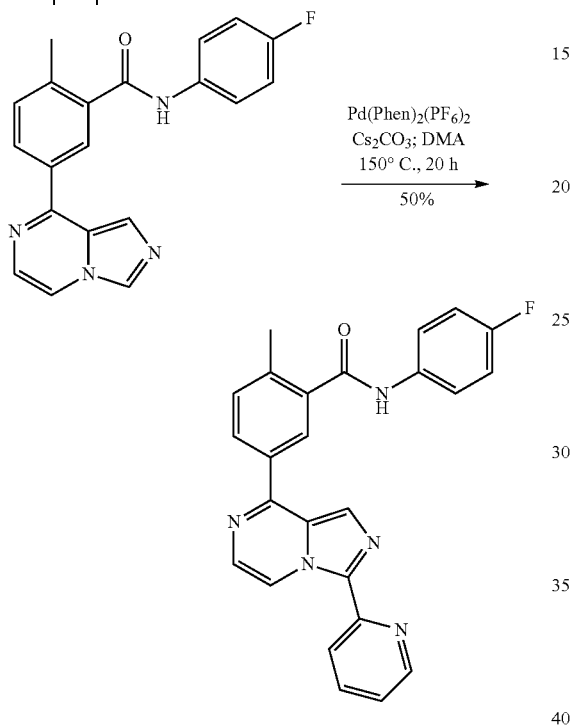

To a suspension of 8-chloroimidazo[1,5-a]pyrazine (300 mg, 1.95 mmol), N-(4-fluorophenyl)-5-(4,4,5,5-tetramethyl-1,3,2-dioxaborolan-2-yl)-2-(trifluoromethyl)benzamide (586 mg, 2.1 mmol), potassium carbonate (224 mg, 1.7 mmol) in DMF/Water (9:1) palladium catalyst (5 mol %) was added. The reaction mixture was heated at about 110° C. for about 60 min. The reaction was diluted with ethyl acetate, filtered through celite, washed with water, brine and concentrated. The residue was purified by prep HPLC using Gilson reverse phase eluting with ACN and water with 0.1% TFA using Luna column to get the N-(4-fluorophenyl)-5-(imidazo[1,5-a]pyrazin-8-yl)-2-methylbenzamide (250 mg, 37% yield). 347.1 (M+1).

To a microwave vial the reagents N-(4-fluorophenyl)-5-(imidazo[1,5-a]pyrazin-8-yl)-2-methylbenzamide (70 mg, 0.2 mmol), 2-iodopyridine (46 mg, 0.22 mmol), Cesium carbonate (73 mg, 0.22 mmol) and the palladium complex Pd(phen)2(PF6)2 Bis(1,10-phenanthroline)palladium Hexafluorophosphate (8 mg, 10 mol %) were added in dimethyl acetamide (2 mL) and heated at about 150° C. for about 20 h. The reaction mixture was purified by prep HPLC using Gilson reverse phase eluting with ACN and water with 0.1% TFA using Luna column to get the title compound N-(4-fluorophenyl)-2-methyl-5-(4,4,5,5-tetramethyl-1,3,2-dioxaborolan-2-yl)benzamide as a TFA salt (10 mg, 45% yield). C25H18FN5O; 424.1 (M+1); 1H NMR (400 MHz, DMSO-d6) δ 10.55 (s, 1H), 9.71 (dd, J=5.0, 1.0 Hz, 1H), 8.79 (ddd, J=4.9, 1.8, 0.9 Hz, 1H), 8.41-8.28 (m, 2H), 8.11 (d, J=7.4 Hz, 2H), 8.02 (td, J=7.7, 1.8 Hz, 1H), 7.93 (d, J=5.0 Hz, 1H), 7.79 (dd, J=8.9, 5.1 Hz, 2H), 7.56 (d, J=7.9 Hz, 1H), 7.48 (ddd, J=7.5, 4.8, 1.2 Hz, 1H), 7.20 (t, J=8.9 Hz, 2H), 2.5 (s, 3H).

Example 55

5-(3-(2,3-difluorophenyl)imidazo[1,2-a]pyridin-8-yl)-N-(4-fluorophenyl)-2-(trifluoromethoxy)benzamide

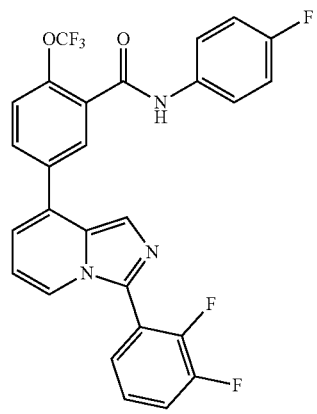 [SMILES: O=C(Nc1ccc(F)cc1)c1cc(-c2cccn3c(-c4cccc(F)c4F)ncc23)ccc1OC(F)(F)F]

Example 55 was synthesized following the procedure explained for the synthesis of Example 42 using 5-bromo-N-(4-fluorophenyl)-2-(trifluoromethoxy)benzamide instead of 3-bromo-2-fluoro-N-(4-fluorophenyl)-6-methylbenzamide. C27H15F6N3O2. 528 (M+1). 1H NMR (400 MHz, DMSO-d6) δ 10.65 (s, 1H), 8.17 (dd, J=7.2, 3.5 Hz, 1H), 8.08-8.00 (m, 2H), 7.83 (s, 1H), 7.77-7.57 (m, 4H), 7.58-7.50 (m, 1H), 7.46-7.37 (m, 1H), 7.24-7.15 (m, 2H), 7.13 (d, J=6.7 Hz, 1H), 6.91 (t, J=6.9 Hz, 1H).

Example 56

2-(3-(2,3-difluorophenyl)imidazo[1,5-a]pyridin-8-yl)-N-(4-fluorophenyl)-5-methylisonicotinamide

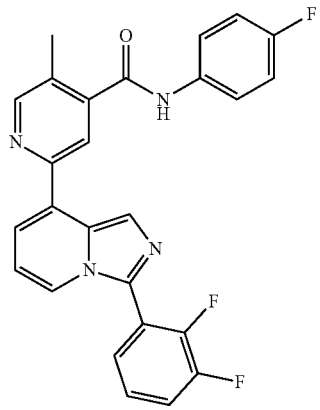 [SMILES: Cc1cnc(-c2cccn3c(-c4cccc(F)c4F)ncc23)cc1C(=O)Nc1ccc(F)cc1]

Example 56 was synthesized following the procedure explained for the synthesis of Example 42 using 2-bromo-N-(4-fluorophenyl)-5-methyl isonicotinamide instead of 3-bromo-2-fluoro-N-(4-fluorophenyl)-6-methylbenzamide.

$C_{26}H_{17}F_3N_4O$. 459 (M+1). $^1$H NMR (400 MHz, Chloroform-d) δ 9.51 (s, 1H), 8.68 (s, 1H), 7.78-7.73 (m, 1H), 7.72 (s, 1H), 7.65 (s, 1H), 7.62-7.54 (m, 2H), 7.38-7.26 (m, 2H), 7.19-7.10 (m, 2H), 7.04-6.95 (m, 2H), 6.68 (t, J=7.0 Hz, 1H), 2.53 (s, 3H).

Example 57

6-(3-(2,3-difluorophenyl)imidazo[1,5-a]pyridin-8-yl)-N-(4-fluorophenyl)-3-methylpicolinamide

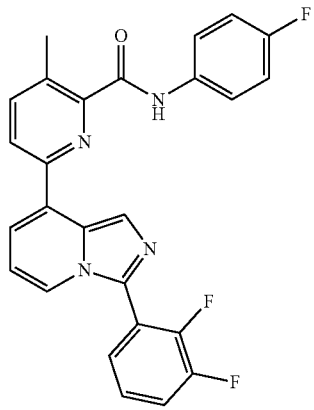

Example 57 was synthesized following the procedure explained for the synthesis of Example 42 using 6-bromo-N-(4-fluorophenyl)-3-methylpicolinamide instead of 3-bromo-2-fluoro-N-(4-fluorophenyl)-6-methylbenzamide. $C_{26}H_{17}F_3N_4O$. 459 (M+1). $^1$H NMR (400 MHz, Chloroform-d) δ 10.30 (s, 1H), 8.14 (d, J=1.0 Hz, 1H), 7.96-7.90 (m, 1H), 7.88 (d, J=8.0 Hz, 1H), 7.84-7.80 (m, 1H), 7.74-7.69 (m, 2H), 7.59-7.52 (m, 1H), 7.39-7.27 (m, 3H), 7.10-7.02 (m, 2H), 6.83 (t, J=7.0 Hz, 1H), 2.91 (s, 3H).

Example 58

5-(3-(2,3-difluorophenyl)imidazo[1,5-a]pyridin-8-yl)-2-methyl-N-(4-(trifluoromethoxy)phenyl)nicotinamide

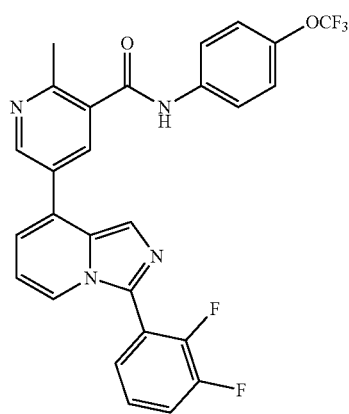 [SMILES: Cc1ncc(-c2cccn3c(-c4cccc(F)c4F)ncc23)cc1C(=O)Nc1ccc(OC(F)(F)F)cc1]

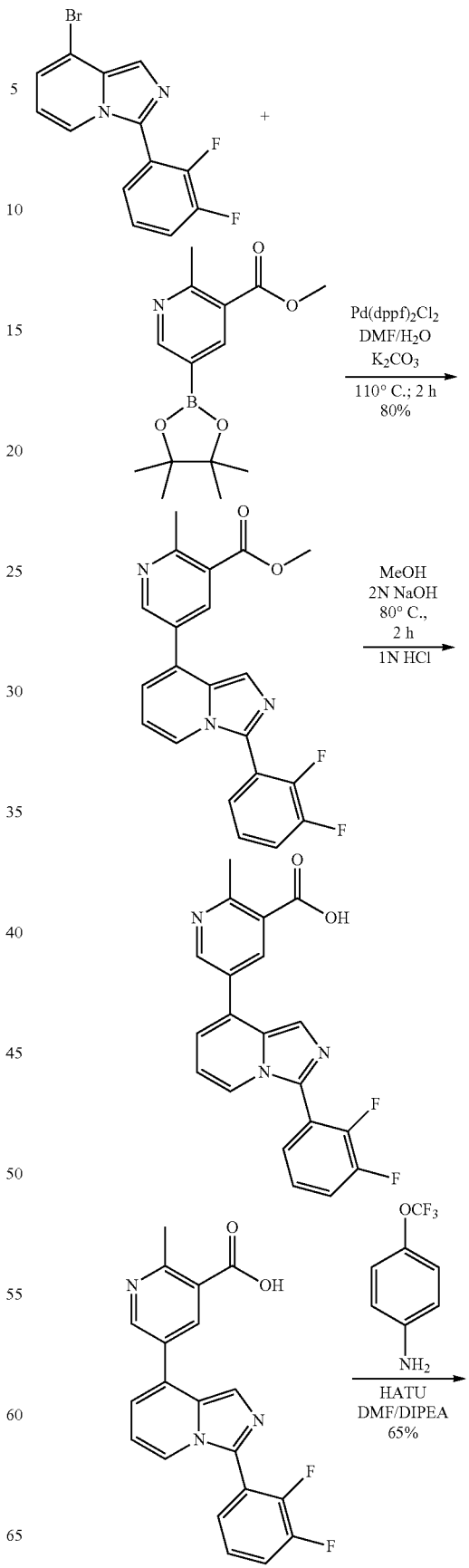

-continued

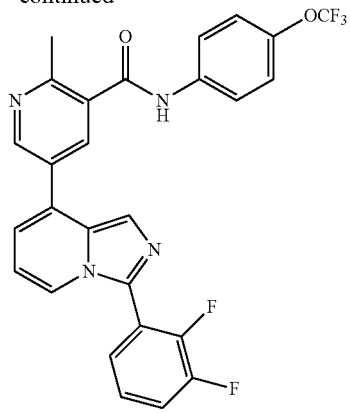

To a suspension of 8-bromo-3-(2,3-difluorophenyl)imidazo[1,5-a]pyridine (475 mg, 1.5 mmol), methyl 2-methyl-5-(4,4,5,5-tetramethyl-1,3-dioxolan-2-yl)nicotinate (512 mg, 1.8 mmol), potassium carbonate (212 mg, 1.5 mmol) in DMF/Water (9:1) palladium catalyst (5 mol %) was added. The reaction mixture was heated at about 110° C. for about 2 h. The reaction was diluted with ethyl acetate, filtered through celite, washed with water, brine and concentrated. The residue was precipitated from ethyl acetate and hexanes to get the product methyl 5-(3-(2,3-difluorophenyl)imidazo[1,5-a]pyridin-8-yl)-2-methylnicotinate (470 mg, 80% yield). 380.1(M+1). 1H NMR (400 MHz, DMSO-d6) δ 9.01 (s, 1H), 8.50 (s, 1H), 8.27-8.10 (m, 1H), 7.74 (s, 1H), 7.65 (q, J=8.8 Hz, 1H), 7.55 (d, J=5.8 Hz, 1H), 7.45 (d, J=9.6 Hz, 1H), 7.14 (d, J=6.7 Hz, 1H), 6.92 (t, J=6.9 Hz, 1H), 3.90 (s, 3H), 2.81 (s, 3H).

To a suspension of methyl 5-(3-(2,3-difluorophenyl)imidazo[1,5-a]pyridin-8-yl)-2-methylnicotinate (500 mg, 1.3 mmol) in methanol (5 mL), 2N sodium hydroxide (105 mg, 2.6 mmol) was added and heated at about 80° C. for about 2 h, during the period, the reaction mixture becomes homogeneous and hydrolysis was complete. The reaction mixture was concentrated. The residue was dissolved in water (10 mL) and acidified with 1N HCl, no product was precipitated. The solvents were distilled off and the product 5-(3-(2,3-difluorophenyl)imidazo[1,5-a]pyridin-8-yl)-2-methylnicotinic acid (450 mg, 93% yield) was used for the next steps. 366.1(M+1). 1H NMR (400 MHz, DMSO-d6) δ 8.99 (d, J=2.4 Hz, 1H), 8.49 (d, J=2.4 Hz, 1H), 8.19 (dd, J=7.3, 3.2 Hz, 1H), 7.73 (d, J=1.0 Hz, 1H), 7.65 (dtd, J=9.8, 8.2, 1.6 Hz, 1H), 7.56 (ddd, J=8.1, 4.8, 1.7 Hz, 1H), 7.43 (td, J=8.1, 3.8 Hz, 1H), 7.14 (d, J=6.6 Hz, 1H), 6.92 (t, J=6.9 Hz, 1H), 2.82 (s, 3H).

To a solution of 5-(3-(2,3-difluorophenyl)imidazo[1,5-a]pyridin-8-yl)-2-methylnicotinic acid (40 mg, 0.1 mmol) and HATU (49 mg, 0.13 mmol) in DMF (2 mL), 4-(trifluoromethoxy)aniline (25 mg, 0.14 mmol) and DIPEA (0.2 mL) were added and stirred at room temperature for about 2 h. After the completion, the reaction mixture was purified by prep HPLC using Gilson reverse phase eluting with ACN and water with 0.1% TFA using Luna column to get the title compound 5-(3-(2,3-difluorophenyl)imidazo[1,5-a]pyridin-8-yl)-2-methyl-N-(4-(trifluoromethoxy)phenyl) nicotinamide (40 mg, 70% yield). C27H17F5N4O2. 525.1 (M+1). 1H NMR (400 MHz, DMSO-d6) δ 10.78 (s, 1H), 9.00 (d, J=2.3 Hz, 1H), 8.34 (d, J=2.3 Hz, 1H), 8.22 (dd, J=7.2, 3.6 Hz, 1H), 7.95 (d, J=0.9 Hz, 1H), 7.87 (d, J=9.1 Hz, 2H), 7.67 (dtd, J=9.9, 8.2, 1.7 Hz, 1H), 7.57 (ddd, J=7.7, 4.9, 1.5 Hz, 1H), 7.45 (dd, J=7.9, 4.7 Hz, 1H), 7.42-7.36 (m, 2H), 7.20 (d, J=6.7 Hz, 1H), 6.97 (t, J=7.0 Hz, 1H), 2.69 (s, 3H).

Example 59

N-(4-cyano-3-(trifluoromethyl)phenyl)-5-(3-(2,3-difluorophenyl)imidazo[1,5-a]pyridin-8-yl)-2-methylnicotinamide

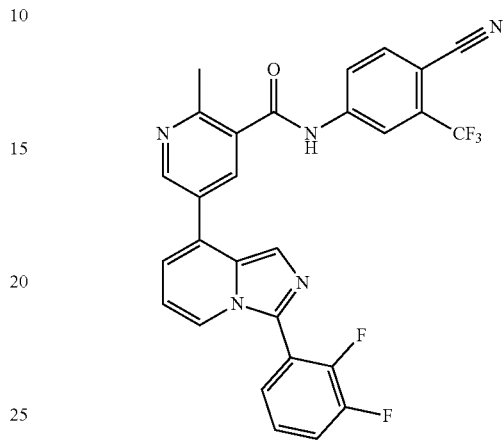

Example 59 was synthesized following the procedure explained for the synthesis of Example 58 using 4-amino-2-(trifluoromethyl)benzonitrile instead of 4-(trifluoromethoxy)aniline. C28H16F5N5O. 534.1 (M+1). 1H NMR (400 MHz, Chloroform-d) δ 8.95 (d, J=2.1 Hz, 1H), 8.74 (s, 1H), 8.09 (t, J=8.9 Hz, 3H), 7.84 (d, J=8.2 Hz, 3H), 7.53 (d, J=8.3 Hz, 1H), 7.45 (d, J=7.1 Hz, 1H), 7.40-7.28 (m, 1H), 6.85 (d, J=6.8 Hz, 1H), 6.77 (t, J=6.8 Hz, 1H), 2.82 (s, 3H).

Example 60

5-(3-(2,3-difluorophenyl)imidazo[1,5-a]pyridin-8-yl)-N-(5-fluoropyridin-2-yl)-2-methylnicotinamide

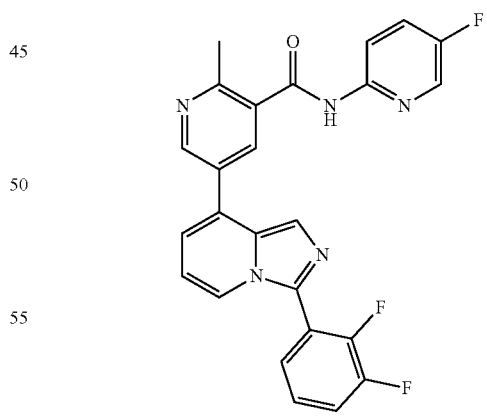

Example 60 was synthesized following the procedure explained for the synthesis of Example 58 using 5-fluoropyridin-2-amine instead of 4-(trifluoromethoxy)aniline. C25H16F3N5O. 460.1 (M+1). 1H NMR (400 MHz, Chloroform-d) δ 8.98 (d, J=2.2 Hz, 1H), 8.50 (s, 1H), 8.41 (dd, J=9.1, 4.1 Hz, 1H), 8.15 (d, J=2.2 Hz, 1H), 8.12 (d, J=2.9 Hz, 1H), 7.86 (dd, J=7.2, 4.2 Hz, 1H), 7.70 (d, J=1.0 Hz, 1H), 7.52 (ddd, J=7.6, 4.4, 1.6 Hz, 2H), 7.40-7.27 (m, 2H), 6.87 (dd, J=6.7, 0.9 Hz, 1H), 6.78 (t, J=6.9 Hz, 1H), 2.85 (s, 3H).0

Example 61

N-(4-chlorophenyl)-5-(3-(2,3-difluorophenyl)imidazo[1,2-a]pyridin-8-yl)-2-methylnicotinamide

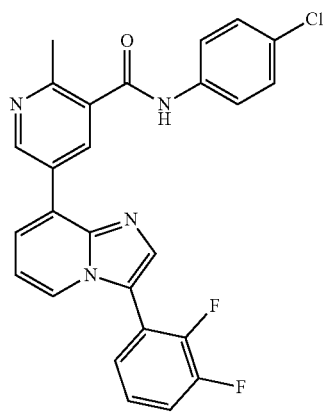 [SMILES: Cc1ncc(-c2cccn3c(-c4cccc(F)c4F)cnc23)cc1C(=O)Nc1ccc(Cl)cc1]

Example 61 was synthesized following the procedure explained for the synthesis of Example 58 using 4-chloroaniline instead of 4-(trifluoromethoxy)aniline. $C_{26}H_{17}ClF_2N_4O$. 475 (M+1). $^1$H NMR (400 MHz, DMSO-d6) δ 10.70 (s, 1H), 8.97 (d, J=2.2 Hz, 1H), 8.31 (d, J=2.2 Hz, 1H), 8.20 (dd, J=7.2, 3.6 Hz, 1H), 7.93 (s, 1H), 7.80-7.72 (m, 2H), 7.70-7.59 (m, 1H), 7.58-751 (m, 1H), 7.48-7.38 (m, 3H), 7.18 (d, J=6.7 Hz, 1H), 6.94 (t, J=7.0 Hz, 1H), 2.67 (s, 3H).

Example 62

2-cyclopropyl-5-(3-(2,3-difluorophenyl)imidazo[1,5-a]pyridin-8-yl)-N-(4-fluorophenyl)benzamide

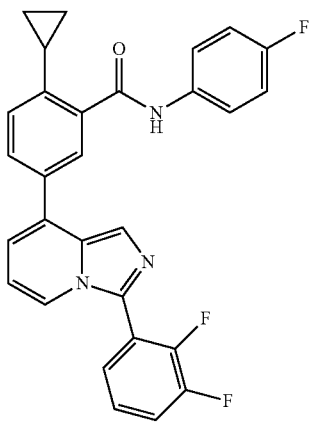 [SMILES: O=C(Nc1ccc(F)cc1)c1cc(-c2cccn3c(-c4cccc(F)c4F)ncc23)ccc1C1CC1]

Example 62 was synthesized following the procedure explained for the synthesis of Example 42 using 5-bromo-2-cyclopropyl-N-(4-fluorophenyl)benzamide instead of 3-bromo-2-fluoro-N-(4-fluorophenyl)-6-methylbenzamide. $C_{29}H_{20}F_3N_3O$. 484 (M+1). $^1$H NMR (400 MHz, Chloroform-d) δ 8.13 (s, 1H), 7.87-7.77 (m, 2H), 7.77-7.66 (m, 2H), 7.66-7.58 (m, 2H), 7.55-7.46 (m, 1H), 7.40-7.26 (m, 2H), 7.15 (d, J=8.0 Hz, 1H), 7.05 (t, J=8.4 Hz, 2H), 6.88 (d, J=6.7 Hz, 1H), 6.78 (t, J=6.9 Hz, 1H), 2.45-2.30 (m, 1H), 1.14-1.04 (m, 2H), 0.93-0.84 (m, 3H).

Example 63

N-(3-bromo-4-fluorophenyl)-5-(3-(2,3-difluorophenyl)imidazo[1,5-a]pyridin-8-yl)-2-methylnicotinamide

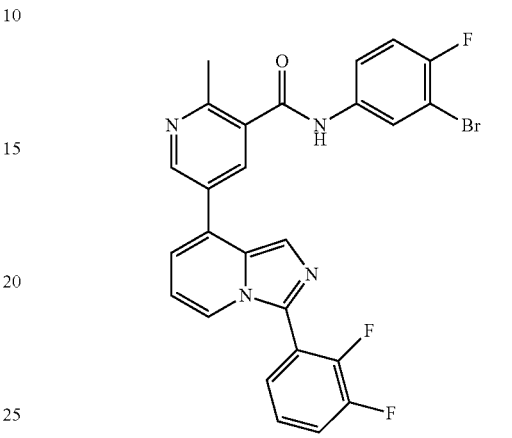

Example 63 was synthesized following the procedure explained for the synthesis of Example 58 using 3-bromo-4-fluoroaniline instead of 4-(trifluoromethoxy)aniline. $C_{26}H_{16}BrF_3N_4O$. 538 (M+1). H NMR (400 MHz, DMSO-d6) δ 10.73 (s, 1H), 8.96 (d, J=2.2 Hz, 1H), 8.30 (d, J=2.3 Hz, 1H), 8.22-8.15 (m, 2H), 7.90 (s, 1H), 7.72-7.48 (m, 3H), 7.48-7.29 (m, 2H), 7.16 (d, J=6.7 Hz, 1H), 6.93 (t, J=6.9 Hz, 1H), 2.66 (s, 3H).

Example 64

N-(4-chloro-2-fluorophenyl)-5-(3-(2,3-difluorophenyl)imidazo[1,5-a]pyridin-8-yl)-2-methylnicotinamide

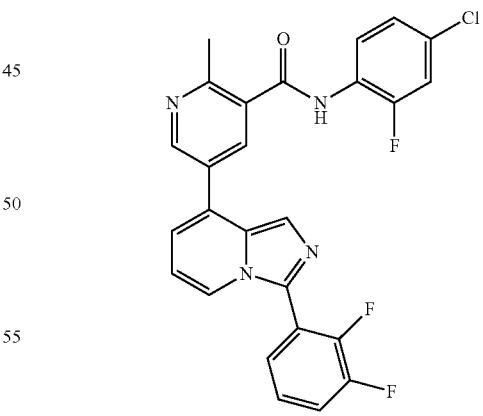

Example 64 was synthesized following the procedure explained for the synthesis of Example 58 using 4-chloro-2-fluoroaniline instead of 4-(trifluoromethoxy)aniline. $C_{26}H_{16}ClF_3N_4O$. 493 (M+1), $^1$H NMR (400 MHz, Chloroform-d) δ 8.97 (d, J=2.2 Hz, 1H), 8.39 (s, 1H), 8.12 (d, J=2.2 Hz, 1H), 7.96-7.79 (m, 2H), 7.65 (s, 1H), 7.54-7.46 (m, 1H), 7.38-7.26 (m, 2H), 7.24-7.14 (m, 2H), 6.86 (dd, J=6.7, 0.9 Hz, 1H), 6.77 (t, J=6.9 Hz, 1H), 2.84 (s, 3H).

Example 65

2-(3-(2,3-difluorophenyl)imidazo[1,5-a]pyridin-8-yl)-N-(4-fluorophenyl)-5-methylpyrimidine-4-carboxamide

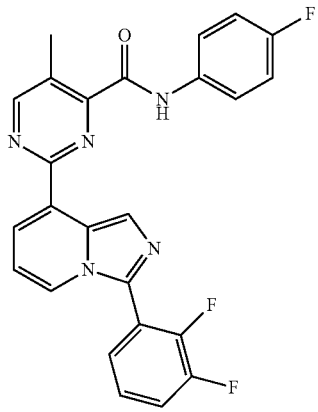 [SMILES: Cc1cnc(-c2cccn3c(-c4cccc(F)c4F)ncc23)nc1C(=O)Nc1ccc(F)cc1]

Example 65 was synthesized following the procedure explained for the synthesis of Example 42 using 2-bromo-N-(4-fluorophenyl)-5-methylpyrimidine-4-carboxamide instead of 3-bromo-2-fluoro-N-(4-fluorophenyl)-6-methylbenzamide. $C_{25}H_{16}F_3N_5O$. 460 (M+1). $^1$HNMR (400 MHz, DMSO-d6) δ 10.83 (s, 1H), 9.08 (s, 1H), 8.48 (d, J=1.0 Hz, 1H), 8.37-8.21 (m, 2H), 7.87-7.78 (m, 2H), 7.65-7.52 (m, 2H), 7.45-7.36 (m, 1H), 7.27-7.18 (m, 2H), 6.99 (t, J=7.0 Hz, 1H), 2.53 (s, 3H).

Example 66

5-(3-(2,3-difluorophenyl)imidazo[1,5-a]pyridin-8-yl)-2-methyl-N-phenylnicotinamide

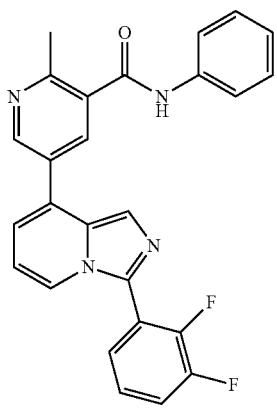 [SMILES: Cc1ncc(-c2cccn3c(-c4cccc(F)c4F)ncc23)cc1C(=O)Nc1ccccc1]

Example 66 was synthesized following the procedure explained for the synthesis of Example 58 using aniline instead of 4-(trifluoromethoxy)aniline. $C_{26}H_{18}F_2N_4O$. 441 (M+1). $^1$H NMR (400 MHz, DMSO-d6) δ 10.55 (s, 1H), 8.95 (d, J=2.3 Hz, 1H), 8.26 (d, J=2.3 Hz, 1H), 8.18 (dd, J=7.4, 3.5 Hz, 1H), 7.89 (s, 1H), 7.76-7.69 (m, 2H), 7.67-7.59 (m, 1H), 7.58-7.51 (m, 1H), 7.46-7.39 (m, 1H), 7.39-7.31 (m, 2H), 7.18-7.08 (m, 2H), 6.92 (t, J=6.9 Hz, 1H), 2.66 (s, 3H).

Example 67

N-(4-(difluoromethoxy)phenyl)-5-(3-(2,3-difluorophenyl)imidazo[1,5-a]pyridin-8-yl)-2-methylnicotinamide

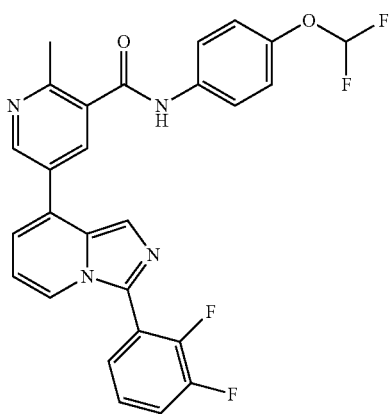 [SMILES: Cc1ncc(-c2cccn3c(-c4cccc(F)c4F)ncc23)cc1C(=O)Nc1ccc(OC(F)F)cc1]

Example 67 was synthesized following the procedure explained for the synthesis of Example 58 using 4-(difluoromethoxy)aniline instead of 4-(trifluoromethoxy)aniline. $C_{27}H_{18}F_4N_4O_2$. 507 (M+1). $^1$H NMR (400 MHz, DMSO-d6) δ 10.64 (s, 1H), 8.96 (d, J=2.2 Hz, 1H), 8.28 (d, J=2.2 Hz, 1H), 8.21-8.16 (m, 1H), 7.90 (s, 1H), 7.83-7.70 (m, 2H), 7.70-7.58 (m, 1H), 7.58-7.48 (m, 1H), 7.48-7.27 (m, 1H), 7.27-7.08 (m, 3H), 7.00-6.83 (m, 1H), 2.66 (s, 3H).

Example 68

N-(3,4-difluorophenyl)-5-(3-(2,3-difluorophenyl)imidazo[1,2-a]pyridin-8-yl)-2-methylnicotinamide

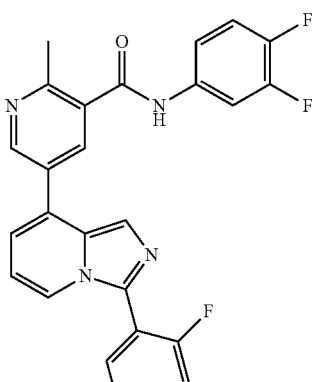

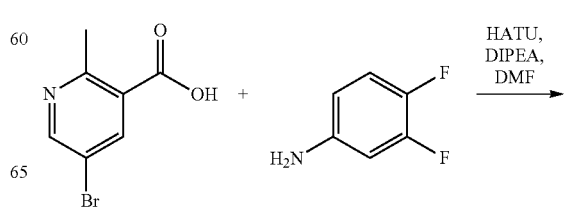

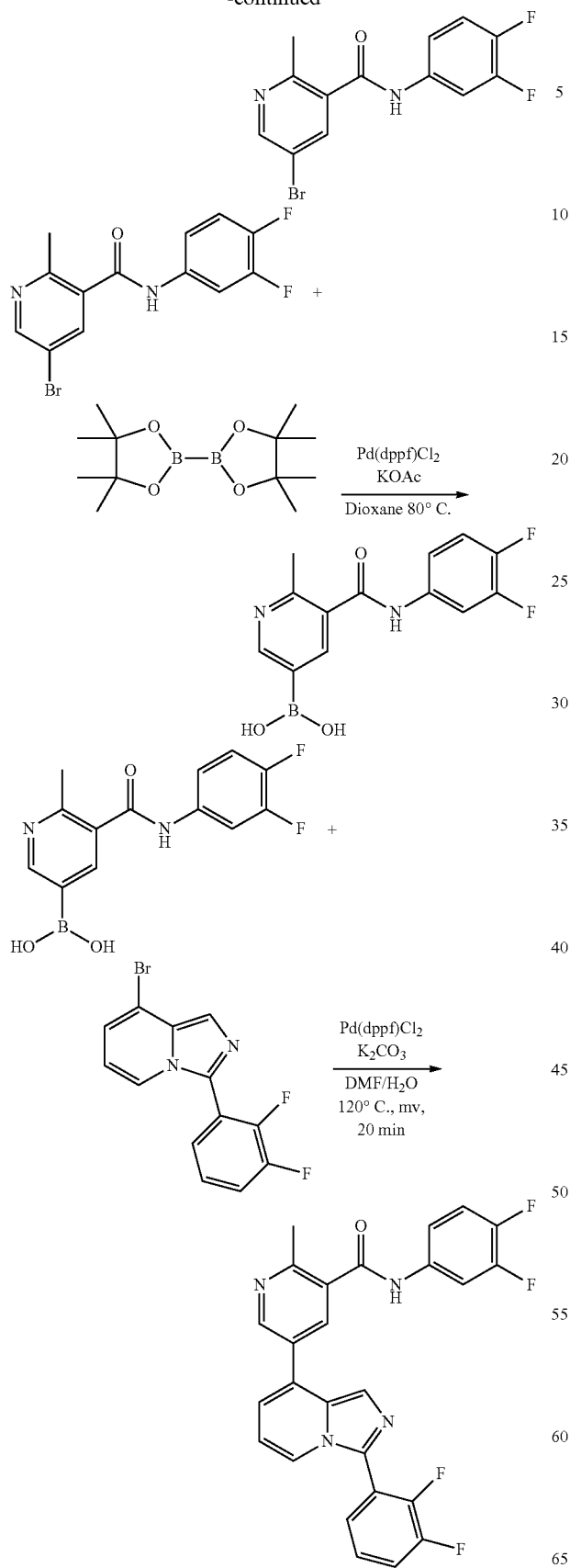

Example 68 was synthesized following the procedure explained for the synthesis of Example 48 using (5-((3,4-difluorophenyl)carbamoyl)-6-methylpyridin-3-yl)boronic acid instead of N-(4-fluorophenyl)-5-(4,4,5,5-tetramethyl-1,3,2-dioxaborolan-2-yl)-2-(trifluoromethyl)benzamide. $C_{26}H_{16}F_4N_4O$. 477 (M+1). $^1$H NMR (400 MHz, DMSO-d6) δ 10.76 (s, 1H), 8.95 (d, J=2.2 Hz, 1H), 8.26 (d, J=2.3 Hz, 1H), 8.17 (dd, J=7.1, 3.1 Hz, 1H), 7.95-7.87 (m, 1H), 7.86 (s, 1H), 7.67-7.58 (m, 1H), 7.57-7.50 (m, 1H), 7.48-7.38 (m, 3H), 7.14 (d, J=6.7 Hz, 1H), 6.91 (t, J=6.9 Hz, 1H), 2.65 (s, 3H).

Example 69

5-(3-(2,3-difluorophenyl)imidazo[1,5-a]pyridin-8-yl)-2-methyl-N-(pyridin-4-yl)nicotinamide

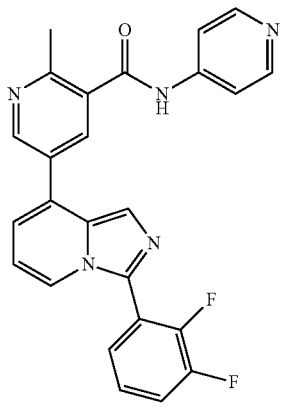 [SMILES: Cc1ncc(-c2cccn3c(-c4cccc(F)c4F)ncc23)cc1C(=O)Nc1ccncc1]

Example 69 was synthesized following the procedure explained for the synthesis of Example 58 using pyridin-4-amine instead of 4-(trifluoromethoxy)aniline. C25H17F2N5O. 442.1 (M+1). 1H NMR (400 MHz, DMSO-d6) δ 11.47 (s, 1H), 9.01 (d, J=2.3 Hz, 1H), 8.73-8.62 (m, 2H), 8.39 (d, J=2.3 Hz, 1H), 8.26-8.16 (m, 1H), 8.06-7.95 (m, 2H), 7.91 (d, J=1.0 Hz, 1H), 7.74-7.59 (m, 1H), 7.56 (dq, J=7.8, 1.8 Hz, 1H), 7.44 (td, J=7.6, 6.9, 2.0 Hz, 1H), 7.18 (d, J=6.6 Hz, 1H), 6.94 (t, J=6.9 Hz, 1H), 2.70 (s, 3H).

Example 70

2-chloro-5-(3-(2,3-difluorophenyl)imidazo[1,5-a]pyridin-8-yl)-N-(4-fluorophenyl)benzamide

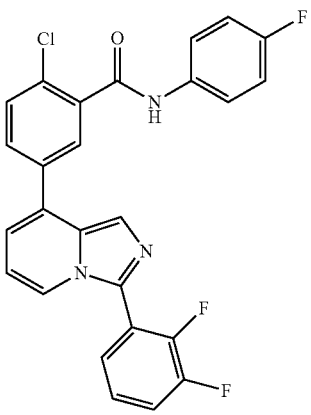 [SMILES: O=C(Nc1ccc(F)cc1)c1cc(-c2cccn3c(-c4cccc(F)c4F)ncc23)ccc1Cl]

Example 70 was synthesized following the procedure explained for the synthesis of Example 48 using (4-chloro-3-((4-fluorophenyl)carbamoyl)phenyl)boronic acid instead of N-(4-fluorophenyl)-5-(4,4,5,5-tetramethyl-1,3,2-dioxaborolan-2-yl)-2-(trifluoromethyl)benzamide.
$C_{26}H_{15}ClF_3N_3O$. 478 (M+1). $^1$H NMR (400 MHz, DMSO-d6) δ 10.67 (s, 1H), 8.18-8.13 (m, 1H), 7.95-7.91 (m, 1H), 7.79-7.71 (m, 4H), 7.66-7.59 (m, 1H), 7.56-7.52 (m, 1H), 7.44-7.38 (m, 1H), 7.22-7.16 (m, 2H), 7.12-7.08 (m, 1H), 6.93-6.87 (m, 1H).

Example 71

5-(3-(2,3-difluorophenyl)imidazo[1,5-a]pyridin-8-yl)-2-methyl-N-(2-methylpyridin-4-yl)nicotinamide

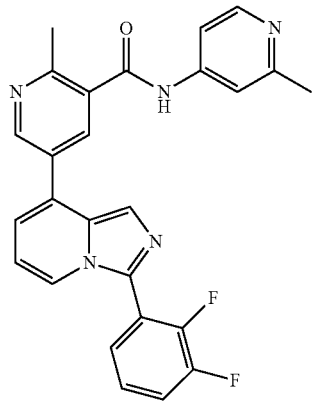 [SMILES: Cc1cc(NC(=O)c2cc(-c3cccn4c(-c5cccc(F)c5F)ncc34)cnc2C)ccn1]

Example 71 was synthesized following the procedure explained for the synthesis of Example 58 using 2-methylpyridin-4-amine instead of 4-(trifluoromethoxy)aniline. $C_{26}H_{19}F_2N_5O$. 456.1 (M+1). 1H NMR (400 MHz, DMSO-d6) δ 11.37 (s, 1H), 9.02 (d, J=2.3 Hz, 1H), 8.55 (d, J=6.4 Hz, 1H), 8.38 (d, J=2.3 Hz, 1H), 8.21 (d, J=7.2 Hz, 1H), 7.91 (d, J=1.0 Hz, 1H), 7.79 (s, 1H), 7.66 (q, J=8.5 Hz, 1H), 7.56 (d, J=7.8 Hz, 1H), 7.52-7.37 (m, 1H), 7.18 (d, J=6.6 Hz, 1H), 6.94 (t, J=6.9 Hz, 1H), 2.69 (s, 3H), 2.60 (s, 3H).

Example 72

5-(3-(2,3-difluorophenyl)imidazo[1,5-a]pyridin-8-yl)-2-methyl-N-(3-(trifluoromethoxy)phenyl)nicotinamide

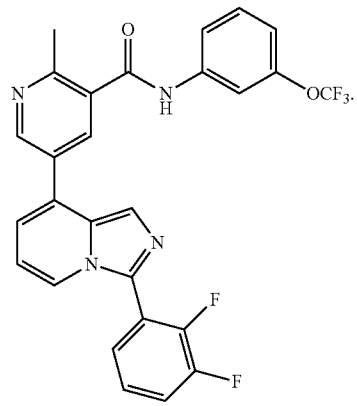 [SMILES: Cc1ncc(-c2cccn3c(-c4cccc(F)c4F)ncc23)cc1C(=O)Nc1cccc(OC(F)(F)F)c1]

Example 72 was synthesized following the procedure explained for the synthesis of Example 58 using 3-(trifluoromethoxy)aniline instead of 4-(trifluoromethoxy)aniline. C27H17F5N4O2. 525.1 (M+1). 1H NMR (400 MHz, DMSO-d6) δ 10.84 (s, 1H), 8.98 (d, J=2.2 Hz, 1H), 8.31 (d, J=2.3 Hz, 1H), 8.20 (dd, J=7.3, 3.2 Hz, 1H), 7.93 (s, 1H), 7.89 (d, J=1.0 Hz, 1H), 7.72-7.61 (m, 2H), 7.56 (ddd, J=8.1, 4.6, 1.6 Hz, 1H), 7.51 (t, J=8.2 Hz, 1H), 7.44 (td, J=8.2, 3.7 Hz, 1H), 7.17 (d, J=6.7 Hz, 1H), 7.15-7.10 (m, 1H), 6.93 (t, J=7.0 Hz, 1H), 2.68 (s, 3H).

Example 73

5-(3-(2,3-difluorophenyl)imidazo[1,5-a]pyridin-8-yl)-N-(4-fluorophenyl-2,3,5,6-d4)-2-methylnicotinamide

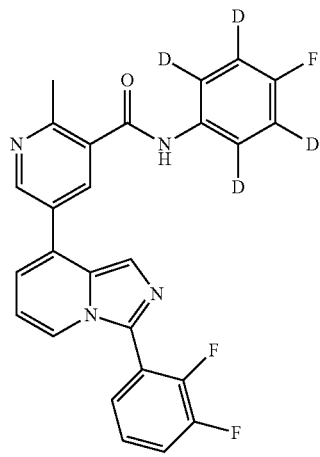 [SMILES: [2H]c1c([2H])c(NC(=O)c2cc(-c3cccn4c(-c5cccc(F)c5F)ncc34)cnc2C)c([2H])c([2H])c1F]

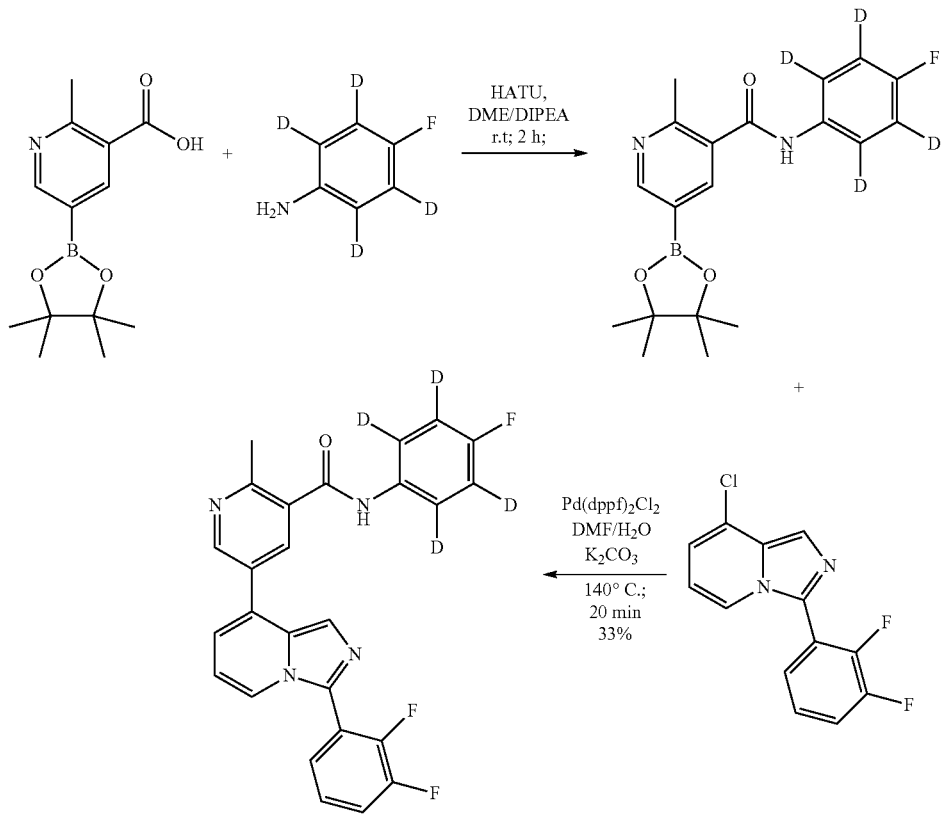 [SMILES: Cc1ncc(B2OC(C)(C)C(C)(C)O2)cc1C(=O)O ; [2H]c1c([2H])c(F)c([2H])c([2H])c1N ; [2H]c1c([2H])c(NC(=O)c2cc(B3OC(C)(C)C(C)(C)O3)cnc2C)c([2H])c([2H])c1F ; [2H]c1c([2H])c(NC(=O)c2cc(-c3cccn4c(-c5cccc(F)c5F)ncc34)cnc2C)c([2H])c([2H])c1F ; Fc1cccc(-c2ncc3c(Cl)cccn23)c1F]

To a solution of the 2-methyl-5-(4,4,5,5-tetramethyl-1,3,2-dioxaborolan-2-yl)nicotinic acid (630 mg, 2.4 mmol) and HATU (908 mg, 2.4 mmol) in DMF (3 mL), 4-fluorobenzene-2,3,5,6-d4-amine (250 mg, 2.2 mmol) and DIPEA (0.5 mL) were added and stirred at room temperature for about 2 h. To the reaction mixture, water (50 mL) was added, stirred for about 30 min, and the product N-((3-bromopyridin-2-yl)methyl)-2,3-difluorobenzamide was filtered, washed with hexanes and dried (280 mg, 45% yield). 279.1 (M+1).

To a suspension of 8-chloro-3-(2,3-difluorophenyl)imidazo[1,5-a]pyridine (285 mg, 1.1 mmol), N-(4-fluorophenyl-2,3,5,6-d4)-2-methyl-5-(4,4,5,5-tetramethyl-1,3,2-dioxaborolan-2-yl)nicotinamide (250 mg, 0.9 mmol), potassium carbonate (124 mg, 0.9 mmol) in DMF/Water (9:1) palladium catalyst (5 mol %) was added. The reaction mixture was subjected to microwave irradiation at 140° C. for about 20 min. The reaction was diluted with ethyl acetate, filtered through celite and concentrated. The residue was purified by prep HPLC using Gilson reverse phase eluting with ACN and water with 0.1% TFA using Luna column, to give the title compound as a TFA salt (135 mg, 33% yield). C26H13D4F3N4O. 463.2 (M+1). 1H NMR (400 MHz, DMSO-d6) δ 10.63 (s, 1H), 8.98 (d, J=2.3 Hz, 1H), 8.29 (d, J=2.3 Hz, 1H), 8.21 (dd, J=7.2, 3.4 Hz, 1H), 7.91 (s, 1H), 7.66 (dtd, J=9.9, 8.2, 1.7 Hz, 1H), 7.56 (ddd, J=7.5, 5.2, 1.7 Hz, 1H), 7.44 (td, J=8.1, 4.1 Hz, 1H), 7.18 (d, J=6.7 Hz, 1H), 6.95 (t, J=7.0 Hz, 1H), 2.68 (s, 3H).

Example 74

5-(3-cyclopentylimidazo[1,5-a]pyridin-8-yl)-N-(4-fluorophenyl)-2-methylnicotinamide

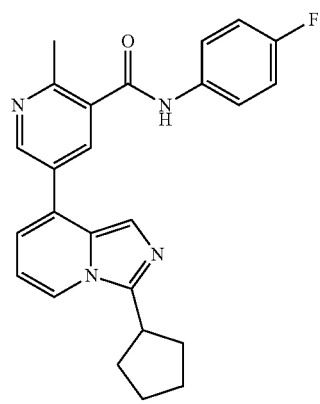 [SMILES: Cc1ncc(-c2cccn3c(C4CCCC4)ncc23)cc1C(=O)Nc1ccc(F)cc1]

Example 74 was made analogously to Example 24 (5-(3-(2,6-difluorophenyl)imidazo[1,5-a]pyridin-8-yl)-N-(4-fluorophenyl)-2-methylnicotinamide) using cyclopentanecarboxylic acid in place of 2,6-difluorobenzoic acid. C25H23FN4O. 415.4 (M+1). 1H NMR (400 MHz, DMSO-d6) δ 10.61 (s, 1H), 8.92 (d, J=2.3 Hz, 1H), 8.43 (s, 1H), 8.21 (d, J=2.3 Hz, 1H), 8.02-7.79 (m, 1H), 7.81-7.72 (m, 2H), 7.21 (q, J=12.7, 10.8 Hz, 3H), 6.98 (d, J=19.6 Hz, 1H), 3.75 (s, 1H), 2.66 (s, 3H), 2.18 (d, J=9.1 Hz, 2H), 1.96-1.66 (m, 6H).

Example 75

N-(4-fluorophenyl)-2-methyl-5-(3-(tetrahydro-2H-pyran-4-yl)imidazo[1,5-a]pyridin-8-yl)nicotinamide

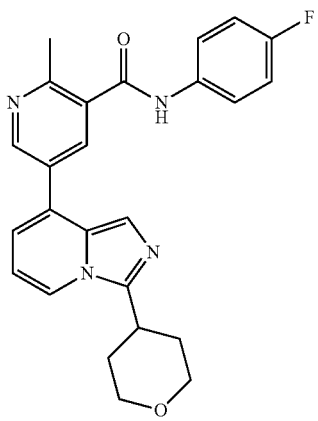 [SMILES: Cc1ncc(-c2cccn3c(C4CCOCC4)ncc23)cc1C(=O)Nc1ccc(F)cc1]

Example 75 was made analogously to Example 24 (5-(3-(2,6-difluorophenyl)imidazo[1,5-a]pyridin-8-yl)-N-(4-fluorophenyl)-2-methylnicotinamide) using tetrahydro-2H-pyran-4-carboxylic acid in place of 2,6-difluorobenzoic acid. $C_{25}H_{23}FN_4O_2$. 431.4 (M+1). $^1$H NMR (400 MHz, DMSO-$d_6$) δ 10.59 (s, 1H), 8.90 (d, J=2.2 Hz, 1H), 8.50 (d, J=7.1 Hz, 1H), 8.19 (d, J=2.3 Hz, 1H), 7.78-7.70 (m, 2H), 7.24-7.15 (m, 2H), 7.13 (s, 1H), 6.95 (d, J=12.4 Hz, 1H), 3.97 (dt, J=11.3, 3.2 Hz, 2H), 3.65 (s, 1H), 3.59-3.48 (m, 2H), 2.64 (s, 3H), 2.31 (p, J=1.9 Hz, 1H), 1.87 (td, J=10.0, 8.8, 3.8 Hz, 3H).

Example 76

N-(4-fluorophenyl)-2-methyl-5-(3-(tetrahydrofuran-3-yl)imidazo[1,5-a]pyridin-8-yl)nicotinamide

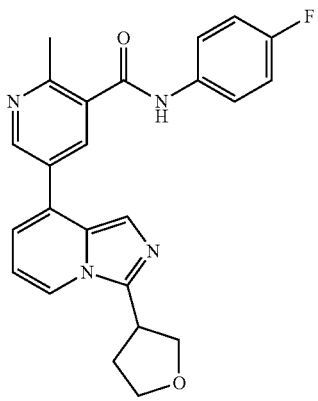 [SMILES: Cc1ncc(-c2cccn3c(C4CCOC4)ncc23)cc1C(=O)Nc1ccc(F)cc1]

Example 76 was made analogously to Example 24 (5-(3-(2,6-difluorophenyl)imidazo[1,5-a]pyridin-8-yl)-N-(4-fluorophenyl)-2-methylnicotinamide) using tetrahydrofuran-3-carboxylic acid in place of 2,6-difluorobenzoic acid. $C_{24}H_{21}FN_4O_2$. 417.3 (M+1). $^1$H NMR (400 MHz, Methanol-$d_4$) δ 8.90 (d, J=2.3 Hz, 1H), 8.54 (d, J=7.3 Hz, 1H), 8.30 (d, J=2.2 Hz, 1H), 8.08 (d, J=1.0 Hz, 1H), 7.76-7.69 (m, 2H), 7.38 (d, J=6.8 Hz, 1H), 7.25 (t, J=7.1 Hz, 1H), 7.19-7.10 (m, 2H), 4.41-4.30 (m, 1H), 4.26-4.13 (m, 3H), 3.96 (dt, J=8.7, 7.6 Hz, 1H), 2.78 (s, 3H), 2.67 (dddd, J=12.9, 9.1, 7.8, 5.0 Hz, 1H), 2.36-2.24 (m, 1H).

Example 77

5-(3-(2,3-difluorophenyl)-7-methylimidazo[1,5-a]pyridin-8-yl)-N-(4-fluorophenyl)-2-methylnicotinamide

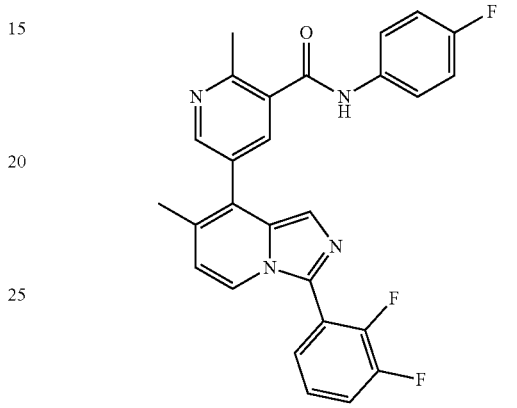

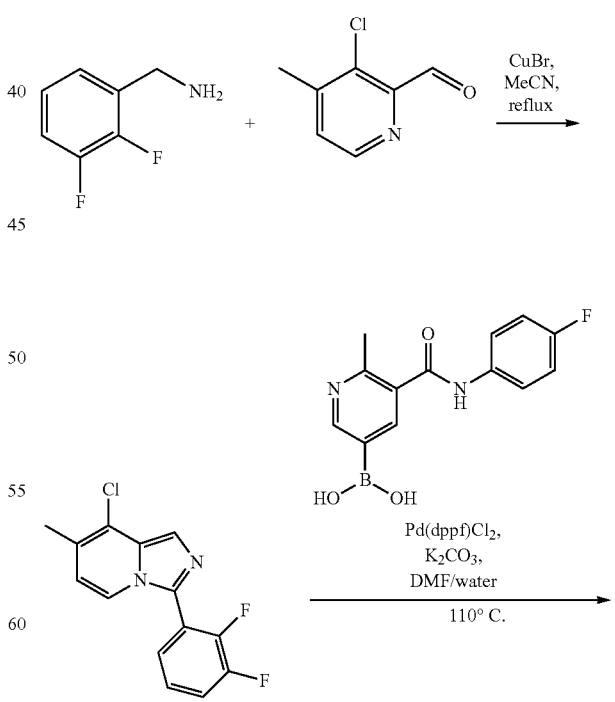

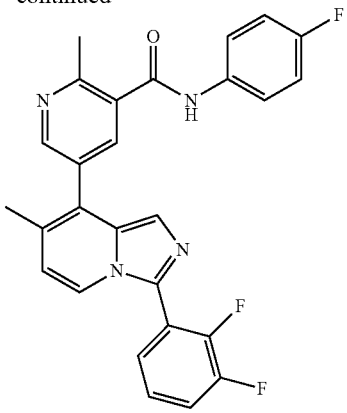

(2,3-difluorophenyl)methanamine (460 mg, 3.21 mmol), 3-chloro-4-methylpicolinaldehyde (1.0 eq), and copper(I) bromide (0.2 eq) were dissolved in MeCN (20.0 mL) and heated to reflux overnight. The reaction was quenched by pouring into ice water and then extracted with EtOAc (3×10 mL). Combined organic layers were concentrated to dryness then purified by FCC to give 8-chloro-3-(2,3-difluorophenyl)-7-methylimidazo[1,5-a]pyridine. (5-((4-fluorophenyl)carbamoyl)-6-methylpyridin-3-yl)boronic acid was then installed via previously described coupling conditions to give 5-(3-(2,3-difluorophenyl)-7-methylimidazo[1,5-a]pyridin-8-yl)-N-(4-fluorophenyl)-2-methylnicotinamide. $C_{27}H_{19}F_3N_4O$. $^1$H NMR (400 MHz, Methanol-$d_4$) δ 8.71 (d, J=2.2 Hz, 1H), 8.13 (dd, J=5.6, 2.7 Hz, 2H), 7.77-7.70 (m, 2H), 7.63-7.53 (m, 2H), 7.51-7.40 (m, 2H), 7.19-7.10 (m, 2H), 6.99 (d, J=7.4 Hz, 1H), 2.81 (s, 3H), 2.31 (s, 3H). 473.3 (M+1).

Example 78

5-(3-(2,3-difluorophenyl)-6-methylimidazo[1,5-a]pyridin-8-yl)-N-(4-fluorophenyl)-2-methylnicotinamide

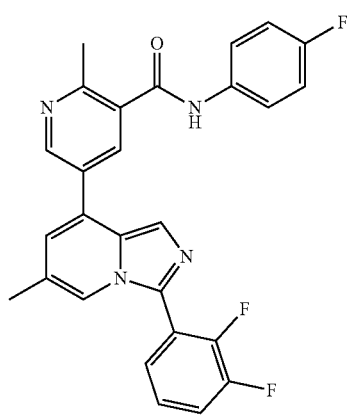 [SMILES: Cc1cc(-c2cnc(C)c(C(=O)Nc3ccc(F)cc3)c2)c2cnc(-c3cccc(F)c3F)n2c1]

Example 78 was made analogously to Example 24 (5-(3-(2,6-difluorophenyl)imidazo[1,5-a]pyridin-8-yl)-N-(4-fluorophenyl)-2-methylnicotinamide) using (3-bromo-5-methylpyridin-2-yl)methanamine hydrochloride in place of (3-chloropyridin-2-yl)methanamine dihydrochloride and 2,3-difluorobenzoic acid in place of 2,6-difluorobenzoic acid. $C_{27}H_{19}F_3N_4O$. 473.3 (M+1). $^1$H NMR (400 MHz, DMSO-$d_6$) δ 10.64 (s, 1H), 9.00 (d, J=2.2 Hz, 1H), 8.32 (d, J=2.4 Hz, 1H), 8.06 (s, 1H), 7.95 (d, J=4.6 Hz, 1H), 7.82-7.73 (m, 2H), 7.73-7.63 (m, 1H), 7.59-7.53 (m, 11-1), 7.49-7.40 (m, 1H), 7.27-7.19 (m, 2H), 7.14 (d, J=2.5 Hz, 1H), 2.69 (s, 3H), 2.32 (d, J=1.2 Hz, 3H).

Example 79

5-(1-chloro-3-(2,3-difluorophenyl)imidazo[1,5-a]pyridin-8-yl)-N-(4-fluorophenyl)-2-methylnicotinamide

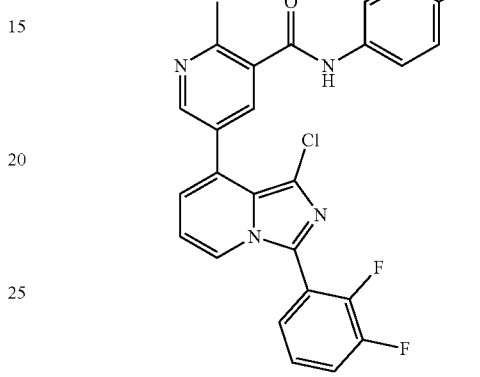

Example 79 was made analogously to the following synthesis for 5-(3-chloro-1-(2,3-difluorophenyl)imidazo[1,5-a]pyridin-5-yl)-N-(4-fluorophenyl)-2-(trifluoromethyl)benzamide, but using 5-(3-(2,3-difluorophenyl)imidazo[1,5-a]pyridin-8-yl)-N-(4-fluorophenyl)-2-methylnicotinamide in place of 5-(1-(2,3-difluorophenyl)imidazo[1,5-a]pyridin-5-yl)-N-(4-fluorophenyl)-2-(trifluoromethylbenzamide. $C_{26}H_{16}ClF_3N_4O$. 493.3/495.3 (M+1). $^1$HNMR (400 MHz, DMSO-$d_6$) δ 10.56 (s, 1H), 8.76 (d, J=2.2 Hz, 1H), 8.25 (dd, J=7.1, 3.7 Hz, 1H), 8.10 (d, J=2.2 Hz, 1H), 7.82-7.73 (m, 2H), 7.68 (dt, J=8.2, 1.9 Hz, 1H), 7.60-7.53 (m, 1H), 7.49-7.41 (m, 1H), 7.21 (t, J=8.9 Hz, 2H), 7.04 (d, J=6.6 Hz, 1H), 6.97 (t, J=6.9 Hz, 1H), 2.68 (s, 3H).

The following synthesis is for 5-(3-chloro-1-(2,3-difluorophenyl)imidazo[1,5-a]pyridin-5-yl)-N-(4-fluorophenyl)-2-(trifluoromethyl)benzamide.

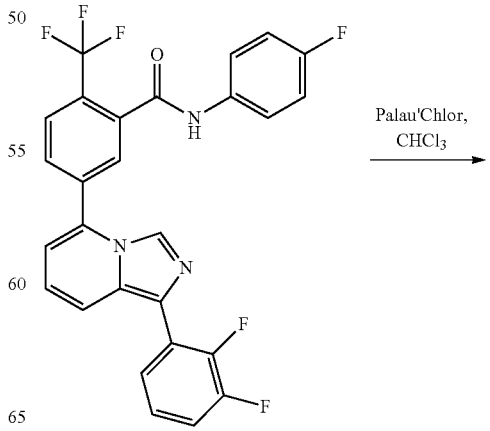

-continued

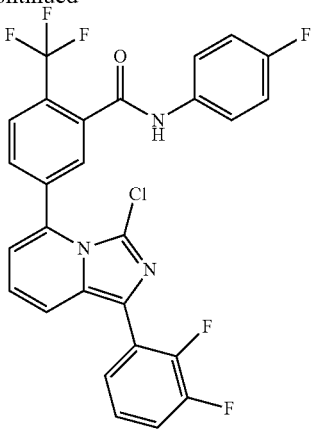

5-(1-(2,3-difluorophenyl)imidazo[1,5-a]pyridin-5-yl)-N-(4-fluorophenyl)-2-(trifluoromethyl)benzamide (13.0 mg, 0.025 mmol) was dissolved in CHCl₃ (1.0 mL) and Palau'Chlor (1.2 eq) was added and the reaction was allowed to stir at room temperature for about 2 hours and 20 mins. The reaction was diluted with water (1.0 mL) and extracted with DCM (3×1 mL). Combined organic layers were concentrated to dryness and purified by reverse-phase prep HPLC to give 5-(3-chloro-1-(2,3-difluorophenyl)imidazo[1,5-a]pyridin-5-yl)-N-(4-fluorophenyl)-2-(trifluoromethyl)benzamide.

Example 80

5-(3-(2-chlorophenyl)imidazo[1,5-a]pyridin-8-yl)-N-(4-fluorophenyl)-2-methylnicotinamide

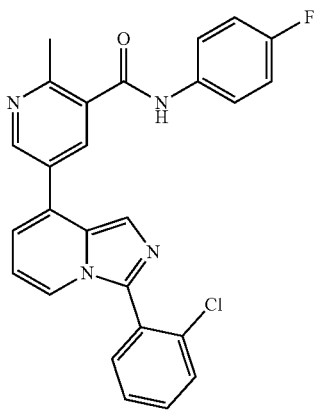

Example 80 was made analogously to Example 24 (5-(3-(2,6-difluorophenyl)imidazo[1,5-a]pyridin-8-yl)-N-(4-fluorophenyl)-2-methylnicotinamide) using 2-chlorobenzoic acid in place of 2,6-difluorobenzoic acid. $C_{26}H_{18}ClFN_4O$. 457.3/459.3 (M+1). ¹H NMR (400 MHz, DMSO-d₆) δ 10.63 (s, 1H), 9.00 (d, J=2.2 Hz, 1H), 8.32 (d, J=2.3 Hz, 1H), 7.97 (s, 1H), 7.88 (d, J=7.2 Hz, 1H), 7.81-7.72 (m, 3H), 7.67 (dtd, J=9.7, 7.7, 1.8 Hz, 2H), 7.59 (td, J=7.5, 1.3 Hz, 1H), 7.27-7.18 (m, 3H), 6.95 (dd, J=8.3, 5.8 Hz, 1H), 2.69 (s, 3H).

Example 81

5-(3-(3-chlorophenyl)imidazo[1,5-a]pyridin-8-yl)-N-(4-fluorophenyl)-2-methylnicotinamide

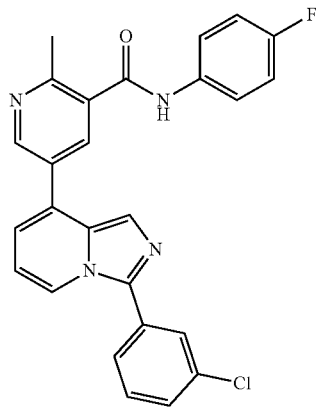

Example 81 was made analogously to Example 24 (5-(3-(2,6-difluorophenyl)imidazo[1,5-a]pyridin-8-yl)-N-(4-fluorophenyl)-2-methylnicotinamide) using 3-chlorobenzoic acid in place of 2,6-difluorobenzoic acid. $C_{26}H_{18}ClFN_4O$. 457.3/459.3 (M+1). NMR (400 MHz, DMSO-d₆) δ10.64 (s, 1H), 8.96 (d, J=2.2 Hz, 1H), 8.57 (d, J=7.2 Hz, 1H), 8.27 (d, J=2.2 Hz, 1H), 7.97-7.89 (m, 2H), 7.86 (dt, J=7.4, 1.6 Hz, 1H), 7.82-7.72 (m, 2H), 7.69-7.56 (m, 2H), 7.27-7.16 (m, 3H), 6.97 (t, J=7.0 Hz, 1H), 2.68 (s, 3H).

Example 82

2-cyclopropyl-5-(3-(2,3-difluorophenyl)imidazo[1,5-a]pyridin-8-yl)-N-(4-fluorophenyl)nicotinamide

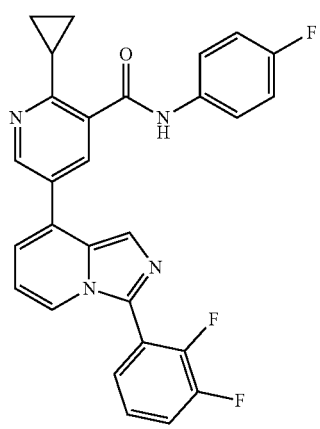 [SMILES: O=C(Nc1ccc(F)cc1)c1cc(-c2cccn3c(-c4cccc(F)c4F)ncc23)cnc1C1CC1]

Example 82 was synthesized following the procedure explained for the synthesis of Example 42 using 5-bromo-2-cyclopropyl-N-(4-fluorophenyl)nicotinamide instead of 3-bromo-2-fluoro-N-(4-fluorophenyl)-6-methylbenzamide. $C_{28}H_{19}F_3N_4O$. 485 (M+1). NMR (400 MHz, DMSO-d6) δ 10.71 (s, 1H), 8.89 (d, J=2.2 Hz, 1H), 8.42-8.16 (m, 2H), 7.91 (s, 1H), 7.83-7.69 (m, 2H), 7.70-7.60 (m, 1H), 7.61-7.48 (m, 1H), 7.46-7.38 (m, 1H), 7.27-7.11 (m, 3H), 6.93 (t, J=7.0 Hz, 1H), 2.46-2.40 (m, 1H), 1.14-108 (m, 2H), 1.06-1.00 (m, 2H).

Example 83

6-(3-(2,3-difluorophenyl)imidazo[1,5-a]pyridin-8-yl)-N-(4-fluorophenyl)picolinamide

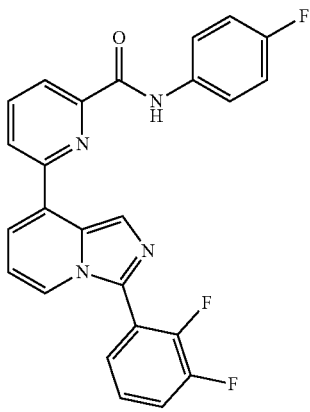 [SMILES: O=C(Nc1ccc(F)cc1)c1cccc(-c2cccn3c(-c4cccc(F)c4F)ncc23)n1]

Example 83 was synthesized following the procedure explained for the synthesis of Example 42 using 6-bromo-N-(4-fluorophenyl)picolinamide instead of 3-bromo-2-fluoro-N-(4-fluorophenyl)-6-methylbenzamide.
$C_{25}H_{15}F_3N_4O$. 445 (M+1). $^1$H NMR (400 MHz, DMSO-d6) δ 10.52 (s, 1H), 8.32-8.14 (m, 5H), 7.90-7.84 (m, 2H), 7.77 (d, J=6.8 Hz, 1H), 7.70-7.60 (m, 1H), 7.59-7.54 (m, 1H), 7.48-7.40 (m, 1H), 7.28-7.18 (m, 2H), 6.99 (t, J=7.0 Hz, 1H).

Example 84

6-(3-(2,3-difluorophenyl)imidazo[1,5-a]pyridin-8-yl)-N-(4-fluorophenyl)picolinamide

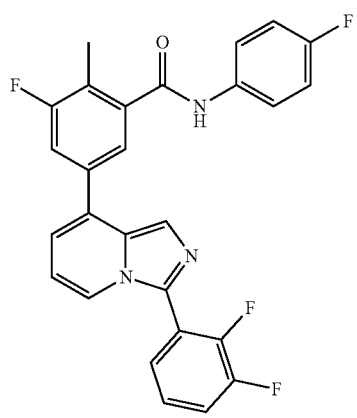 [SMILES: Cc1c(F)cc(-c2cccn3c(-c4cccc(F)c4F)ncc23)cc1C(=O)Nc1ccc(F)cc1]

Example 84 was synthesized following the procedure explained for the synthesis of Example 42 using 5-bromo-3-fluoro-N-(4-fluorophenyl)-2-methylbenzamide instead of 3-bromo-2-fluoro-N-(4-fluorophenyl)-6-methylbenzamide.
$C_{27}H_{17}F_4N_3O$. 476 (M+1). $^1$H NMR (400 MHz, DMSO-d6) δ 10.33 (s, 1H), 8.24-8.16 (m, 1H), 7.96-7.84 (m, 1H) 7.80-7.70 (m, 4H), 7.65-7.52 (m, 2H), 7.47-7.37 (m, 1H), 7.33-7.11 (m, 3H), 6.94-6.89 (m, 1H), 2.45-1.78 (m, 3H).

Example 85

5-(3-(2,3-difluorophenyl)imidazo[1,5-a]pyridin-8-yl)-3-fluoro-N-(4-fluorophenyl)-2-methylbenzamide

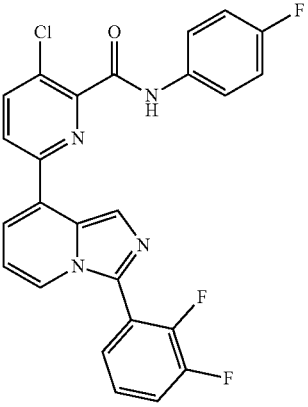 [SMILES: O=C(Nc1ccc(F)cc1)c1nc(-c2cccn3c(-c4cccc(F)c4F)ncc23)ccc1Cl]

Example 85 was synthesized following the procedure explained for the synthesis of Example 42 using 6-bromo-3-chloro-N-(4-fluorophenyl)picolinamide instead of 3-bromo-2-fluoro-N-(4-fluorophenyl)-6-methylbenzamide.
$C_{25}H_{14}ClF_3N_4O$. 479 (M+1). $^1$H NMR (400 MHz, Methanol-d4) δ 8.70 (s, 1H), 8.34-8.07 (m, 3H), 7.83-7.36 (m, 6H), 7.20-6.91 (m, 4H).

Example 86

5-(3-(2,3-dichlorophenyl)imidazo[1,5-a]pyridin-8-yl)-N-(4-fluorophenyl)-2-methylnicotinamide

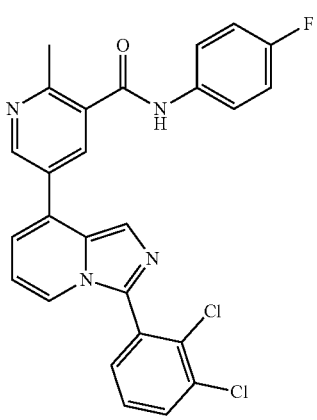

Example 86 was made analogously to Example 24 (5-(3-(2,6-difluorophenyl)imidazo[1,5-a]pyridin-8-yl)-N-(4-fluorophenyl)-2-methylnicotinamide) using 2,3-dichlorobenzoic acid in place of 2,6-difluorobenzoic acid. $C_{26}H_{17}Cl_2FN_4O$. 491.2/493.3 (M+1). $^1$H NMR (400 MHz, DMSO-d$_6$) δ 10.63 (s, 1H), 9.00 (d, J=2.2 Hz, 1H), 8.33 (d, J=2.2 Hz, 1H), 7.98-7.87 (m, 3H), 7.82-7.73 (m, 2H), 7.66 (dd, J=7.7, 1.7 Hz, 1H), 7.59 (t, J=7.8 Hz, 1H), 7.27-7.17 (m, 3H), 6.94 (t, J=6.9 Hz, 1H), 2.69 (s, 3H).

Example 87

5-(3-(2-chloro-3-fluorophenyl)imidazo[1,5-a]pyridin-8-yl)-N-(4-fluorophenyl)-2-methylnicotinamide

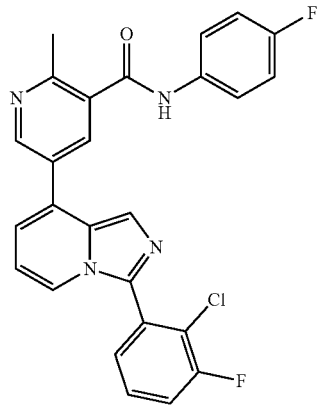

Example 87 was made analogously to Example 24 (5-(3-(2,6-difluorophenyl)imidazo[1,5-a]pyridin-8-yl)-N-(4-fluorophenyl)-2-methylnicotinamide) using 2-chloro-3-fluorobenzoic acid in place of 2,6-difluorobenzoic acid. $C_{26}H_{17}ClF_2N_4O$. 475.3/477.3 (M+1). $^1$H NMR (400 MHz, DMSO-$d_6$) δ 10.63 (s, 1H), 9.00 (d, J=2.2 Hz, 1H), 8.33 (d, J=2.2 Hz, 1H), 7.99 (d, J=7.1 Hz, 1H), 7.94 (s, 1H), 7.82-7.73 (m, 2H), 7.72-7.57 (m, 2H), 7.54 (dt, J=7.5; 1.3 Hz, 1H), 7.27-7.18 (m, 3H), 6.94 (t, J=6.9 Hz, 1H), 2.69 (s, 3H).

Example 88

5-(3-(3-chloro-2-fluorophenyl)imidazo[1,5-a]pyridin-8-yl)-N-(4-fluorophenyl)-2-methylnicotinamide

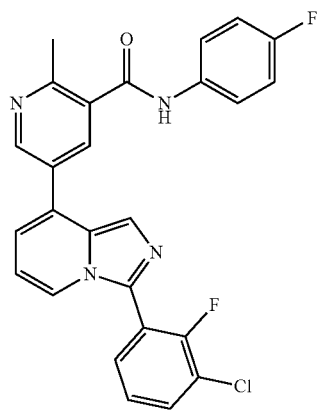

Example 88 was made analogously to Example 24 (5-(3-(2,6-difluorophenyl)imidazo[1,5-a]pyridin-8-yl)-N-(4-fluorophenyl)-2-methylnicotinamide) using 3-chloro-2-fluorobenzoic acid in place of 2,6-difluorobenzoic acid. $C_{26}H_{17}ClF_2N_4O$. 475.3/477.3 (M+1). $^1$H NMR (400 MHz, DMSO-$d_6$) δ 10.64 (s, 1H), 8.99 (d, J=2.1 Hz, 1H), 8.32 (d, J=2.1 Hz, 1H), 8.18 (dd, J=7.3, 3.9 Hz, 1H), 7.95 (d, J=2.1 Hz, 1H), 7.87-7.68 (m, 4H), 7.46 (t, J=7.9 Hz, 1H), 7.28-7.17 (m, 3H), 7.00-6.91 (m, 1H), 2.69 (s, 3H).

Example 89

5-(3-(2,4-difluorophenyl)imidazo[1,5-a]pyridin-8-yl)-N-(4-fluorophenyl)-2-methylnicotinamide

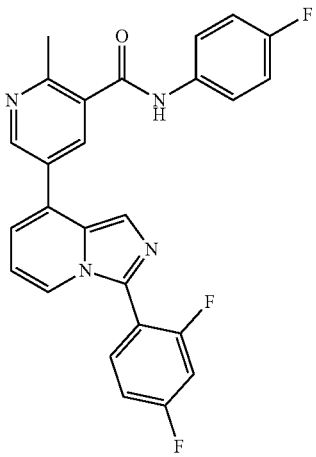 [SMILES: Cc1ncc(-c2cccn3c(-c4ccc(F)cc4F)ncc23)cc1C(=O)Nc1ccc(F)cc1]

Example 89 was made analogously to Example 24 (5-(3-(2,6-difluorophenyl)imidazo[1,5-a]pyridin-8-yl)-N-(4-fluorophenyl)-2-methylnicotinamide) using 2,4-difluorobenzoic acid in place of 2,6-difluorobenzoic acid. $C_{26}H_{17}F_3N_4O$. 459.4 (M+1). $^1$H NMR (400 MHz, DMSO-$d_6$) δ 10.64 (s, 1H), 8.98 (d, J=2.2 Hz, 1H), 8.30 (d, J=2.2 Hz, 1H), 8.09 (dd, J=7.2, 3.6 Hz, 1H), 7.94 (s, 1H), 7.86-7.74 (m, 3H), 7.57 (ddd, J=10.6, 9.3, 2.5 Hz, 1H), 7.36 (td, J=8.5, 2.6 Hz, 1H), 7.26-7.16 (m, 3H), 6.95 (t, J=7.0 Hz, 1H), 2.68 (s, 3H).

Example 90

5-(3-cyclopropylimidazo[1,5-a]pyridin-8-yl)-N-(4-fluorophenyl)-2-methylnicotinamide

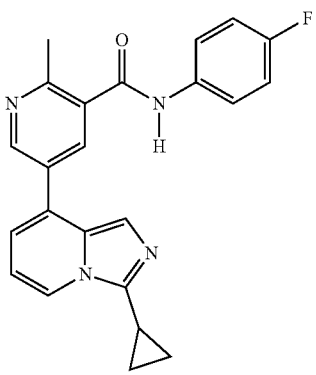 [SMILES: Cc1ncc(-c2cccn3c(C4CC4)ncc23)cc1C(=O)Nc1ccc(F)cc1]

Example 90 was synthesized following the procedure explained for the synthesis of Example 17 using cyclopropanoic acid instead of pyridazine-3-carboxylic acid, and replacing N-(4-fluorophenyl)-5-(4,4,5,5-tetramethyl-1,3,2-dioxaborolan-2-yl)-2-(trifluoromethyl)benzamide with N-(4-fluorophenyl)-2-methyl-5-(4,4,5,5-tetramethyl-1,3,2-dioxaborolan-2-yl)nicotinamide. $C_{23}H_{19}FN_4O$. 387.1 (M+1). 1H NMR (400 MHz, DMSO-d6) δ 10.62 (s, 1H), 8.92 (d, J=2.3 Hz, 1H), 8.57 (d, J=7.2 Hz, 1H), 8.22 (d, J=2.3 Hz, 1H), 8.05 (s, 1H), 7.86-7.64 (m, 2H), 7.29 (d, J=6.8 Hz, 1H), 7.22 (t, J=8.9 Hz, 2H), 7.15 (t, J=7.0 Hz, 1H), 2.67 (s, 3H), 2.54 (dd, J=8.9, 4.9 Hz, 1H), 1.22 (dd, J=8.2, 2.8 Hz, 2H), 1.18-1.03 (m, 2H).

Example 91

5-(3-cyclobutylimidazo[1,5-a]pyridin-8-yl)-N-(4-fluorophenyl)-2-methylnicotinamide

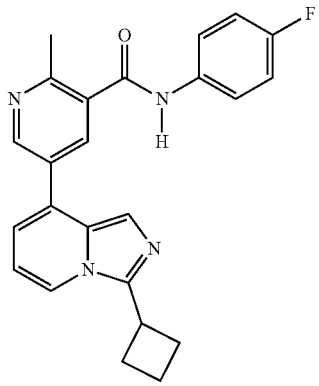 [SMILES: Cc1ncc(-c2cccn3c(C4CCC4)ncc23)cc1C(=O)Nc1ccc(F)cc1]

Example 91 was synthesized following the procedure explained for the synthesis of Example 17 using cyclobutanoic acid instead of pyridazine-3-carboxylic acid, and replacing N-(4-fluorophenyl)-5-(4,4,5,5-tetramethyl-1,3,2-dioxaborolan-2-yl)-2-(trifluoromethyl)benzamide with N-(4-fluorophenyl)-2-methyl-5-(4,4,5,5-tetramethyl-1,3,2-dioxaborolan-2-yl)nicotinamide. $C_{24}H_{21}FN_4O$. 401.2 (M+1). 1H NMR (400 MHz, DMSO-d6) δ 10.64 (s, 1H), 8.93 (d, J=2.3 Hz, 1H), 8.35 (d, J=7.2 Hz, 1H), 8.27-8.16 (m, 2H), 7.84-7.70 (m, 2H), 7.32 (d, J=6.8 Hz, 1H), 7.23 (t, J=8.9 Hz, 2H), 7.14 (t, J=7.0 Hz, 1H), 4.39-4.14 (m, 1H), 2.68 (s, 3H), 2.57-2.52 (m, 4H), 2.15 (dt, J=10.7, 8.9 Hz, 1H), 1.97 (dt, J=7.1, 3.3 Hz, 1H).

Example 92

5-(1-bromo-3-(2,3-difluorophenyl)imidazo[1,5-a]pyridin-8-yl)-N-(4-fluorophenyl)-2-methylnicotinamide

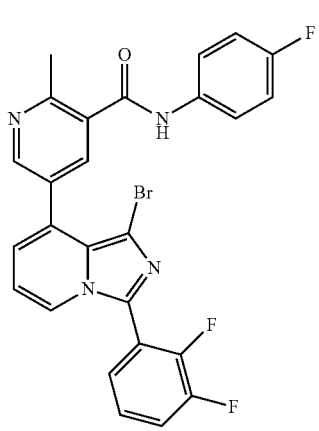 [SMILES: Cc1ncc(-c2cccn3c(-c4cccc(F)c4F)nc(Br)c23)cc1C(=O)Nc1ccc(F)cc1]

Example 92 was made analogously to Example 80 (5-(1-chloro-3-(2,3-difluorophenyl)imidazo[1,5-a]pyridin-8-yl)-N-(4-fluorophenyl)-2-methylnicotinamide) using N-bromosuccinimide in place of Palau'Chloride. $C_{26}H_{16}BrF_3N_4O$. 537.3/539.3 (M+1). $^1$H NMR (400 MHz, DMSO-d$_6$) δ 10.54 (s, 1H), 8.75 (d, J=2.2 Hz, 1H), 8.30-8.25 (m, 1H), 8.09 (d, J=2.2 Hz, 1H), 7.79-7.73 (m, 2H), 7.73-7.65 (m, 1H), 7.59-7.54 (m, 1H), 7.45 (dd, J=7.8, 4.7 Hz, 1H), 7.25-7.17 (m, 2H), 7.04-6.95 (m, 2H), 2.68 (s, 3H).

Example 93

5-(3-cyclohexylimidazo[1,5-a]pyridin-8-yl)-N-(4-fluorophenyl)-2-methylnicotinamide

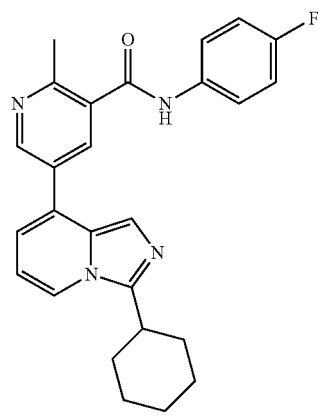 [SMILES: Cc1ncc(-c2cccn3c(C4CCCCC4)ncc23)cc1C(=O)Nc1ccc(F)cc1]

Example 93 was made analogously to Example 24 (5-(3-(2,6-difluorophenyl)imidazo[1,5-a]pyridin-8-yl)-N-(4-fluorophenyl)-2-methylnicotinamide) using cyclohexanecarboxylic acid in place of 2,6-difluorobenzoic acid. $C_{26}H_{25}FN_4O$. 429.4 (M+1). $^1$H NMR (400 MHz, DMSO-d$_6$) δ 10.66 (s, 1H), 8.93 (d, J=2.2 Hz, 1H), 8.69 (d, J=7.3 Hz, 1H), 8.33 (s, 1H), 8.26 (d, J=2.3 Hz, 1H), 7.81-7.73 (m, 2H), 7.38 (d, J=6.8 Hz, 1H), 7.26-7.18 (m, 3H), 3.59 (tt, J=12.0, 3.4 Hz, 1H), 2.68 (s, 3H), 2.02 (d, J=12.4 Hz, 2H), 1.86 (dt, J=12.9, 3.3 Hz, 2H), 1.82-1.61 (m, 3H), 1.57-1.43 (m, 21-1), 1.36-1.22 (m, 1H).

Example 94

2-(azetidin-1-yl)-5-(3-(2,3-difluorophenyl)imidazo[1,5-a]pyridin-8-yl)-N-(4-fluorophenyl)nicotinamide

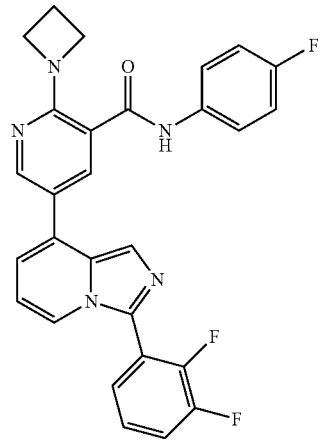 [SMILES: O=C(Nc1ccc(F)cc1)c1cc(-c2cccn3c(-c4cccc(F)c4F)ncc23)cnc1N1CCC1]

Example 94 was synthesized following the procedure explained for the synthesis of Example 42 using 2-(azetidin-1-yl)-5-bromo-N-(4-fluorophenyl)nicotinamide instead of 3-bromo-2-fluoro-N-(4-fluorophenyl)-6-methylbenzamide. C28H20F3N5O. 500.0 (M+1). 1H NMR (400 MHz, DMSO-d6) δ 10.53 (s, 1H), 8.59 (d, J=2.3 Hz, 1H), 8.10 (dd, J=7.4, 3.7 Hz, 1H), 8.05 (d, J=2.2 Hz, 1H), 7.88 (s, 1H), 7.76-7.69 (m, 2H), 7.66-7.59 (m, 1H), 7.57-7.51 (m, 1H), 7.46-7.38 (m, 1H), 7.22-7.15 (m, 2H), 7.05 (d, J=6.7 Hz, 1H), 6.89 (t, J=7.0 Hz, 1H), 4.06 (t, J=7.5 Hz, 4H), 2.30 (p, J=7.5 Hz, 2H).

General Synthetic Sequence of Formula II
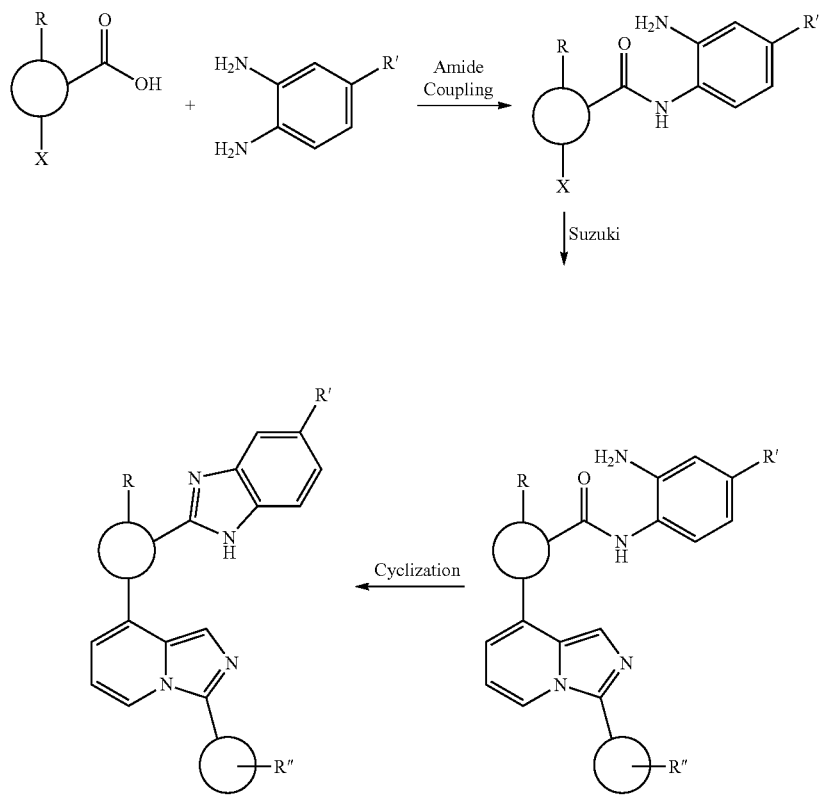
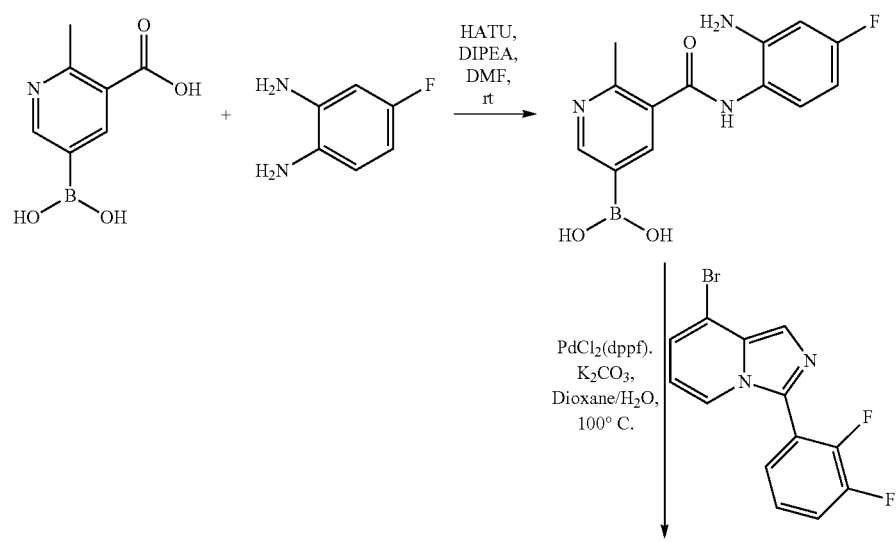

-continued
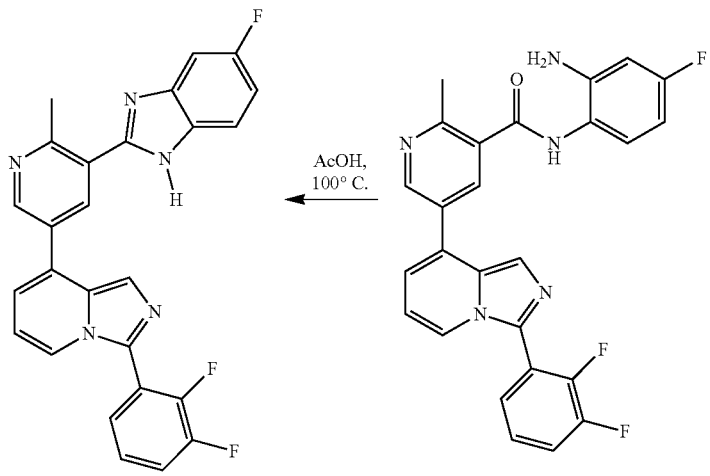
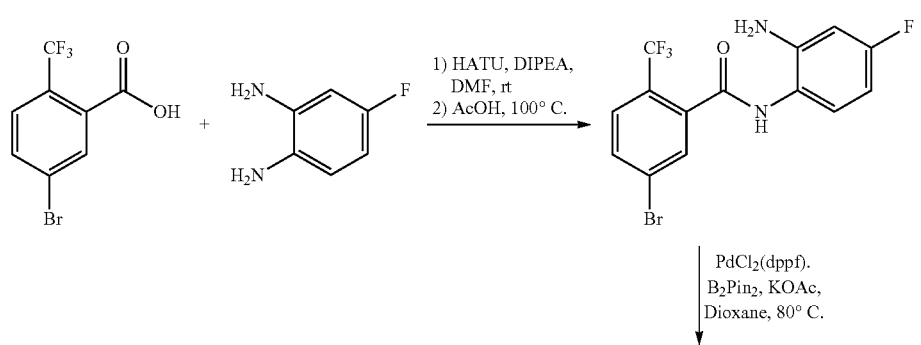
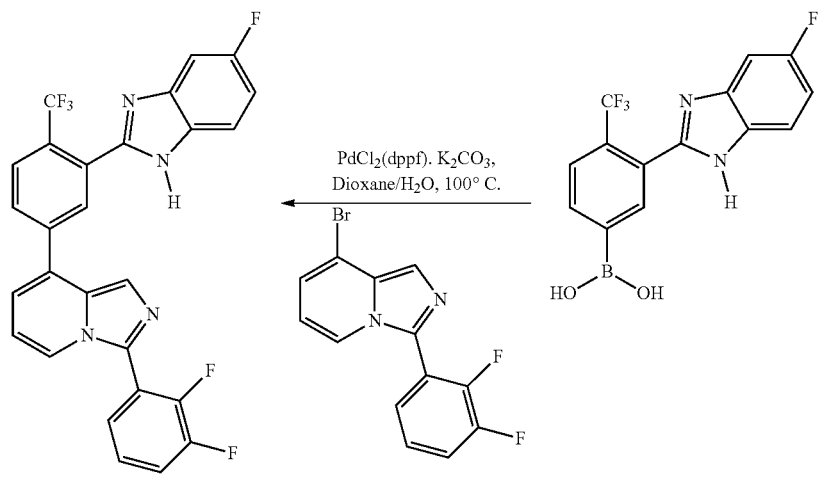

General Synthesis of Formula II

Example 95

2-(5-(3-(2,3-difluorophenyl)imidazo[1,5-a]pyridin-8-yl)-2-(trifluoromethyl)phenyl)-5-fluoro-1H-benzo[d]imidazole

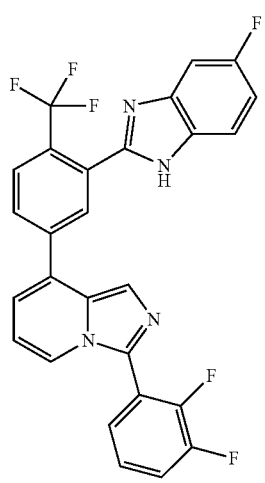 [SMILES: Fc1ccc2[nH]c(-c3cc(-c4cccn5c(-c6cccc(F)c6F)ncc45)ccc3C(F)(F)F)nc2c1]

Synthesis of N-(2-amino-4-fluorophenyl)-5-bromo-2-(trifluoromethyl)benzamide: N-(2-amino-4-fluorophenyl)-5-bromo-2-(trifluoromethyl)benzamide was prepared analogously to Example 97, using 5-bromo-2-(trifluoromethyl) benzoic acid (427 mg, 1.586 mmol, 1 equiv) in place of 5-borono-2-methylnicotinic acid. N-(2-amino-4-fluorophenyl)-5-bromo-2-(trifluoromethyl)benzamide was purified by silica gel chromatography (0-80% EtOAc/hexanes) and isolated as a white solid (408 mg, 68% yield). LC-MS m/z: 377.6 (M+1).

Synthesis of 2-(5-bromo-2-(trifluoromethyl)phenyl)-5-fluoro-1H-benzo[d]imidazole: 2-(5-bromo-2-(trifluoromethyl)phenyl)-5-fluoro-1H-benzo[d]imidazole was prepared analogously to Example 97, using N-(2-amino-4-fluorophenyl)-5-bromo-2-(trifluoromethyl)benzamide (190 mg, 0.504 mmol, 1 equiv) in place of N-(2-amino-4-fluorophenyl)-5-(3-(2,3-difluorophenyl)imidazo[1,5-a]pyridin-8-yl)-2-methylnicotinamide. 2-(5-bromo-2-(trifluoromethyl)phenyl)-5-fluoro-1H-benzo[d]imidazole was purified by silica gel chromatography (0-100% EtOAc/hexanes) and isolated as a white solid (138 mg, 76% yield). LC-MS m/z: 359.7 (M+1).

Synthesis of (3-(5-fluoro-1H-benzo[d]imidazol-2-yl)-4-(trifluoromethyl)phenyl)boronic acid: To a mixture of 2-(5-bromo-2-(trifluoromethyl)phenyl)-5-fluoro-1H-benzo[d]imidazole (138 mg, 0.384 mmol, 1 equiv), B$_2$Pin$_2$ (146 mg, 0.576 mmol, 1.5 equiv), Pd(dppf)Cl$_2$ (12 mg, 0.019 mmol, 5 mol %) and KOAc (94 mg, 0.961 mmol, 2.5 equiv), in a sealed microwave vial, was added freshly degassed dioxane (3 mL). The reaction was stirred at 80° C., overnight. The reaction mixture was concentrated in vacuo then diluted with DMF/water. The crude product was purified by HPLC (10-100% ACN/water). (3-(5-fluoro-1H-benzo[d]imidazol-2-yl)-4-(trifluoromethyl)phenyl)boronic acid was isolated as a white solid (65 mg, 52% yield). LC-MS m/z: 325.1 (M+1).

Synthesis of 2-(5-(3-(2,3-difluorophenyl)imidazo[1,5-a]pyridin-8-yl)-2-(trifluoromethyl)phenyl)-5-fluoro-1H-benzo[d]imidazole: 2-(5-(3-(2,3-difluorophenyl)imidazo[1,5-a]pyridin-8-yl)-2-(trifluoromethyl)phenyl)-5-fluoro-1H-benzo[d]imidazole was prepared analogously to Example 97 using (3-(5-fluoro-1H-benzo[d]imidazol-2-yl)-4-(trifluoromethyl)phenyl)boronic acid (24 mg, 0.074 mmol, 1 equiv) in place of (5-((2-amino-4-fluorophenyl)carbamoyl)-6-methylpyridin-3-yl)boronic acid. 2-(5-(3-(2,3-difluorophenyl)imidazo[1,5-a]pyridin-8-yl)-2-(trifluoromethyl)phenyl)-5-fluoro-1H-benzo[d]imidazole was isolated as a yellow solid (19 mg, 50% yield). C$_{27}$H$_{14}$F$_6$N$_4$. 509.5 (M+1). $^1$HNMR (400 MHz, DMSO-d6) δ 8.22 (td, J=11.5, 11.0, 2.5 Hz, 3H), 8.14 (d, J=8.2 Hz, 1H), 7.94 (d, J=1.0 Hz, 1H), 7.74-7.61 (m, 2H), 7.57 (ddd, J=8.1, 4.8, 1.6 Hz, 1H), 7.51 (dd, J=9.3, 2.5 Hz, 1H), 7.44 (td, J=8.1, 3.9 Hz, 1H), 7.25 (d, J=6.7 Hz, 1H), 7.17 (ddd, J=9.9, 8.8, 2.5 Hz, 1H), 6.97 (t, J=7.0 Hz, 1H). $^{19}$F NMR (376 MHz, DMSO-d6) δ-57.47 (s, 3F), -75.36 (s, 6F), -120.04 (m,1F), -137.81--138.17 (m, 2F).

Example 96

2-(2-chloro-5-(3-(2,3-difluorophenyl)imidazo[1,5-a]pyridin-8-yl)phenyl)-5-fluoro-1H-benzo[d]imidazole

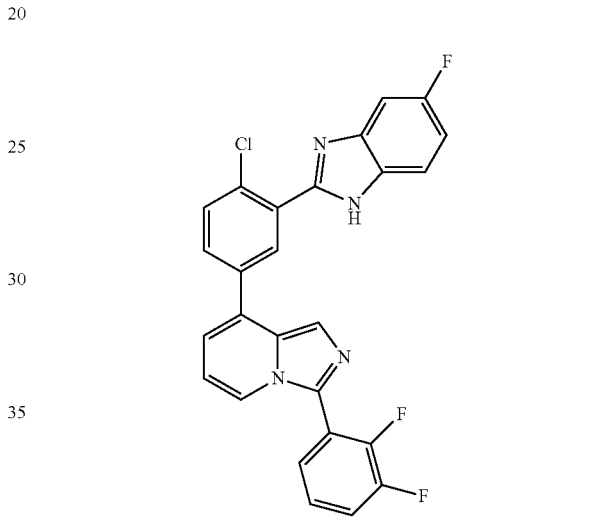

Synthesis of (3-((2-amino-4-fluorophenyl)carbamoyl)-4-chlorophenyl)boronic acid: (3-((2-amino-4-fluorophenyl)carbamoyl)-4-chlorophenyl)boronic acid was prepared analogously to Example 97, using 5-borono-2-chlorobenzoic acid (349 mg, 1.74 mmol, 1 equiv) in place of 5-borono-2-methylnicotinic acid. (3-((2-amino-4-fluorophenyl)carbamoyl)-4-chlorophenyl)boronic acid was purified by HPLC (20-100% ACN/water) and isolated as a white solid.

Synthesis of N-(2-amino-4-fluorophenyl)-2-chloro-5-(3-(2,3-difluorophenyl)imidazo[1,5-a]pyridin-8-yl)benzamide: N-(2-amino-4-fluorophenyl)-2-chloro-5-(3-(2,3-difluorophenyl)imidazo[1,5-a]pyridin-8-yl)benzamide was prepared analogously to Example 97, using (3-((2-amino-4-fluorophenyl)carbamoyl)-4-chlorophenyl)boronic acid (80 mg, 0.189 mmol, 1 equiv) in place of (5-((2-amino-4-fluorophenyl)carbamoyl)-6-methylpyridin-3-yl)boronic acid. The title compound was purified by HPLC (20-100% ACN/water) and isolated as a white solid (40 mg, 43% yield).

Synthesis of 2-(2-chloro-5-(3-(2,3-difluorophenyl)imidazo[1,5-a]pyridin-8-yl)phenyl)-5-fluoro-1H-benzo[d]imidazole: 2-(2-chloro-5-(3-(2,3-difluorophenyl)imidazo[1,5-a]pyridin-8-yl)phenyl)-5-fluoro-1H-benzo[d]imidazole was prepared analogously to Example 97 using N-(2-amino-4-fluorophenyl)-2-chloro-5-(3-(2,3-difluorophenyl)imidazo[1,5-a]pyridin-8-yl)benzamide (44 mg, 0.07 mmol, 1 equiv) in place of N-(2-amino-4-fluorophenyl)-5-(3-(2,3-difluorophenyl)imidazo[1,5-a]pyridin-8-yl)-2-methylnicotinamide.

2-(2-chloro-5-(3-(2,3-difluorophenyl)imidazo[1,5-a]pyridin-8-yl)phenyl)-5-fluoro-1H-benzo[d]imidazole was isolated as a yellow solid (14 mg, 45% yield). C$_{26}$H$_{14}$ClF$_3$N$_4$. 475.7 (M+1). $^1$H NMR (400 MHz, DMSO-d6) δ 8.30 (d, J=2.2 Hz, 1H), 8.21 (dd, J=7.2, 3.4 Hz, 1H), 7.99 (dd, J=8.4, 2.3 Hz, 1H), 7.87 (d, J=8.4 Hz, 2H), 7.73 (dd, J=8.9, 4.8 Hz, 1H), 7.66 (dtd, J=9.8, 8.2, 1.6 Hz, 1H), 7.60-7.51 (m, 2H), 7.44 (td, J=8.1, 4.1 Hz, 1H), 7.24-7.15 (m, 2H), 6.95 (t, J=6.9 Hz, 1H). $^{19}$F NMR (376 MHz, DMSO-d6) δ-75.25 (s, 3F), −119.54 (m, 1F), −137.44 (m, 2F).

Example 97

2-(5-(3-(2,3-difluorophenyl)imidazo[1,5-a]pyridin-8-yl)-2-methylpyridin-3-yl)-5-fluoro-1H-benzo[d]imidazole

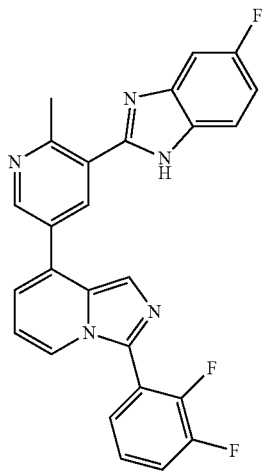 [SMILES: Cc1ncc(-c2cccn3c(-c4cccc(F)c4F)ncc23)cc1-c1nc2cc(F)ccc2[nH]1]

Synthesis of (5-((2-amino-4-fluorophenyl)carbamoyl)-6-methylpyridin-3-yl)boronic acid: To a solution of 5-borono-2-methylnicotinic acid (0.316 g, 1.74 mmol, 1.1 equiv), 4-fluorobenzene-1,2-diamine (0.20 g, 1.59 mmol, 1.0 equiv) and HATU (0.90 g, 2.38 mmol, 1.5 equiv) in DMF (5 mL) was added DIPEA (0.55 mL, 0.41 g, 3.17 mmol, 2 equiv). The reaction was stirred at room temperature overnight. The reaction mixture was subsequently diluted with DMF/water and purified by HPLC (10-70% ACN/water). (5-((2-amino-4-fluorophenyl)carbamoyl)-6-methylpyridin-3-yl)boronic acid was isolated as a white solid (0.25 g, 39% yield). LC-MS m/z: 290.1 (M+1).

Synthesis of N-(2-amino-4-fluorophenyl)-5-(3-(2,3-difluorophenyl)imidazo[1,5-a]pyridin-8-yl)-2-methylnicotinamide: To a mixture of (5-((2-amino-4-fluorophenyl)carbamoyl)-6-methylpyridin-3-yl)boronic acid (35 mg, 0.087 mmol, 1 equiv), 8-bromo-3-(2,3-difluorophenyl)imidazo[1,5-a]pyridine (27 mg, 0.087 mmol, 1 equiv), Pd(dppf)Cl$_2$ (2.6 mg, 0.004 mmol, 5 mol %) and K$_2$CO$_3$ (24 mg, 0.174 mmol, 2 equiv), in a sealed microwave vial, was added freshly degassed DMF/H$_2$O (1 mL, 9:1). The reaction was stirred at 100° C., overnight. The reaction mixture was diluted with DMF/water and purified by HPLC (10-100% ACN/water). N-(2-amino-4-fluorophenyl)-5-(3-(2,3-difluorophenyl)imidazo[1,5-a]pyridin-8-yl)-2-methylnicotinamide was isolated as a white solid (40 mg, 78% yield). LC-MS m/z: 474.5 (M+1).

Synthesis of 2-(5-(3-(2,3-difluorophenyl)imidazo[1,5-a]pyridin-8-yl)-2-methylpyridin-3-yl)-5-fluoro-1H-benzo[d]imidazole: A solution of N-(2-amino-4-fluorophenyl)-5-(3-(2,3-difluorophenypimidazo[1,5-a]pyridin-8-yl)-2-methylnicotinamide (40 mg, 0.06 mmol, 1 equiv) in AcOH (1 mL) was stirred overnight at 100° C. The reaction mixture was subsequently concentrated in vacuo, diluted with DMF/water and purified by HPLC. 2-(5-(3-(2,3-difluorophenyl)imidazo[1,5-a]pyridin-8-yl)-2-methylpyridin-3-yl)-5-fluoro-1H-benzo[d]imidazole was isolated as a yellow solid (15 mg, 39% yield). C$_{26}$H$_{16}$F$_3$N$_5$. 456.5 (M+1). $^1$H NMR (400 MHz, DMSO-d6) δ 9.02 (d, J=2.2 Hz, 1H), 8.60 (d, J=2.2 Hz, 1H), 8.23 (d, J=7.8 Hz, 1H), 7.96 (d, J=1.0 Hz, 1H), 7.74 (dd, J=8.8, 4.8 Hz, 1H), 7.67 (dtd, J=10.2, 8.6, 1.8 Hz, 1H), 7.61-7.52 (m, 2H), 7.45 (td, J=7.8, 7.4, 2.8 Hz, 1H), 7.26-7.15 (m, 2H), 6.98 (t, J=6.9 Hz, 1H), 2.95 (s, 3H). $^{19}$F NMR (376 MHz, DMSO-d$_6$) δ-75.31 (s, 6F), −119.66 (m, 1F), −138.01 (m, 2F).

Example 98

2-(5-(3-(2,3-difluorophenyl)imidazo[1,5-a]pyridin-8-yl)-2-(trifluoromethyl)pyridin-3-yl)-5-fluoro-1H-benzo[d]imidazole

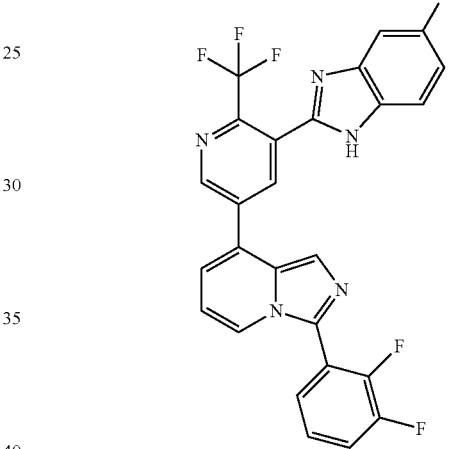

Synthesis of N-(2-amino-4-fluorophenyl)-5-bromo-2-(trifluoromethyl)nicotinamide: N-(2-amino-4-fluorophenyl)-5-bromo-2-(trifluoromethyl)nicotinamide was prepared analogously to Example 97, using 5-bromo-2-(trifluoromethyl)nicotinic acid (214 mg, 0.793 mmol, 1 equiv) in place of 5-borono-2-methylnicotinic acid. N-(2-amino-4-fluorophenyl)-5-bromo-2-(trifluoromethyl)nicotinamide was purified by silica gel chromatography (0-80% EtOAc/hexanes) and isolated as a white solid (289 mg, 96% yield). LC-MS m/z: 378.7 (M+1).

Synthesis of 2-(5-bromo-2-(trifluoromethyl)pyridin-3-yl)-5-fluoro-1H-benzo[d]imidazole: 2-(5-bromo-2-(trifluoromethyl)pyridin-3-yl)-5-fluoro-1H-benzo[d]imidazole was prepared analogously to Example 97, using N-(2-amino-4-fluorophenyl)-5-bromo-2-(trifluoromethyl)nicotinamide (286 mg, 0.756 mmol, 1 equiv) in place of N-(2-amino-4-fluorophenyl)-5-(3-(2,3-difluorophenyl)imidazo[1,5-a]pyridin-8-yl)-2-methylnicotinamide. N-(2-amino-4-fluorophenyl)-5-bromo-2-(trifluoromethyl)nicotinamide was purified by silica gel chromatography (0-100% EtOAc/hexanes) and isolated as a white solid (243 mg, 89% yield). LC-MS m/z: 360.7 (M+1).

Synthesis of (5-(5-fluoro-1H-benzo[d]imidazol-2-yl)-6-(trifluoromethyl)pyridin-3-yl)boronic acid: (5-(5-fluoro-1H-benzo[d]imidazol-2-yl)-6-(trifluoromethyl)pyridin-3-yl)boronic acid was prepared analogously to Example 95, using 2-(5-bromo-2-(trifluoromethyl)pyridin-3-yl)-5-fluoro-1H-benzo[d]imidazole (243 mg, 0.675 mmol, 1 equiv) in place of 2-(5-bromo-2-(trifluoromethyl)phenyl)-5-fluoro-1H-benzo[d]imidazole. (5-(5-fluoro-1H-benzo[d]imidazol-2-yl)-6-(trifluoromethyl)pyridin-3-yl)boronic acid was isolated as a white solid (125 mg, 57% yield). LC-MS m/z: 326.1 (M+1).

Synthesis of 2-(5-(3-(2,3-difluorophenyl)imidazo[1,5-a]pyridin-8-yl)-2-(trifluoromethyl)pyridin-3-yl)-5-fluoro-1H-benzo[d]imidazole: 2-(5-(3-(2,3-difluorophenyl)imidazo[1,5-a]pyridin-8-yl)-2-(trifluoromethyl)pyridin-3-yl)-5-fluoro-1H-benzo[d]imidazole was prepared analogously to Example 97 using (5-(5-fluoro-1H-benzo[d]imidazol-2-yl)-6-(trifluoromethyl)pyridin-3-yl)boronic acid (44 mg, 0.10 mmol, 1 equiv) in place of (5-((2-amino-4-fluorophenyl)carbamoyl)-6-methylpyridin-3-yl)boronic acid. 2-(5-(3-(2,3-difluorophenyl)imidazo[1,5-a]pyridin-8-yl)-2-(trifluoromethyl)pyridin-3-yl)-5-fluoro-1H-benzo[d]imidazole was isolated as a yellow solid (11 mg, 18% yield). $C_{26}H_{13}F_6N_5$ 510.6 (M+1). $^1$H NMR (400 MHz, DMSO-d6) δ 9.30 (d, J=2.1 Hz, 1H), 8.71 (d, J=2.1 Hz, 1H), 8.28 (dd, J=7.3, 2.8 Hz, 1H), 8.00 (d, J=1.0 Hz, 1H), 7.72 (dd, J=8.8, 4.9 Hz, 1H), 7.69-7.62 (m, 1H), 7.57 (ddd, J=8.2, 4.4, 1.7 Hz, 1H), 7.53 (dd, J=9.4, 2.5 Hz, 1H), 7.45 (td, J=8.1, 3.3 Hz, 1H), 7.34 (d, J=6.7 Hz, 1H), 7.17 (ddd, J=9.9, 8.9, 2.6 Hz, 1H), 6.99 (t, J=7.0 Hz, 1H). $^{19}$F NMR (376 MHz, DMSO-d6) δ-62.23 (s, 3F), −75.30 (s, 3F), −120.16 (m, 1F), −138.01 (m, 1F).

Example 99

2-(5-(3-(2,3-difluorophenyl)imidazo[1,5-a]pyridin-8-yl)-2-methylpyridin-3-yl)-1H-benzo[d]imidazole

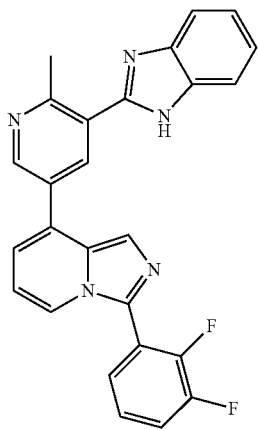 [SMILES: Cc1ncc(-c2cccn3c(-c4cccc(F)c4F)ncc23)cc1-c1nc2ccccc2[nH]1]

Synthesis of N-(2-aminophenyl)-5-(3-(2,3-difluorophenyl)imidazo[1,5-a]pyridin-8-yl)-2-methylnicotinamide: N-(2-aminophenyl)-5-(3-(2,3-difluorophenyl)imidazo[1,5-a]pyridin-8-yl)-2-methylnicotinamide was prepared analogously to Example 97, using 5-(3-(2,3-difluorophenyl)imidazo[1,5-a]pyridin-8-yl)-2-methylnicotinic acid (15 mg, 0.041 mmol, 1 equiv) and benzene-1,2-diamine (9 mg, 0.082 mmol, 2 equiv) in place of 5-borono-2-methylnicotinic acid and 4-fluorobenzene-1,2-diamine. N-(2-aminophenyl)-5-(3-(2,3-difluorophenyl)imidazo[1,5-a]pyridin-8-yl)-2-methylnicotinamide was purified by HPLC (20-90% ACN/water) and isolated as a white solid (16 mg, 84% yield). LC-MS m/z: 456.5 (M+1).

Synthesis of 2-(5-(3-(2,3-difluorophenyl)imidazo[1,5-a]pyridin-8-yl)-2-methylpyridin-3-yl)-1H-benzo[d]imidazole: 2-(5-(3-(2,3-difluorophenyl)imidazo[1,5-a]pyridin-8-yl)-2-methylpyridin-3-yl)-1H-benzo[d]imidazole was prepared analogously to Example 97, using N-(2-aminophenyl)-5-(3-(2,3-difluorophenyl)imidazo[1,5-a]pyridin-8-yl)-2-methylnicotinamide (16 mg, 0.028 mmol, 1 equiv) in place of N-(2-amino-4-fluorophenyl)-5-(3-(2,3-difluorophenyl)imidazo[1,5-a]pyridin-8-yl)-2-methylnicotinamide. 2-(5-(3-(2,3-difluorophenyl)imidazo[1,5-a]pyridin-8-yl)-2-methylpyridin-3-yl)-1H-benzo[d]imidazole was isolated as a white solid (3 mg, 14% yield). $C_{26}H_{17}F_2N_5$. 438.6 (M+1). $^1$H NMR (400 MHz, DMSO-d6) δ 8.99 (d, J=2.2 Hz, 1H), 8.56 (d, J=2.2 Hz, 1H), 8.20 (d, J=7.2 Hz, 1H), 7.93 (d, J=1.0 Hz, 1H), 7.72 (d, J=5.9 Hz, 2H), 7.64 (q, J=9.2, 8.8 Hz, 1H), 7.58-7.52 (m, 1H), 7.46-7.38 (m, 1H), 7.34 (d, J=6.3 Hz, 2H), 7.21 (d, J=6.7 Hz, 1H), 6.94 (t, J=6.9 Hz, 1H), 2.92 (s, 3H). $^{19}$F NMR (376 MHz, DMSO-d6) δ-74.76 (s, 3F), −138.07 (m, 1F).

Biological Examples

Activity testing was conducted in the Examples below using methods described herein and those well known in the art.

Example 509

Cell-Based (HeLa) Assay for Measurement of IDO1 Inhibition

To measure IDO1 inhibition in tissue culture, HeLa cells were treated with a test compound in the presence of IFNγ, which induces IDO1 expression. Following incubation, cell supernatants were assayed for kynurenine levels, an indicator of IDO1 activity.

H1-HeLa cells (ATCC #CRL-1958) were seeded in 384-well plates (Greiner #82051-282) at a volume of 50 in DMEM (Corning #15-018-CM) supplemented with 10% FBS (Corning #35-011-CV) and 1% P/S/G (Corning #30-009-CL) at a density of 1,250 cells/well and incubated overnight at 37° C., 5% $CO_2$/100% humidity. The following day, the test compounds were added in DMSO (0.5% final) at various concentrations, and IDO1 was inducibly expressed by the addition of 50 uL/well of 50 ng/mL of INFγ(Peprotech #300-02) in cell plating media. As a positive control, 50 uL of the cell plating media without IFNγ was added to several wells. Following a 48 hour incubation, the plates were spun down at 1,200 RPM for 5 min at 10° C. 65 µL/well of the supernatant was then transferred to new 384-well plates (Thermo #262160) that contained 10 uL/well of 30% TCA (Sigma #T0699), and the plates were sealed and incubated at 60° C. for 30 min. The plates were then centrifuged for 15 min at 2,000 RPM at 10° C. 40 µL/well of the supernatant was transferred to new 384-well plates (Thermo #262160) and was reacted with 40 µL/well of 2% (w/v) p-dimethylaminobenzaldehyde (Sigma #156417) in glacial acetic acid (Sigma #A6283). The reaction was incubated at room temperature for 10 min and absorbance at 480 nm was read using a PerkinElmer Envision plate reader.

Data in Table 1 were normalized based on positive (−IFNγ) and negative (+IFNγ) controls and $EC_{50}$ values were calculated from the fit of the dose-response curves to a four-parameter equation. All $EC_{50}$ values represent geometric mean values of a minimum of four determinations. These assays generally produced results within 2-fold of the reported mean.

TABLE 1

| Example No. | Name | EC$_{50}$ (nM) |
|---|---|---|
| 1 | 5-(3-(2-carbamoylphenyl)-[1,2,4]triazolo[4,3-a]pyridin-8-yl)-N-(4-fluorophenyl)-2-methylbenzamide | 5341.49 |
| 2 | N-(4-fluorophenyl)-2-methyl-5-(3-(5-methyl-1,3,4-oxadiazol-2-yl)imidazo[1,5-a]pyridin-8-yl)benzamide | 3841.6 |
| 3 | N-(4-fluorophenyl)-2-methyl-5-(3-(1-methyl-1H-1,2,3-triazol-5-yl)imidazo[1,5-a]pyridin-8-yl)benzamide | 2193.17 |
| 4 | N-(4-fluorophenyl)-2-methyl-5-(3-(2-methylpyridin-3-yl)-[1,2,4]triazolo[4,3-a]pyridin-8-yl)benzamide | 2161.83 |
| 5 | 5-(3-(4-fluoro-2-methylphenyl)-[1,2,4]triazolo[4,3-a]pyridin-8-yl)-N-(4-fluorophenyl)-2-methylbenzamide | 1405.5 |
| 6 | 2-(8-(3-((4-fluorophenyl)carbamoyl)-4-(trifluoromethyl)phenyl)imidazo[1,5-a]pyridin-3-yl)isonicotinamide | 1328.54 |
| 7 | 5-(3-(1,2,3-oxadiazol-5-yl)imidazo[1,5-a]pyridin-8-yl)-N-(4-fluorophenyl)-2-methylbenzamide | 1215.27 |
| 8 | N-(4-fluorophenyl)-5-(3-(1-methyl-1H-1,2,3-triazol-5-yl)imidazo[1,5-a]pyridin-8-yl)-2-(trifluoromethyl)benzamide | 1203.91 |
| 9 | N-(4-fluorophenyl)-2-methyl-5-(3-phenyl-[1,2,4]triazolo[4,3-a]pyridin-8-yl)benzamide | 808.937 |
| 10 | 5-(3-(4-cyanopyridin-2-yl)imidazo[1,5-a]pyridin-8-yl)-N-(4-fluorophenyl)-2-(trifluoromethyl)benzamide | 712.008 |
| 11 | N-(4-fluorophenyl)-2-methyl-5-(3-(pyridin-3-yl)-[1,2,4]triazolo[4,3-a]pyridin-8-yl)benzamide | 682.82 |
| 12 | N-(4-fluorophenyl)-2-methyl-5-(3-(o-tolyl)-[1,2,4]triazolo[4,3-a]pyridin-8-yl)benzamide | 402.685 |
| 13 | N-(4-fluorophenyl)-5-(3-(1-methyl-1H-imidazol-4-yl)imidazo[1,5-a]pyridin-8-yl)-2-(trifluoromethyl)benzamide | 364.707 |
| 14 | N-(4-fluorophenyl)-2-methyl-5-(3-(1-methyl-1H-imidazol-4-yl)imidazo[1,5-a]pyridin-8-yl)benzamide | 322.487 |
| 15 | 5-(3-(3-cyanopyridin-2-yl)imidazo[1,5-a]pyridin-8-yl)-N-(4-fluorophenyl)-2-(trifluoromethyl)benzamide | 274.198 |
| 16 | N-(4-fluorophenyl)-2-methyl-5-(3-(2-(trifluoromethyl)phenyl)imidazo[1,5-a]pyridin-8-yl)nicotinamide | 239.011 |
| 17 | N-(4-fluorophenyl)-5-(3-(pyridazin-3-yl)imidazo[1,5-a]pyridin-8-yl)-2-(trifluoromethyl)benzamide | 236.514 |
| 18 | 5-(3-(3-fluoro-2-(trifluoromethyl)phenyl)imidazo[1,5-a]pyridin-8-yl)-N-(4-fluorophenyl)-2-methylnicotinamide | 211.108 |
| 19 | N-(4-fluorophenyl)-5-(3-(3-fluoropyridin-2-yl)imidazo[1,5-a]pyridin-8-yl)-2-methylnicotinamide | 198.517 |
| 20 | 5-(3-(2,3-difluorophenyl)-[1,2,4]triazolo[4,3-a]pyridin-8-yl)-N-(4-fluorophenyl)-2-methylbenzamide | 192.257 |
| 21 | N-(4-fluorophenyl)-5-(3-(quinolin-4-yl)imidazo[1,5-a]pyridin-8-yl)-2-(trifluoromethyl)benzamide | 183.265 |
| 22 | N-(4-fluorophenyl)-2-methyl-5-(3-(m-tolyl)imidazo[1,5-a]pyridin-8-yl)nicotinamide | 134.926 |
| 23 | N-(4-fluorophenyl)-5-(3-(4-fluoropyridin-2-yl)imidazo[1,5-a]pyridin-8-yl)-2-methylnicotinamide | 111.948 |
| 24 | 5-(3-(2,6-difluorophenyl)imidazo[1,5-a]pyridin-8-yl)-N-(4-fluorophenyl)-2-methylnicotinamide | 103.71 |
| 25 | N-(4-fluorophenyl)-2-methyl-5-(3-(pyrimidin-2-yl)imidazo[1,5-a]pyridin-8-yl)nicotinamide | 68.985 |
| 26 | N-(4-fluorophenyl)-5-(3-(pyrimidin-4-yl)imidazo[1,5-a]pyridin-8-yl)-2-(trifluoromethyl)benzamide | 66.423 |

TABLE 1-continued

| Example No. | Name | EC$_{50}$ (nM) |
|---|---|---|
| 27 | 5-(3-(3,5-difluorophenyl)imidazo[1,5-a]pyridin-8-yl)-N-(4-fluorophenyl)-2-methylnicotinamide | 61.684 |
| 28 | 2-(3-(2,3-difluorophenyl)imidazo[1,5-a]pyridin-8-yl)-N-(4-fluorophenyl)-5-(trifluoromethyl)isonicotinamide | 57.876 |
| 29 | N-(4-fluorophenyl)-2-methyl-5-(3-(o-tolyl)imidazo[1,5-alpyridin-8-yl)nicotinamide | 44.718 |
| 30 | 5-(3-(2,5-difluorophenyl)imidazo[1,5-a]pyridin-8-yl)-N-(4-fluorophenyl)-2-methylnicotinamide | 39.02 |
| 31 | N-(4-fluorophenyl)-5-(3-(pyridin-3-yl)imidazo[1,5-a]pyridin-8-yl)-2-(trifluoromethyl)benzamide | 38.304 |
| 32 | 5-(3-(1H-pyrazol-3-yl)imidazo[1,5-a]pyridin-8-yl)-N-(4-fluorophenyl)-2-(trifluoromethyl)benzamide | 34.862 |
| 33 | N-(4-fluorophenyl)-5-(3-(pyridin-2-yl)imidazo[1,5-a]pyridin-8-yl)-2-(trifluoromethyl)benzamide | 31.111 |
| 34 | 5-(3-(2,3-difluorophenyl)imidazo[1,5-a]pyridin-8-yl)-N-(4-fluorophenyl)-2-methylbenzamide | 29.432 |
| 35 | N-(4-fluorophenyl)-5-(3-(3-fluorophenyl)imidazo[1,5-a]pyridin-8-yl)-2-methylnicotinamide | 26.768 |
| 36 | N-(4-fluorophenyl)-5-(3-(pyrazin-2-yl)imidazo[1,5-a]pyridin-8-yl)-2-(trifluoromethyl)nicotinamide | 25.178 |
| 37 | N-(4-fluorophenyl)-2-methyl-5-(3-(pyrimidin-2-yl)imidazo[1,5-a]pyridin-8-yl)benzamide | 24.241 |
| 38 | 6-(3-(2,3-difluorophenyl)imidazo[1,5-a]pyridin-8-yl)-N-(4-fluorophenyl)-3-(trifluoromethyl)picolinamide | 23.81 |
| 39 | N-(4-fluorophenyl)-5-(3-(3-fluorophenyl)imidazo[1,5-a]pyridin-8-yl)-2-(trifluoromethyl)benzamide | 23.305 |
| 40 | N-(4-fluorophenyl)-2-methyl-5-(3-(oxazol-2-yl)imidazo[1,5-alpyridin-8-yl)benzamide | 23.061 |
| 41 | 2-(difluoromethyl)-5-(3-(2,3-difluorophenyl)imidazo[1,5-a]pyridin-8-yl)-N-(4-fluorophenyl)benzamide | 19.786 |
| 42 | 3-(3-(2,3-difluorophenyl)imidazo[1,5-a]pyridin-8-yl)-2-fluoro-N-(4-fluorophenyl)-6-methylbenzamide | 17.748 |
| 43 | 5-(3-(2,3-difluorophenyl)imidazo[1,5-a]pyridin-8-yl)-N-(4-fluorophenyl)-2-methylnicotinamide | 17.179 |
| 44 | 5-(3-(2,3-difluorophenyl)-1-methylimidazo[1,5-a]pyridin-8-yl)-N-(4-fluorophenyl)-2-(trifluoromethyl)benzamide | 16.911 |
| 45 | N-(4-fluorophenyl)-5-(3-(pyrimidin-2-yl)imidazo[1,5-a]pyridin-8-yl)-2-(trifluoromethyl)benzamide | 16.43 |
| 46 | N-(4-fluorophenyl)-5-(3-(oxazol-2-yl)imidazo[1,5-a]pyridin-8-yl)-2-(trifluoromethyl)benzamide | 16.139 |
| 47 | 5-(3-(2,3-difluorophenyl)imidazo[1,5-a]pyridin-8-yl)-N-(4-fluorophenyl)-2-(trifluoromethyl)nicotinamide | 16.021 |
| 48 | 5-(3-(2,3-difluorophenyl)imidazo[1,5-a]pyridin-8-yl)-N-(4-fluorophenyl)-2-(trifluoromethyl)benzamide | 15.854 |
| 49 | N-(4-fluorophenyl)-5-(3-(2-fluorophenyl)imidazo[1,5-a]pyridin-8-yl)-2-methylnicotinamide | 15.737 |
| 50 | 5-(3-(2,3-difluorophenyl)-[1,2,4]triazolo[4,3-b]pyridazin-8-yl)-N-(4-fluorophenyl)-2-methylnicotinamide | 1887.55 |
| 51 | 5-(3-(2,3-difluorophenyl)imidazo[1,5-a]pyrazin-8-yl)-N-(4-fluorophenyl)-2-methylbenzamide | 656.005 |
| 52 | N-(4-fluorophenyl)-2-methyl-5-(3-(o-tolyl)imidazo[1,5-a]pyrazin-8-yl)benzamide | 3111.2 |
| 53 | N-(4-fluorophenyl)-2-methyl-5-(3-(m-tolyl)imidazo[1,5-a]pyrazin-8-yl)benzamide | 2376.4 |
| 54 | N-(4-fluorophenyl)-2-methyl-5-(3-(pyridin-2-yl)imidazo[1,5-a]pyrazin-8-yl)benzamide | 2631.22 |
| 55 | 5-(3-(2,3-difluorophenyl)imidazo[1,5-a]pyridin-8-yl)-N-(4-fluorophenyl)-2-(trifluoromethoxy)benzamide | 14.958 |

TABLE 1-continued

| Example No. | Name | EC$_{50}$ (nM) |
|---|---|---|
| 56 | 2-(3-(2,3-difluorophenyl)imidazo[1,5-a]pyridin-8-yl)-N-(4-fluorophenyl)-5-methylisonicotinamide | 85.669 |
| 57 | 6-(3-(2,3-diflurophenyl)imidazo[1,5-a]pyridin-8-yl)-N-(4-fluorophenyl)-3-methylpicolinamide | 76.82 |
| 58 | 5-(3-(2,3-difluorophenyl)imidazo[1,5-a]pyridin-8-yl)-2-methyl-N-(4-(trifluoromethoxy)phenyl)nicotinamide | 110.043 |
| 59 | N-(4-cyano-3-(trifluoromethyl)phenyl)-5-(3-(2,3-difluorophenyl)imidazo[1,5-a]pyridin-8-yl)-2-methylnicotinamide | 226.621 |
| 60 | 5-(3-(2,3-difluorophenyl)imidazo[1,5-a]pyridin-8-yl)-N-(5-fluoropyridin-2-yl)-2-methylnicotinamide | 21.12 |
| 61 | N-(4-chlorophenyl)-5-(3-(2,3-difluorophenyl)imidazo[1,5-a]pyridin-8-yl)-2-methylnicotinamide | 29.902 |
| 62 | 2-cyclopropyl-5-(3-(2,3-difluorophenyl)imidazo[1,5-a]pyridin-8-yl)-N-(4-fluorophenyl)benzamide | 15.2 |
| 63 | N-(3-bromo-4-fluorophenyl)-5-(3-(2,3-difluorophenyl)imidazo[1,5-a]pyridin-8-yl)-2-methylnicotinamide | 306.773 |
| 64 | N-(4-chloro-2-fluorophenyl)-5-(3-(2,3-difluorophenyl)imidazo[1,5-a]pyridin-8-yl)-2-methylnicotinamide | 24.287 |
| 65 | 2-(3-(2,3-difluorophenyl)imidazo[1,5-a]pyridin-8-yl)-N-(4-fluorophenyl)-5-methylpyrimidine-4-carboxamide | 398.521 |
| 66 | 5-(3-(2,3-difluorophenyl)imidazo[1,5-a]pyridin-8-yl)-2-methyl-N-phenylnicotinamide | 15.326 |
| 67 | N-(4-(difluoromethoxy)phenyl)-5-(3-(2,3-difluorophenyl)imidazo[1,5-a]pyridin-8-yl)-2-methylnicotinamide | 79.524 |
| 68 | N-(3,4-difluorophenyl)-5-(3-(2,3-difluorophenyl)imidazo[1,5-a]pyridin-8-yl)-2-methylnicotinamide | 100.587 |
| 69 | 5-(3-(2,3-difluorophenyl)imidazo[1,5-a]pyridin-8-yl)-2-methyl-N-(pyridin-4-yl)nicotinamide | 57.647 |
| 70 | 2-chloro-5-(3-(2,3-difluorophenyl)imidazo[1,5-a]pyridin-8-yl)-N-(4-fluorophenyl)benzamide | 12.196 |
| 71 | 5-(3-(2,3-difluorophenyl)imidazo[1,5-a]pyridin-8-yl)-2-methyl-N-(2-methylpyridin-4-yl)nicotinamide | 656.021 |
| 72 | 5-(3-(2,3-difluorophenyl)imidazo[1,5-a]pyridin-8-yl)-2-methyl-N-(3-(trifluoromethoxy)phenyl)nicotinamide | 379.772 |
| 73 | 5-(3-(2,3-difluorophenyl)imidazo[1,5-a]pyridin-8-yl)-N-(4-fluorophenyl-2,3,5,6-d4)-2-methylnicotinamide | 23.913 |
| 74 | 5-(3-cyclopentylimidazo[1,5-a]pyridin-8-yl)-N-(4-fluorophenyl)-2-methylnicotinamide | 459.677 |
| 75 | N-(4-fluorophenyl)-2-methyl-5-(3-(tetrahydro-2H-pyran-4-yl)imidazo[1,5-a]pyridin-8-yl)nicotinamide | 591.058 |
| 76 | N-(4-fluorophenyl)-2-methyl-5-(3-(tetrahydrofuran-3-yl)imidazo[1,5-a]pyridin-8-yl)nicotinamide | 5000 |
| 77 | 5-(3-(2,3-difluorophenyl)-7-methylimidazo[1,5-a]pyridin-8-yl)-N-(4-fluorophenyl)-2-methy(nicotinamide | 729.997 |
| 78 | 5-(3-(2,3-difluorophenyl)-6-methylimidazo[1,5-a]pyridin-8-yl)-N-(4-fluorophenyl)-2-methylnicotinamide | 894.993 |
| 79 | 5-(l-chloro-3-(2,3-difluorophenyl)imidazo[1,5-a]pyridin-8-yl)-N-(4-fluorophenyl)-2-methylnicotinamide | 117.965 |
| 80 | 5-(3-(2-chlorophenyl)imidazo[1,5-a]pyridin-8-yl)-N-(4-fluorophenyl)-2-methylnicotinamide | 19.285 |
| 81 | 5-(3-(3-chlorophenyl)imidazo[1,5-a]pyridin-8-yl)-N-(4-fluorophenyl)-2-methylnicotinamide | 235.483 |
| 82 | 2-cyclopropyl-5-(3-(2,3-difluorophenyl)imidazo[1,5-a]pyridin-8-yl)-N-(4-fluorophenyl)nicotinamide | 17.507 |
| 83 | 6-(3-(2,3-difluorophenyl)imidazo[1,5-a]pyridin-8-yl)-N-(4-fluorophenyl)picolinamide | 207.411 |
| 84 | 5-(3-(2,3-difluorophenyl)imidazo[1,5-a]pyridin-8-yl)-3-fluoro-N-(4-fluorophenyl)-2-methylbenzamide | 75.284 |
| 85 | 3-chloro-6-(3-(2,3-difluorophenyl)imidazo[1,5-a]pyridin-8-yl)-N-(4-fluorophenyl)picolinamide | 51.987 |
| 86 | 5-(3-(2,3-dichlorophenyl)imidazo[1,5-a]pyridin-8-yl)-N-(4-fluorophenyl)-2-methylnicotinamide | 30.778 |
| 87 | 5-(3-(2-chloro-3-fluorophenyl)imidazo[1,5-a]pyridin-8-yl)-N-(4-fluorophenyl)-2-methylnicotinamide | 13.263 |
| 88 | 5-(3-(3-chloro-2-fluorophenyl)imidazo[1,5-a]pyridin-8-yl)-N-(4-fluorophenyl)-2-methylnicotinamide | 49.505 |
| 89 | 5-(3-(2,4-difluorophenyl)imidazo[1,5-a]pyridin-8-yl)-N-(4-fluorophenyl)-2-methylnicotinamide | 30.615 |
| 90 | 5-(3-cyclopropylimidazo[1,5-a]pyridin-8-yl)-N-(4-fluorophenyl)-2-methylnicotinamide | 2938.7 |
| 91 | 5-(3-cyclobutylimidazo[1,5-a]pyridin-8-yl)-N-(4-fluorophenyl)-2-methylnicotinamide | 888.075 |
| 92 | 5-(1-bromo-3-(2,3-difluorophenyl)imidazo[1,5-a]pyridin-8-yl)-N-(4-fluorophenyl)-2-methylnicotinamide | 272.745 |
| 93 | 5-(3-cyclohexylimidazo[1,5-a]pyridin-8-yl)-N-(4-fluorophenyl)-2-methylnicotinamide | 249.662 |
| 94 | 2-(azetidin-1-yl)-5-(3-(2,3-difluorophenyl)imidazo[1,5-a]pyridin-8-yl)-N-(4-fluorophenyl)nicotinamide | 123.677 |
| 95 | 2-(5-(3-(2,3-difluorophenyl)imidazo[1,5-a]pyridin-8-yl)-2-(trifluoromethyl)phenyl)-5-fluoro-1H-benzo[d]imidazole | 24.276 |
| 96 | 2-(2-chloro-5-(3-(2,3-difluorophenyl)imidazo[1,5-a]pyridin-8-yl)phenyl)-5-fluoro-1H-benzo[d]imidazole | 67.237 |
| 97 | 2-(5-(3-(2,3-difluorophenyl)imidazo[1,5-a]pyridin-8-yl)-2-methylpyridin-3-yl)-5-fluoro-1H-benzo[d]imidazole | 64.932 |
| 98 | 2-(5-(3-(2,3-difluorophenyl)imidazo[1,5-a]pyridin-8-yl)-2-(trifluoromethyl)pyridin-3-yl)-5-fluoro-1H-benzo[d]imidazole | 36.648 |
| 99 | 2-(5-(3-(2,3-difluorophenyl)imidazo[1,5-a]pyridin-8-yl)-2-methylpyridin-3-yl)-1H-benzo[d]imidazo1e | 59.88 |

What is claimed is:

1. A compound of Formula I:

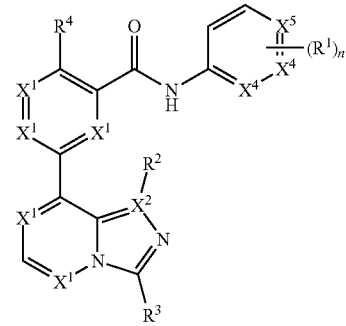

I wherein $X^1$ at each location in Formula I is independently N, CH, or $CX^R$;

$X^2$ is N or C, wherein $R^2$ is absent when $X^2$ is N;

$X^4$ at each location in Formula I is independently N, CH, or $CR^1$;

$X^5$ is CH, $CX^R$, or $CR^1$;

$X^R$ is hydrogen, halogen, $C_{1-3}$ haloalkyl, or $C_{1-6}$ alkyl;

$R^1$ is hydrogen, deuterium, halogen, —CN, —OCF$_3$, —OCHF$_2$, or —CF$_3$, wherein n is 0-5 and where if n is >1, $R^1$ can be independently the same or different from each other;

$R^2$ is hydrogen, halogen, C$_{1-6}$ alkyl, or an unsubstituted or substituted aryl with one, two, or three substituents independently selected from halogen, —CN, C$_{1-6}$ haloalkyl, and C$_{1-6}$ alkyl;

$R^3$ is C$_{3-6}$ cycloalkyl, C$_{3-6}$ heterocycle, or mono or bicyclic aryl or heteroaryl, wherein each mono or bicyclic aryl or heteroaryl is unsubstituted or substituted with one, two, or three substituents independently selected from halogen, —CN, C$_{1-6}$ haloalkyl, and C$_{1-6}$ alkyl; and $R^4$ is halogen, C$_{1-6}$ alkyl, C$_{1-6}$ haloalkyl, —OCF$_3$, C$_{3-6}$ cycloalkyl, or a 4-12 membered heterocycle, or a pharmaceutically acceptable salt thereof.

2. A compound of Formula I$_a$:

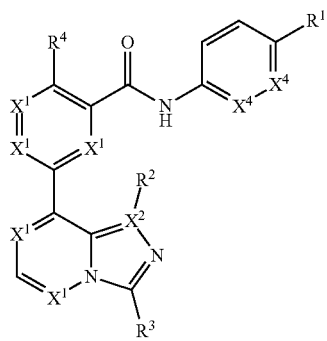

wherein
- $X^1$ at each location of Formula Ia is independently N, CH, or CX$^R$;
- $X^2$ is N or C, wherein $R^2$ is absent when $X^2$ is N;
- $X^4$ at each location of Formula Ia is independently N, CH, or CR$^1$;
- $X^R$ is hydrogen, halogen, C$_{1-3}$ haloalkyl, or C$_{1-6}$ alkyl;
- $R^1$ is hydrogen, deuterium, halogen, —CN, —OCF$_3$, —OCHF$_2$, or —CF$_3$, wherein $R^1$ can be independently the same or different from each other;
- $R^2$ is absent when $X^2$ is N; or $R^2$ is hydrogen, halogen, C$_{1-6}$ alkyl, or an unsubstituted or substituted aryl with one, two, or three substituents independently selected from halogen, —CN, C$_{1-6}$ haloalkyl, and C$_{1-6}$ alkyl;
- $R^3$ is C$_{3-6}$ cycloalkyl, C$_{3-6}$ heterocycle, or mono or bicyclic aryl or heteroaryl, wherein each mono or bicyclic aryl or heteroaryl is unsubstituted or substituted with one, two, or three substituents independently selected from halogen, —CN, C$_{1-6}$ haloalkyl, and C$_{1-6}$ alkyl; and
- $R^4$ is halogen, C$_{1-6}$ alkyl, C$_{1-6}$ haloalkyl, —OCF$_3$, C$_{3-6}$ cycloalkyl, or a 4-12 membered heterocycle, or a pharmaceutically acceptable salt thereof.

3. A compound of Formula I$_b$:

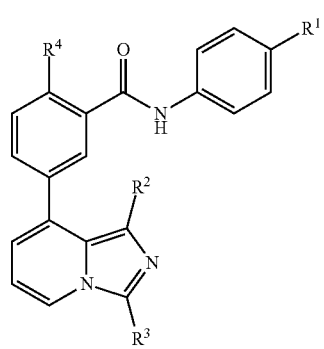

wherein
- $R^1$ is halogen;
- $R^2$ is hydrogen, C$_{1-3}$ alkyl, or an unsubstituted or substituted aryl with one, two, or three substituents independently selected from halogen, —CN, C$_{1-3}$ haloalkyl, and C$_{1-3}$ alkyl;
- $R^3$ is a C$_{3-6}$ cycloalkyl, C$_{3-6}$ heterocycle, or mono or bicyclic aryl or heteroaryl, wherein each mono or bicyclic aryl or heteroaryl is unsubstituted or substituted with one, two, or three substituents independently selected from halogen, —CN, C$_{1-3}$ haloalkyl, and C$_{1-3}$ alkyl; and
- $R^4$ is halogen, C$_{1-3}$ alkyl, C$_{1-3}$ haloalkyl, —OCF$_3$, C$_{3-6}$ cycloalkyl, or 4-12 membered heterocycle, or a pharmaceutically acceptable salt thereof.

4. A compound of Formula I$_c$:

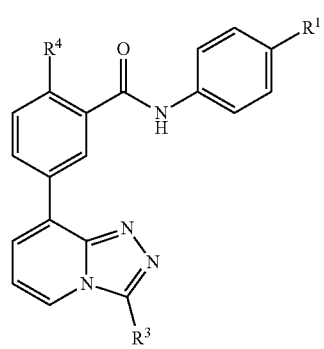

wherein
- $R^1$ is halogen;
- $R^3$ is a C$_{3-6}$ cycloalkyl, C$_{3-6}$ heterocycle, or mono or bicyclic aryl or heteroaryl, wherein each mono or bicyclic aryl or heteroaryl is unsubstituted or substituted with one, two, or three substituents independently selected from halogen, —CN, C$_{1-3}$ haloalkyl, and C$_{1-3}$ alkyl; and
- $R^4$ is halogen, C$_{1-3}$ alkyl, C$_{1-3}$ haloalkyl, —OCF$_3$, C$_{3-6}$ cycloalkyl, or 4-12 membered heterocycle, or a pharmaceutically acceptable salt thereof.

5. A compound of Formula I$_e$:

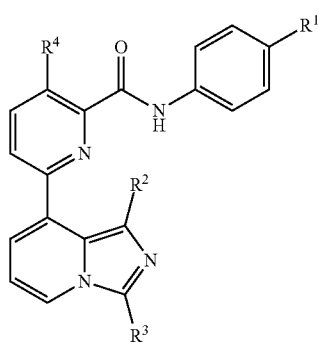

wherein
 R$^1$ is halogen;
 R$^2$ is hydrogen, halogen, C$_{1-3}$ alkyl, C$_{1-3}$ haloalkyl, —OCF$_3$, C$_{3-6}$ cycloalkyl, or 4-12 membered heterocycle;
 R$^3$ is a C$_{3-6}$ cycloalkyl, C$_{3-6}$ heterocycle, or mono or bicyclic aryl or heteroaryl, wherein each mono or bicyclic aryl or heteroaryl is unsubstituted or substituted with one, two, or three substituents independently selected from halogen, —CN, C$_{1-3}$ haloalkyl, and C$_{1-3}$ alkyl; and
 R$^4$ is halogen, C$_{1-6}$ alkyl, C$_{1-6}$ haloalkyl, —OCF$_3$, C$_{3-6}$ cycloalkyl, or a 4-12 membered heterocycle,
or a pharmaceutically acceptable salt thereof.

6. A compound of Formula I$_f$:

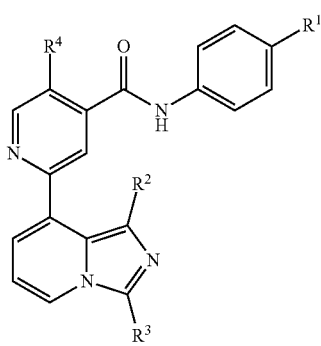

wherein
 R$^1$ is halogen;
 R$^2$ is hydrogen, C$_{1-3}$ alkyl, or an unsubstituted or substituted aryl with one, two, or three substituents independently selected from halogen, —CN, C$_{1-3}$ haloalkyl, and C$_{1-3}$ alkyl;
 R$^3$ is a C$_{3-6}$ cycloalkyl, C$_{3-6}$ heterocycle, or mono or bicyclic aryl or heteroaryl, wherein each mono or bicyclic aryl or heteroaryl is unsubstituted or substituted with one, two, or three substituents independently selected from halogen, —CN, C$_{1-3}$ haloalkyl, and C$_{1-3}$ alkyl; and
 R$^4$ is halogen, C$_{1-3}$ alkyl, C$_{1-3}$ haloalkyl, —OCF$_3$, C$_{3-6}$ cycloalkyl, or 4-12 membered heterocycle,
or a pharmaceutically acceptable salt thereof.

7. A compound of Formula I$_h$:

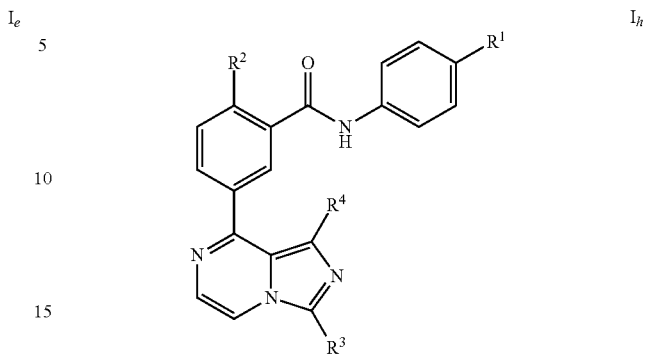

wherein
 R$^1$ is halogen;
 R$^2$ is hydrogen, C$_{1-3}$ alkyl, or an unsubstituted or substituted aryl with one, two, or three substituents independently selected from halogen, —CN, C$_{1-3}$ haloalkyl, and C$_{1-3}$ alkyl;
 R$^3$ is a 5-10 membered mono or bicyclic aryl or heteroaryl, wherein each mono or bicyclic aryl or heteroaryl is unsubstituted or substituted with one, two, or three substituents independently selected from halogen, —CN, C$_{1-3}$ haloalkyl, and C$_{1-3}$ alkyl; and
 R$^4$ is C$_{1-3}$ alkyl or C$_{1-3}$ haloalkyl,
or a pharmaceutically acceptable salt thereof.

8. A compound of Formula I$_i$:

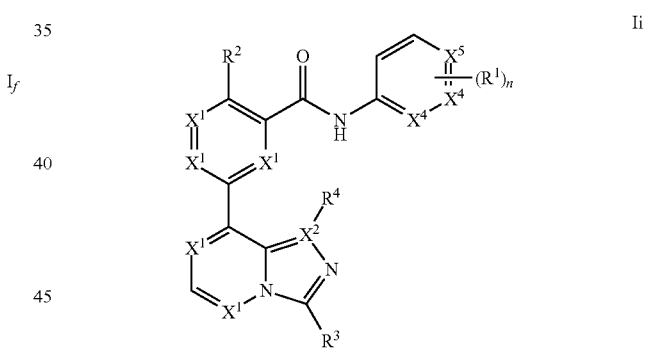

wherein
 X$^1$ at each location in Formula Ii is independently N, CH, or CX$^R$;
 X$^2$ is N or C, wherein R$^2$ is absent when X$^2$ is N;
 X$^4$ at each location in Formula Ii is independently N, CH, or CR$^1$;
 X$^5$ is N, CH, or CR$^1$;
 X$^R$ is hydrogen, halogen, C$_{1-3}$ haloalkyl, or C$_{1-6}$ alkyl;
 R$^1$ is hydrogen, deuterium, halogen, —CN, —OCF$_3$, —OCHF$_2$, C$_{1-3}$ haloalkyl, or C$_{1-6}$ alkyl, wherein n is 0-5 and R$^1$ can be independently the same or different from each other;
 R$^2$ is hydrogen, halogen, C$_{1-6}$ alkyl, or an unsubstituted or substituted aryl with one, two, or three substituents independently selected from halogen, —CN, C$_{1-6}$ haloalkyl, and C$_{1-6}$ alkyl;
 R$^3$ is C$_{3-6}$ cycloalkyl, C$_{3-6}$ heterocycle, or mono or bicyclic aryl or heteroaryl, wherein each mono or bicyclic aryl or heteroaryl is unsubstituted or substituted with one, two, or three substituents independently selected from halogen, —CN, $C_{1-6}$ haloalkyl, $C_{1-6}$ alkyl, and —C(O)N($R^5$)($R^6$);

$R^4$ is halogen, $C_{1-6}$ alkyl, $C_{1-6}$ haloalkyl, —OCF$_3$, $C_{3-6}$ cycloalkyl, or a 4-12 membered heterocycle;

$R^5$ is hydrogen or $C_{1-6}$ alkyl; and $R^6$ is hydrogen or $C_{1-6}$ alkyl, or a pharmaceutically acceptable salt thereof.

9. The compound of claim 1, or a pharmaceutically acceptable salt thereof, wherein $R^1$ is fluoro, chloro, or bromo.

10. The compound of claim 1, or a pharmaceutically acceptable salt thereof, wherein $R^2$ is hydrogen or $C_{1-3}$ alkyl.

11. The compound of claim 1, or a pharmaceutically acceptable salt thereof, wherein $R^2$ is hydrogen.

12. The compound of claim 1, or a pharmaceutically acceptable salt thereof, wherein $R^3$ is a 5-10 membered mono or bicyclic aryl or heteroaryl, wherein each mono or bicyclic aryl or heteroaryl is unsubstituted or substituted with one or two substituents independently selected from halogen, —CN, $C_{1-3}$ haloalkyl, and $C_{1-3}$ alkyl.

13. The compound of claim 8, or a pharmaceutically acceptable salt thereof, wherein $R^3$ is selected from the group consisting of:

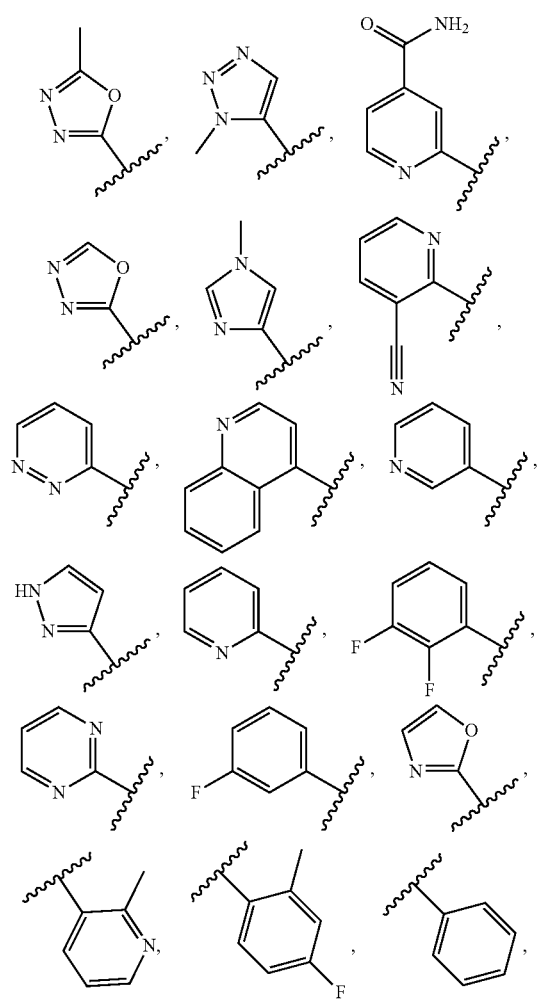

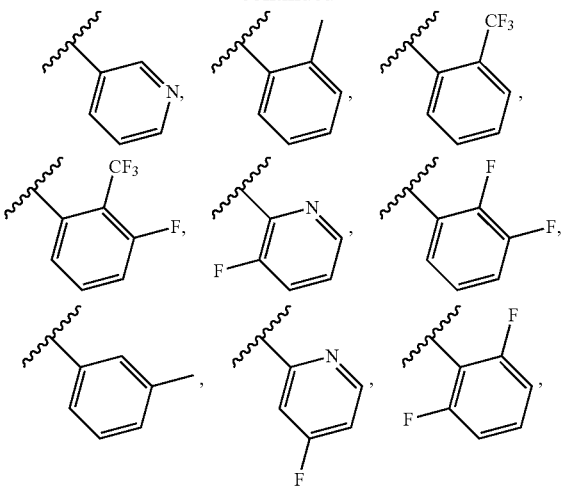

-continued

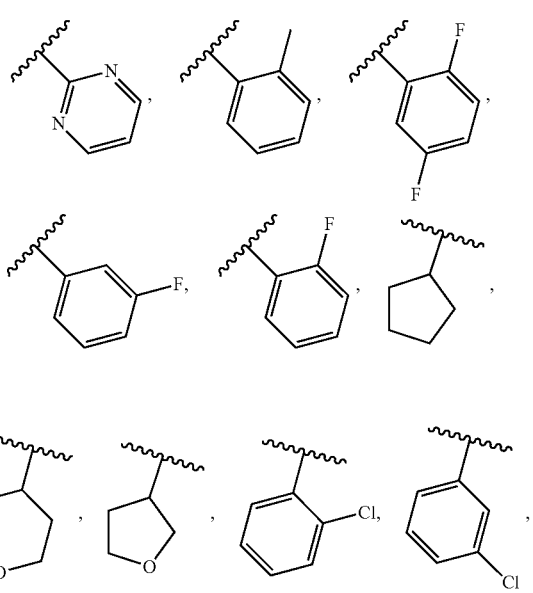

14. The compound of claim 1, or a pharmaceutically acceptable salt thereof, wherein $R^4$ is methyl, —CF$_3$, —CHF$_2$, —OCF$_3$, or $C_{4-6}$ heterocycle.

15. A compound selected from the group consisting of:
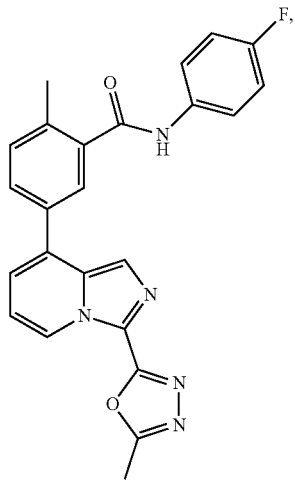
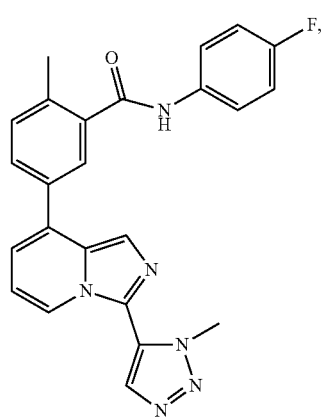
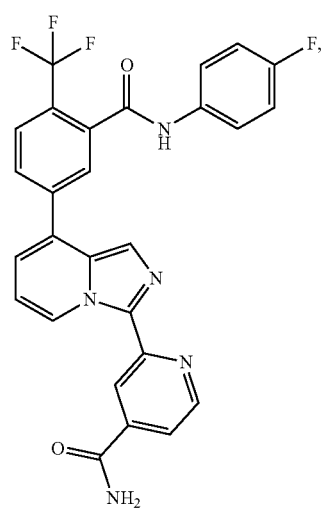
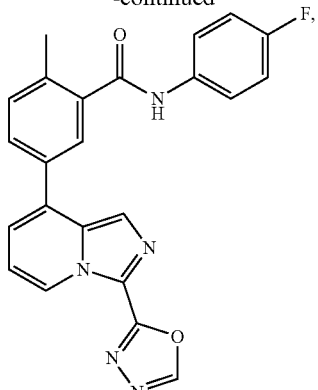
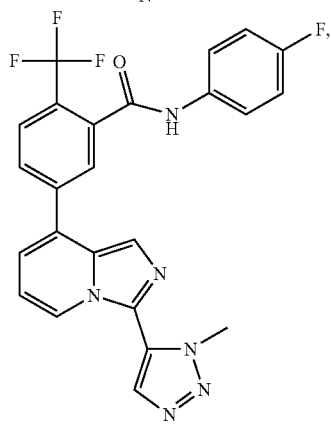
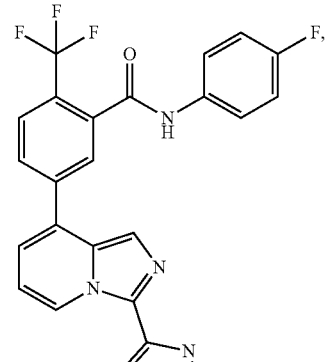
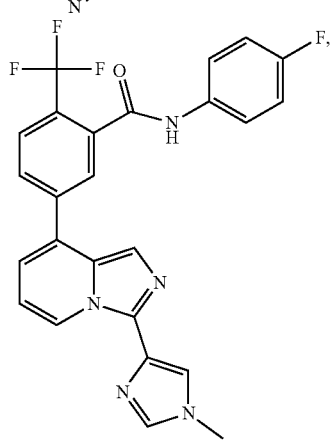

247
-continued
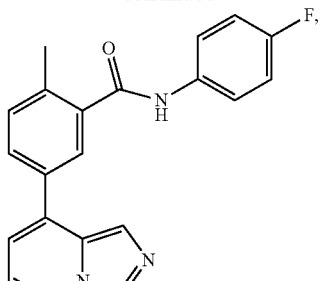
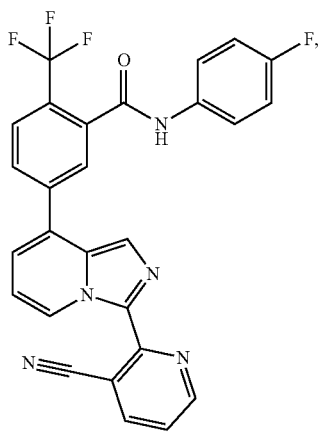
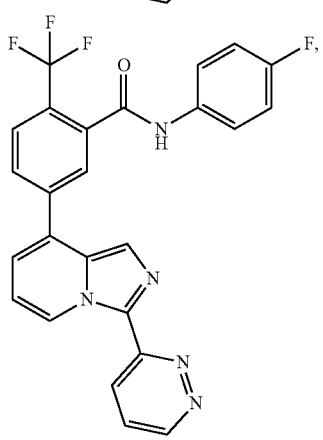
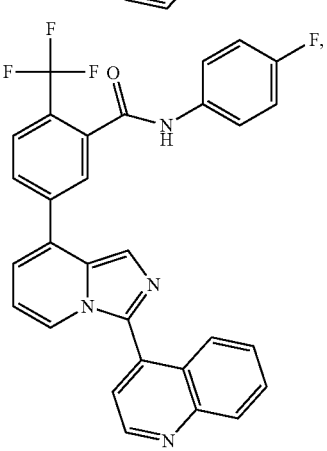
248
-continued
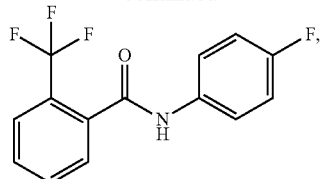
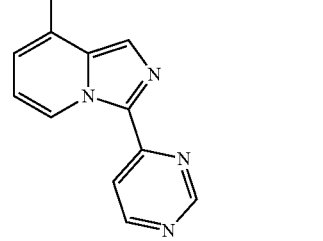
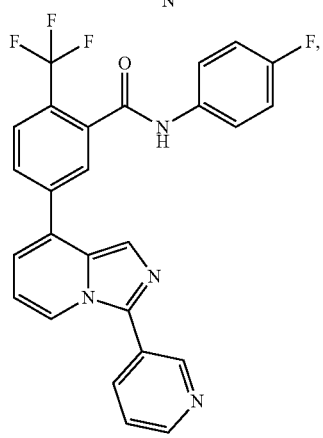
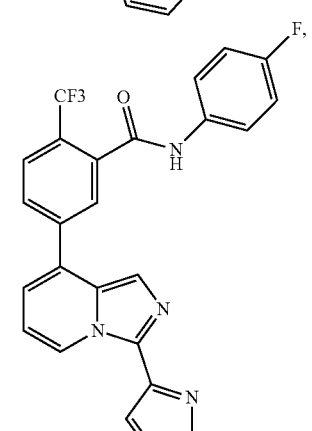
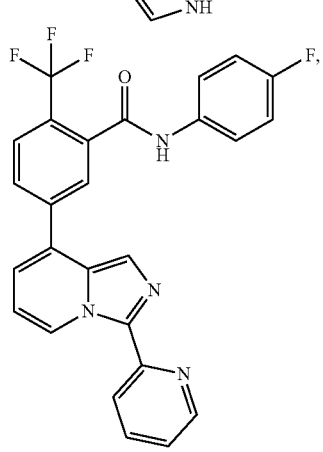

249
-continued
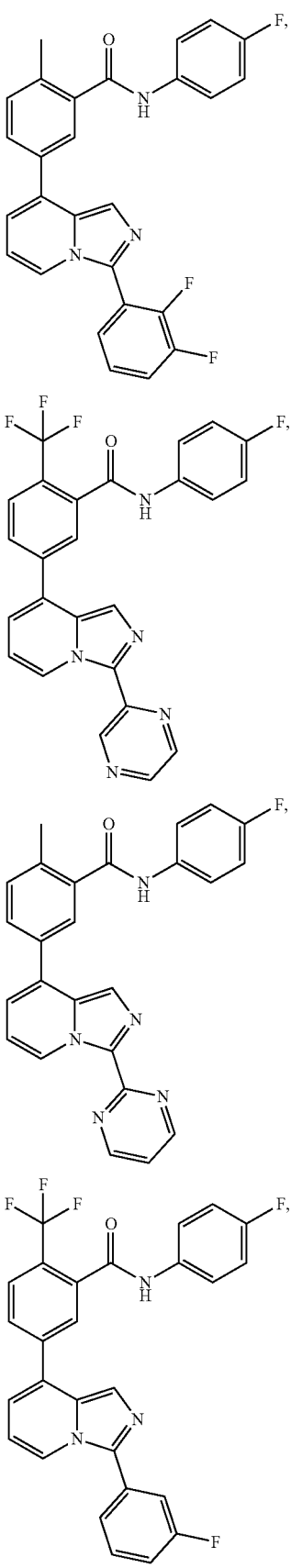
250
-continued
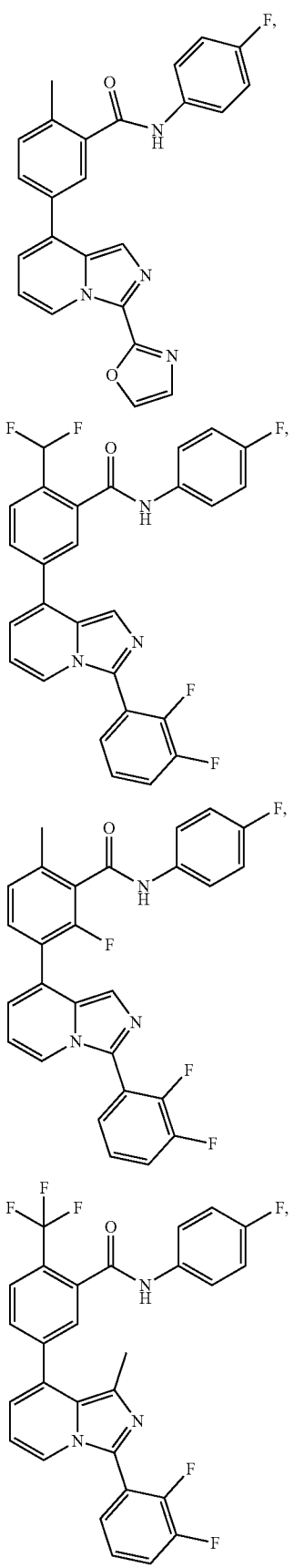

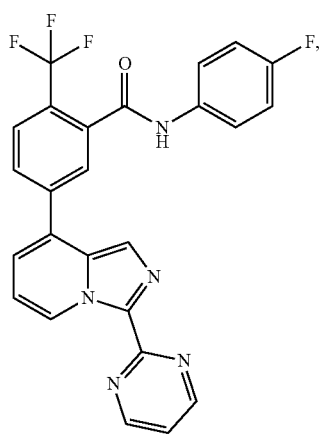
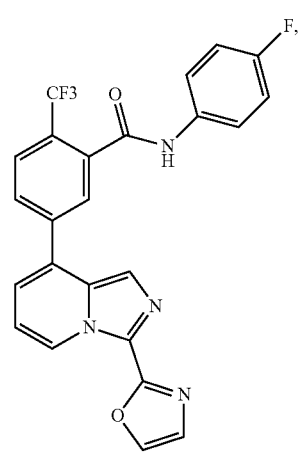
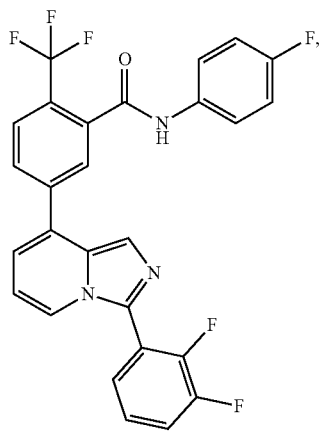
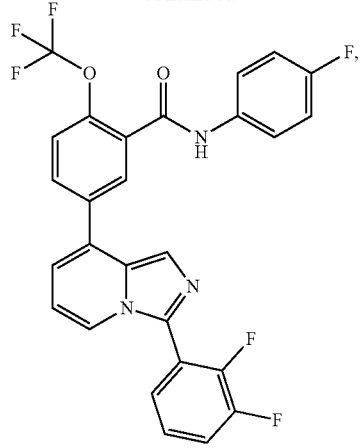
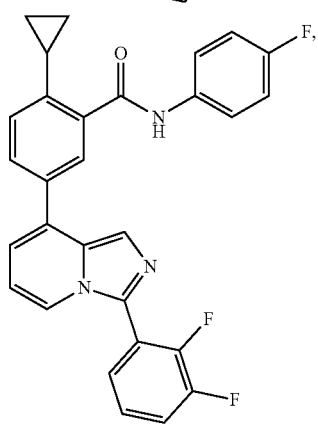
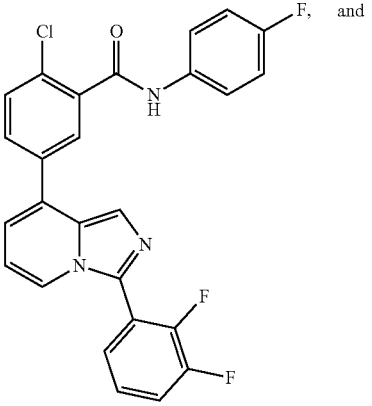
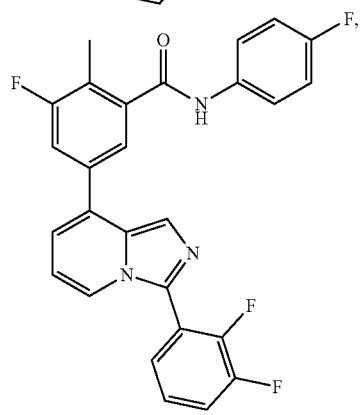
or a pharmaceutically acceptable salt thereof.

16. A compound selected from the group consisting of:
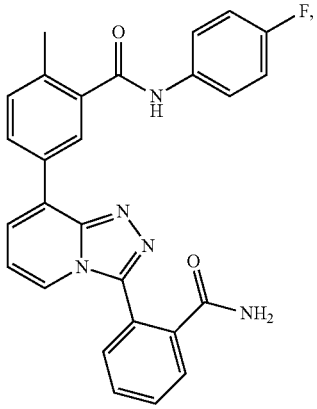
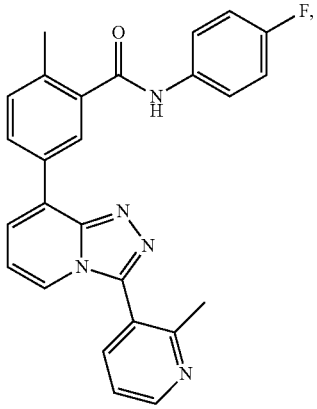
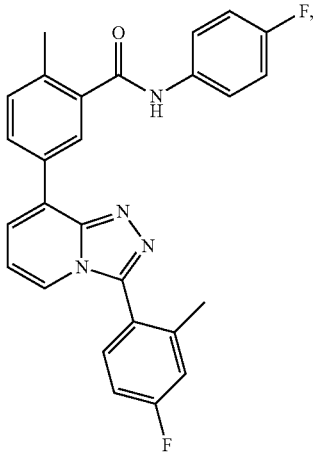
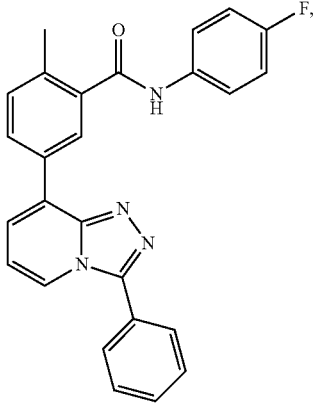
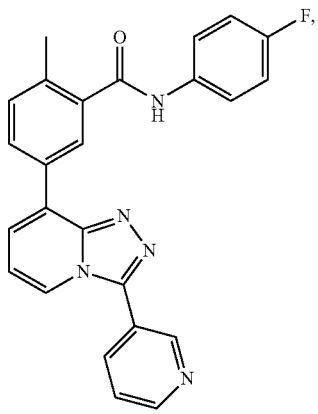
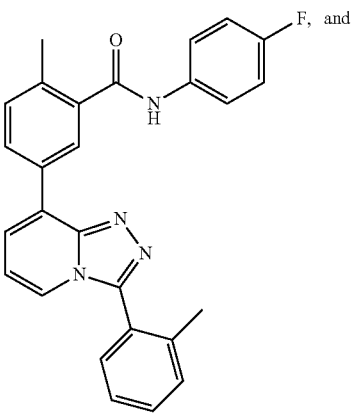
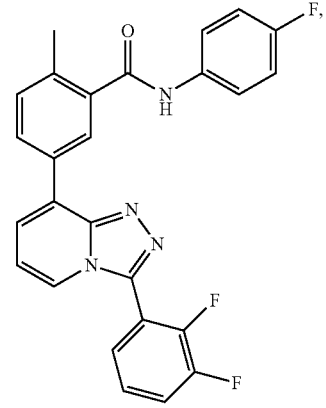
or a pharmaceutically acceptable salt thereof.

17. A compound selected from the group consisting of:
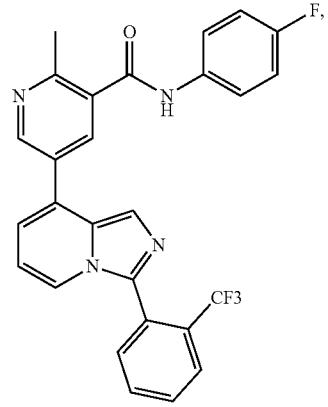
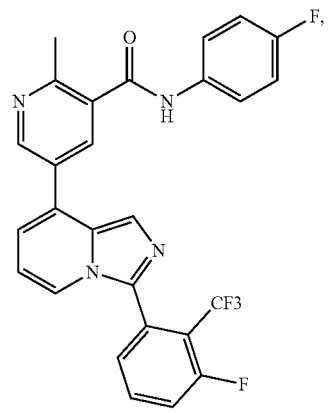
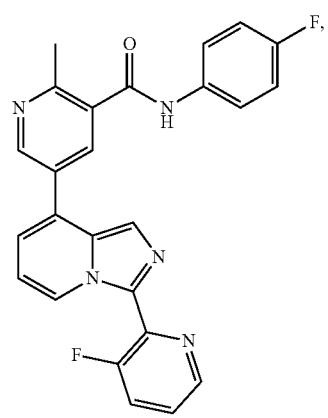
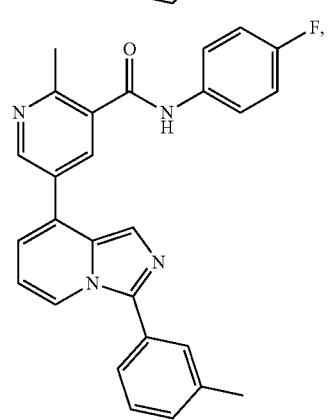
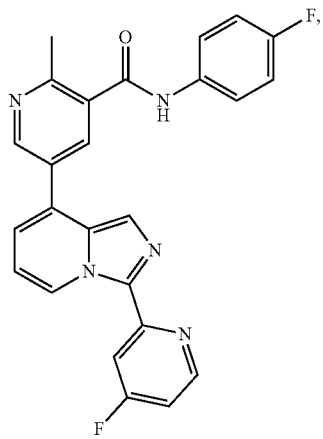
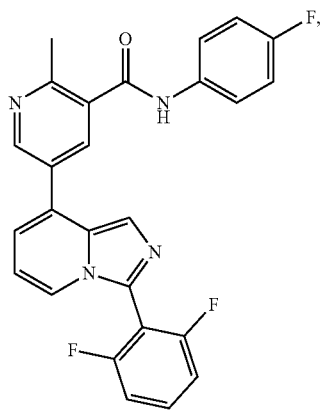
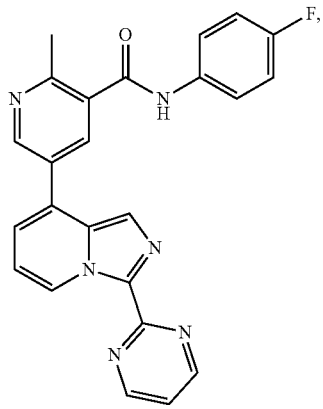
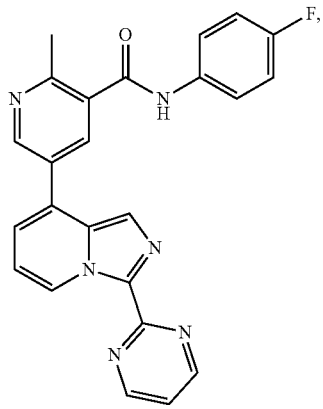

-continued
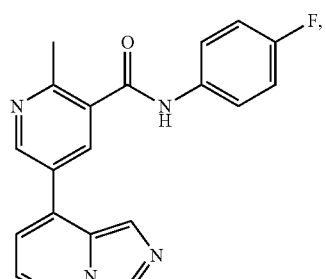
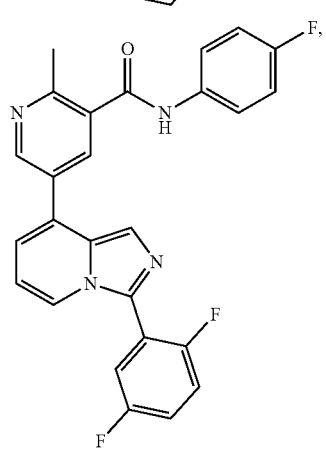
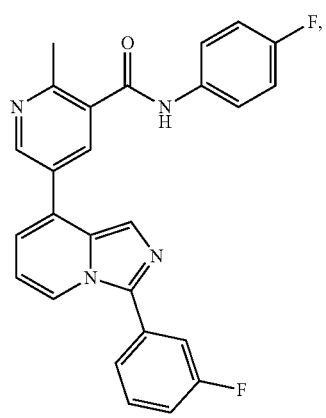
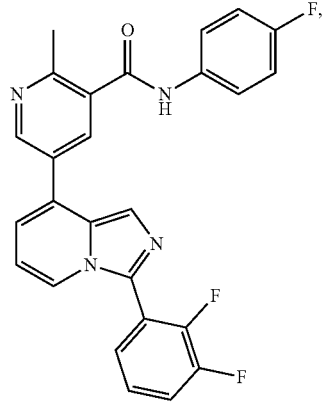
-continued
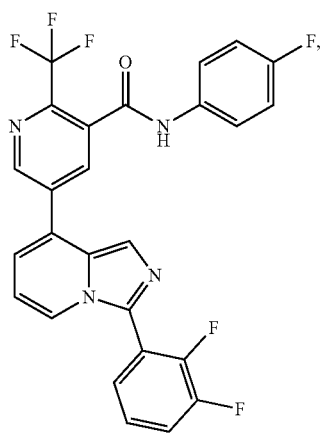
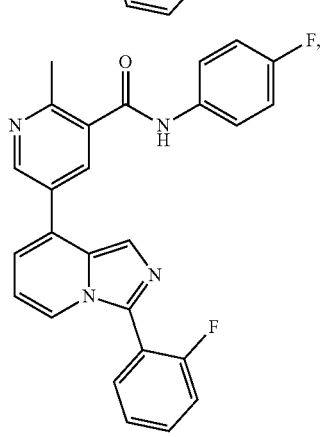
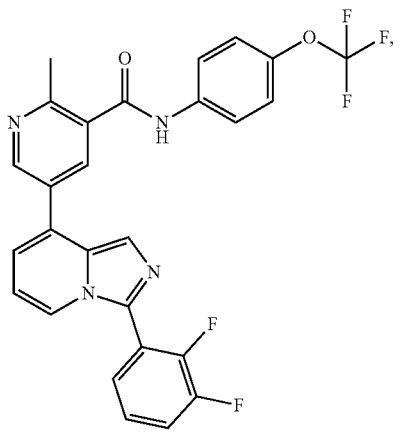
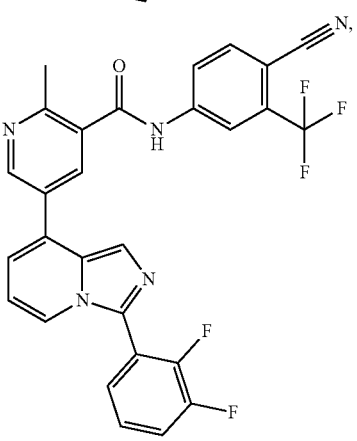

259
-continued
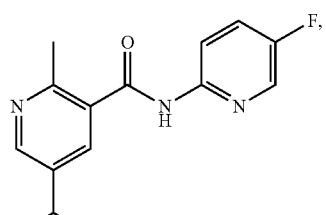
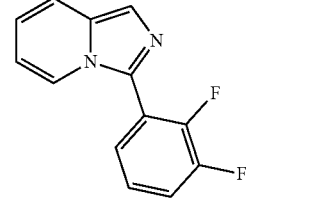
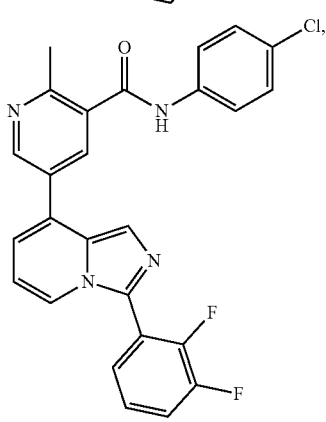
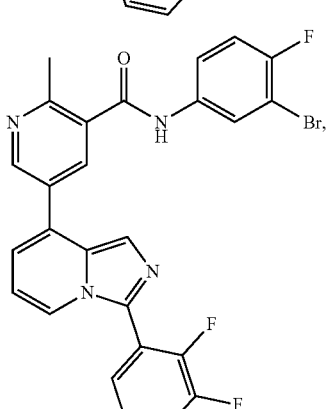
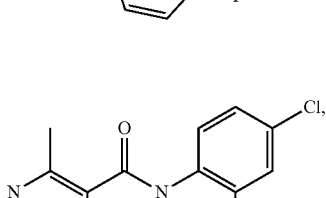
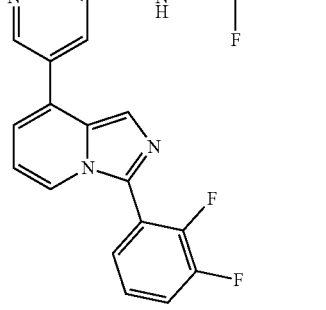
260
-continued
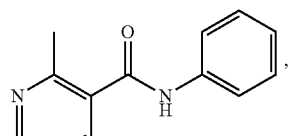
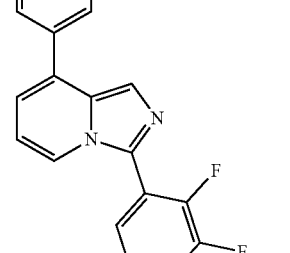
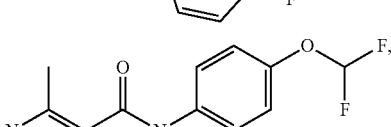
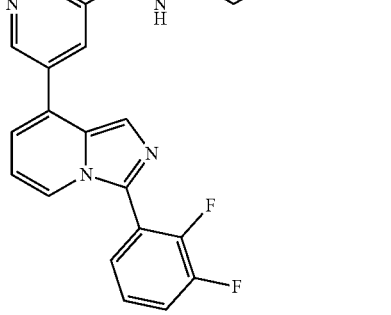
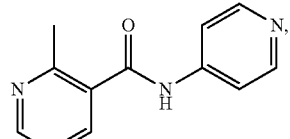
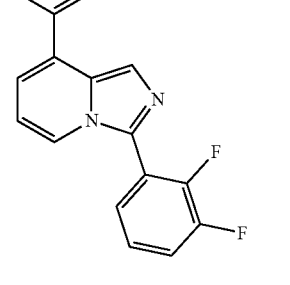

261
-continued
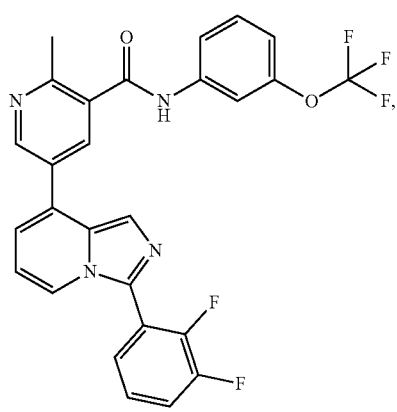
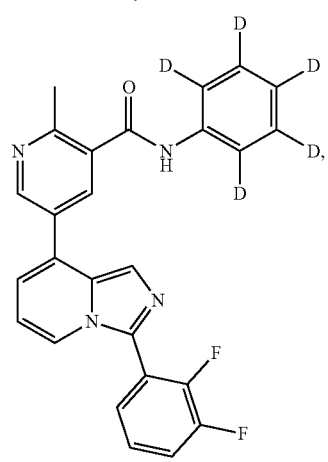
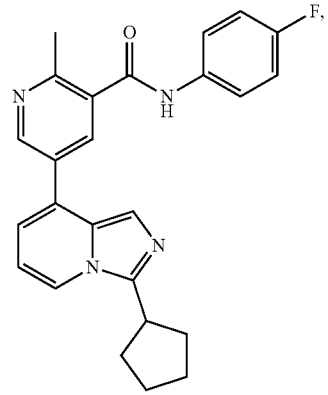
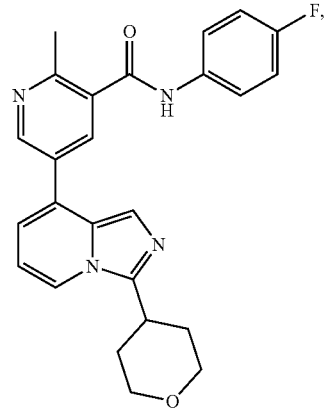
262
-continued
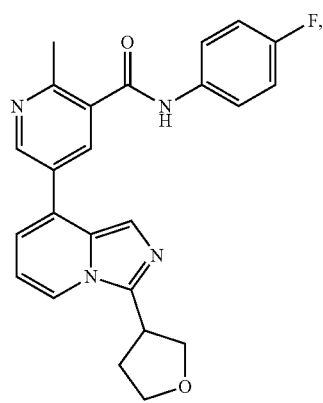
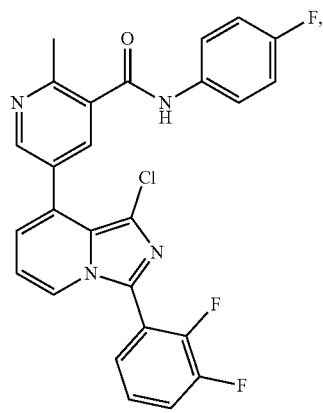
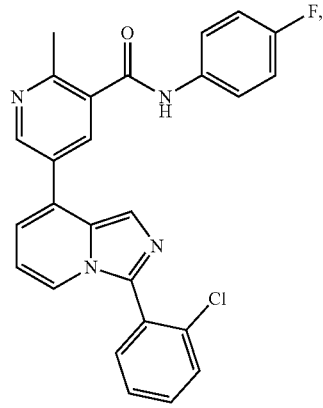
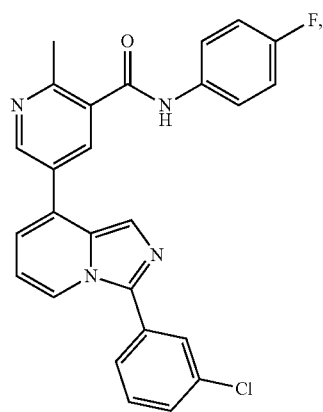

263
-continued
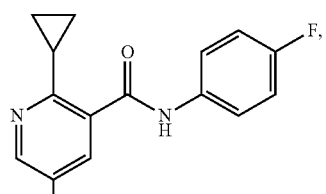
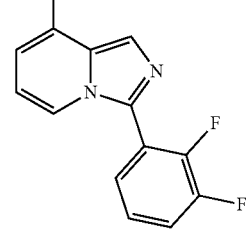
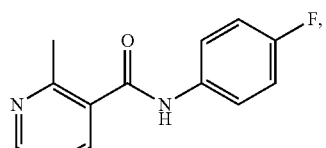
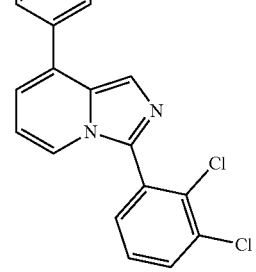
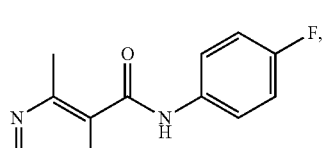
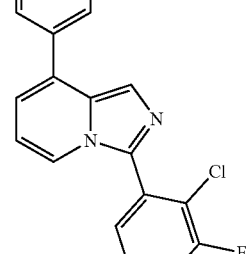
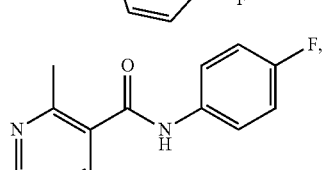
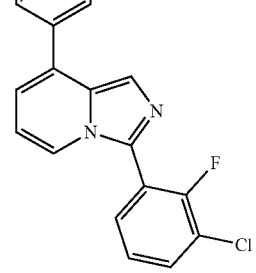
264
-continued
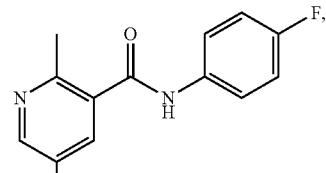
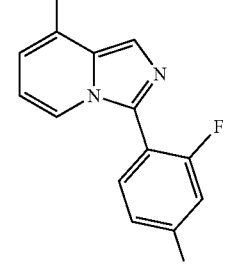
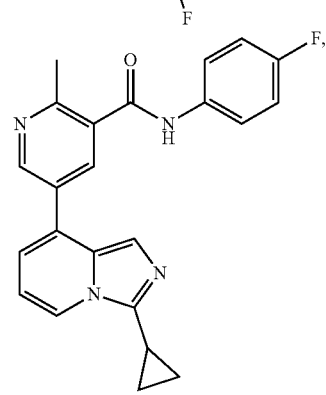
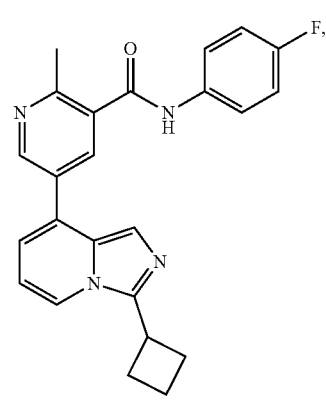
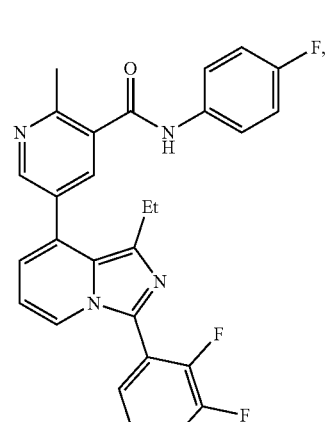

265
-continued
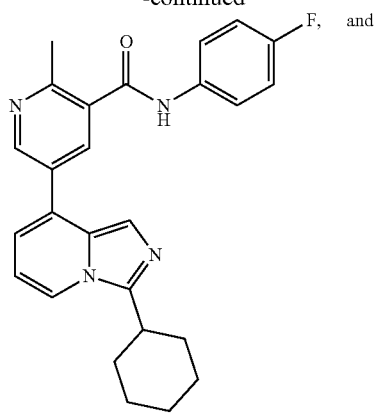
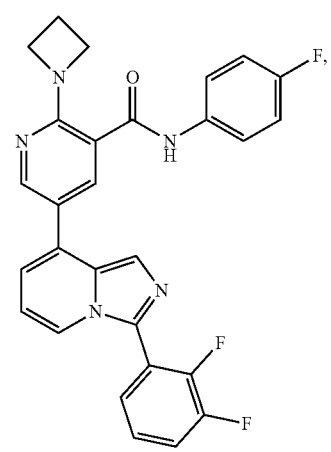
or a pharmaceutically acceptable salt thereof.
18. A compound selected from the group consisting of:
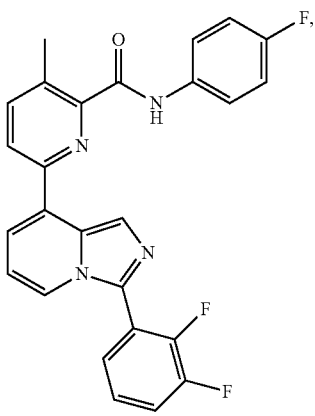
266
-continued
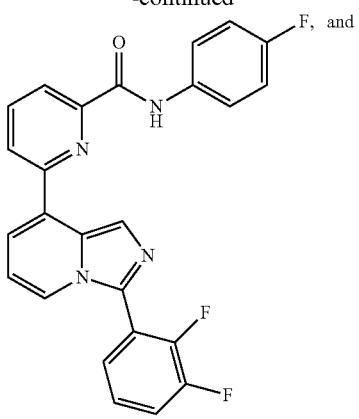
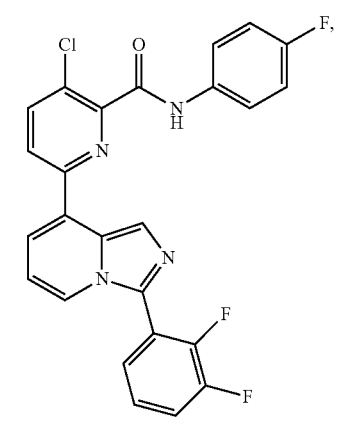
or a pharmaceutically acceptable salt thereof.
19. The compound of claim 1, or a pharmaceutically acceptable salt thereof, selected from the group consisting of:
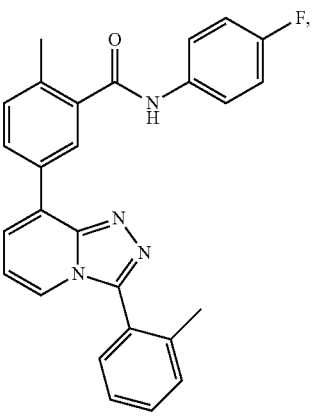

267
-continued
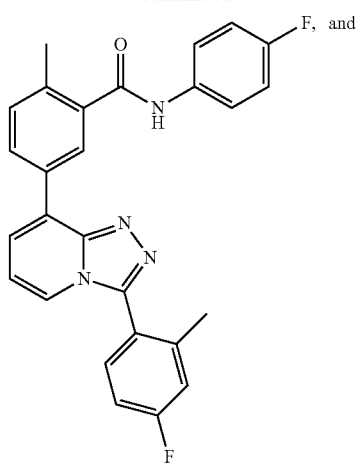
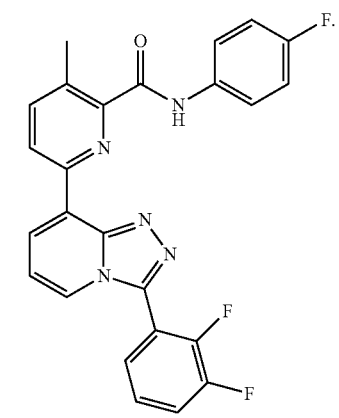
20. The compound of claim 1, or a pharmaceutically acceptable salt thereof, selected from the group consisting of:
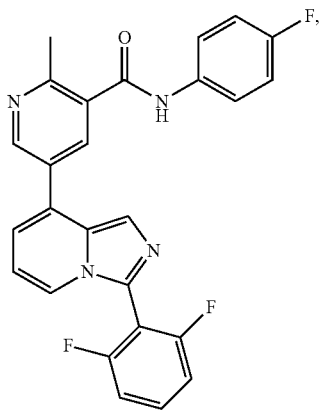
268
-continued
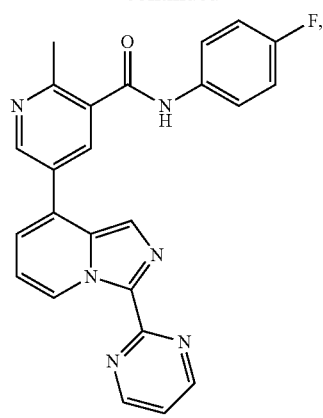
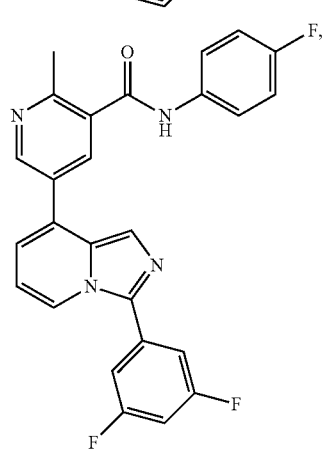
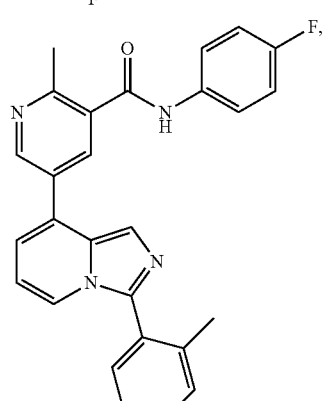
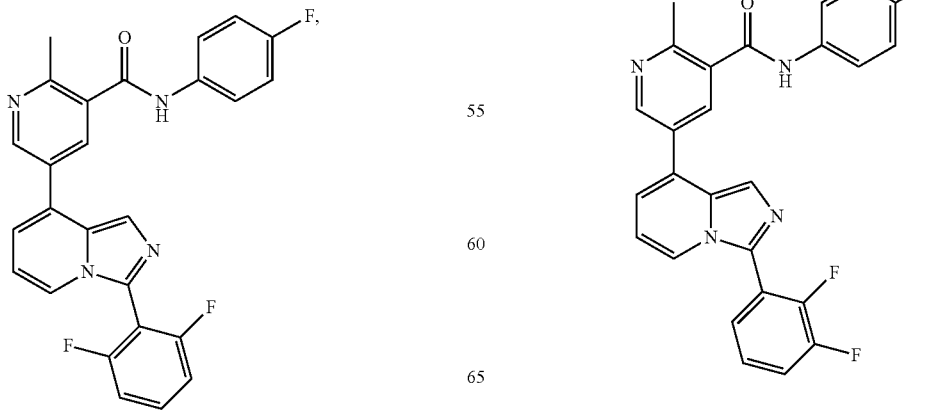

269
-continued
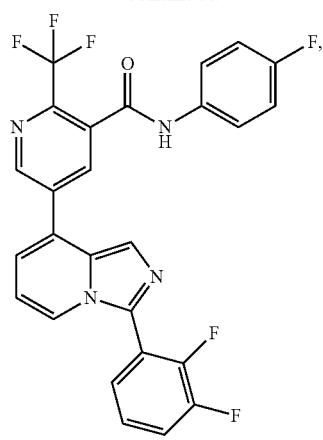
270
-continued
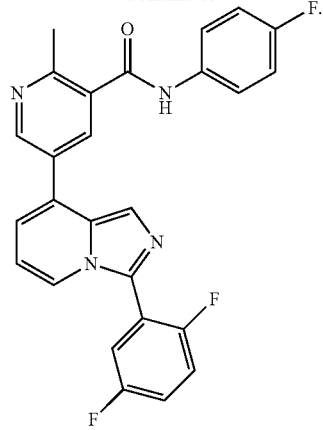
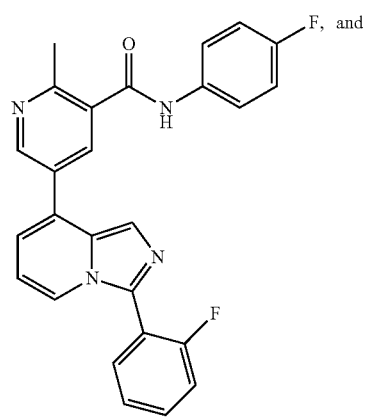
21. The compound of claim 1, or a pharmaceutically acceptable salt thereof, wherein the compound is
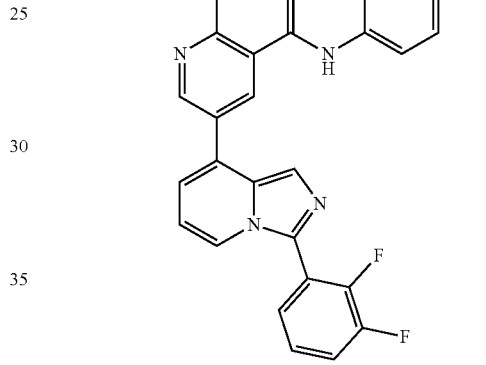
22. A pharmaceutical composition comprising a compound of claim 1, or a pharmaceutically acceptable salt thereof, and at least one pharmaceutically acceptable carrier.
* * * * *